(12) United States Patent  
Parma et al.

(10) Patent No.: US 6,280,932 B1  
(45) Date of Patent: *Aug. 28, 2001

(54) HIGH AFFINITY NUCLEIC ACID LIGANDS TO LECTINS

(75) Inventors: David H Parma; Brian Hicke; Philippe Bridonneau; Larry Gold, all of Boulder, CO (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/952,793

(22) PCT Filed: Jun. 5, 1996

(86) PCT No.: PCT/US96/09455

§ 371 Date: Nov. 21, 1997

§ 102(e) Date: Nov. 21, 1997

(87) PCT Pub. No.: WO96/40703

PCT Pub. Date: Dec. 19, 1996

Related U.S. Application Data

(63) Continuation-in-part of application No. 08/479,724, filed on Jun. 7, 1995, now Pat. No. 5,780,228, and a continuation-in-part of application No. 08/472,256, filed on Jun. 7, 1995, now Pat. No. 6,001,988, and a continuation-in-part of application No. 08/472,255, filed on Jun. 7, 1995, now Pat. No. 5,766,853, and a continuation-in-part of application No. 08/477,829, filed on Jun. 7, 1995, now abandoned, which is a continuation-in-part of application No. 07/714,131, filed on Jun. 10, 1991, now Pat. No. 5,475,096, which is a continuation-in-part of application No. 07/536,428, filed on Jun. 11, 1990, now abandoned.

(51) Int. Cl.[7] ............................. C12Q 1/68; C07H 19/00; C07H 21/00; C07H 21/02

(52) U.S. Cl. ............................. 435/6; 435/91.1; 435/91.2; 435/7.1; 536/22.1; 536/23.1; 536/24.33; 530/300

(58) Field of Search ................................. 435/6, 7.1, 91.1, 435/91.2; 536/22.1, 23.1, 24.33; 530/300

(56) References Cited

U.S. PATENT DOCUMENTS

| | | | |
|---|---|---|---|
| 5,270,163 | 12/1993 | Gold et al. | 435/6 |
| 5,459,015 | 10/1995 | Janjic et al. | 435/6 |
| 5,472,841 | 12/1995 | Jayasena et al. | 435/6 |
| 5,475,096 | 12/1995 | Gold et al. | 536/26 |
| 5,476,766 | 12/1995 | Gold et al. | 435/6 |
| 5,484,891 | 1/1996 | Lasky et al. | 530/387.3 |
| 5,489,677 | 2/1996 | Sanghvi et al. | 536/22.1 |
| 5,496,938 | 3/1996 | Gold et al. | 536/22.1 |
| 5,503,978 | 4/1996 | Schneider et al. | 435/6 |
| 5,527,894 | 6/1996 | Gold et al. | 536/22.1 |
| 5,543,293 | 8/1996 | Gold et al. | 435/6 |
| 5,567,588 | 10/1996 | Gold et al. | 435/6 |
| 5,580,737 | 12/1996 | Polisky et al. | 435/6 |
| 5,587,468 | 12/1996 | Allen et al. | 536/22.1 |
| 5,595,877 | 1/1997 | Gold et al. | 435/6 |
| 5,723,323 | 3/1998 | Kauffman et al. | 435/172.3 |
| 5,780,228 | * 7/1998 | Parma et al. | 435/6 |
| 6,001,988 | * 12/1999 | Parma et al. | 536/24.3 |

FOREIGN PATENT DOCUMENTS

| | | |
|---|---|---|
| 2 183 661 | 6/1987 | (GB). |
| WO 89/06694 | 7/1989 | (WO). |
| WO 91/19813 | 12/1991 | (WO). |
| WO 92/14843 | 9/1992 | (WO). |

OTHER PUBLICATIONS

Biolabs Catalogs, pp. 60–61, 1986.*

(List continued on next page.)

*Primary Examiner*—Jezia Riley  
(74) *Attorney, Agent, or Firm*—Swanson & Bratschun, L.L.C.

(57) ABSTRACT

This invention discloses high-affinity oligonucleotide ligands to lectins, specifically nucleic acid ligands having the ability to bind to the lectins, wheat germ agglutinin, L-selectin and P-selectin. Also disclosed are the methods for obtaining such ligands.

50 Claims, 19 Drawing Sheets

OTHER PUBLICATIONS

Cassels et al. (1990) J. of Biol. Chem. 265:14127.
DeFrees and Gaeta (1993) J. Am. Chem. Soc. 115:7549.
Ellington & Szostak (1990) Abstracts of papers presented at the 1990 meeting on RNA Processing, Cold Spring Harbor Laboratory, Cold Spring Harbor, NY, p. 84.
Foxall et al. (1992) J. Cell Biol. 117:895.
Glick et al. (1991) J. Biol. Chem. 266:23660.
Green et al. (1995) Glycobiology 5:29.
Imundo et al. (1995) Proc. Natl. Acad. Sci. USA 92:3019.
Jacob et al. (1995) Biochemistry 34:1210.
Joyce (1989) Gene 82:83.
Joyce & Inoue (1989) Nucleic Acids Research 17:711.
Karlsson (1989) Annu. Rev. Biochem. 58:309.
Kinzler & Vogelstein (1989) Nucleic Acids Research 17:3645.
Kramer et al. (1974) J. Mol. Biol. 89:719.
Lee (1992) FASEB 6:3193.
Levisohn & Spiegelman (1969) Proc. Natl. Acad. Sci. USA 63:805.
Levisohn & Spiegelman (1968) Proc. Natl. Acad. Sci. USA 60:866.
Ma et al. (1993) Circulation 88:649.
Martens et al. (1995) J. Biol. Chem. 270:21129.
Mihelcic et al. (1994) Blood 84:2322.
Monsigny et al. (1979) Eur. J. Biochem. 98:39.
Mulligan et al.(1993) Nature 364:149.
Mulligan et al. (1993) J. Immun. 151:6410.
Mulligan et al. (1993) J. Exp. Med. 178:623.
Mulligan et al. (1992) J. Clin. Invest. 90:1600.
Mulligan et al. (1994) J. Immun., pp. 832–840.
Nagata and Burger (1974) J. Biol. Chem. 249:3116.
Nelson et al. (1993) J. Clin. Invest. 91:1157.
Nelson et al. (1994) J. Biol. Chem. 269:15060.
Nelson et al. (1993) Blood 82:3253.
Oliphant et al. (1989) Mol. Cell. Biol. 9:2944.
Oliphant & Struhl (1988) Nucleic Acids Research 16:7673.
Oliphant & Struhl (1987) Methods in Enzymology 155:568.
Oliphant et al. (1986) Gene 44:177.
Orlandi et al. (1992) J. Cell Biol. 116:901.
Petri (1991) ASM News 57:299.
Phillips et al. (1990) Science 250:1130.
Robertson & Joyce (1990) Nature 344:467.
Saitoh et al. (1991) FEBS 282:385.
Seekamp et al. (1991) Amer. J. Pathol. 144:592.
Sherblom et al. (1994) J. Biol. Chem. 263:5418.
Singleton and Sainsbury (1987) in Dictionary of Microbiology and Molecular Biology, ($2^{nd}$ ed.) John Wiley & Sons, New York, p. 493.
Thiesen & Bach (1990) Nucleic Acids Research 18:3203.
Todderud et al. (1992) J. Leuk. Biol. 52:85.
Tyrrell et al. (1991) Proc. Natl. Acad. Sci. USA 88:10372.
Van Landschoot et al. (1977) Eur. J. Biochem. 79:275.
Watowich et al. (1994) Structure 2:719.
Watson et al. (1991) Nature 349:164–166.
Watson et al. (1990) J. Cell. Biol. 110:2221.
Winn et al. (1993) J. Clin. Invest. 92:2042.
Wright (1993) J. Mol. Biol. 232:620.
Yednock et al. (1987) J. Cell. Biol. 104:713.
Yuen et al. (1994) J. Biol. Chem. 269:1595.
Szostak, "Structure and Activity of Ribozymes," in Redesigning the Molecules of Life, (S.A. Benner ed.) Springer–Verlag Berlin Heidelberg, pp. 87–113, (1988).

* cited by examiner

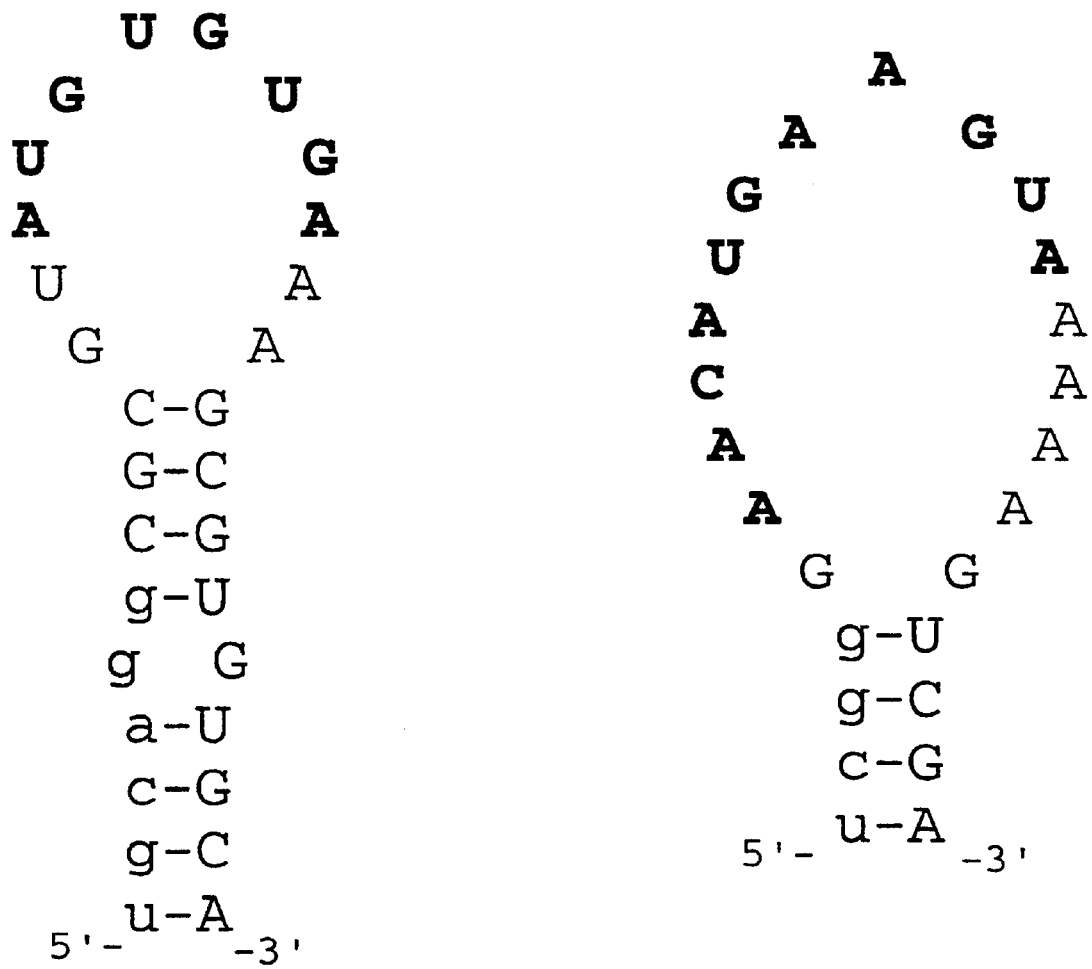
FIGURE 7A
FIGURE 7B
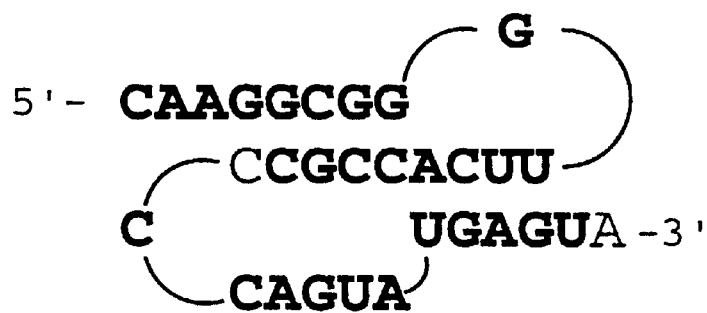
FIGURE 7C

```
                        Base Pairs
    Y  T_15
  G    A      AT   TA   GC   CG   GT   TG   GA   AG   AA   OTHER
    Y-R       2    13   3    6    --   --   --   --   --   --
    G-A       --   --   3    --   --   --   21   --   --   --
 10 G-C       --   --   24   --   --   --   --   --   --   --
    A |
    A |
    C-G_20    --   --   --   24   --   --   --   --   --   --
    A-T       18   4    1    1    --   --   --   --   --   --
  5 T-A       4    18   --   --   1    --   1    --   --   --
    G A       --   8    --   --   --   --   12   1    2    1
    N-N'      12   3    7    --   --   1    --   --   --   1
    N-N'_25   --   2    8    11   1    --   --   2    --   --
    N-N'      4    --   1    3    4    --   2    --   1    9
5'- N  N -3'  1    --   1    3    1    --   2    2    1    13
```

FIGURE 12

```
         U U
        U   U      AU   UA   GC   CG   GU   UG   AG   GA   OTHER
         G-C                 21
         Y-R'           11   10
         G-A                                              21
         C-G             6   15
         R-Y'       9    1   11
     R Y R-Y'      13    1    6    1
   A       |
   A
   Y U C Y-R'           13    5    3
         N-N'       4    3    4    6    2    1    1
         R-Y'       7    3    7         3                   1
         G-C'       1    2   13    3                        2
         N-N'       3    2    5    1                   2    8
         N-N'       3    2    3    2                   5    6
         5'   3'
```

FIGURE 15

```
         N2-16
         N   N
         N   N        AU      UA      GC      CG      GU      OTHER
         R-Y'          9      --       2      --       1        1
         K-M'         --       4       8      --      --        1

… # HIGH AFFINITY NUCLEIC ACID LIGANDS TO LECTINS

RELATEDNESS OF THE APPLICATION

This application is a 35 USC § 371 national phase of PCT/US96/09455, filed Jun. 5, 1996, which is a continuation-in-part of each of the following: U.S. Ser. No. 08/479,724, filed Jun. 7, 1995, now U.S. Pat. No. 5,780,228; U.S. Ser. No. 08/472,256, filed Jun. 7, 1995, now U.S. Pat. No. 6,001,988; U.S. Ser. No. 08/472,255, filed Jun. 7, 1995, now U.S. Pat. No. 5,766,853; and U.S. Ser. No. 08/477,829, filed Jun. 7, 1995, now abandoned. Each of the foregoing applications filed on Jun. 7, 1995, is a continuation-in-part of U.S. Ser. No. 07/714,131, filed Jun. 10, 1991, now U.S. Pat. No. 5,475,096, which is a continuation-in-part of U.S. Ser. No. 07/536,428, filed Jun. 11, 1990, now abandoned.

FIELD OF THE INVENTION

Described herein are methods for identifying and preparing high-affinity nucleic acid ligands to lectins. Lectins are carbohydrate binding proteins. The method utilized herein for identifying such nucleic acid ligands is called SELEX, an acronym for Systematic Evolution of Ligands by EXponential enrichment. Specifically disclosed herein are high-affinity nucleic acid ligands to wheat germ agglutinin (WGA), L-selectin, E-selectin, and P-selectin.

BACKGROUND OF THE INVENTION

The biological role of lectins (non-enzymatic carbohydrate-binding proteins of non-immune origin; I. J. Goldstein et al., 1980, Nature 285:66) is inextricably linked to that of carbohydrates. One function of carbohydrates is the modification of physical characteristics of glyco-conjugates (i.e., solubility, stability, activity, susceptibility to enzyme or antibody recognition), however, a more interesting and relevant aspect of carbohydrate biology has emerged in recent years; the carbohydrate portions of glyco-conjugates are information rich molecules (N. Sharon and H. Lis, 1989, Science 246:227–234; K. Drickamer and M. Taylor, 1993, Annu. Rev. Cell Biol. 9:237–264; A. Varki, 1993, Glycobiol. 3:97–130). Within limits, the binding of carbohydrates by lectins is specific (i.e., there are lectins that bind only galactose or N-acetylgalactose; other lectins bind mannose; still others bind sialic acid and so on; K. Drickamer and M. Taylor, supra). Specificity of binding enables lectins to decode information contained in the carbohydrate portion of glyco-conjugates and thereby mediate many important biological functions.

Numerous mammalian, plant, microbial and viral lectins have been described (I. Ofek and N. Sharon, 1990, Current Topics in Microbiol. and Immunol. 151:91–113; K. Drickamer and M. Taylor, supra; I. J. Goldstein and R. D. Poretz, 1986, in The Lectins, p.p. 33–247; A. Varki, supra). These proteins mediate a diverse array of biological processes which include: trafficking of lysosomal enzymes, clearance of serum proteins, endocytosis, phagocytosis, opsonization, microbial and viral infections, toxin binding, fertilization, immune and inflammatory responses, cell adhesion and migration in development and in pathological conditions such as metastasis. Roles in symbiosis and host defense have been proposed for plant lectins but remain controversial. While the functional role of some lectins is well understood, that of many others is understood poorly or not at all.

The diversity and importance of processes mediated by lectins is illustrated by two well documented mammalian lectins, the asialoglycoprotein receptor and the serum mannose binding protein, and by the viral lectin, influenza virus hemagglutinin. The hepatic asialoglycoprotein receptor specifically binds galactose and N-acetylgalactose and thereby mediates the clearance of serum glycoproteins that present terminal N-acetylgalactose or galactose residues, exposed by the prior removal of a terminal sialic acid. The human mannose-binding protein (MBP) is a serum protein that binds terminal mannose, fucose and N-acetylglucosamine residues. These terminal residues are common on microbes but not mammalian glyco-conjugates. The binding specificity of MBP constitutes a non-immune mechanism for distinguishing self from non-self and mediates host defense through opsonization and complement fixation. Influenza virus hemagglutinin mediates the initial step of infection, attachment to nasal epithelial cells, by binding sialic acid residues of cell-surface receptors.

The diversity of lectin mediated functions provides a vast array of potential therapeutic targets for lectin antagonists. Both lectins that bind endogenous carbohydrates and those that bind exogenous carbohydrates are target candidates. For example, antagonists to the mammalian selectins, a family of endogenous carbohydrate binding lectins, may have therapeutic applications in a variety of leukocyte-mediated disease states Inhibition of selectin binding to its receptor blocks cellular adhesion and consequently may be useful in treating inflammation, coagulation, transplant rejection, tumor metastasis, rheumatoid arthritis, reperfusion injury, stroke, cyocardial infarction, burns, psoriasis, multiple sclerosis, bacterial sepsis, hypovolaemic and traumatic shock, acute lung injury, and ARDS.

The selectins, E-, P- and L-, are three homologous C-type lectins that recognize the tetrasaccharide, sialyl-Lewis$^x$ (C. Foxall et al, 1992, J. Cell Biol. 117,895–902). Selectins mediate the initial adhesion of neutrophils and monocytes to activated vascular endothelium at sites of inflammation (R. S. Cotran et al., 1986, J. Exp. Med. 164 661-; M. A. Jutila et al., 1989, J. Immunol. 143,3318-; J. G. Geng et al., 1990, Nature, 757; U. H. Von Adrian et al., 1994, Am J. Physiol. Heart Circ. Physiol. 263, H 1034–H1044). In addition, L-selectin is responsible for the horning of lymphocytes to peripheral and mesenteric lymph nodes (W. M. Gallatin et al., 1983, Nature 304,30; T. K. Kishimoto et al., 1990, Proc. Natl. Acad. Sci. 87,2244-) and P-selectin mediates the adherence of platelets to neutrophils and monocytes (S- C. Hsu-Lin et al., 1984, J. Biol. Chem. 259,9121).

Selectin antagonists (antibodies and carbohydrates) have been shown to block the extravasation of neutrophils at sites of inflammation (P. Piscueta and F. W. Luscinskas, 1994, Am. J. Pathol. 145, 461–469), to be efficacious in animal models of ischemia/reperfusion (A. S. Weyrich et al., 1993, J. Clin. Invest. 91,2620–2629; R. K. Winn et al., 1993, J. Clin. Invest. 92, 2042–2047), acute lung injury (M. S. Mulligan et al., 1993, J. Immunol. 151, 6410–6417; A Seekamp et al., 1994, Am. J. Pathol. 144, 592–598), insulitis/diabetes (S. D. Yang et al., 1993, Proc. Natl. Acad. Sci. 90,10494–10498), meningitis (C. Granet et al., 1994, J. Clin. Invest. 93, 929–936), hemorrhagic shock (R. K. Winn et al., 1994, Am J. Physiol. Heart Circ. Physiol. 267, H2391–H2397) and transplantation. In addition, selectin expression has been documented in models of arthritis (R. Jamar et al., 1995, Radiology 194, 843–850), experimental allergic encephalomyelitis (J. M. Dopp et al., 1994, J. Neuroimmunol. 54, 129–144), cutaneous inflammation (A. Siber et al., 1994, Lab. Invest. 70, 163–170) glomerulonephritis (P. G. Tipping et al., 1994, Kidney Int. 46, 79–88), on leukaemic cells and colon carcinomas (R. M. Lafrenie et al., 1994, Eur. J. Cancer [A] 30A, 2151–2158) and L-selectin receptors have been observed in myelinated regions of the central nervous system (K. Huang et al., 1991, J. Clin. Invest. 88, 1778–1783). These animal model data strongly support the expectation of a therapeutic role for selectin antagonists in a wide variety of disease states in which host tissue damage is neutrophil-mediated.

Other examples of lectins that recognize endogenous carbohydrates are CD22β, CD23, CD44 and sperm lectins (A. Varki, 1993, Glycobil.3, 97–130; P. M. Wassarman, 1988, Ann. Rev. Biochem. 57, 415–442). CD22β is involved in early stages of B lymphocyte activation; antagonists may modulate the immune response. CD23 is the low affinity IgE receptor; antagonists may modulate the IgE response in allergies and asthma. CD44 binds hyaluronic acid and thereby mediates cell/cell and cell/matrix adhesion; antagonists may modulate the inflammatory response. Sperm lectins are thought to be involved in sperm/egg adhesion and in the acrosomal response; antagonists may be effective contraceptives, either by blocking adhesion or by inducing a premature, spermicidal acrosomal response.

Antagonists to lectins that recognize exogenous carbohydrates may have wide application for the prevention of infectious diseases. Many viruses (influenza A, B and C; Sendhi, Newcastle disease, coronavirus, rotavirus, encephalomyelitis virus, enchephalomyocarditis virus, reovirus, paramyxovirus) use lectins on the surface of the viral particle for attachment to cells, a prerequisite for infection; antagonists to these lectins are expected to prevent infection (A. Varki, 1993, Glycobiol.3, 97–130). Similarly colonization/infection strategies of many bacteria utilize cell surface lectins to adhere to mammalian cell surface glycoconjugates. Antagonists to bacterial cell surface lectins are expected to have therapeutic potential for a wide spectrum of bacterial infections, including: gastric (*Helicobacter pylori*), urinary tract (*E. coli*), pulmonary (*Klebsiella pneumoniae, Stretococcus pneumoniae, Mycoplasma pneumoniae*) and oral (*Actinomyces naeslundi* and *Actinomyces viscosus*) colonization/infection (S N. Abraham, 1994, Bacterial Adhesins, in The Handbook of Immunopharmacology; Adhesion Molecules, C. D. Wegner, ed; B. J. Mann et al., 1991, Proc. Natl. Acad. Sci 88, 3248–3252). A specific bacterial mediated disease state is *Pseudomonas aeruginosa* infection, the leading cause of morbidity and mortality in cystic fibrosis patients. The expectation that high affinity antagonists will have efficacy in treating *P. Aeruginosa* infection is based on three observations. First, a bacterial cell surface, GalNAcβ1-4Gal binding lectin mediates infection by adherence to asialogangliosides (αGM1 and αGM2) of pulmonary epithelium (L. Imundo et al., 1995, Proc. Natl. Acad. Sci 92, 3019–3023). Second, in vitro, the binding of *P. aeruginosa* is competed by the gangliosides' tetrasaccharide moiety, Galβ1-3-GalNAcβ1-4-Galβ1-4-Glc. Third, in vivo, instillation of antibodies of Pseudomonas surface antigens can prevent lung and pleural damage (J. F. Pittet et al., 1993, J. Clin. Invest. 92, 1221–1228).

Non-bacterial microbes that utilize lectins to initiate infection include *Entamoeba histalytica* (a Gal specific lectin that mediates adhesion to intestinal mucosa; W. A. Petri, Jr., 1991, AMS News 57:299–306) and *Plasmodium faciparum* (a lectin specific for the terminal Neu5Ac(a2-3) Gal of glycophorin A of erthrocytes; P. A. Orlandi et al., 1992, J. Cell Biol. 116:901–909). Antagonists to these lectins are potential therapeutics for dysentery and malaria.

Toxins are another class of proteins that recognize exogenous carbohydrates (K- A Karlsson, 1989, Ann. Rev. Biochem. 58:309–350). Toxins are complex, two domain molecules, composed of a functional and a cell recognition/adhesion domain. The adhesion domain is often a lectin (i.e., bacterial toxins: pertussis toxin, cholera toxin, heat labile toxin, verotoxin and tetanus toxin; plant toxins: ricin and abrin). Lectin antagonists are expected to prevent these toxins from binding their target cells and consequently to be useful as antitoxins.

There are still other conditions for which the role of lectins is currently speculative. For example, genetic mutations result in reduced levels of the serum mannose-binding protein (MBP). Infants who have insufficient levels of this lectin suffer from severe infections, but adults do not. The high frequency of mutations in both oriental and Caucasian populations suggests a condition may exist in which low levels of serum mannose-binding protein are advantageous. Rheumatoid arthritis (RA) may be such a condition. The severity of RA is correlated with an increase in IgG antibodies lacking terminal galactose residues on Fe region carbohydrates (A. Young et al., 1991, Arth. Rheum. 34, 1425–1429; I. M. Roitt et al., 1988, J. Autoimm. 1, 499–506). Unlike their normal counterpart, these gal-deficient carbohydrates are substrates for MBP. MBP/IgG immunocomplexes may contribute to host tissue damage through complement activation. Similarly, the eosinophil basic protein is cytotoxic. If the cytotoxicity is mediated by the lectin activity of this protein, then a lectin antagonist may have therapeutic applications in treating eosinophil mediated lung damage.

Lectin antagonists may also be useful as imaging agents or diagnostics. For example, E-selectin antagonists may be used to image inflamed endothelium. Similarly antagonists to specific serum lectins, i.e. mannose-binding protein, ay also be useful in quantitating protein levels.

Lectins are often complex, multi-domain, multimeric proteins. However, the carbohydrate-binding activity of mammalian lectins is normally the property of a carbohydrate recognition domain or CRD. The CRDs of mammalian lectins fall into three phylogenetically conserved classes: C-type, S-type and P-type (K. Drickamer and M. E. Taylor, 1993, Annu. Rev. Cell Biol. 9, 237–264). C-type lectins require $Ca^{++}$ for ligand binding, are extracellular membrane and soluble proteins and, as a class, bind a variety of carbohydrates. S-type lectins are most active under reducing conditions, occur both intra- and extracellularly, bind β-galactosides and do not require $Ca^{++}$. P-type lectins bind mammose 6-phosphate as their primary ligand.

Although lectin specificity is usually expressed in terms of monosaccharides and/or oligosaccharides (i.e., MPB binds mannose, fucose and N-acetylglucosamine), the affinity for monosaccharides is weak. The dissociation constants for monomeric saccharides are typically in the millimolar range (Y. C. Lee, 1992, FASEB J. 6:3193–3200; G. D. Glick et al., 1991, J Biol. Chem. 266–23660–23669; Y. Nagata and M. M. Burger, 1974, J. Biol. Chem. 249:116–3122).

Co-crystals of MPP complexed with mannose oligomers offer insight into the molecular limitations on affinity and specificity of C-type lectins (W. I. Weis et al., 1992, Nature 360:127–134; K. Drickamer, 1993, Biochem. Soc. Trans. 21:456–459). The 3- and 4-hydroxy groups of mannose form coordination bonds with bound $Ca^{++}$ ion #2 and hydrogen bonds with glutamic acid (185 and 193) and asparagine (187 and 206). The limited contacts between the CRD and bound sugar are consistent with its spectrum of monosaccharide binding; N-acetylglucosamine has equatorial 3- and 4-hydroxyls while fucose has similarly configured hydroxyls at the 2 and 3 positions.

The affinity of the mannose-binding protein and other lectins for their natural ligands is greater than that for monosaccharides. Increased specificity and affinity can be accomplished by establishing additional contacts between a protein and its ligand (K. Drickamer, 1993, supra) either by 1) additional contacts with the terminal sugar (i.e., chicken hepatic lectin binds N-acetylglucose amine with greater affinity that mannose or fucose suggesting interaction with the 2-substituent); 2) clustering of CRDs for binding complex oligosaccharides (i.e., the mammalian asialylglycoprotein receptor); 3) interactions with additional saccharide residues (i.e., the lectin domain of selectins appears to interact with two residues of the tetrasaccharide sialyl-Lewis$^x$: with the charged terminal residue, sialic acid, and with the fucose residue; wheat germ agglutinin appears to interact with all three residues of trimers of N-acetylglucosamine); or by 4) contacts with a non-carbohydrate portion of a glyco-protein.

The low affinity of lectins for mono- and oligo-saccharides presents major difficulties in developing high affinity antagonists that may be useful therapeutics. Approaches that have been used to develop antagonists are similar to those that occur in nature: 1) addition or modification of substituents to increase the number of interactions; and 2) multimerization of simple ligands.

The first approach has had limited success. For example, homologous of sialic acid have been analyzed for affinity to influenza virus hemagglutinin (S. J. Watowich et al. 1994, Structure 2:719–731). The dissociation constants of the best analogues are 30 to 300 $\mu$M which is only 10 to 100-fold better than the standard monosaccharide.

Modifications of carbohydrate ligands to the selectins have also had limited success. In static ELISA competition assays, sialyl-Lewis$^a$ and sialyl-Lewis$^x$ have IC$_{50}$s of 220 $\mu$M and 750 $\mu$M, respectively, for the inhibition of the binding of an E-selectin/IgG chimera to immobilized sialyl-Lewis$^x$ (R. M. Nelson et al., 1993, J. Clin. Invest. 91, 1157–1166). The IC$_{50}$ of a sialyl-Lewis$^a$ derivative (addition of an aliphatic aglycone to the GlcNAc and replacement of the N-acetyl with an NH$_2$ group) improved 10-fold to 21 $\mu$M. Similarly, removal of the N-acetyl from sialyl-Lewis$^x$ improves inhibition in an assay dependent manner (C. Foxall et al., 1992, J. Cell Biol. 117, 895–902; S. A. DeFrees et al., 1993, J. Am. Chem. Soc. 115,7549–7550).

The second approach, multimerization of simple ligands, can lead to dramatic improvements in affinity for lectins that bind complex carbohydrates (Y. C. Lee, supra). On the other hand, the approach does not show great enhancement for lectins that bind simple oligosaccharides; dimerizing sialyl-Lewis$^x$, a minimal carbohydrate ligand for E-selectin, improves inhibition approximately 5-fold (S. A. DeFrees et al., supra).

An alternative approach is to design compounds that are chemically unrelated to the natural ligand. In the static ELISA competition assays inositol polyanions inhibit L- and P-selectin binding with IC$_{50}$s that range from 1.4 $\mu$M to 2.8 mM (O. Cecconi et al., 1994, J. Biol. Chem. 269, 15060–15066). Synthetic oligopeptides, based on selectin amino acid sequences, inhibit neutrophil binding to immobilized P-selectin with IC$_{50}$s ranging from 50 $\mu$M to 1 mM (J- G Geng et al., 1992, J of Biol. Chem. 267,19846–19853).

Lectins are nearly ideal targets for isolation of antagonists by SELEX technology described below. The reason is that oligonucleotide ligands that are bound to the carbohydrate binding site can be specifically eluted with the relevant sugar(s). Oligonucleotide ligands with affinities that are several orders of magnitude greater than that of the competing sugar can be obtained by the appropriate manipulation of the nucleic acid ligand to competitor ratio. Since the carbohydrate binding site is the active site of a lectin, essentially all ligands isolated by this procedure will be antagonists. In addition, these SELEX ligands will exhibit much greater specificity that monomeric and oligomeric saccharides.

A method for the in vitro evolution of nucleic acid molecules with highly specific binding to target molecules has been developed. This method, Systematic Evolution of Ligands by EXponential enrichment, termed SELEX, is described in U.S. patent application Ser. No. 07/536,428, entitled "Systematic Evolution of Ligands by Exponential Enrichment," now abandoned, U.S. patent application Ser. No. 07/714,131, filed Jun. 10, 1991, entitled "Nucleic Acid Ligands," now U.S. Pat No. 5,475,096, U.S. patent application Ser. No. 07/931,473, filed Aug. 17, 1992, entitled "Methods for Identifying Nucleic Acid Ligands," now U.S. Pat. No. 5,270,163 (see also PCT/US91/04078), each of which is herein specifically incorporated by reference. Each of these applications, collectively referred to herein as the SELEX Patent Applications, describes a fundamentally novel method for making a nucleic acid ligand to any desired target molecule.

SELEX method involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific, high affinity nucleic acid ligands to the target molecule.

The basic SELEX method has been modified to achieve a number of specific objectives. For example, U.S. patent application Ser. No. 07/960,093, filed Oct. 14, 1992, entitled "Method for Selecting Nucleic Acids on the Basis of Structure," describes the use of SELEX in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands" describes a SELEX based method for selecting nucleic acid ligands containing photoreactive groups capable of binding and/or photocrosslinking to and/or photoinactivating a target molecule. U.S. patent application Ser. No. 08/134,028, filed Oct. 7, 1993, entitled "High-Affinity Nucleic Acid Ligands That Discriminate Between Theophylline and Caffeine," describes a method for identifying highly specific nucleic acid ligands able to discriminate between closely related molecules, termed Counter-SELEX. U.S. patent application Ser. No. 08/143,564, filed Oct. 25, 1993, entitled "Systematic Evolution of Ligands by EXponential Enrichment: Solution SELEX," describes a SELEX-based method which achieves highly efficient partitioning between oligonucleotides having high and low affinity for a target molecule. U.S. patent application Ser. No. 07/964,624, filed Oct. 21, 1992, entitled "Nucleic Acid Ligands to HIV-RT and HIV-1

Rev," now U.S. Pat. No. 5,496,938, describes methods for obtaining improved nucleic acid ligands after SELEX has been performed. U.S. patent application Ser. No. 08/400,440, filed Mar. 8, 1995, entitled "Systematic Evolution of Ligands by EXponential Enrichment: Chemi-SELEX," now U.S. Pat. No. 5,705,337, describes methods for covalently linking a ligand to its target.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified nucleic acid ligands containing modified nucleotides are described in U.S. patent application Ser No. 08/117,991, filed Sep. 8, 1993, entitled "High Affinity Nucleic Acid Ligands Containing Modified Nucleotides," that describes oligonucleotides containing nucleotide derivatives chemically modified at the 5- and 2'-positions of pyrimidines. U.S. patent application Ser. No. 08/134,028, supra, describes highly specific nucleic acid ligands containing one or more nucleotides modified with 2'-amino (2'-$NH_2$), 2'-fluoro (2'-F), and/or 2'-O-methyl (2'-OMe). U.S. patent application Ser. No. 08/264,029, filed Jun. 22, 1994, entitled "Novel Method of Preparation of 2' Modified Pyrimidine Intramolecular Nucleophilic Displacement," describes novel methods for making 2'-modified nucleosides.

The SELEX method encompasses combining selected oligonucleotides with other selected oligonucleotides as described in U.S. patent application Ser. No. 08/284,063, filed Aug. 2, 1994, entitled "Systematic Evolution of Ligands by Exponential Enrichment: Chimeric SELEX", now U.S. Pat. No. 5,637,459. The SELEX method also includes combining the selected nucleic acid ligands with non-oligonucleotide functional units and U.S. patent application Ser. No. 08/234,997, filed Apr. 28, 1994, entitled "Systematic Evolution of Ligands by Exponential Enrichment: Blended SELEX", now U.S. Pat. No. 5,683,867, and U.S. patent application Ser. No. 08/434,465, filed May 4, 1995, entitled "Nucleic Acid Ligand Complexes", now U.S. Pat. No. 6,011,020. These applications allow the combination of the broad array of shapes and other properties, and the efficient amplification and replication properties, of oligonucleotides with the desirable properties of other molecules. Each of the above described patent applications which describe modifications of the basic SELEX procedure are specifically incorporated by reference herein in their entirety.

The present invention applies the SELEX methodology to obtain nucleic acid ligands to lectin targets. Lectin targets, or lectins, include all the non-enzymatic carbohydrate-binding proteins of non-immune origin, which include, but are not limited to, those described above.

Specifically, high affinity nucleic acid ligands to wheat germ agglutinin, and various selectin proteins have been isolated. For the purposes of the invention the terms wheat germ agglutinin, wheat germ lectin and WGA are used interchangeably. Wheat germ agglutinin (WGA) is widely used for isolation, purification and structural studies of glyco-conjugates. As outlined above, the selectins are important anti-inflammatory targets. Antagonists to the selectins modulate extravasation of leukocytes at sites of inflammation and thereby reduce neutrophil caused host tissue damage. Using the SELEX technology, high affinity antagonists of L-selectin, E-selectin and P-selectin mediated adhesion are isolated.

BRIEF SUMMARY OF THE INVENTION

The present invention includes methods of identifying and producing nucleic acid ligands to lectins and the nucleic acid ligands so identified and produced. More particularly, nucleic acid ligands are provided that are capable of binding specifically to Wheat Germ Agglutinin (WGA), L-Selectin, E-selectin and P-selectin.

Further included in this invention is a method of identifying nucleic acid ligands and nucleic acid ligand sequences to lectins comprising the steps of (a) preparing a candidate mixture of nucleic acids, (b) partitioning between members of said candidate mixture on the basis of affinity to said lectin, and (c) amplifying the selected molecules to yield a mixture of nucleic acids enriched for nucleic acid sequences with a relatively higher affinity for binding to said lectin.

More specifically, the present invention includes the nucleic acid ligands to lectins identified according to the above-described method, including those ligands to Wheat Germ Agglutinin listed in Table 2, those ligands to L-selectin listed in Tables 8, 12 and 16, and those ligands to P-selectin listed in Tables 19 and 25. Additionally, nucleic acid ligands to E-selectin and serum mannose binding protein are provided. Also included are nucleic acid ligands to lectins that are substantially homologous to any of the given ligands and that have substantially the same ability to bind lectins and antagonize the ability of the lectin to bind carbohydrates. Further included in this invention are nucleic acid ligands to lectins that have substantially the same structural form as the ligands presented herein and that have substantially the same ability to bind lectins and antagonize the ability of the lectin to bind carbohydrates.

The present invention also includes modified nucleotide sequences based on the nucleic acid ligands identified herein and mixtures of the same.

The present invention also includes the use of the nucleic acid ligands in therapeutic, prophylactic and diagnostic applications.

BRIEF DESCRIPTION OF THE FIGURES

FIG. 7 shows hairpin secondary structures for representative L-selectin 2'$NH_2$ RNA ligands: (a) F13.32 (SEQ. ID NO: 67), family I; (b) 6.16 (SEQ. ID NO: 84), family III; and (c) F14.12 (SEQ. ID NO: 78), family II. Nucleotide sequence is in standard one letter code. Invariant nucleotides are in bold type. Nucleotides derived from fixed sequence are in lower case.

FIG. 12 shows the consensus hairpin secondary structure for family 1 ssDNA ligands to L-selectin. Nucleotide sequence is in standard one letter code. Invariant nucleotides are in bold type. The base pairs at highly variable positions are designated N-N'. To the right of the stem is a matrix showing the number of occurances of particular base pairs for the position in the stem that is on the same line.

FIG. 15 shows the consensus hairpin secondary structures for 2'-F RNA ligands to L-selectin. Nucleotide sequence is in standard one letter code. Invariant nucleotides are in bold type. The base pairs at highly variable positions are designated N-N'. To the right of the stem is a matrix showing the number of occurances of particular base pairs for the position in the stem that is on the same line.

FIG. 16 shows the consensus hairpin secondary structures for 2'-F RNA ligands to P-selectin. Nucleotide sequence is in standard one letter code. Invariant nucleotides are in bold type. The base pairs at highly variable positions are designated N-N'. To the right of the stem is a matrix showing the number of occurances of particular base pairs for the position in the stem that is on the same line.

DETAILED DESCRIPTION OF THE INVENTION

Figure 1A:
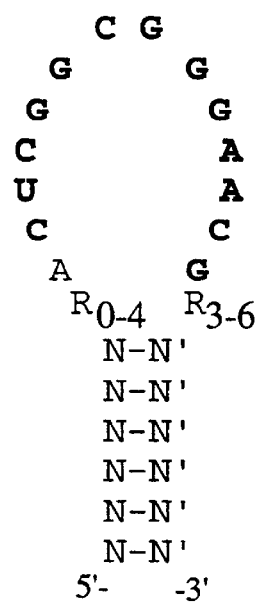
FIG. 1 shows consensus hairpin secondary structure for WGA 2'-$NH_2$ RNA ligands: (a) family 1, (b) family 2 and (c) family 3. Nucleotide sequence is in standard one letter code. Invariant nucleotides are in bold type. Nucleotides derived from fixed sequence are in lower case.

This application describes high-affinity nucleic acid ligands to lectins identified through the method known as SELEX. SELEX is described in U.S. patent application Ser. No. 07/536,428, entitled "Systematic Evolution of Ligands by EXponential Enrichment", now abandoned; U.S. patent application Ser. No. 07/714,131, filed Jun. 10, 1991, entitled "Nucleic Acid Ligands", now U.S. Pat. No. 5,475,096; U.S. patent application Ser. No. 07/931,473, filed Aug. 17, 1992, entitled "Methods for Identifying Nucleic Acid Ligands", now U.S. Pat. No. 5,270,163, (see also PCT/US91/04078). These applications, each specifically incorporated herein by reference, are collectively called the SELEX Patent Applications.

IN its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 0.05–50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for partitioning nucleic acids within a candidate mixture; and methods for amplifying partitioned nucleic acids to generate enriched candidate mixture. The SELEX Patent applications also describe ligands obtained to a number of target species, including both protein targets where the protein is and is not a nucleic acid binding protein.

This invention also includes the ligands as described above, wherein certain chemical modifications are made in order to increase the in vivo stability of the ligand or to enhance or mediate the delivery of the ligand. Examples of such modifications include chemical substitutions at the sugar and/or phosphate and/or base positions of a given nucleic acid sequence. See, e.g., U.S. patent application Ser. No. 08/117,991, filed Sep. 8, 1993, entitled "High Affinity Nucleic Acid Ligands Containing Modified Nucleotides" which is specifically incorporated herein by reference. Additionally, in co-pending and commonly assigned U.S. patent application Ser. No. 07/964,624, filed Oct. 21, 1992 ('624), now U.S. Pat. No. 5,496,938, methods are described for obtaining improved nucleic acid ligands after SELEX has been performed. The '624 application, entitled "Nucleic Acid Ligands to HIV-RT and HIV-1 Rev," is specifically incorporated herein by reference. Further included in the '624 patent are methods for determining the three-dimensional structures of nucleic acid ligands. Such methods include mathematical modeling and structure modifications of the SELEX-derived ligands, such as chemical modifications and nucleotide substitution. Other modifications are known to one of ordinary skill in the art. Such modifications may be made post-SELEX (modification of previously identified unmodified ligands) or by incorporation into the SELEX process. Additionally, the nucleic acid ligands of the invention can be complexed with various other compounds, including but not limited to, lipophilic compounds or non-immunogenic, high molecular weight compounds. Lipophilic compounds include, but are not limited to, cholesterol, dialkyl glycerol, and diacyl glycerol. Non-immunogenic, high molecular weight compounds include, but are not limited to, polyethylene glycol, dextran, albumin and magnetite. The nucleic acid ligands described herein can be complexed with a lipophilic compound (e.g., cholesterol) or attached to or encapsulated in a complex comprised of lipophilic components (e.g., a liposome). The complexed nucleic acid ligands can enhance the cellular uptake of the nucleic acid ligands by a cell for delivery of the nucleic acid ligands to an intracellular target. The complexed nucleic acid ligands can also have enhanced pharmacokinetics and stability. U.S. patent application Ser. No. 08/434,465, filed May 4, 1995, entitled "Nucleic Acid Ligand Complexes," now U.S. Pat. No. 6,011,020, which is herein incorporated by reference describes a method for preparing a therapeutic or diagnostic complex comprised of a nucleic acid ligand and a lipophilic compound or a non-immunogenic, high molecular weight compound.

The methods described herein and the nucleic acid ligands identified by such methods are useful for both therapeutic and diagnostic purposes. Therapeutic uses include the treatment or prevention of diseases or medical conditions in human patients. Many of the therapeutic uses are described in the background of the invention, particularly, nucleic acid ligands to selectins are useful as anti-inflammatory agents. Antagonists to the selectins modulate extravasion of leukocytes at sites of inflammation and thereby reduce neutrophil caused host tissue damage. Diagnostic utilization may include both in vivo or in vitro diagnostic applications. The SELEX method generally, and the specific adaptations of the SELEX method taught and claimed herein specifically, are particularly suited for diagnostic applications. SELEX identifies nucleic acid ligands that are able to bind targets with high affinity and with surprising specificity. These characteristics are, of course, the desired properties one skilled in the art would seek in a diagnostic ligand.

The nucleic acid ligands of the present invention may be routinely adapted for diagnostic purposes according to any umber of techniques employed by those skilled in the art. Diagnostic agents need only be able to allow the user to identify the presence of a given target at a particular locale or concentration. Simply the ability to form binding pairs with the target may be sufficient to trigger a positive signal for diagnostic purposes. Those skilled in the art would also be able to adapt any nucleic acid ligand by procedures known in the art to incorporate a labeling tag in order to track the presence of such ligand. Such a tag could be used in a number of diagnostic procedures. The nucleic acid ligands to lectin, particularly selectins, described herein may specifically be used for identification of the lectin proteins.

SELEX provides high affinity ligands of a target molecule. This represents a singular achievement that is unprecedented in the field of nucleic acids research. The present invention applies the SELEX procedure to lectin targets. Specifically, the present invention describes the identification of nucleic acid ligands to Wheat Germ Agglutinin, and the selectins, specifically, L-selectin, P-selectin and E-selectin. In the Example section below, the experimental parameters used to isolate and identify the nucleic acid ligands to lectins are described.

In order to produce nucleic acids desirable for use as a pharmaceutical, it is preferred that the nucleic acid ligand (1) binds to the target in a manner capable of achieving the desired effect on the target; (2) be as small as possible to obtain the desired effect; (3) be as stable as possible; and (4) be a specific ligand to the chosen target. In most situations, it is preferred that the nucleic acid ligand have the highest possible affinity to the target.

In the present invention, a SELEX experiment was performed in search of nucleic acid ligands with specific high affinity for Wheat Germ Agglutinin from a degenerate library containing 50 random positions (50N). This invention includes the specific nucleic acid ligands to Wheat Germ Agglutinin shown in Table 2 (SEQ ID NOS: 4–55), identified by the methods described in Examples 1 and 2. Specifically, RNA ligands containing 2'-NH$_2$ modified pyrimidines are provided. The scope of the ligands covered by this invention extends to all nucleic acid ligands of Wheat Germ Agglutinin, modified and unmodified, identified according to the SELEX procedure. More specifically, this invention includes nucleic acid sequences that are substantially homologous to the ligands shown in Table 2. By substantially homologous it is meant a degree of primary sequence homology in excess of 70%, most preferably in excess of 80%. A review of the sequence homologies of the ligands of Wheat Germ Agglutinin shown in Table 2 shows that sequences with little or no primary homology may have substantially the same ability to bind Wheat Germ Agglutinin. For these reasons, this invention also includes nucleic acid ligands that have substantially the same ability to bind Wheat Germ Agglutinin as the nucleic acid ligands shown in Table 2. Substantially the same ability to bind Wheat Germ Agglutinin means that the affinity is within a few orders of magnitude of the affinity of the ligands described herein. It is well within the skill of those of ordinary skill in the art to determine whether a given sequence—substantially homologous to those specifically described herein—has substantially the same ability to bind Wheat Germ Agglutinin.

In the present invention, SELEX experiments were performed in search of nucleic acid ligands with specific high affinity for L-selectin from degenerate libraries containing 30 or 40 random positions (30N or 40N). This invention includes the specific nucleic acid ligands to L-selectin shown in Tables 8, 12 and 16 (SEQ ID NOS; 67–117, 129–180, 185–196 and 293–388), identified by the methods described in Examples 7, 8, 13, 14, 22 and 23. Specifically, RNA ligands containing 2'-NH$_2$ or 2'-F pyrimidines and ssDNA ligands are provided. The scope of the ligands covered by this invention extends to all nucleic acid ligands of L-selectin, modified and unmodified, identified according to the SELEX procedure. More specifically, this invention includes nucleic acid sequences that are substantially homologous to the ligands shown in Tables 8, 12 and 16. By substantially homologous it is meant a degree of primary sequence homology in excess of 70%, most preferably in excess of 80%. A review of the sequence homologies of the ligands of L-selectin shown in Tables 8, 12 and 16 shows that sequences with little or no primary homology may have substantially the same ability to bind L-selectin. For these reasons, this invention also includes nucleic acid ligands that have substantially the same ability to bind L-selectin as the nucleic acid ligands shown in Tables 8, 12 and 16. Substantially the same ability to bind L-selectin means that the affinity is within a few orders of magnitude of the affinity of the ligands described herein. It is well within the skill of those of ordinary skill in the art to determine whether a given sequence—substantially homologous to those specifically described herein—has substantially the same ability to bind L-selectin.

In the present invention, SELEX experiments were performed in search of nucleic acid ligands with specific high affinity for P-selectin from degenerate libraries containing 50 random positions (50N). This invention includes the specific nucleic acid ligands to P-selectin shown in Tables 19 and 25 (SEQ ID NOS: 199–247 and 251–290), identified by the methods describe din Examples 27, 28, 35 and 36. Specifically, RNA ligands containing 2'-NH$_2$ and 2'F pyrimidines are provided. The scope of the ligands covered by this invention extends to all nucleic acid ligands of P-selectin, modified and unmodified, identified according to the SELEX procedure. More specifically, this invention includes nucleic acid sequences that are substantially homologous to the ligands shown in Tables 19 and 25. By substantially homologous it is meant a degree of primary sequence homology in excess of 70%, most preferably in excess of 80%. A review of the sequence homologies of the ligands of P-selectin shown in Tables 19 and 25 shows that sequences with little or no primary homology may have substantially the same ability to bind P-selectin. For these reasons, this invention also includes nucleic acid ligands that have substantially the same ability to bind P-selectin as the nucleic acid ligands shown in Tables 19 and 25. Substantially the same ability to bind P-selectin means that the affinity is within a few orders of magnitude of the affinity of the ligands described herein. It is well within the skill of those of ordinary skill in the art to determine whether a given sequence—substantially homologous to those specifically described herein—has substantially the same ability to bind P-selectin.

In the present invention, a SELEX experiment was performed in search of nucleic acid ligands with specific high affinity for E-selectin from a degenerate library containing 40 random positions (40N). This invention includes specific nucleic acid ligands to E-selectin identified by the methods described in Example 40. The scope of the ligands covered by this invention extends to all nucleic acid ligands of E-selectin, modified and unmodified, identified according to the SELEX procedure.

Additionally, the present invention includes multivalent Complexes comprising the nucleic acid ligands of the invention. The multivalent Complexes increase the binding energy to facilitate better binding affinities through slower off-rates of the nucleic acid ligands. The multivalent Complexes may be useful at lower doses than their monomeric counterparts. In addition, high molecular weight polyethylene glycol was included in some of the Complexes to decrease the in vivo clearance rate of the Complexes. Specifically, nucleic acid ligands to L-selection were placed in multivalent Complexes.

As described above, because of their ability to selectively bind lectins, the nucleic acid ligands to lectins described herein are useful as pharmaceuticals. This invention, therefore, also includes a method for treating lectin-mediated diseases by administration of a nucleic acid ligand capable of binding to a lectin.

Therapeutic compositions of the nucleic acid ligands may be administered parenterally by injection, although other effective administration forms, such as intraarticular injection, inhalant mists, orally active formulations, transdermal iontophoresis or suppositories, are also envisioned. One preferred carrier is physiological saline solution, but it is contemplated that other pharmaceutically acceptable carriers may also be used. In one preferred embodiment, it is envisioned that the carrier and the ligand constitute a physiologically-compatible, slow release formation. The primary solvent in such a carrier may be either aqueous or non-aqueous in nature. In addition, the carrier may contain other pharmacologically-acceptable excipients for modifying or maintaining the pH, osmolarity, viscosity, clarity, color, sterility, stability, rate of dissolution, or odor of the formulation. Similarly, the carrier may contain still other pharmacologically-acceptable excipients for modifying or maintaining the stability, rate of dissolution, release, or absorption of the ligand. Such excipients are those substances usually and customarily employed to formulate dosages for parental administration in either unit dose or multi-dose form.

Once the therapeutic composition has been formulated, it may be stored in sterile vials as a solution, suspension, gel, emulsion, solid, or dehydrated or lyophilized powder. Such formulations maybe stored either in a ready to use form or requiring reconstitution immediately prior to administration. The manner of administering formulations containing nucleic acid ligands for systemic delivery may be via subcutaneous, intramuscular, intravenous, intranasal or vaginal or rectal suppository.

Well established animal models exist or many of the disease states which are candidates for selectin antagonist therapy. Models available for testing the efficacy of oligonucleotide selectin antagonists include:

1) mouse models for peritoneal inflammation (P. Pizcueta and F. W. Luscinskas, 1994, Am. J. Pathol. 145, 461–469), diabetes (A. C. Hanninen et al., 1992, J. Clin. Invest. 92, 2509–2515), lymphocyte trafficking (L. M. Bradley et al., 1994, J. Exp. Med., 2401–206), glomerulonephritis (P. G. Tipping et al., 1994, Kidney Int. 46, 79–88), experimental allergic encephalomyelitis (j. M. Dopp et al., 1994, J. Neuroimmunol, 54; 129–144), acute inflammation in human/SCID mouse chimera (H.-C. Yan et al., 1994, J. Immunol. 152, 3053–3063), endotoxin-mediated inflammation (W. E. Sanders et al., 1992, Blood 80, 795–800);

2) rat models for acute lung injury (m. S. Milligan et al., 1994, J. Immunol. 152, 832–840), hind limb ischemia/reperfusion injury (A. Seekamp et al., 1994, Am. J. Pathol 144, 592–598), remote lung injury (A. Seekamp et al., 1994, supra; D. L. Carden et al., 1993, J. Appl. Physiol 75, 2529–2543), neutrophil rolling on mesenteric venules (K. Ley et al., 1993, Blood 82, 1632–1638), myocardial infarction ischemia reperfusion injury (D. Altavilla et al., 1994, Eur. J. Pharmacol. Environ. Toxicol. Pharmacol. 270, 45–51);

3) rabbit models for hemorrhagic shock (R. K. Winn et al., 1994, Am. J. Physiol. Heart Circ. Physiol. 267, H2391–H2397), ear ischemia reperfusion injury (D. Mihelcic et al., 1994, Bollod 84, 2333–2328) neutrophil rolling on mesenteric venules (A. M. Olofsson et al., Blood 84, 2749–2758), experimental meningtis (C. Granert et al., 1994, J. Clin. Invest. 93, 929–936); lung, peritoneal and subcutaneous bacterial infection (S. R. Sharer et al., 1993, J. Immunol. 151, 4982–4988), myocardial ischemia/repefusion (G. Montrucchio et al., 1989, Am. J. Physiol. 256, H1236-H1246), central nervous system ischemic injury (W. M. Clark et al., 1991, Stroke 22, 877–883);

4) cat models for myocardial infraction ischemia reperfusion injury (M. Buerke et al., 1994, J. Pharmacol. Exp. Ther. 271, 134–142);

5) dog models for myocardial infraction ischemia reperfusion injury (D. J. Lefer et al., 1994, Circulation 90, 2390–2401);

6) pig models for arthritis (F. Jamar et al., 1995, Radiology 194, 843–850);

7) rhesus monkey models for cutaneous inflammation (A. Siber et al., Lab. Invest. 70, 163–175);

8) cynomolgus monkey models for renal transplants (S.-L. Wee, 1991, Transplant. Prod. 23, 279–280); and 9) baboon models for dacron grafts (T. Palabrica et al., 1992, Nature 359, 848–851), septic, traumatic and hypovolemic shock (H. Redl et al., 1991, Am. J. Pathol. 139, 461–466).

The nucleic acid ligands to lectins described herein are useful as pharmaceuticals and as diagnostic reagents.

EXAMPLES

The following examples are illustrative of certain embodiments of the invention and are not to be constructed as limiting the present invention in any way. Examples 1–6 describe identification and characterization of 2'-NH$_2$ RNA ligands to Wheat Germ Agglutinin. Examples 7–12 described identification and characterization of 2'-NH$_2$ RNA ligands to L-selectin. Examples 13–21 describe identification and characterization of ssDNA ligands to L-selectin. Examples 22–25 describe identification and characterization of 2'-FRNA ligands to L-selectin. Example 26 describes identification of ssDNA ligands to P-selectin. Examples 27–39 describes identification and characterization of 2'-NH$_2$ and 2'-FRNA ligands to P-selectin. Example 40 describes identification of nucleic acid ligands to E-selectin.

EXAMPLE 1

Nucleic Acid Ligands to Wheat Germ Agglutinin

The experimental procedures outlined in this Example were used to identify and characterize nucleic acid ligands to wheat germ agglutinin (WGA) as described in Examples 2–6.

Experimental Procedures

A) Materials

Wheat Germ Lectin (Triticum vulgare) Sepharose 6MB beads were purchased from Pharmacia Biotech. Wheat Germ Lectin, Wheat Germ Agglutinin, and WGA are used interchangeably herein. Free Wheat Germ Lectin (Triticum vulgare) and all other lectins were obtained from E Y Laboratories; methyl-α-D-mannopyranoside was from Calbiochem and N-acetyl-D-glucosamine, GlcNAc, and the trisaccharide N N'N'-triacetylchitotriose, (GlcNAc)$_3$, were purchased from Sigma Chemical Co. The 2'-NH$_2$ modified CTP and UTP were prepared according to Pieken et al., (1991, Science 253:314–317), DNA oligonucleotides were synthesized by Operon. All other reagents and chemicals were purchased from commercial sources. Unless otherwise indicated, experiments utilized Hanks' Balanced Salt Solutions (HBSS; 1.3 mM CaCl$_2$, 5.0 mM KCl, 0.3 mM KH$_2$PO$_4$, 0.5 mM MgCl$_2$.6H$_2$O, 0.4 mM MgSO$_4$.7H$_2$O, 138 mM NaCl, 4.0 mM NaHCO$_3$, 0.3 mM Na$_2$HPO4, 5.6 mM D-Glucose; GibcoBRL).

B) SELEX

The SELEX procedure is described in detail in U.S. Pat. No. 5,270,163 and elsewhere. In the wheat germ agglutinin SELEX experiment, the DNA template for the initial RNA pool contained 50 random nucleotides, flanked by N9 5' and 3' fixed regions (50N9) 5' gggaaaagcgaaucauacacaaga-50N-gcuccgccagagaccaaccgagaa 3'(SEQ ID NO:1). All C and U have 2'-NH$_2$ substituted for 2'-OH for ribose. The primers for the PCR were the following: 5' Primer 5'taatacgactcac-tatagggaaaagcgaatcatacacaaga 3'(SEQ ID NO:2) and 3' Primer 5'ttctcggttggtctctggcggagc 3'(SEQ ID NO:3). The fixed regions of the starting random pool include DNA primer annealing sites for PCR and cDNA synthesis as well as the consensus T7 promoter region to allow in vitro transcription. These single-stranded DNA molecules were converted into double-stranded transcribable templates by PCR amplification. PCR conditions were 50 mM KCl, 10 mM Tris-Cl, pH 8.3, 0.1% Triton X-100, 7.5 mM $MgCl_2$, 1 mM of each dATP, dCTP, dGTP, and dTTP, and 25 U/ml of Taq DNA polymerase. Transcription reactions contained 5 mM DNA template, 5 units/$\mu$l T7 RNA polymerase, 40 mM Tris-Cl (pH 8.0), 12 mM $MgCl_2$, 5 mM DTT, 1 mM spermidine, 0.002% Triton X-100, 4% PEG 8000, 2 mM each of 2'-OH ATP, 2'-OH GTP, 2'-$NH_2$ CTP, 2'-$NH_2$ UTP, and 0.31 mM $\alpha$-$^{32}$P 2'-OH ATP.

The strategy for partitioning WGA/RNA complexes from unbound RNA was 1) to incubate the RNA pool with WGA immobilized on sepharase beads; 2) to remove unbound RNA by extensive washing; and 3) to specifically elute RNA molecules bound at the carbohydrate binding site by incubating the washed beads in buffer containing high concentrations of $(GlcNAc)_3$. The SELEX protocol is outlined in Table 1.

The WGA density on Wheat Germ Lectin Sepharose 6MB beads is approximately 5 mg/ml of gel of 116 $\mu$M (manufacturer's specifications). After extensive washing in HBSS, the immobilized WGA was incubated with RNA at room temperature for 1 to 2 hours in a 2 ml siliconized column with constant rolling (Table 1). Unbound RNA was removed by extensive washing with HBSS. Bound RNA was eluted as two fractions; first, nonspecifically eluted RNA was removed by incubating and washing with 10 mM methyl-$\alpha$-D-mannopyranoside in HBSS (Table 1; rounds 1–4) or with HBSS (Table 1; rounds 5–11); second, specifically eluated RNA was removed by incubating and washing with 0.5 to 10 mM $(GlcNAc)_3$ in HBSS (Table 1). The percentage of input RNA that was specifically eluted is recorded in Table 1.

The specifically eluted fraction was processed for use in the following round. Fractions eluted from immobilized WGA were heated at 90° C. for 5 minutes in 1% SDS, 2% $\beta$-mercaptoethanol and extracted with phenol/chloroform. RNA was reverse transcribed into cDNA by AMV reverse transcriptase at 48° C. for 60 min in 50 mM Tris-Cl pH (8.3), 60 mM NaCl, 6 mM $Mg(OAc)_2$, 10 mM DTT, 100 pmol DNA primer, 0.4 mM each of dNTPs, and 0.4 unit/$\mu$l AMV RT PCR amplification of this cDNA resulted in approximately 500 pmol double-stranded DNA, transcripts of which were used to initiate the next round of SELEX.

D) Nitrocellulose Filer Binding Assay

As described in SELEX Patent Applications, a nitrocellulose filter partitioning method was used to determine the affinity of RNA ligands for WGA and for other proteins. Filter discs (nitrocellulose/cellulose acetate mixed matrix, 0.45 $\mu$m pore size, Millipore; or pure nitrocellulose, 0.45 $\mu$m pore size, Bio-Rad) were placed on a vacuum manifold and washed with 4 ml of HBSS buffer under vacuum. Reaction mixtures, containing $^{32}$P labeled RNA pools and unlabeled WGA, were incubated in HBSS for 10 min at room temperature, filtered, and then immediately washed with 4 ml HBSS. The filters were air-dried and counted in a Beckman LS6500 liquid scintillation counter without floor.

WGA is a homodimer, molecular weight 43.2 kD, with 4 GlcNAc binding sites per dimer. For affinity calculations, we assume one RNA ligand binding site per monomer (two per dimer). The monomer concentration is defined as 2 times the dimer concentration. The equilibrium dissociation constant, $K_d$, for an RNA pool or specific ligand that binds monoplasically is given by the equation $$K_d=[P_f][R_f]/[RP]$$

where,

[Rf]=free RNA concentration

[Pf]=free WGA monomer concentration

[RP]=concentration of RNA/WGA monomer complexes $K_d$=dissociation constant

A rearrangement of this equation, in which the fraction of RNA bound at equilibrium is expressed as a function of the total concentration of the reactants, was used to calculate Kds of monophasic binding curves:

$$q=(P_T+R_T+K_d-((P_T+R_T+K_d)^2-4\ P_T R_T)^{1/2})$$

q=fraction of RNA bound $[P_T]$=total WGA monomer concentration $[R_T]$=total RNA concentration $K_d$s were determined by least square fitting of the data points using the graphics program Kaleidagraph (Synergy Software, Reading, Pa.).

E) Cloning and Sequencing

The sixth and eleventh round PCR products were re-amplified with primers which contain a BamHl or a EcoR1 restriction endonuclease recognition site. Using these restriction sites the DNA sequences were inserted directionally into the pUC18 vector. These recombinant plasmids were transformed into *E. coli* strain JM109 (Stratagene, La Jolla, Ca.). Plasmid DNA was prepared according to the alkaline hydrolysis method (Zhou et al., 1990 Biotechniques 8:172–173) and about 72 clones were sequenced using the Sequenase protocol (United States Biochemical Corporation, Cleveland, Ohio). The sequences are provided in Table 2.

F) Competitive Binding Studies

Competitive binding experiments were performed to determine if RNA ligands and $(GlcNAc)_3$ bind the same site on WGA. A set of reaction mixtures containing $\alpha^{37}$P labeled RNA ligand and unlabeled WGA, each at a fixed concentration (Table 5), was incubated in HBSS for 15 min at room temperature with $(GlcNAc)_3$. Individual reaction mixtures were then incubated with a $(GlcNAc)_3$ dilution from a 2-fold dilution series for 15 minutes. The final $(GlcNAc)_3$ concentrations ranged from 7.8 $\mu$M to 8.0 mM (Table 5). The reaction mixtures were filtered, processed and counted as described in "Nitrocellulose Filter Binding Assay," paragraph D above.

Competition titration experiments were analyzed by the following equation to determine the concentration of the protein [P] as a function of the total concentration of competitor added, $[C_T]$:

$$0=[P](1+K_L[L_T]/(1+K_L[P])+K_C[C_T]/(1+K_C[P]))-P_T$$

where $L_T$ is the concentration of initial ligand, $K_L$ is the binding constant of species L to the protein (assuming 1:1 stiochiometry) and Kc is the binding constant of species C to the protein (assuming 1:1 stiochiometry). Since ti is difficult to obtain a direction solution for equation 1, iteration to determine values of [P] to a precision of $1\times10^{-15}$ was used. Using these values of [P], the concentration of protein-ligand complex [PL] as a function of $[C_T]$ was determined by the following equation:

$$[PL]=K_L[L_T][P]/(1+K_L[P])$$

Since the ezperimental data is expressed in terms of %[PL], the calculated concentration of [PL] was normalized by the initial concentration of [PLo] before addition of the competitor. ([PLo] was calculated using the quadratic solution for the standard binding equation for the conditions used. The maximum (M) and minimum (B) % [PL] was allowed to float during the analysis as shown in the following equation.

$$\%[PL]=[PL]/[PLo]*(M-B)+B$$

A non-linear least-squares fitting procedure was used as described by P. R. Bevington (1969) Data Reduction and Error Analysis for the Physical Sciences, McGraw-Hill publishers. The program used was originally written by Stanley J. Gill in MatLab and modified for competition analysis by Stanley C. Gill. The data were fit to equations 1–3 to obtain best fit parameters for $K_C$, M and B as a function of [Cr] while leaving $K_L$ and $P_T$ fixed.

G) Inhibition of WGA Agglutinating Activity

Agglutination is a readily observed consequence of the interaction of a lectin with cells and requires that individual lectin molecules crosslink two or more cells. Lectin mediated agglutination can be inhibited by sugars with appropriate specificity. Visual assay of the hemagglutinating activity of WGA and the inhibitory activity of RNA ligands, GlcNAc and (GlcNAc)₃ was made in Falcon round bottom 96 well microtiter plates, using sheep erythrocytes. Each well contained 54 µl of erythrocytes (2.5×10⁸ cells/ml) and 54 µl of test solution.

To titrate WGA agglutinating activity, each test solution contained a WGA dilution from a 4-fold dilution series. The final WGA concentrations range from 0.1 pM to 0.5 µM. For inhibition assays, the test solutions contained 80 nM WGA (monomer)and a dilution from a 4-fold dilution series of the designated inhibitor. Reaction mixtures were incubated at room temperature for 2 hours, after which time no changes were observed in the precipitation patterns of erythrocytes. These experiments were carried out in Gelatin Veronal Buffer (0.15 mM CaCl₂, 141 mM NaCl, 0.5 mM MgCl₂, 0.1% gelatin, 1.8 mM sodium barbital, and 3.1 mM barbituric acid, pH 7.3–7.4; Sigma #G-6514).

In the absence of agglutination, erythrocytes settle as a compact pellet. Agglutinated cells form a more diffuse pellet. Consequently, in visual tests, the diameter of the pellet is diagnostic for agglutination. The inhibition experiments included positive and negative controls for agglutination and appropriate controls to show that the inhibitors alone did not alter the normal precipitation pattern.

EXAMPLE 2

RNA Ligands to WGA

A. SELEX

The starting RNA library for SELEX, randomized 50N9 (SEQ ID NO:1), contained approximately 2×10¹⁵ molecules (2 nmol RNA). The SELEX protocol is outlined in Table 1. Binding of randomized RNA to WGA is undetectable at 36 µM WGA monomer. The dissociation constant of the interaction is estimated to be <4 mM.

The percentage of input RNA eluated by (GlcNAc)₃ increased from 0.05% in the first round, to 28.5% in round 5 (Table 1). The bulk $K_d$ of round 5 RNA was 600 nM (Table 1). Since an additional increase in specifically eluted RNA was not observed in round 6a (Table 1), round 6 was repeated (Table 1, round 6b) with two modifications to increase the stringency of selection: the volume of gel, and hence the mass of WGA, was reduced ten fold; and RNA was specifically eluted with increasing concentrations of (GlCNAc)₃, in stepwise fashion, with only the last eluted RNA processed for the following round. The percentage of specifically eluted RNA increased from 5.7% in round 6b to 21.4% in round 8, with continued improvement in the bulk $K_d$ (260 nM, round 8 RNA, Table 1).

For rounds 9 through 11, the WGA mass was again reduced ten fold to further increase stringency. The $K_d$ of round 11 RNA was 68 nM. Sequencing of the bulk starting RNA pool and sixth and eleventh round RNA revealed some nonrandomness in the variable region at the sixth round and increased nonrandomess at round eleven.

To monitor the progess of SELEX, ligands were cloned and sequenced from round 6b and round 11. From each of two rounds, 36 randomly picked clones were sequenced. Sequences were aligned manually and are shown in Table 2.

B. RNA Sequences

From the sixth and eleventh rounds, respectively, 27 of 29 and 21 of 35 sequenced ligands were unique. The number before the "." in the ligand name indicates whether it was closed from the round 6 or round 11 pool. Only a portion of the entire clone is shown in Table 2 (SEQ ID NOS: 4–55). The entire evolved random region is shown in upper case letters. Any portion of the fixed region is shown in lower case letters. By definition, each clone includes both the evolved sequence and the associated fixed region, unless specifically stand otherwise. A unique sequence is operationally defined as one that differs from all others by these or more nucleotides. In Table 2, ligands sequences are shown in standard single letter code (Cornish-Bowden, 1985 NAR 13: 3021–3030). Sequences that were isolated more than once are indicated by the parenthetical number, (n), following the ligand isolate number. These clones fall into nine sequence families (1–9) and a group of unrelated sequences (Orphans).

The distribution of families from round six to eleven provides a clear illustration of the appearance and disappearance of ligand families in response to increased selective pressure (Table 2). Family 3, predominant (11/29 ligands) in round 6, has nearly disappeared (2/34) by round 11. Similarly, minor families 6 through 9 virtually disappear. In contrast, only one (family 1) of round eleven's predominant families (1, 2, and 5) was detected in round six. The appearance and disappearance of families roughly correlates with their binding affinities.

Alignment (Table 2) defines consensus sequences for families 1–4 and 6–9 (SEQ ID NOS:56–63). The consensus sequences of families 1–3 are long (20, 16 and 16, respectively) and very highly conserved. The consensus sequences of families 1 and 2 contain two sequences in common; the trinucleotide TCG and the pentanucleotide ACGAA. A related tetranucleotide, AACG, occurs in family 3. The variation in position of the consensus sequences within the variable regions indicates that the ligands do not require a specific sequence from either the 5' or 3' fixed region.

The consensus sequences of family 1 and 2 are flanked by complementary sequences 5 or more nucleotides in length. These complementary sequences are not conserved and the majority include minor discontinuities. Family 3 also exhibits flanking complementary sequences, but these are more variable in length and structure and utilize two nucleotide pairs of conserved sequence.

Confidence in the family 4 consensus sequence (Table 2) is limited by the small number of ligands, the variability of spacing and high G content. The pentanucleotide, RCTGG, also occurs in families 5 and 8. Ligands of family 5 show other sequence similarities to those of family 4, especially to ligand 11.28.

C. Affinities

The dissociation constants for representative members of families 1–9 and orphan ligands were determined by nitrocellulose filter binding experiments and are listed in Table 3. These calculations assume one RNA ligand binding site per WGA monomer. At the highest WGA concentration tested (36 μM WGA monomer), binding of random RNA is not observed, indicating a $K_d$ at least 100-fold higher than the protein concentration or >4 mM.

The data in Table 3 define several characteristics of ligand binding. First, RNA ligands to WGA bid monophasically. Second, the range of measured dissociation constants is 1.4 nM to 840 nM. Third, the binding for a number of ligands, most of which were sixth round isolates, was less than 5% at the highest WGA concentration tested. The dissociation constants of these ligands are estimated to be greater than 20 μM. Fourth, on average eleventh round isolates have higher affinity than those from the sixth round. Fifth, the SELEX probably was not taken to completion; the best ligand (11.20) (SEQ ID NO:40) is not the dominant species. Since the SELEX was arbitrarily stopped at the 11th round, it is not clear that 11.20 would be the ultimate winner. Sixth, even though the SELEX was not taken to completion, as expected, RNA ligands were isolated that bind WGA with much greater affinity than do mono- or oligosaccharides, (ie, the affinity of 11.20 is $5\times10^5$ greater than that of GlcNAc, Kd=760 μM, and 850 better than that of (GlcNAc)$_3$, Kd=12 μM; Y. Nagata and M. Burger, 1974, supra). This observation validates the proposition that competitive elution allows the isolation of oligonucleotide ligands with affinities that are several orders of magnitude greater than that of the competing sugar.

In addition these data show that even under conditions of high target density 116 pmol WGA dimer/μl of beads, it is possible to overcome avidity problems and recover ligands with nanomolar affinities. From the sixth to the eleventh round (Table 2), in response to increased selective pressure as indicated by the improvement in bulk $K_d$ (Table 1), sequence families with lower than average affinity (Table 3) are eliminated from the pool.

EXAMPLE 3

Specificity of RNA Ligands to WGA

The affinity of WGA ligands 6.8, 11.20 and 11.24 (SEQ ID NOS: 13, 40, and 19) for GlcNAc binding lectins from *Ulex europoeus, Datura stramonium* and *Canavalia ensiformis* were determined by nitrocellulose partitioning. The results of this determination are shown in Table 4. The ligands are highly specific for WGA. For example, the affinity of ligand 11:20 for WGA is 1,500, 8,000 and <15,000 fold greater than it is for the *U. europoeus, D. strammonium* and *C. ensiformis* lectins, respectively. The 8,000 fold difference in affinity for ligand 11,20 exhibited by T. vulgare and D. stramonium compares to a 3 to 10 fold difference in their affinity for oligomers of GlCNAc and validates the proposition that competitive elution allows selection of oligonucleotide ligands with much greater specificity that monomeric and oligomeric saccharides (J. F. Crowley et al., 1984, Arch. Biochem. and Biophys. 231:524–533; Y. Nagata and M. Burger, 1974, supra; J-P. Priva et al., FEBS Letters 46:229–232).

EXAMPLE 4

Competitive Binding Studies

If an RNA ligand a carbohydrate bind a common site, then binding of the RNA ligand is expected to be competitively inhibited by the carbohydrate. Furthermore, if the oligonucleotides ligands bind exclusively to carbohydrate binding sites, inhibition is expected to be complete at high carbohydrate concentrations. In the experiments reported in Table 5, dilutions of unlabeled (GlcNAc)$_3$, from a 2-fold dilution series, were added to three sets of binding reactions that contained WGA and an α-$^{32}$P labeled RNA ligand (6.8, 11.20 or 11.24 (SEQ ID NOS:13, 40 and 19); [RNA]$_{final}$= [WGA]$_{final}$=15 nM). After a 15 minute incubation at room temperature, the reactions were filtered and processed as in standard binding experiments.

Qualitatively, it is clear that RNA ligands bind only to sites at which (GlcNAc)$_3$ binds, since inhibition is complete at high (GlcNAc)$_3$ concentrations (Table 5). These data do not rule out the possibility that (GlcNAc)$_3$ binds one or more sites that are not bound by these RNA ligands.

Quantitatively, these data fit a simple model of competitive inhibition (Table 5) and give estimates of 8.4, 10.9, and 19.4 μM for the Kd of (GlCNAc)$_3$. These estimates are in good agreement with literature values (12 μM @4 C, Nagata and Burger, 1974, supra; 11 μM @ 10.8 C, Van Landschoot et al., 1977, Eur. J. Biochem. 79:275–283; 50 μM, M. Monsigny et al., 1979, Eur J. Biochem. 98:39–5). These data confirm the proposition that competitive elution with a specific carbohydrate targets the lectin's carbohydrate binding site.

EXAMPLE 5

Inhibition of WGA Agglutinating Activity

At 0.5 μM, RNA ligands 6.8 and 11.20 (SEQ ID NO: 13 and 40) completely inhibit WGA mediated agglutination of sheep erythrocytes (Table 6). Ligand 11.24 (SEQ ID NO: 19) is not as effective, showing only partial inhibition at 2 μM, the highest concentration tested (Table 6). (GlcNAc)$_3$ and GlCNAc completely inhibit agglutination at higher concentrations, 8 μM and 800 μM, respectively, (Table 6; Monsigny et al., supra). The inhibition of agglutination varifies the proposition that ligands isolated by this procedure will be antagonists of lectin function. Inhibition also suggests that more than one RNA ligand is bound per WGA dimer, since agglutination is a function of multiple carbohydrate binding sites.

An alternative interpretation for the inhibition of agglutination is that charge repulsion prevents negatively charged WGA/RNA complexes from binding carbohydrates (a necessary condition for agglutination) on negatively charged cell surfaces. This explanation seems unlikely for two reasons. First, negatively charged oligonucleotide ligands selected against an immobilized purified protein are known to bind to the protein when it is presented in the context of a cell surface (see Example 10, L-selectin cell binding). Second, negatively charged (pI=4) succinylated WGA is as effective as native WGA (pI=8.5) in agglutinating erythrocytes (M. Monsigny et al., supra).

EXAMPLE 6

Secondary Structure of High Affinity WGA Ligands

In favorable instances, comparative analysis of aligned sequences allows deduction of secondary structure and structure-function relationships. If the nucleotides at two positions in a sequence covary according to Watson-Crick base pairing rules, then the nucleotides at these positions are apt to be paired. Nonconserved sequences, especially those that vary in length are not apt to be directly involved in function, while highly conserved sequence are likely to be directly involved.

Figure 1B:
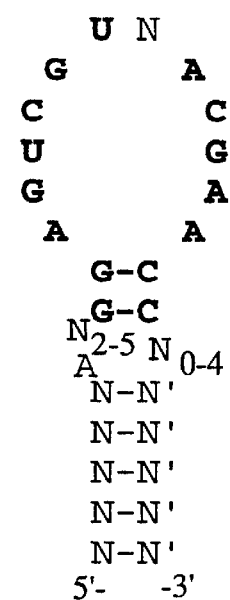
Figure 1C:
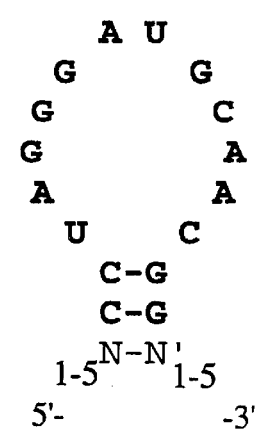

Comparative analyses of both family 1 and 2 sequences each yield a hairpin structure with a large, highly conserved loop (FIGS. 1a and 1b). Interactions between loop nucleotides are likely but they are not defined by these data. The stems of individual ligands vary in sequence, length and structure (i.e., a variety of bulges and internal loops are allowed; Table 2). Qualitatively it is clear that the stems are validated by Watson/Crick covariation and that by the rules of comparative analysis the stems are not directly involved in binding WGA. Family 3 can form a similar hairpin in which 2 pairs of conserved nucleotides are utilized in the stem (FIG. 1c).

If it is not possible to fold the ligands of a sequence family into homologous structure, their assignment to a single family in questionable. Both ligand 11.7, the dominant member of family 4, and ligand 11.28 can be folded into two plane G-quartets. However, this assignment is speculative: 1) 11.28 contains five GG dinucleotides and one GGGG tetranucleotide allowing other G-quartets; and 2) ligands 11.2 and 11.33 cannot form G-quartets. On the other hand, all ligands can form a hairpin with the conserved sequence GAGRFTNCRT in the loop. However, the conserved sequence RCTGGC (Table 2) does not have a consistent role in these hairpins.

Multiple G-quartet structures are possible for Family 5. One of these resembles the ligand 11.7 G-quartet. No convincing hairpin structural are possible for ligand 11.20.

EXAMPLE 7

2'-NH$_2$RNA Ligands to Human L-Selectin

The experimental procedures outlined in this Example were used to identify and characterize the 2'-NH$_2$ RNA ligands to human L-selectin in Examples 8–12. Experimental Procedures
A) Materials LS-Rg is a chimeric protein in which the extracellular domain of human L-selectin is joined to the Fc domain of a human G2 immunoglobulin (Norgard et al., 1993, PNAS 90:1068–1072), ES-Rg, PS-Rg and CD22β-Rg are analogous constructs of E-selectin, P-selectin and CD22β joined to a human G1 immunoglobulin Fc domain (R. M. Nelson et al., 1993, supra; I. Stamenkovic et al., 1991, Cell 66, 1133–1144). Purified chimera were provided by A. Varki. Soluble P-selectin was purchased from R&D Systems. Protein A Sepharose 4 Fast Flow beads were purchased from Pharmacia Biotech. Anti-L-selectin monoclonal antibodies; SK11 was obtained from Becton-Dickinson, San Jose, Calif.; DREG-56, an L-selectin specific monoclonal antibody, was purchased from Endogen, Cambridge, Mass. The 2'-NH$_2$ modified CTP and UTP were prepared according to Picken et al. (1991, Science 253;314–317). DNA oligonucleotides were synthesized by Operon. All other reagents and chemicals were purchased from commercial sources. Unless otherwise indicated, experiments utilized HSMC buffer (1 mM CaCl$_2$, 1 mM MgCl$_2$, 150 mM NaCl, 20.0 mM HEPES, pH 7.4).
B) SELEX The SELEX procedure is described in detail in U.S. Pat. No. 5,270,163 and elsewhere. The nucleotide sequence of the synthetic DNA template for the LS-Rg SELEX was randomized at 40 positions. This variable region was flanked by N7 5' and 3'fixed regions (40N7). 40N7 transcript has the sequence 5'gggaggacgaugcgg-40N-cagacgacucgcccga 3'(SEQ ID NO:64). All C and U have 2'-NH$_2$ substituted for 2'-OH on the ribose. The primers for the PCR were the following:

N7.5'Primer 5'taatacgactcactatagggaggacgatgcgg3'(SEQ ID NO:65)

N7 3'Primer 5'tcgggcgagtcgtcctg 3' (SEQ ID NO:66)

The fixed regions include primer annealing sites for PCR and cDNA synthesis as well as a consensus T7 promoter to allow in vitro transcription. The initial RNA pool was made by first Klenow extending 1 nmol of synthetic single strand DNA and then transcribing the resulting double stranded molecules with T7 RNA polymerase. Klenow extension conditions: 3.5 nmols primer 5N7, 1.4 nmols 40N7, 1X Klenow Buffer, 0.4 mM each of dATP, dCTP, dGTP and dTTP in a reaction volume of 1 ml.

For subsequent rounds, eluted RNA was the template for AMV reverse transcriptase mediated synthesis of single-stranded cDNA. These single-stranded DNA molecules were converted into double-stranded transcription templates by PCR amplification. PCR conditions wee 50 mM KCl, 10 mM Tris-Cl, pH 8.3, 7.5 mM MgCl$_2$, 1 mM of each dATP, dCTP, dGTP, and dTTP, and 25 U/ml of Taq DNA polymerase. Transcription reactions contained 0.5 mM DNA template, 200 nM T7 RNA polymerase, 80 mM HEPES (pH 8.0), 12 mM MgCl$_2$, 5 mM DTT, 2 mM spermidine, 2 mM each of 2'-OH ATP, 2'-OH GTP, 2'-NH$_2$ CTP, 2'-NH$_2$ UTP, and 250 nM α-$^{32}$P2'-OH ATP.

The strategy for partitioning LS-Rg/RNA complexes from unbound RNA is outlined in Tables 7a and 7b. First, the RNA pool was incubated with LS-Rg immobilized on protein A sepharose beads in HSMC buffer. Second, the unbound RNA was removed by extensive washing. Third, the RNA molecules bound at the carbohydrate binding site were specifically eluted by incubating the washed beads in HMSC buffer containing 5 mM EDTA in place of divalent cations. The 5 mM elution was followed by a non-specific 50 mM EDTA elution. LS-Rg was coupled to protein A sepharose beads according to the manufacturer's instructions (Pharmacia Biotech).

The 5 mM EDTA elution is a variation of a specific site elution strategy. Although it is not a priori as specific as elution by carbohydrate competition, it is a general strategy for C-type (calcium dependent binding) lectins and is a practical alternative when the cost and/or concentration of the required carbohydrate competitor is unreasonable (as is the case with sialyl-Lewis$^x$). This scheme is expected to be fairly specific for ligands that form bonds with the lectin's bound Ca$^{++}$ because the low EDTA concentration does not appreciably increase the buffer's ionic strength and the conformation of C-type lectins is only subtly altered in the absence of bound calcium (unpublished observations cited by K. Drickamer, 1993, Biochem. Soc. Trans. 21:456–459).

In the initial SELEX rounds, which were performed at 4° C., the density of immobilized LS-Rg was 16.7 pmols/µl of Protein A Sepharose 4 Fast Flow beads. In later rounds, the density of LS-Rg was reduced (Tables 7a and 7b), as needed, to increase the stringency of selection. At the seventh round, the SELEX was branched and continued in parallel at 4° C. (Table 7a) and at room temperature (Table 7b). Wash and elution buffers were equilibrated to the relevant incubation temperature. Beginning with the fifth round, SELEX was often done at more than one LS-Rg density. In each branch, the eluted material from only one LS-Rg density was carried forward.

Before each round, RNA was batch adsorbed to 100 µl of protein A sepharose beads for 1 hour in a 2 siliconized column. Unbound RNA and RNA eluted with minimal washing (two volumes) were combined and used for SELEX input material. For SELEX, extensively washed, immobilized LS-Rg was batch incubated with pre-adsorbed RNA for 1 to 2 hours in a 2 ml siliconized column with constant rocking. Unbound RNA was removed by extensive batch washing (200 to 500 μl HSMC/wash). Bound RNA was eluted as two fractions; first, bound RNA was eluted by incubating and washing columns with 5 mM EDTA in HSMC without divalent cations; second, the remaining elutable RNA was removed by incubating and/or washing with 50 mM EDTA in HSMC without divalents. The percentage of input RNA that was eluted is recorded in Tables 7a and 7b. In every round, an equal volume of protein A sepharose bends without LS-Rg was treated identically to the SELEX beads to determine background binding. All unadsorbed, wash and eluted fractions were counted in a Beckman LS6500 scintillation counter in order to monitor each round of SELEX.

The eluted fractions were processed for use in the following round (Tables 7a and 7b). After extracting with phenol/chloroform and precipitating with isopropanol/ethanol (1:1, v/v), the RNA was reverse transcribed into cDNA by AMV reverse transcriptase either 1) at 48° C. for 15 minutes and then 65° C. for 15 minutes or 2) at 37° C. and 48° C. for 15 minutes each, in 50 mM Tris-Cl pH (8.3), 60 mM NaCl, 6 mM $Mg(OAc)_2$, 10 mM DTT, 100 pmol DNA primer, 0.4 mM each of dNTPs, and 0.4 unit/μl AMV RT. Transcripts of the PCR product were used to initiate the next round of SELEX.

C) Nitrocellulose Filter Binding Assay

As described in SELEX Patent Applications, a nitrocellulose filter partitioning method was used to determine the affinity of RNA ligands for LS-Rg and for other proteins. Filter discs (nitrocellulose/cellulose acetate mixed matrix, 0.45 μm pore size, Millipore) were placed on a vacuum manifold and washed with 2 ml of HSMC buffer under vacuum. Reaction mixtures, containing $^{32}P$ labeled RNA pools and unlabeled LS-Rg, were incubated in HSMC for 10–20 min at 4° C., room temperature or 37° C., filtered, and then immediately washed with 4 ml HSMC at the same temperature. The filter were air-dried and counted in a Beckman LS6500 liquid scintillation counter without fluor.

LS-Rg is a dimeric protein that is the expression product of a recombinant gene constructed by fusing the DNA sequence that encodes the extracellular domains of human L-selectin to the DNA that encodes a human $IgG_2$ Fc region. For affinity calculations, we assume one RNA ligand binding site per LS-Rg monomer (two per dimer). The monomer concentration is defined as 2 times the LS-Rg dimer concentration. The equilibrium dissociation constant, K, for an RNA pool or specific ligand that binds monophasically is given by the equation $$Kd=[Pf][Rf]/[RP]$$

where

[Rf]=free RNA concentration

[Pf]=free LS-Rg monomer concentration

[RP]=concentration of RNA/LS-Rg complete $K_d$=dissociation constant

A rearrangement of this equation, in which the fraction of RNA bound at equilibrium is expressed as a function of the total concentration of the reactants, was used to calculate Kds of monophasic binding curves:

$$q=(P_T+R_T+K_d-((P_T+R_T+K_d)^2-4P_TR_T)^{1/2})$$

q=fraction of RNA bound $[P_T]$=2×(total SL-Rg concentration)

$[R_T]$=total RNA concentration

Many ligands and evolved RNA pools yield biphasic binding curves. Biphasic binding can be described as the binding of two affinity species that are not in equilibrium. Biphasic binding data were evaluated with the equation $$q=2P_t+R_t+Kd_1+Kd_2-[(P_t+X_1R_1+K_{d1})^2-4P_tX_1R_t]^{1/2}-[(P_t+X_2R_t+K_{d2})^2-4P_tX_2R_t]^{1/2},$$

where $X_1$ and $X_2$ are the mole fractions of affinity species $R_1$ and $R_2$ and $K_{d1}$ and $K_{d2}$ are the corresponding dissociation constants. $K_d$s were determined by least square fitting $K_d$s were determined by least square fitting of the data points using the graphics program Kaleidagraph (Synergy Software, Reading, Pa.).

D) Cloning and Sequencing

Sixth, thirteenth (RT) and fourteenth (4° C.) round PCR products were reamplified with primers which contain either a BamHI or a HinDIII restriction endonuclease recognition site. Using these restriction sites, the DNA sequences were inserted directionally into the pU9 vector. These recombinant plasmids were transformed into *E. coli* strain DH5a (Life Technologies, Gaithersburg, Md.). Plasmid DNA was prepared according to the alkaline hydrolysis method (PERFECTprep, 5"-3", Boulder, Colo.). Approximately 150 clones were sequenced using the Sequenase protocol (Amersham, Arlington Heights, Ill.). The resulting ligand sequences are shown in Table 8.

E) Cell Binding studies

The ability of evolved ligand pools and cloned ligands to bind to L-selectin presented in the context of a cell surface was tested in experiments with isolated human peripheral blood mononuclear cells (PBMCs). Whole blood, collected from normal volunteers, was anticoagulated with 5 mM EDTA. Six milliliters of blood were layered on a 6 ml Histopaque gradient in 15 ml polypropylene tube and centrifuged (700 g) at room temperature for 30 minutes. The mononuclear cell layer was collected, diluted in 10 ml of $Ca^{++}/Mg^{++}$-free DPBS (DPBS(-); Gibco 14190–029) and centrifuged (225 g) for 10 minutes at room temperature. Cell pellets from two gradients were combined, resuspended in 10 ml of DPBS(-) and recentrifuged as described above. These pellets were resuspended in 100 μl of SMHCK buffer supplemented with 1% BSA. Cells were counted in a hemocytometer, diluted to $2\times10^7$ cells/ml in SMHCK/1% BSA and immediately added to binding assays. Cell viability was monitored by trypan blue exclusion.

For cell binding assays, a constant number of cells were titrated with increasing concentration of radiolabeled ligand. The test ligands were serially diluted in DPBS(-)(1%BSA to 2-times the desired final concentration approximately 10 minutes before use. Equal volumes (25 μl) of each ligand dilution and the cell suspension ($2\times10^7$ cells/ml) were added to 0.65 ml eppendorf tubes, gently vortexed and incubated on ice for 30 minutes. At 15 minutes the tubes were revortexed. The ligand/PBMC suspension was layered over 50 μl of ice cold phthalate oil (1:1=dinonyl:dibutyl phthalate) and microfuged (14,000 g) for 5 minutes at 4° C. Tubes were frozen in dry ice/ethanol, visible pellets amputated into scintillation vials and counted in Beckman LS6500 scintillation counter as described in Example 7, paragraph C.

The specificity of binding to PBMCs was tested by competition with the L-selectin specific blocking monoclonal antibody, DREG-56, while saturability of biding was tested by competition with unlabeled RNA. Experimental procedure and conditions were like those for PBMC binding experiments, except that the radiolabeled RNA ligand (final concentration 5 mM) was added to serial dilutions of the competitor before mixing with PBMCs.

F) Inhibition of Selectin Binding to sialyl-Lewis$^x$

The ability of evolved RNA pools or cloned ligands to inhibit the binding of LS-Rg to sialyl-Lewis$^x$ was tested in competive ELISA assays (C. Foxall et al., 1992, supra). For these assays, the wells of Corning (25801) 96 well microtiter plates were coated with 100 ng of a sialyl-Lewis$^x$/BSA conjugate, air dried overnight, washed with 300 µl of PBS(−) and then blocked with 1% BSA in SHMCK for 60 min at room temperature. RNA ligands were incubated with LS-Rg in SHMCK/1% BSA at room temperature for 15 min. After removal of the blocking solution, 50 µl of LS-Rg (10 nM) or a LS-Rg (10 nM)/RNA ligand mix was added to the coated, blocked wells and incubated at room temperature for 60 minutes. The binding solutions was removed, wells were washed with 300 µl of PBS(−) and then probed with HRP conjugated anti-human IgG, at room temperature to quantitate LS-Rg binding. After a 30 minutes incubaton at room temperature in the dark with OPD peroxidase substrate (Sigma P9187), the extent of LS-Rg binding and percent inhibition was determined from the OD$_{450}$.

EXAMPLE 8

2'-NH$_2$ RNA Ligands to Human L-selectin

A. SELEX

The starting RNA pool for SELEX, randomized 40N7 (SEQ ID NO: 63), contained approximately 10$^{15}$ molecules (1 nmol RNA). The SELEX protocol is outlined in Tables 7a and 7b and Example 7. The dissociation constant of randomized RNA to LS-Rg is estimated to be approximately 10 µM. No difference was observed in the RNA elution profiles with 5 mM EDTA from SELEX and background beads for rounds 1 and 2, while the 50 mM elution produced a 2–3 fold excess over background (Table 7a). The 50 mM eluted RNA from rounds 1 and 2 were amplified for the input material for rounds 2 and 3, respectively. Beginning in round 3, the 5 mM elution from SELEX beads was significantly higher than background and was processed for the next round's input RNA. The percentage of input RNA eluted by 5 mM EDTA increased from 0.5% in the first round to 8.4% in round 5 (Table 7a). An additional increase in specifically eluted RNA from the 10 µM LS-Rg beads was not observed in round 6 (Table 7a). To increase the stringency of selection, the density of immobilized LS-Rg was reduced ten fold in round 5 with further reductions in protein density at later rounds. The affinity of the selected pools rapidly increased and the pools gradually evolved biphasic binding characteristics.

Binding experiments with 6th round RNA revealed that the affinity of the evolving pool for L-selectin was temperature sensitive. Beginning with round 7, the SELEX was branched; one branch was continued at 4° C. (Table 7a) while the other was conducted at room temperature (Table 7b). Bulk sequencing of 6th, 13th (rm temp) and 14th (4° C.) RNA pools revealed noticeable non-randomness at round six and dramatic non-randomess at the later rounds. The 6th round RNA bound monophasically at 4° C. with a dissociation constant of approximately 40 nM, while the 13th and 14th round RNAs bound biphasically with high affinity Kds of approximately 700 pM. The molar fraction of the two pools that bound with high affinity were 25% and 65%, respectively. The binding of all tested pools required divalent cations. In the absence of divalent cations, the Kds of the 13th and 14th round pools increased to 45 nM and 480 nM, respectively (HSMC, minus Ca$^{++}$/Mg$^{++}$, plus 2 mM EDTA).

To monitor the progress of SELEX, ligands were cloned and sequenced from rounds 6, 13 (rm temp) and 14 (4° C.). Sequences were aligned manually and with the aid of a computer program that determines consensus sequences from frequently occurring local alignments.

B. Sequences

In Table 8, ligand sequences are shown in standard single letter code (Cornish-Bowden, 1985 NAR 13: 3021–3030). The letter/number combination before the "." in the ligand name indicates whether it was cloned from the round 6, 13 or 14 pools. Only the evolved random region is shown in Table 8. Any portion of the fixed region is shown in lower case letters. By definition, each clone includes both the evolved sequence and the associated fixed region, unless specifically stated otherwise. From the sixth, thirteenth and fourteenth rounds, respectively, 26 of 48, 8 of 24 and 9 of 70 sequenced ligands were unique. A unique sequence is operationally defined as one that differs from all others by three or more nucleotides. Sequences that were isolated more than once, are indicated by the parenthetical number, (n), following the ligand isolate number. These clones fall into thirteen sequence families (I–XIII) and a group of unrelated sequences (Orphans)(SEQ ID NOs:67–117).

Two families, I and III, are defined by ligands from multiple lineages. Both families occur frequently in round 6, but only one family III ligand was identified in the final rounds. Six families (IV, V, VI, VII, VIII, and possibly II) are each defined by just two lineages which limits confidence in their consensus sequences. Five families (IX through XIII) are defined by a single lineage which precludes determination of consensus sequences.

Ligands from family II dominate the final rounds: 60/70 ligands in round 14 and 9/24 in round 13. Family II is represented by three mutational variations of a single sequence. One explanation for the recovery of a single lineage is that the ligand's information content is extremely high and was therefore represented by a unique species in the starting pool. Family II ligands were not detected in the sixth round which is consistent with a low frequency in the initial population. An alternative explanation is sampling error. Note that a sequence of questionable relationship was detected in the sixth round.

The best defined consensus sequences are those of family I. AUGUGUA (SEQ ID NO:118), and a family III, AACAIGAAGIA (SEQ ID NO:120), as shown in Table 8. Family III has two additional, variably spaced sequences, AGUC and ARUUAG, that may be conserved. The tetranucleotide AUGW is found in the consensus sequence of families I, III, and VII and in families II, VIII and IX. If this sequence is significant, it suggests that the conserved sequences of ligands of family VIII are circularly permuted. The sequence AGAA is found in the consensus sequences of families IV and VI and in families X and XIII.

C. Affinities

The dissociation constants for representative ligands from rounds 13 and 14, including all orphans, were determined by nitrocellulose filter binding experiments are described in Example 7 and the results are listed in Table 9. These calculations assume two RNA ligand binding sites per chimera. The affinity of random RNA cannot be reliably determined but is estimated to be approximately 10 µM.

In general, ligands bind monophasically with dissociation constants ranging from 50 pM to 15 nM at 4° C. Some of the highest affinity ligands bind biphasically. Although ligands of families I, VII, X and orphan F14.70 bind about equally well at 4° C. and room temperature, in general the affinities decrease with increasing temperature. The observed affinities substantiate the proposition that it is possible to isolate oligonucleotide ligands with affinities that are several orders of magnitude greater than that of carbohydrate ligands.

EXAMPLE 9

Specificity of 2'-NH$_2$ RNA Ligands to L-Selectin

The affinity of L-selectin ligands to ES-Rg, PS-Rg and CD22β-Rg were determined by nitrocellulose partitioning as described in Example 7. As indicated in Table 10, the ligands are highly specific for L-selectin. In general, a ligand's affinity for ES-Rg is $10^3$-fold lower and that for PS-Rg is about $10^4$-fold less than for LS-Rg. Binding above background is not observed for CD22β-Rg at the highest protein concentration tested (660 nM), indicating that ligands do not bind the Fc domain of the chimeric constructs nor do they have affinity for the sialic acid binding site of an unrelated lectin. The specificity of oligonucleotide ligand binding contrasts sharply with the binding of cognate carbohydrates by the selectins and confirms the proposition that SELEX ligands will have greater specificity than carbohydrate ligands.

EXAMPLE 10

Binding of L-Selectin 2'-NH$_2$ RNA Ligands to Human PBMCs

Figure 2:
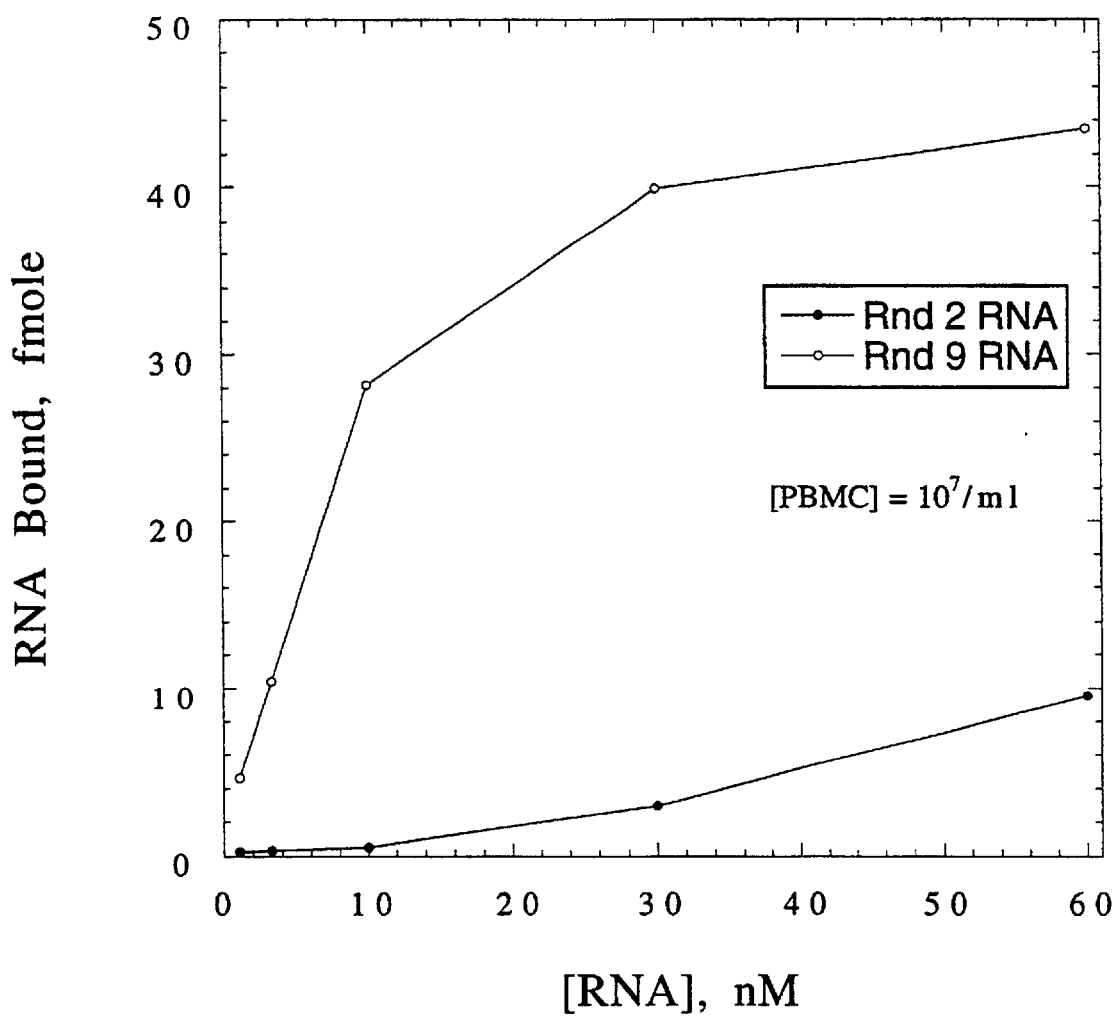
FIG. 2 shows binding curves for the L-selectin SELEX second and ninth round 2'-$NH_2$ RNA pools to peripheral blood lymphocytes (PBMCs).
Figure 3:
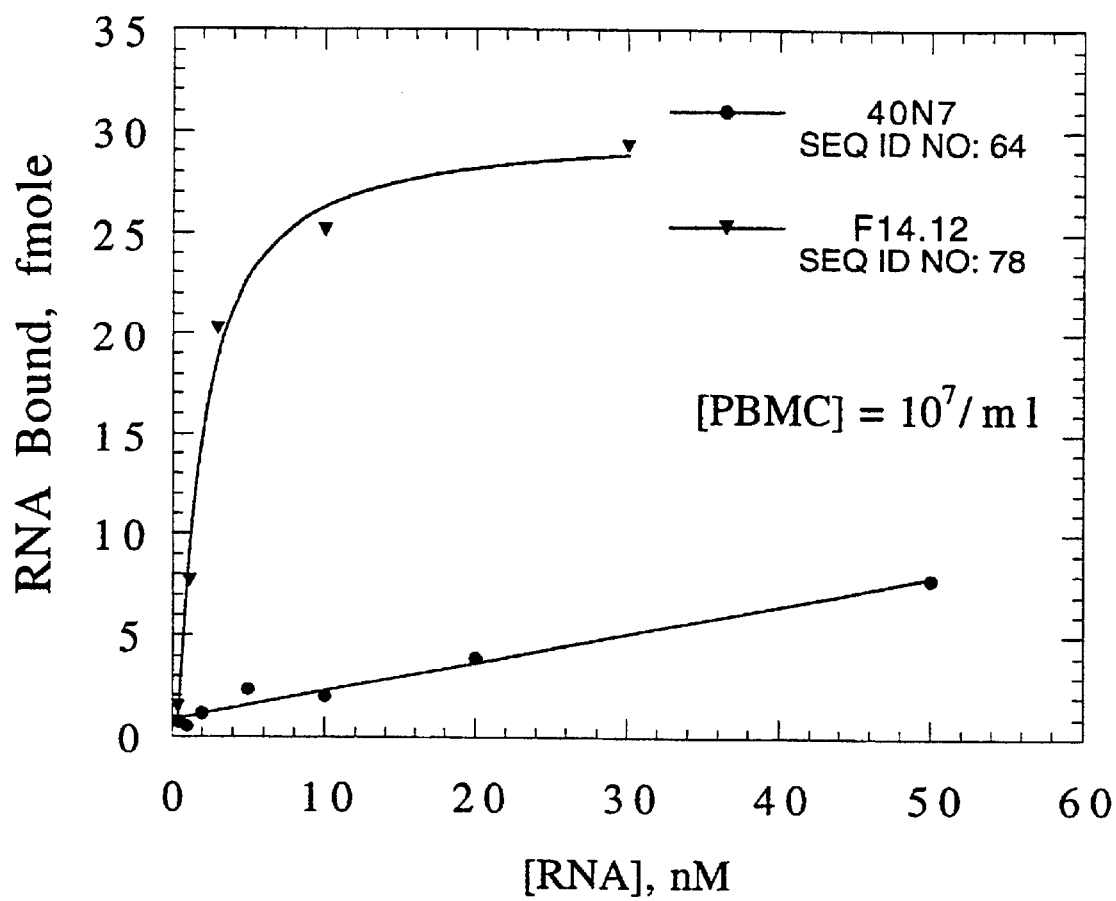
FIG. 3 shows binding curves for random 40N7 2'-$NH_2$ RNA (SEQ ID NO: 64) and the cloned L-selectin ligand, F14.12 (SEQ ID NO: 78), to peripheral blood lymphocytes (PBMC).
Figure 4:
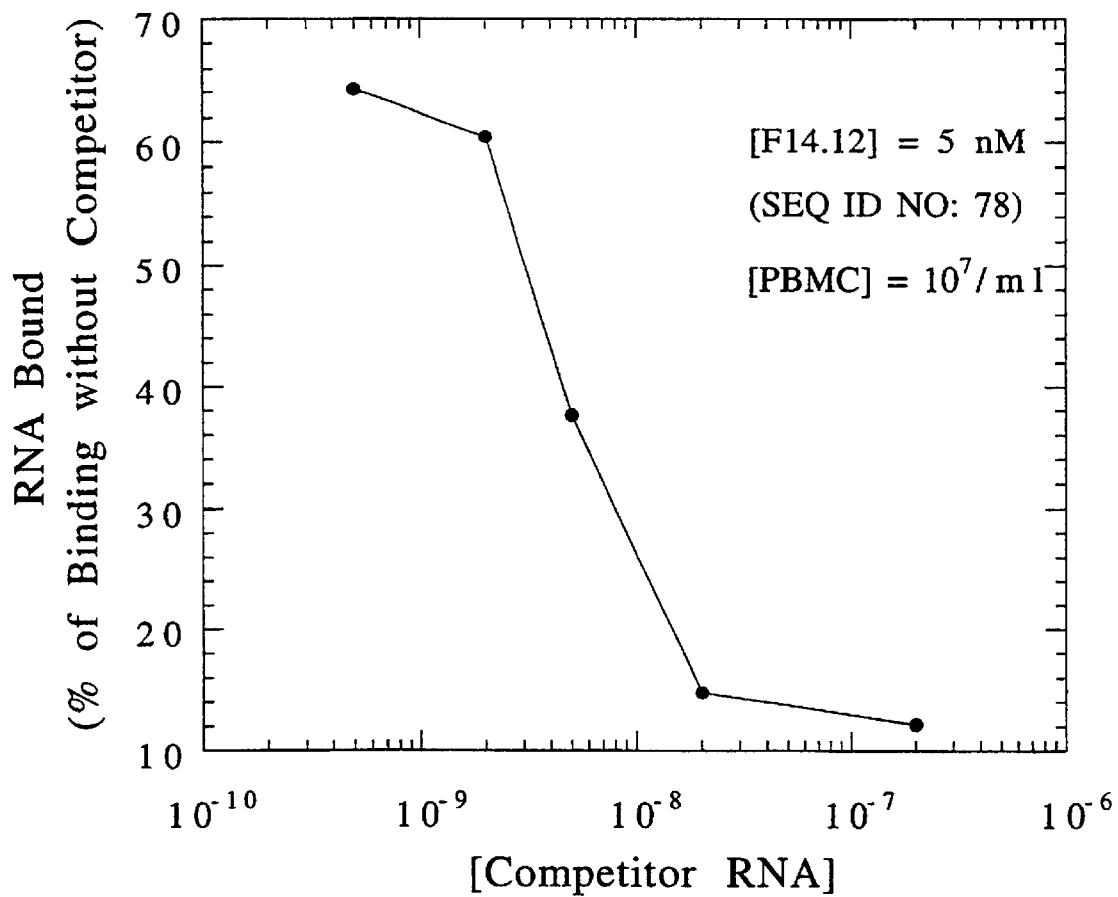
FIG. 4 shows the results of a competition experiment in which the binding of 5 nM $^{32}$P-labeled F14.12 (SEQ ID NO: 78) to PBMCs ($10^7$/ml) is competed with increasing concentrations of unlabeled F14.12 (SEQ ID NO: 78). RNA Bound equals 100×(net counts bound in the presence of competitor/net counts bound in the absence of competitor).
Figure 5:
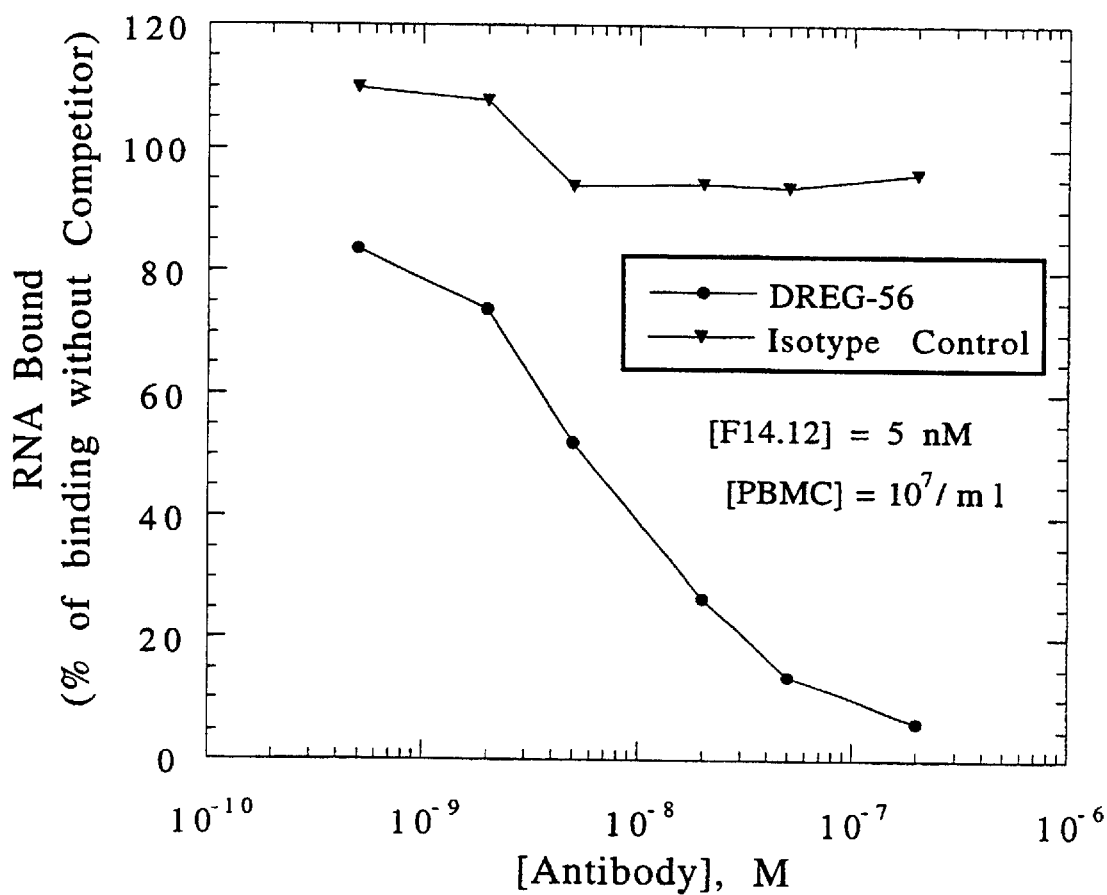
FIG. 5 shows the results of a competition experiment in which the binding of 5 nM $^2$P-labeled F14.12 (SEQ ID NO: 78) to PBMCs ($10^7$/ml) is competed with increasing concentrations of the blocking monoclonal anti-L-selectin antibody, DREG-56, or an isotype matched, negative control antibody. RNA Bound equals 10033 (net counts bound in the presence of competitor/net counts bound in the absence of competitor).

Since the L-selectin ligands were isolated against purified, immobilized protein, it is essential to demonstrate that they bind L-selectin presented in the context of a cell surface. Comparison of 2nd and 9th round RNAs (FIG. 2) shows that the evolved (9th round) ligand pool binds isolated PBMCs with high affinity and, as expected for specific binding, in a saturable fashion. The binding of round 2 RNA appears to be non-saturable as is characteristic of non-specific binding. The cloned ligand, F14.12 (SEQ ID NO: 78), also binds in a saturable fashion with a dissociation constant of 1.3 nM, while random 40N7 (SEQ ID NO: 64) resembles round 2 RNA (FIG. 3). The saturability of binding is confirmed by the data in FIG. 4; >90% of 5 nM $^{32}$P-labeled F14.12 RNA binding is competed by excess cold RNA. Specificity is demonstrated by the results in FIG. 5; binding of 5 nM $^{32}$P-labeled F14.12 RNA is completely competed by the anti-L-selectin blocking monoclonal antibody, DREG-56, but is unaffected by an isotype-matched irrelevant antibody. These data validate the feasibility of using immobilized, purified protein to isolate ligands against a cell surface protein and the binding specificity of F14.12 to L-selectin in the context of a cell surface.

EXAMPLE 11

Inhibition of Binding to Sialyl-Lewis$^x$

Oligonucleotide ligands, eluted by 2–5 mM EDTA, are expected to derive part of their binding energy from contacts with the lectin domain's bound Ca$^{++}$ and consequently, are expected to compete with sialyl-Lewis$^x$ for binding. The ability of ligand F14.12 (SEQ ID NO: 78) to inhibit LS-Rg binding to immobilized sialyl-Lewis$^x$ was determined by competition ELISA assays. As expected, 4 mM EDTA reduced LS-Rg binding 7.4-fold, while 20 mM round 2 RNA did not inhibit LS-Rg binding. Carbohydrate binding is known to be Ca$^{++}$ dependent; the affinity of round 2 RNA is too low to bind 10 nM LS-Rg (Table 7).

Figure 6:
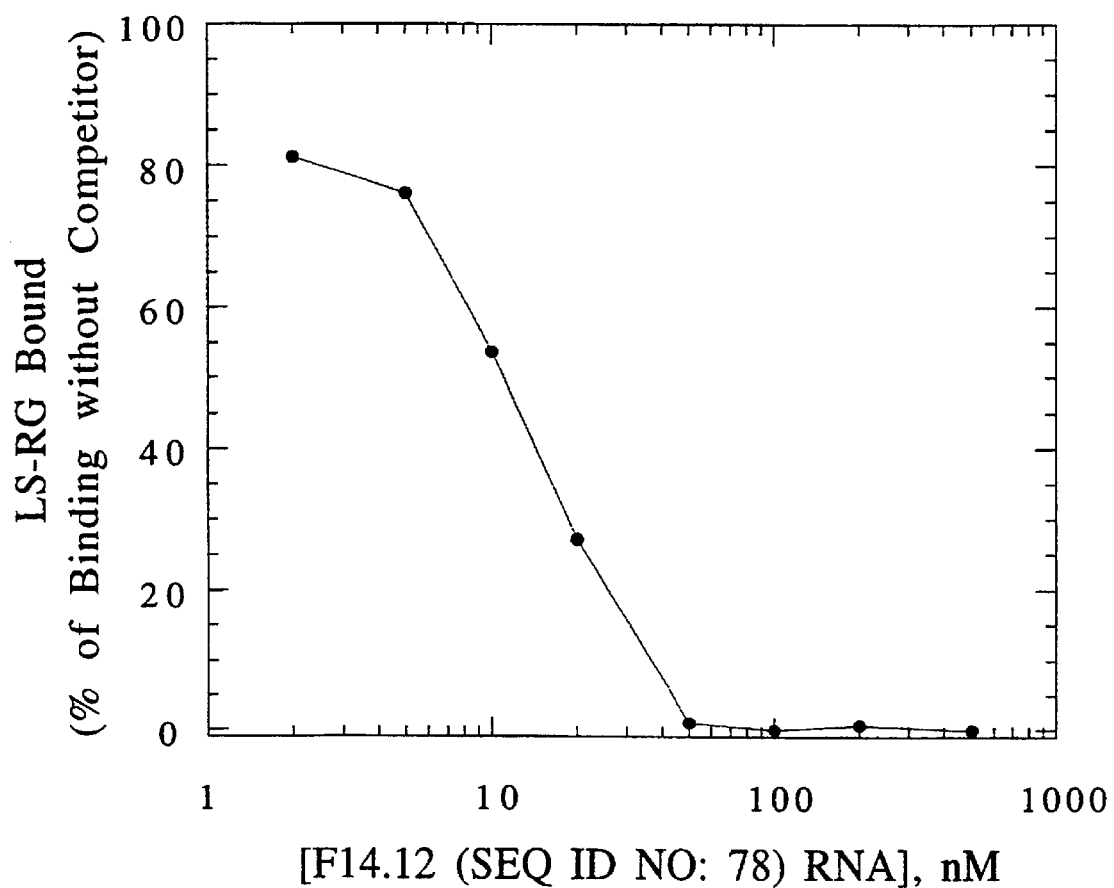
FIG. 6 shows the results of a competitive ELISA assay in which the binding of soluble LS-Rg to immobilized sialyl-Lewis$^x$/BSA conjugates is competed with increasing concentrations of unlabeled F14.12 (SEQ ID NO: 78). Binding of LS-Rg was monitored with an HRP conjugated anti-human IgG antibody. LS-Rg Bound equals 100␣33 ($OD_{450}$ in the presence of competitor)/($OD_{450}$ in the absence of competitor). The observed $OD_{450}$ was corrected for nonspecific binding by subtracting the $OD_{450}$ in the absence of LS-Rg from the experimental values. In the absence of competitor the $OD_{450}$ was 0.324 and in the absence of LS-Rg 0.052. Binding of LS-Rg requires divalent cations; in the absence of competitor, replacement of $Ca^{++}/Mg^{++}$ with 4 mM EDTA reduced the $OD_{450}$ to 0.045.

In this assay F14.12 RNA inhibits LS-Rg binding in a concentration dependent manner with an IC$_{50}$ of about 10 nM (FIG. 6). Complete inhibition is observed at 50 nM F14.12. The observed inhibition is reasonable under the experimental conditions; the Kd of F14.12 at room temperature is about 1 nM (Table 9) and 10 nM LS-Rg is 20 nM binding sites. These data verify that RNA ligands compete with sialyl-Lewis$^x$ for LS-Rg binding and support the contention that low concentrations of EDTA specifically elute ligands that bind the lectin domain's carbohydrate binding site.

EXAMPLE 12

Secondary Structure of High Affinity 2'-NH$_2$ Ligands to L-Selectin

In favorable instances, comparative analysis of aligned sequences allows deduction of secondary structure and structure-function relationships. If the nucleotides at two positions in a sequence covary according to Watson-Crick base pairing rules, then the nucleotides at these positions are apt to be paired. Nonconserved sequences, especially those that vary in length are not apt to be directly involved in function, while highly conserved sequences are likely to be directly involved.

Comparative analysis of the family I alignment suggests a hairpin structure in which the consensus sequence, AUGUGUGA, is contained within a variable size loop (FIG. 7a). The stem sequences are not conserved and may be either 5' or 3'-fixed or variable sequence. The one ligand that does not form a stem, F14.25 (SEQ ID NO: 73), has a significantly lower affinity than the other characterized ligands (Table 9).

The proposed structure for family III is also a hairpin with the conserved sequence, AACAUGAAGUA, contained within a variable length loop (FIG. 7b). The 5'-half of the stem is 5'-fixed sequence which may account in part for the less highly conserved sequence, AGUC.

Although there is no alignment data for family II, the sequence folds into a pseudoknot (FIG. 7c). Three attractive features of this model are 1) the helices stack on one another, 2) the structure utilizes only variable sequence and 3) the structure is compatible with the major variant sequences.

EXAMPLE 13 ssDNA Ligands to Human L-Selectin

The experimental procedures outlined in this Example were used to identify and characterize ssDNA ligands to human L-selectin as described in Examples 14–21.

Experimental Procedures

A) Materials

Unless otherwise indicated, all materials used in the ssDNA SELEX against the L-selectin/IgG2 chimera, LS-Rg, were identical to those of Example 7, paragraph A. The buffer for SELEX experiments was 1 mM CaCl$_2$, 1 mM MgCl$_2$, 100 mM NaCl, 10.0 mM HEPES, pH 7.4. The buffer for all binding affinity experiments differed from the above in containing 125 mM NaCl, 5 mM KCl, and 20 mM HEPES, pH 7.4.

B) SELEX

The SELEX procedure is described in detail in U.S. Pat. No. 5,270,163 and elsewhere. The strategy used for this ssDNA SELEX is essentially identical to that described in Example 7, paragraph B except as noted below. The nucleotide sequence of the synthetic DNA template for the LS-Rg SELEX was randomized at 40 positions. This variable region was flanked by BH 5' and 3' fixed regions. The random DNA template was termed 40BH (SEQ ID NO: 126) and had the following sequence: 5'-ctacctacgatctgactagc<40N>gcttactctcatgtagttcc-3'. The primers for the PCR were the following: 5' Primer:

5'-ctacctacgatctgactagc-3' (SEQ ID NO: 127) and 3' Primer: 5'-ajajaggaactacatgagagtaagc-3'; j=biotin (SEQ ID NO: 128). The fixed regions include primer annealing sites for PCR amplification. The initial DNA pool contained 500 pmols of each of two types of single-stranded DNA: 1) synthetic ssDNA and 2) PCR amplified, ssDNA from 1 nmol of synthetic ssDNA template.

For subsequent rounds, eluted DNA was the template for PCR amplification. PCR conditions were 50 mM KCl, 10 mM Tris-Cl, pH 8.3, 7.5 mM $MgCl_2$, 1 mM of each dATP, dCTP, dGTP, and dTTP and 25 U/ml of the Stoffel fragment of Taq DNA polymerase. After PCR amplification, double stranded DNAs were end-labeled using $\gamma^{32}$P-ATP. Complementary strands were separated by electrophoresis through an 8% polyacrylamide/7M urea gel. Strand separation results from the molecular weight difference of the strands due to biotintylation of the 3' PCR primer. In the final rounds, DNA strands were separated prior to end labelling in order to achieve high specific activity. Eluted fractions were processed by ethanol precipitation.

The strategy for partitioning LS-Rg/ssDNA complexes from unbound ssDNA was as described in Example 7, paragraph B, except that 2 mM EDTA was utilized for specific elution. The SELEX strategy is outlined in Table 11.

C) Nitrocellulose Filter Binding Assay

As described in SELEX Patent Applications and in Example 7, paragraph C, a nitrocellulose filter partitioning method was used to determine the affinity of ssDNA ligands for LS-Rg and for other proteins. For these experiments a Gibco BRL 96 well manifold was substituted for the 12 well Millipore manifold used in Example 7 and radioactivity was determined with a Fujix BAS100 phosphorimager. Binding data were analyzed as described in Example 7, paragraph C.

D) Cloning and Sequencing

Thirteenth, fifteenth and seventeenth round PCR products were re-amplified with primers which contain either a BamHI or a HinDIII restriction endonuclease recognition site. Approximately 140 ligands were cloned and sequenced using the procedures described in Example 7, paragraph D. The resulting sequences are shown in Table 12.

E) Cell Binding Studies

The ability of evolved ligand pools to bind to L-selectin presented in the context of a cell surface was tested in experiments with isolated human peripheral blood mononuclear cells (PBMCs) as described in Example 7, paragraph E.

Flow Cytometry

Binding of oligonucleotides to leukocytes was tested in flow cytometry applications. Briefly, peripheral blood mononuclear cells (PBMC) were purified on histoplaque by standard techniques. Cells (500 cells/mL) were incubated with fluorescein labeled oligonucleotide in 0.25 mL SMHCK buffer (140 mM NaCl, 1 mM $MgCl_2$, 1 mM $CaCl_2$, 5 mM, KCl, 20 mM HEPES pH 7.4, 8.9 mM NaOH, 0.1% (w/v) BSA, 0.1% (w/v) sodium azide) at room temperature for 15 minutes. Fluorescent staining of cells was quantified on a FACSCaliber fluorescent activated cell sorter (Becton Dickinson, San Jose, Calif.).

To examine the ability of oligonucleotides to bind leukocytes in whole blood, 25 μl aliquots of heparinised whole blood were stained for 30 min at 22° C. with 2 μg Cy5PE labeled anti-CD45 (generous gift of Ken Davis, Becton-Dickinson) and 0.15 μM FITC-LD201T1 (synthesized with a 5'-Fluorescein phosphoramidite by Operon Technologies, Alameda, Calif.; SEQ ID NO: 185). To determine specificity, other samples were stained with FITC-LD201T1 in the presence of 0.3 μM DREG-56 or 7 μM unlabeled LD201T1; or cells were reassayed after addition of 4 mM EDTA. The final concentration of whole blood was at least 70% (v/v). Stained, concentrated whole blood was diluted 1/15 in 140 mM NaCl, 5 mM KCl, 1 mM $MgCl_2$, 1 mM $CaCl_2$, 20 mM HEPES pH 7.4, 0.1% bovine serum albumin and 0.1% $NaN_3$ immediately prior to flow cytometry on a Becton-Dickinson FACS Calibur. Lymphocytes and granulocytes were gated using side scatter and CD45CyPE staining.

F) Synthesis and Characterization of Multimeric Oligonucleotide Ligands

Synthesis of Branched Dimeric Oligonucleotide Complexes

Figure 8A:
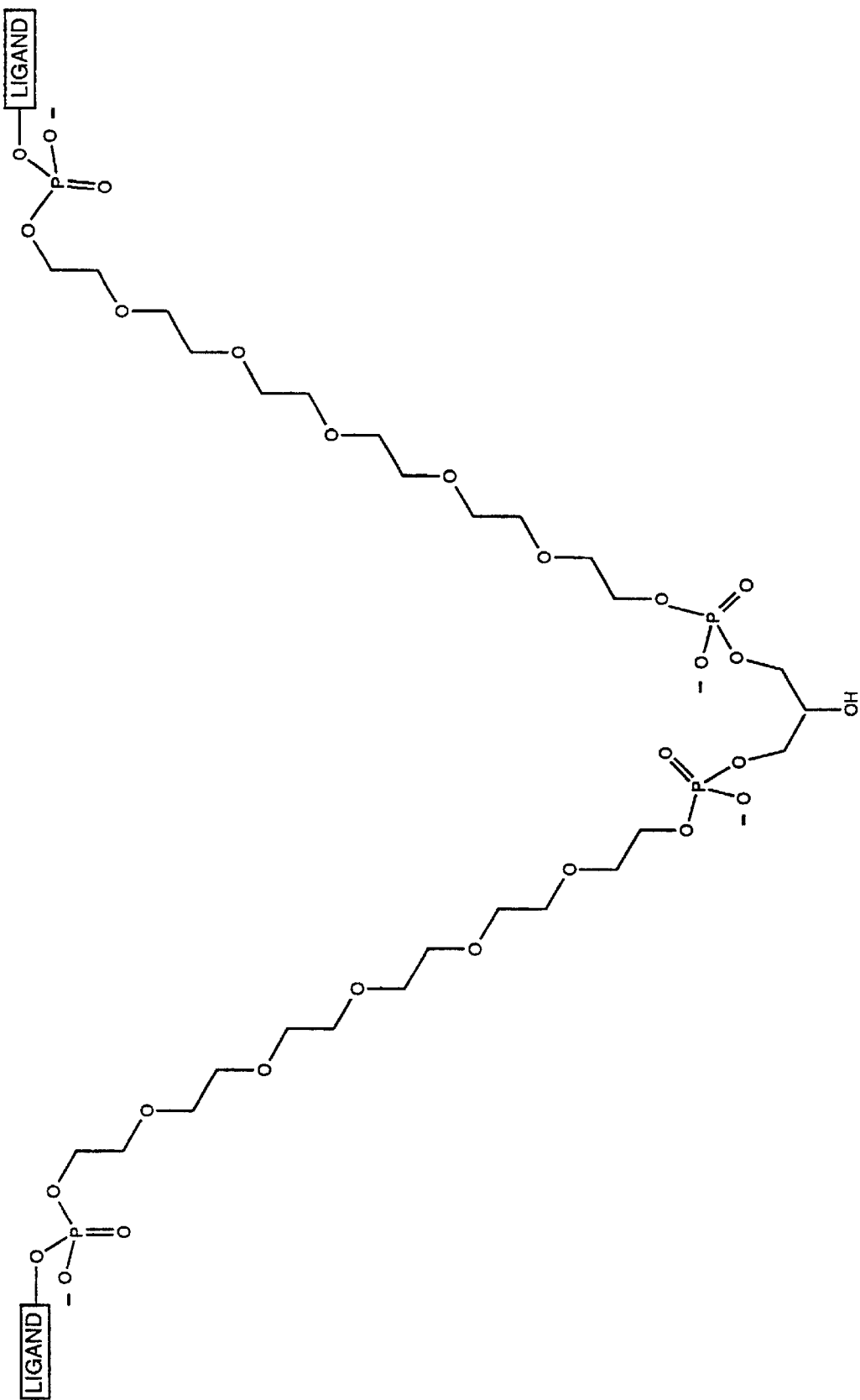
FIG. 8 shows a schematic representation of each dimeric and multimeric oligonucleotide complex: (a) dimeric branched oligonucleotide; (b) multivalent sterptavidin/bio-oligonucleotide complex (A: streptavidin; B: biotin); (c) dimeric dumbell oligonucleotide; (d) dimeric fork oligonucleotide.

Dimeric oligonucleotides were synthesized by standard solid state processes, with initiation from a 3'-3' Symmetric Linking CPG (Operon, Alameda, Calif.). Branched complexes contain two copies of a truncated L-selectin DNA ligand, each of which is linked by the 3' end to the above CPG via a five unit ethylene glycol spacer (FIG. 8A). Each ligand is labeled with a fluorescein phosphoramidite at the 5' end (Glen Research, Sterling, Va.). Branched dimers were made for 3 truncates of LD201T1 (SEQ ID NO: 142). The truncated ligands used were LD201T4 (SEQ ID NO: 187), LD201T10 (SEQ ID NO: 187) and LD201T1 (SEQ ID NO: 185). Branched dimers were purified by gel electrophoresis.

Synthesis of Multivalent Biotintylated-DNA Ligand/Streptavidin Complexes

Figure 8B:
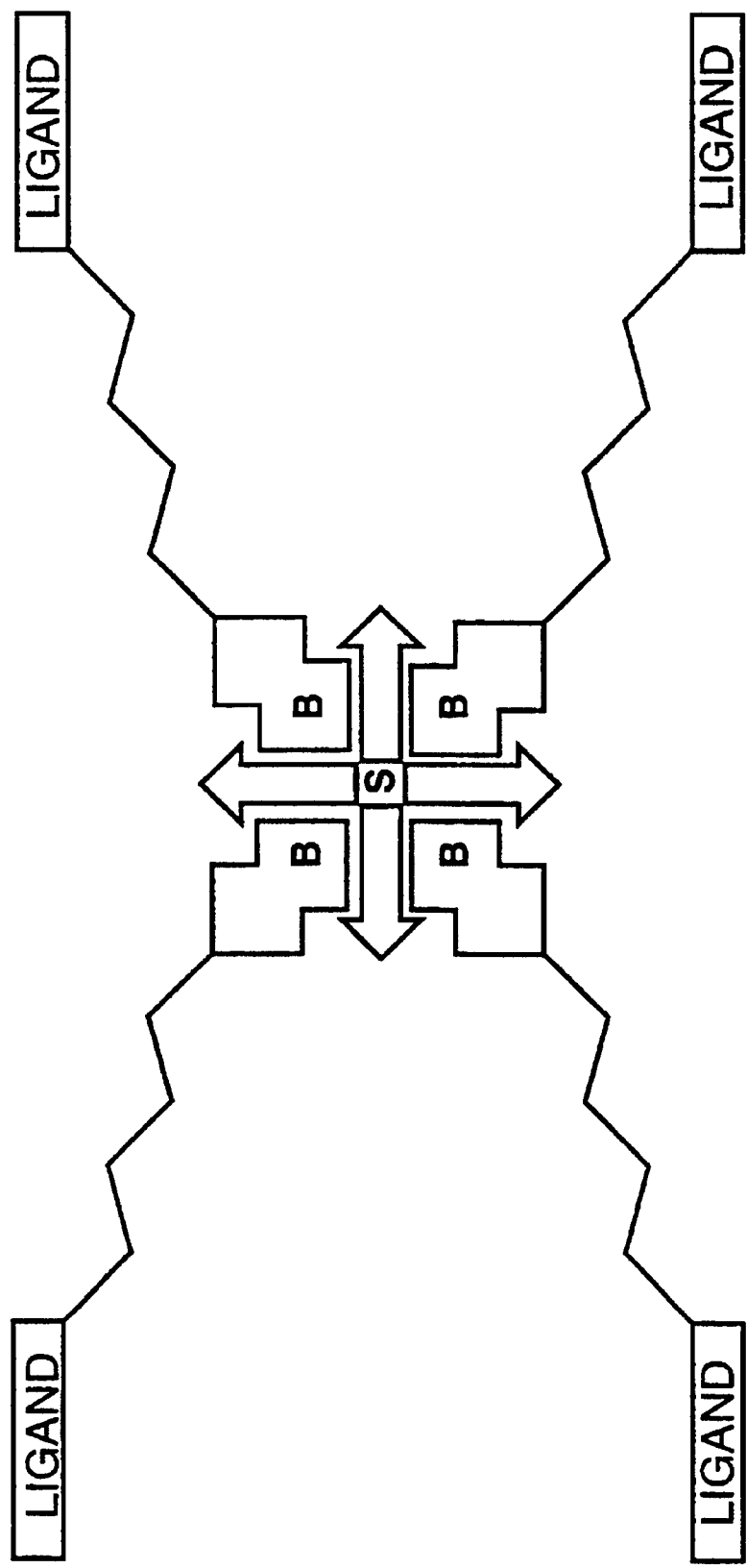

Multivalent oligonucleotide complexes were produced by reacting biotintylated DNA ligands with either fluorescein or phycoerythrin labeled streptavidin (SA-FITC, SA-PE, respectively) (FIG. 8B). Streptavidin (SA) is a tetrameric protein, each subunit of which has a biotin binding site. 5' and 3' biotintylated DNAs were synthesized by Operon Technologies, Inc (Alameda, Calif.) using BioTEG and BioTEG CPG (Glen Research, Sterling, Va.), respectively. The expected stoichiometry is 2 to 4 DNA molecules per complex. SA/bio-DNA complexes were made for 3 truncates of LD201 (SEQ ID NO: 142). The truncated ligands were LD201T4 (SEQ ID NO: 187), LD201T10 (SEQ ID NO: 188) and LD201T1 (SEQ ID NO: 185). The bio-DNA/SA multivalent complexes were generated by incubating biotin modified oligonucleotide (1 mM) and fluoroscein labeled streptavidin (0.17 mM) in 150 mM NaCl, 20 mM HEPES pH 7.4 at room temperature for at least 2 hours. Oligonucleotide-streptavidin complexes were used directly from the reaction mixture without additional purification of the Complex from free streptavidin or oligonucleotide.

Synthesis of a Dumbell Dimer Multivalent Complex

Figure 8C:
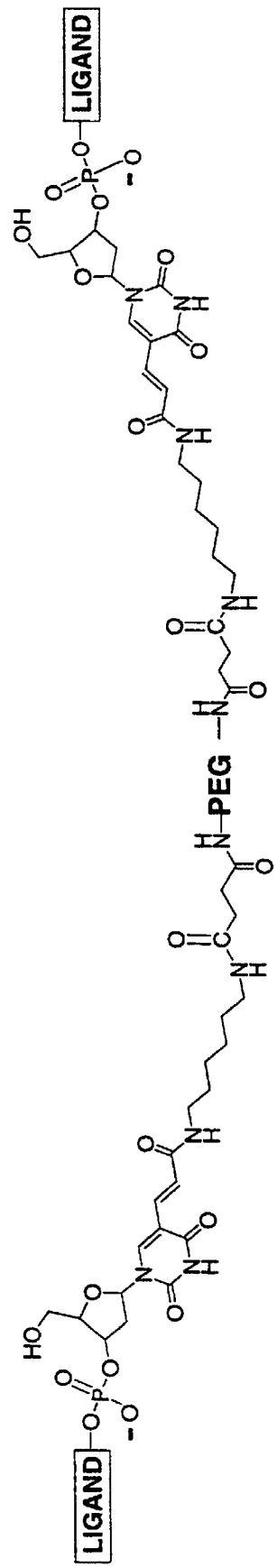

A "dumbell" DNA dimer complex was formulated from a homobifunctional N-hydroxysuccinimidyl (or NHS) active ester of polyethelene glycol, PEG 3400 MW, and a 29 mer DNA oligonucleotide, NX303 (SEQ ID NO: 196), having a 5' terminal Amino Modifier C6 dT (Glen Research) and a 3'-3' terminal phosphodiester linkage (FIG. 8C). NX303 is a truncate of LD201 (SEQ ID NO: 142). The conjugation reaction was in DMSO with 1% TEA with excess equivalents of the DNA ligand to PEG. The PEG conjugates were purified from the free oligonucleotide by reverse phase chromatography. The dimer was then purified from the monomer by anion exchange HPLC. The oligonucleotide was labeled at the 5' terminus with fluorescein as previously described.

Synthesis of a Fork Dimer Multivalent Complex

Figure 8D:
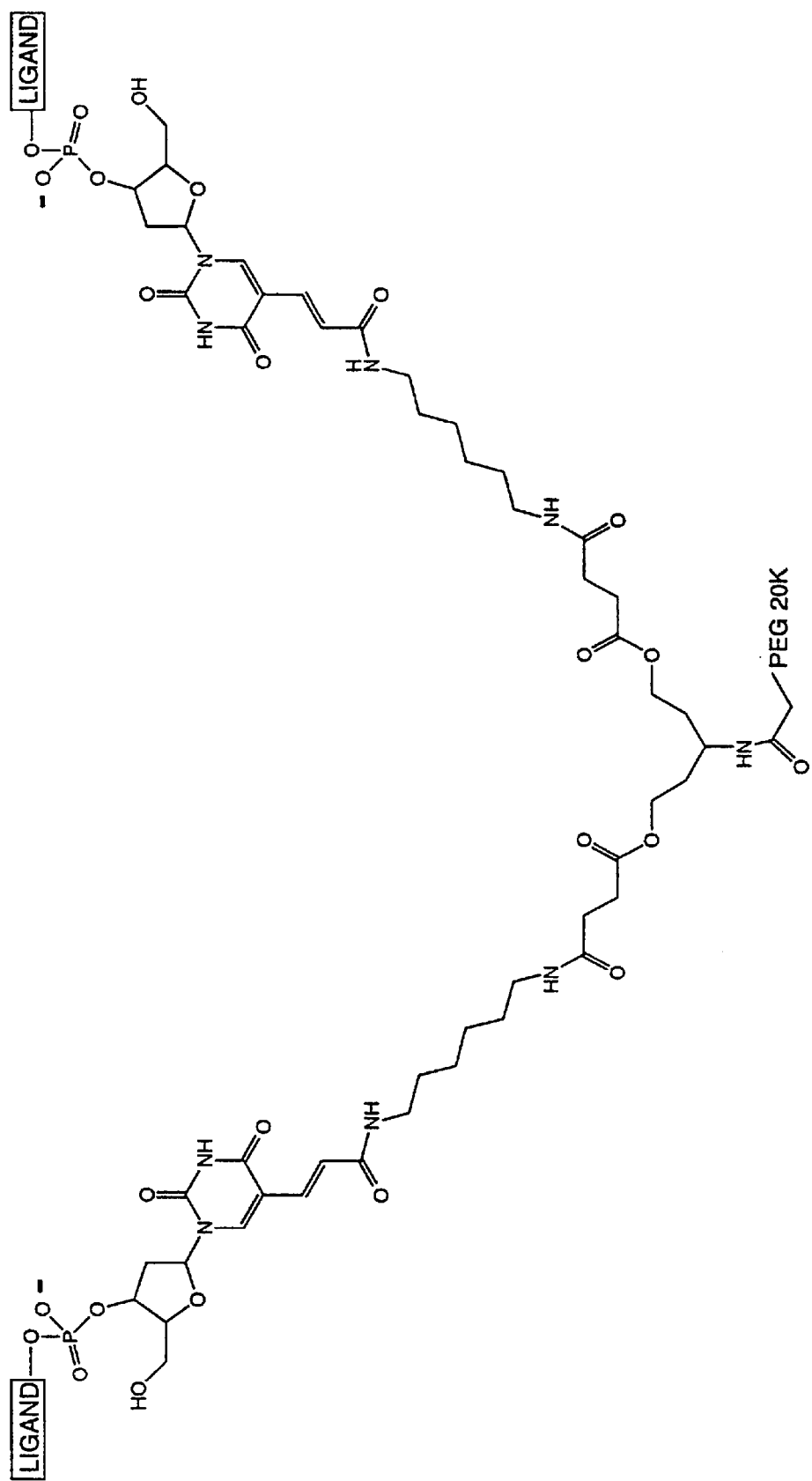

To synthesize the fork dimer multivalent complex (FIG. 8D), a glycerol was attached by its 2-position to one terminus of a linear PEG molecule (MW 20 kD) to give the bis alcohol. This was further modified to the bis succinate ester, which was activated to the bis N-hydroxysuccinimidyl active ester. The active ester was conjugated to the primary amine at the 5' terminus of the truncated DNA nucleic acid ligand NX303 (SEQ ID NO: 196). The conjugation reaction was in DMSO with 1% TEA with excess equivalents of the DNA ligand to PEG. The PEG conjugates were purified away from the free oligonucleotide by reverse phase chromatography. The dimer was then purified away from the monomer by anion exchange HPLC. The oligonucleotide was labeled at the 5' terminus with fluorescein as previously described.

Characterization of Multimeric Oligonucleotide Ligands

The binding of dimeric and multimeric oligonucleotide complexes to human peripheral blood mononuclear cells was analyzed by flow cytometry as described in Example 13, paragraph D.

G) Photo-Crosslinking

A photo-crosslinking version of DNA ligand LD201T4 (SEQ ID NO: 187) was synthesized by replacing nucleotide T15 (FIG. 12) with 5-bromo-deoxyuracil. 4 nmol of $^{32}$P-labeled DNA was incubated with 4 nmol L-selectin-Rg in 4 ml 1×SHMCK+0.01% human serum albumin (w/v), then irradiated at ambient temperature with 12,500 pulses from an excimer laser at a distance of 50 cm and at 175 mJ/pulse. Protein and DNA were precipitated with 400 μl 3 M sodium acetate and 8.4 ml ethanol followed by incubation at −70 degrees C. Precipitated material was centrifuged, vacuum dried and resuspended in 100 μl 0.1 M Tris pH 8.0, 10 mM $CaCl_2$. Forty-five μg chymotrypsin were added and after 20 min at 37 degrees C., the material was loaded onto an 8% polyacrylamide/7 M urea/1×TBE gel and electrophoresed until the xylene cyanole had migrated 15 cm. The gel was soaked for 5 min in 1×TBE and then blotted for 30 min at 200 mAmp in 1×TBE onto Immobilon-P (Millipore). The membrane was washed for 2 min in water, air dried, and an autoradiograph taken. A labeled band running slower than the free DNA band, representing a chymotryptic peptide crosslinked to LD201T4, was observed and the autoradiograph was used as a template to excise this band from the membrane. The peptide was sequenced by Edman degradation, and the resulting sequence was LEKTLP__SRSYY. The blank residue corresponds to the crosslinked amino acid, F82 of the lectin domain.

H) Lymphocyte Trafficking Experiments

Human PBMC were purified from heparinised blood by a Ficoll-Hypaque gradient, washed twice with HBSS (calcium/magnesium free) and labeled with $^{51}$Cr (Amersham). After labeling, the cells were washed twice with HBSS (containing calcium and magnesium) and 1% bovine serum albumin (Sigma). Female SCID mice (6–12 weeks of age) were injected intravenously with $2\times10^6$ cells. The cells were either untreated or mixed with either 13 pmol of antibody (DREG-56 or MEL-14), or 4, 1, or 0.4 nmol of modified oligonucleotide (synthesis described below). One hour later the animals were anesthetized, a blood sample taken and the mice were euthanised. PLN, MLN, Peyer's patches, spleen, liver, lungs, thymus, kidneys and bone marrow were removed and the counts incorporated into the organs determined by a Packard gamma counter. In a second protocol, $2\times10^6$ human PBMC, purified, labeled, and washed as described above, were injected intravenously into female SCID mice without antibody or oligonucleotide pretreatment. One to 5 min prior to injecting the cells, the animals were injected with either 15 pmol DREG-56 or 4 nmol modified oligonucleotide. Counts incorporated into organs were quantified as described above.

Synthesis of modified nucleotides NX288 (SEQ ID NO: 193) and NX303 (SEQ ID NO: 196) was initiated by coupling to a dT-5'-CE polystyrene support (Glen Research), resulting in a 3'-3' terminal phosphodiester linkage, and having a 5' terminal an Amino Modifier C6 dT (Glen Research). Once NX288 and NX303 were synthesized, a 20,000 MW PEG2-NHS ester (Shearwater Polymers, Huntsville, Ala.) was then coupled to the oligonucleotide through the 5' amine moiety. The molar ration, PEG:oligo, in the reactions was from 3:1 to 10:1. The reactions were performed in 80:20 (v:v) 100 mM borate buffer pH 8: DMF at 37° C. for one hour.

I) Inhibition of L-selectin Binding to Sialyl Lewis$^x$

SLe$^x$-BSA (Oxford GlycoSystems, Oxford, UK) in 1×PBS, without $CaCl_2$ and $MgCl_2$, (GIBCO/BRL) was immobilized at 100 ng/well onto a microtiter plate by overnight incubation at 22° C. The wells were blocked for 1 h with the assay buffer consisting of 20 mM HEPES, 111 mM NaCl, 1 mM $CaCl_2$, 1 mM $MgCl_2$, 5 mM KCl, 8.9 mM NaOH, final pH 8, and 1% globulin-free BSA (Sigma). The reaction mixtures, incubated for 90 min with orbital shaking, contained 5 nM L-Selectin-Rg, a 1:100 dilution of anti-human IgG-peroxidase conjugate (Sigma), and 0–50 nM of competitor in assay buffer. After incubation, the plate was washed with BSA-free assay buffer to remove unbound chimera-antibody complex and incubated for 25 min with O-phenylenediamine dihydrochloride peroxidase substrate (Sigma) by shaking in the dark at 22° C. Absorbance was read at 450 nm on a Bio-Kinetics Reader, Model EL312e (Bio-Tek Instruments, Laguna Hills, Calif.). Values shown represent the mean±s.e from duplicate, or triplicate, samples from one representative experiment.

EXAMPLE 14 ssDNA Ligands to L-Selectin

A. SELEX

The starting ssDNA pool for SELEX, randomized 40BH (SEQ ID NO: 126), contained approximately $10^{15}$ molecules (1 nmol ssDNA). The dissociation constant of randomized ssDNA to LS-Rg is estimated to be approximately 10 μM. The SELEX protocol is outlined in Table 11.

The initial round of SELEX was performed at 4° C. with an LS-Rg density of 16.7 pmol/μl of protein A sepharose beads. Subsequent rounds were at room temperature except as noted in Table 11. The 2 mM EDTA elution was omitted from rounds 1–3. The signal to noise ratio of the 50 mM EDTA elution in these three rounds was 50, 12 and 25, respectively (Table 11). These DNAs were amplified for the input materials of rounds 2–4. Beginning with round 4, a 2 mM EDTA elution was added to the protocol. In this and all subsequent rounds, the 2 mM EDTA eluted DNA was amplified for the next round's input material.

To increase the stringency of selection, the density of immobilized LS-Rg was reduced ten fold in round 4 with further reductions in protein as needed to increase the stringency of selectin (Table 11). Under these conditions a rapid increase in the affinity of the selected pools was observed (Tables 11); at 4° C., the dissociation constant of round 7 ssDNA was 60 nM.

Binding experiments with 7th round DNA revealed that the affinity of the evolving pool for L-selectin was weakly temperature sensitive (Kds: 60 nM, 94 nM and 230 nM at 4° C., room temperature and 37° C., respectively). To enhance the selection of ligands that bind at physiological temperature, rounds 8, 13, 16 and 17 were performed at 37° C. Although temperature sensitive, the affinity of round 15 ssDNA was optimal at room temperature (160 pM), with 3-fold higher Kds at 4° C. and 37° C.

Bulk sequencing of DNA pools indicates some non-randomness at round 5 and dramatic non-randomness at round 13. Ligands were cloned and sequenced from rounds 13, 15, and 17. Sequences were aligned manually and with the aid of a NeXstar computer program that determines consensus sequences from frequently occurring local alignments.

B. Sequences

In Table 12, ligand sequences are shown in standard single letter code (Cornish-Bowden, 1985 NAR 13: 3021–3030). Only the evolved random region is shown in Table 12. Any portion of the fixed region is shown in lower case letters. By definition, each clone includes both the evolved sequences and the associated fixed region, unless specifically stated otherwise. A unique sequence is operationally defined as one that differs from all others by three or more nucleotides. Sequences that were isolated more than once are indicated by the parenthetical number, (n), following the ligand isolate number. These clones fall into six families and a group of unrelated sequences or orphans (Table 12) (SEQ ID NOs: 129–180).

Family 1 is defined by ligands from 33 lineages and has a well defined consensus sequence, TACAAGGYGYTA-VACGTA (SEQ ID NO: 181). The conservation of the CAAGG and ACG and their 6 nucleotide spacing is nearly absolute (Table 12). The consensus sequence is flanked by variable but complementary sequences that are 3 to 5 nucleotides in length. The statistical dominance of family 1 suggests that the properties of the bulk population are a reflection of those of family 1 ligands. Note that ssDNA family I and 2'-NH$_2$ family I share a common sequence, CAAGGCG and CAAGGYG, respectively.

Family 2 is represented by a single sequence and is related to family 1. The ligand contains the absolutely conserved CAAGG and highly conserved ACG of family 1 although the spacing between the two elements is strikingly different (23 compared to 6 nucleotides).

Families 4–6 are each defined by a small number of ligands which limits confidence in their consensus sequence, while family 7 is defined by a single sequence which precludes determination of a consensus. Family 5 appears to contain two conserved sequences, AGGGT and RCACGAYACA, the positions of which are circularly permuted.

C. Affinities

The dissociation constants of representative ligands from Table 12 are shown in Table 13. These calculations assume two ssDNA ligand binding sites per chimera. The affinity of random ssDNA cannot be reliably determined but is estimated to be approximately 10 $\mu$M.

At room temperature, the dissociation constants range from 43 pM to 1.8 nM which is at least a 5×10$^3$ to 2×10$^5$ fold improvement over randomized ssDNA (Table 13). At 37° C., the Kds range from 130 pM to 23 nM. The extend of temperature sensitivity varies from insensitive (ligands LD122 and LD127 (SEQ ID NO: 159 and 162)) to 80-fold (ligand LD112 (SEQ ID NO: 135)). In general, among family 1 ligands the affinity of those from round 15 is greater than that of those from round 13. For the best ligands (LD208, LD227, LD230 and LD233 (SEQ ID NOS: 133, 134, 132, and 146)), the difference in affinity at room temperature and 37° C. is about 4-fold.

The observed affinities of the evolved ssDNA ligand pools reaffirm our proposition that it is possible to isolate oligonucleotide ligands with affinities that are several orders of magnitude greater than that of carbohydrate ligands.

EXAMPLE 15

Specificity of ssDNA Ligands to L-Selectin

The affinity of representative cloned ligands for LS-Rg, ES-Rg, PS-Rg, CD22β-Rg and WGA was determined by nitrocellulose partitioning and the results shown in Table 14. The ligands are highly specific for L-selectin. The affinity for ES-Rg is about 10$^3$-fold lower and that for PS-Rg is about 5×10$^3$-fold less than for LS-Rg. Binding above background is not observed for CD22β-Rg or for WGA at 0.7 and 1.4 $\mu$M protein, respectively, indicating that ligands neither bind the Fc domain of the chimeric constructs nor have affinity for unrelated sialic acid binding sites.

The specificity of oligonucleotide ligand binding contrasts sharply with the binding of cognate carbohydrates by the selectins and reconfirms the proposition that SELEX ligands will have greater specificity than carbohydrate ligands.

EXAMPLE 16

Cell Binding Studies

Figure 9:
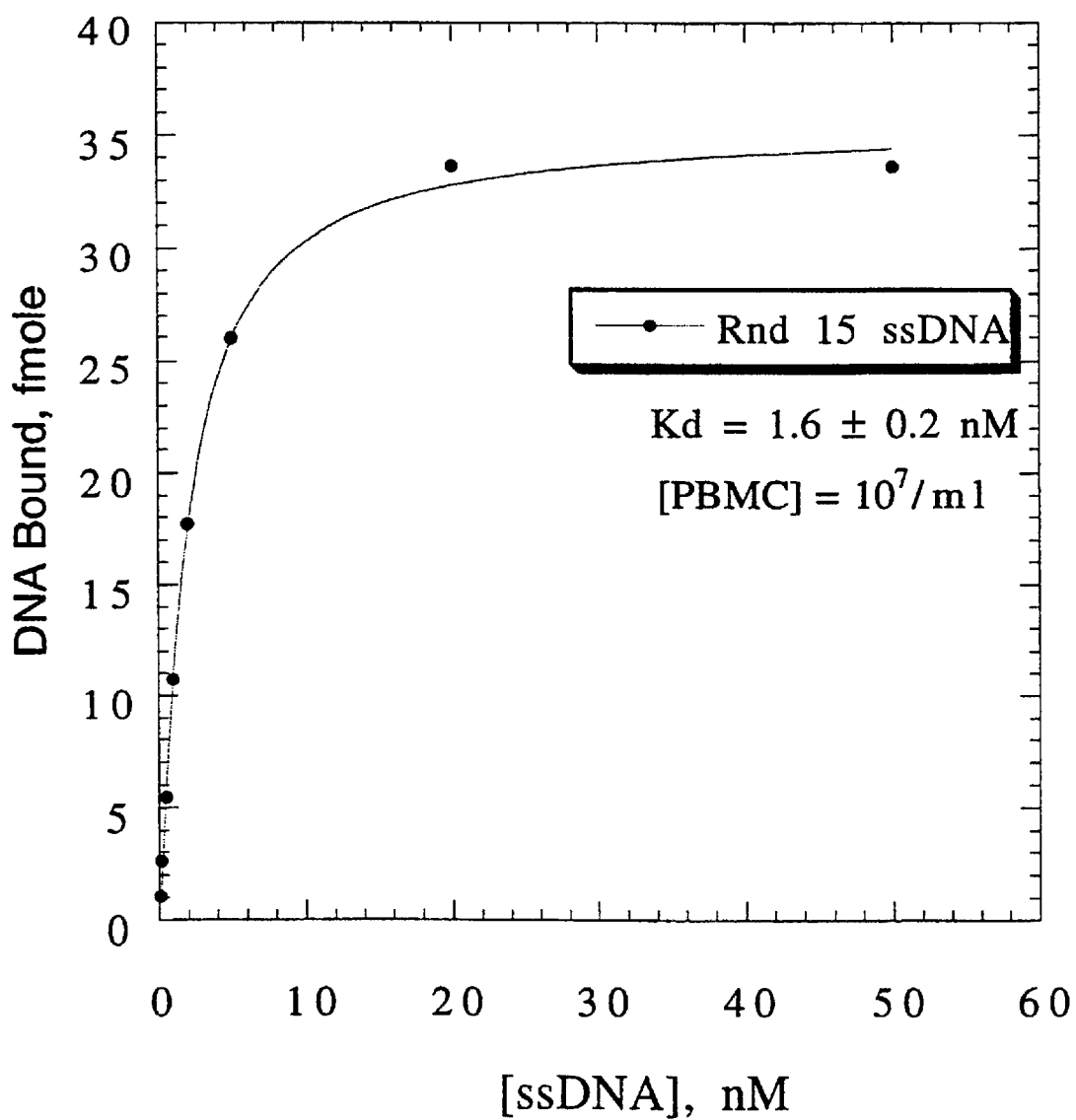
FIG. 9 shows binding curves for the L-selectin SELEX fifteenth round ssDNA pool to PBMCs ($10^7$/ml).
Figure 10:
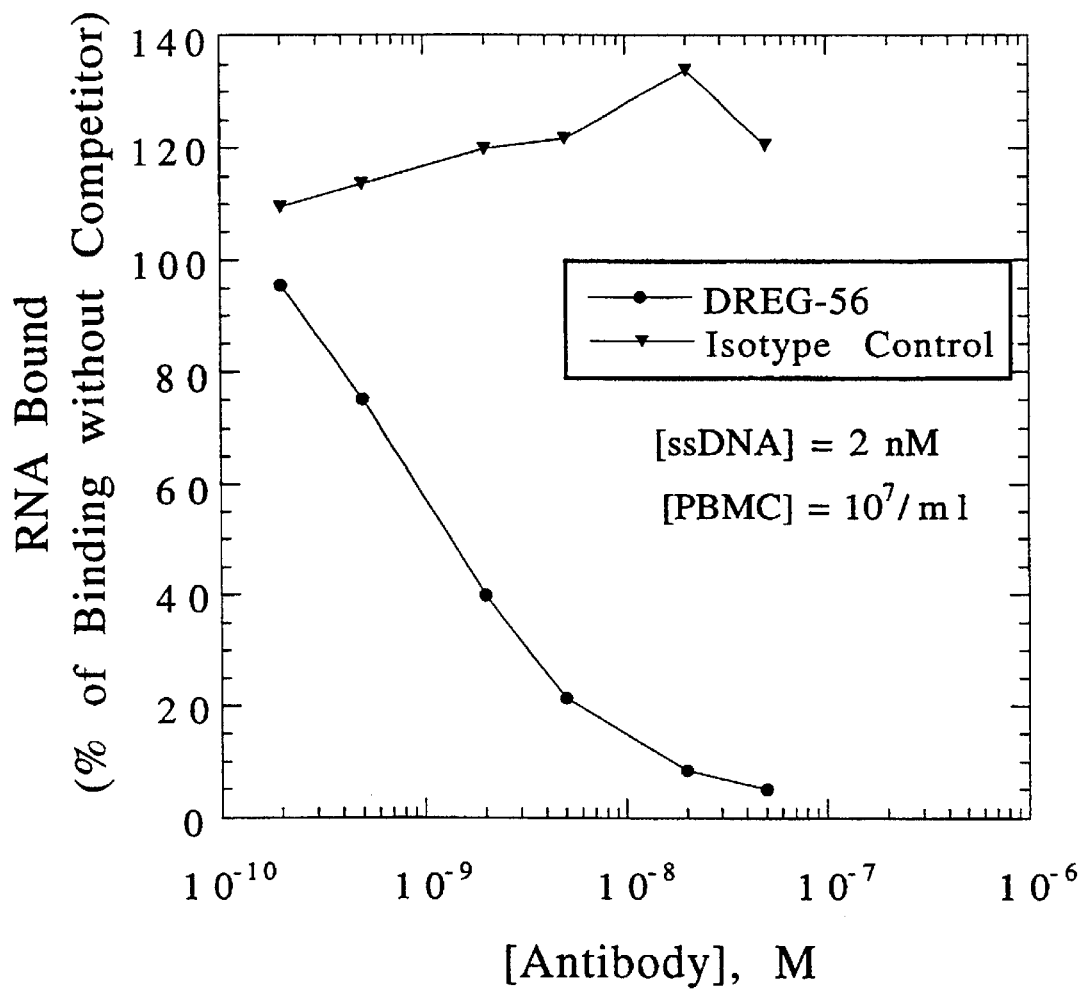
FIG. 10 shows the results of a competition experiment in which the binding of 2 nM $^{32}$P-labeled found 15 ssDNA to PBMCs ($10^7$/ml) is competed with increasing concentrations of the blocking monoclonal anti-L-selectin antibody, DREG-56, or an isotype matched, negative control antibody. RNA Bound equals 100×(net counts bound in the presence of competitor/net counts bound in the absence of competitor).

Round 15 ssDNA pool was tested for its ability to bind to L-selectin presented in the context of a peripheral blood mononuclear cell surface as described in Example 13, paragraph E. The evolved pool was tested both for affinity and for specificity by competition with an anti-L-selectin monoclonal antibody. FIG. 9 shows that the round 15 ssDNA pool binds isolated PBMCs with a dissociation constant of approximately 1.6 nM and, as is expected for specific binding, in a saturable fashion. FIG. 10 directly demonstrates specificity of binding; in this experiment, binding of 2 nM $^{32}$P-labeled round 15 ssDNA is completely competed by the anti-L-selectin blocking monoclonal antibody, DREG-56, but is unaffected by an isotype-matched irrelevant antibody. In analogous experiments, LD201T1 (SEQ ID NO: 185) was shown to bind human PBMC with high affinity. Binding was saturable, divalent cation dependent, and blocked by DREG-56.

These data validate the feasibility of using immobilized, purified protein to isolate ligands against a cell surface protein and demonstrate the specific binding of the round 15 ssDNA pool and of ligand LD201T1 to L-selectin in the context of a cell surface.

Figure 11B:
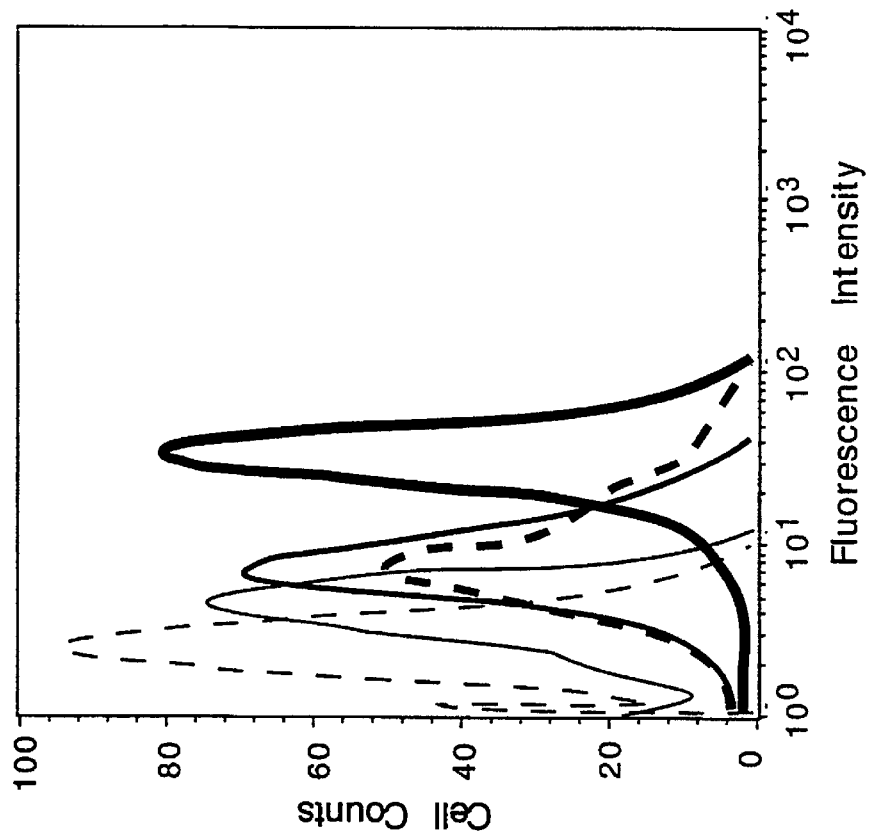
FIG. 11 shows L-selectin specific binding of LD201T1 (SEQ ID NO: 185) to human lymphocytes and granulocytes in whole blood. a, FITC-LD201T1 binding to lymphocytes is competed by DREG-56, unlabeled LB201T1, and inhibited by EDTA. b, FITC-LD201T1 binding to granulocytes is competed by DREG-56, unlabeled LD201T1, and inhibited by EDTA. All samples were stained with 0.15 mM FITC-LD201T1; thick line: FITC-LD201T1 only; thick dashed line: FITC LD201T1 with 0.3 mM DREG-56; medium thick line: FITC-LD201T1 with 7 mM unlabeled NX280; thin line: FITD-LD201T1 stained cells, reassayed after addition of 4 mM EDTA; thin dashed line: autofluorescence.
Figure 11A:
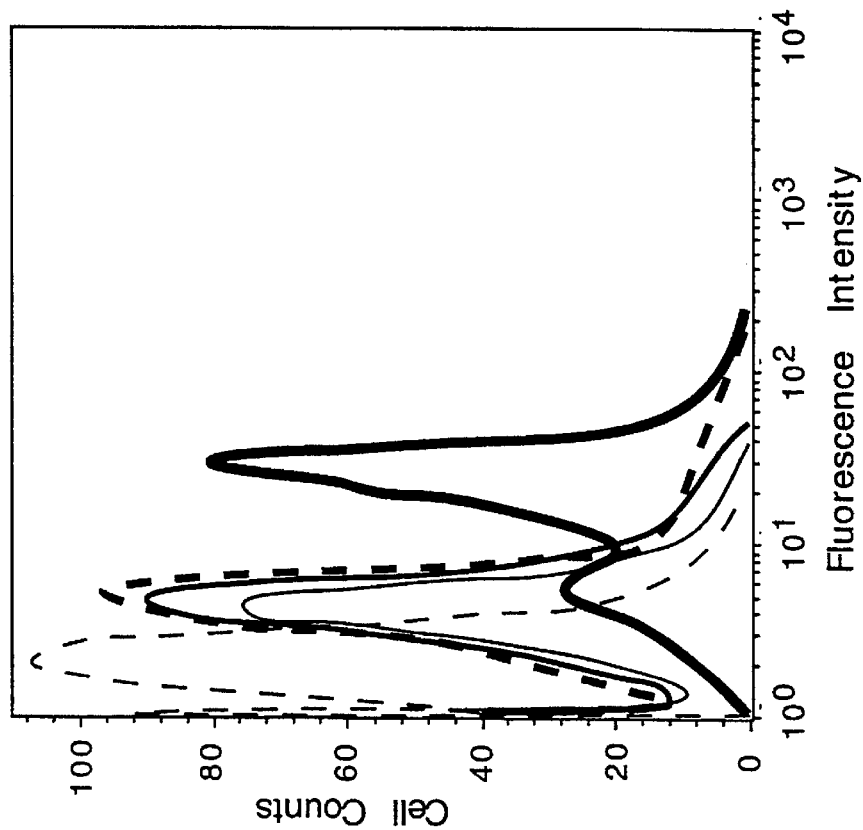
Figure 13:
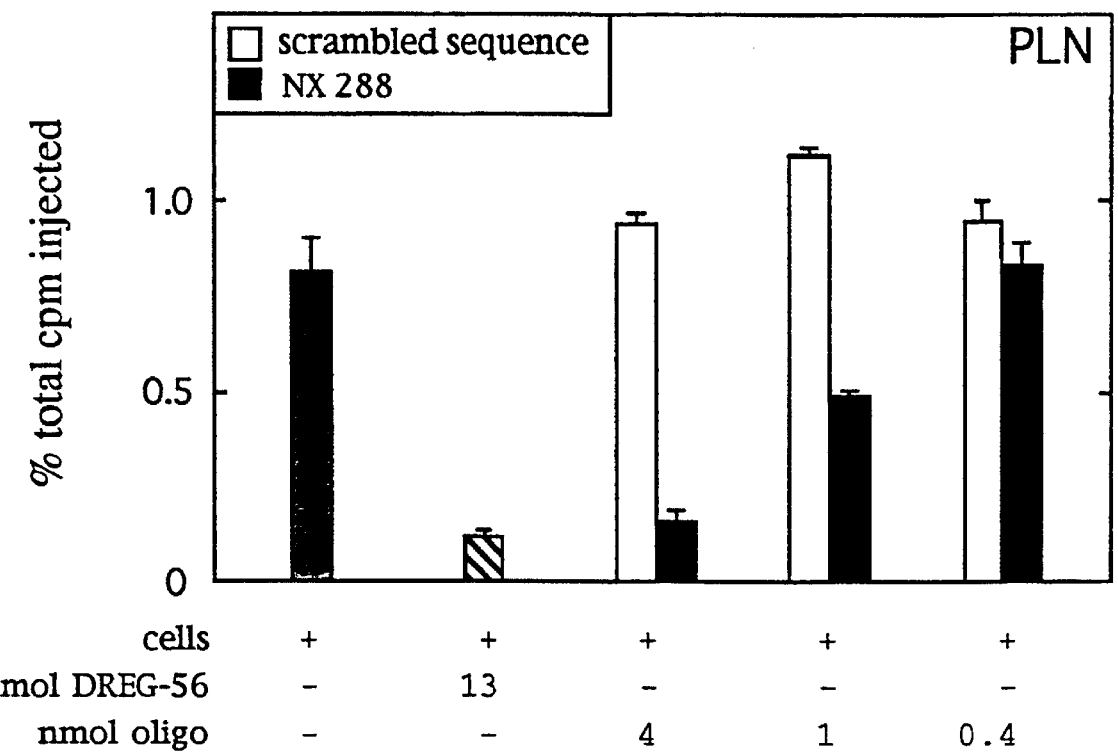
FIG. 13 shows that in vitro pre-treatment of human PBMC with NX288 (SEQ ID NO: 193) inhibits lymphocyte trafficking to SCID mouse PLN. Human PBMC were purified from heparinised blood by a Ficoll-Hypaque gradient, washed twice with HBSS (calcium/magnesium free) and labeled with $^{51}$Cr (Amersham). After labeling, the cells were washed twice with HBSS (containing calcium and magnesium) and 1% bovine serum albumin (Sigma). Female SCID mice (6–12 weeks of age) were injected intravenously with $2\times10^6$ cells. The cells were either untreated or mixed with either 13 pmol of antibody (DREG-56 or MEL-14), or 4, 1, or 0.4 nmol of modified oligonucleotide. One hour later the animals were anaesthetised, a blood sample taken and the mice were euthanised. PLN, MLN, Peyer's patches, spleen, liver, lungs, thymus, kidneys and bone marrow were removed and the counts incorporated into the organs determined by a Packard gamma counter. Values shown represent the mean±s.e. of triplicate samples, and are representative of 3 experiments.

The binding of LD201T1 to leukocytes in whole blood was examined by flow cytometry. Fluorescein isothiocyanate (FITC)-conjugated LD201T1 specifically bind human lymphocytes and neutrophils (FIG. 11A/B); binding is inhibited by competition with DREG-56, unlabeled LD201, and by the addition of 4 mM EDTA (FIG. 11A/B). These cell binding studies demonstrate that LD201T1 bind saturably and specifically to human L-selectin on lymphocytes and neutrophils.

EXAMPLE 17

Secondary Structure of High Affinity ssDNA Ligands to L-Selectin

In favorable instances, comparative analysis of aligned sequences allows deduction of secondary structure and structure-function relationships. If the nucleotides at two positions in a sequence covary according to Watson-Crick base pairing rules, then the nucleotides at these positions are apt to be paired. Nonconserved sequences, especially those that vary in length are not apt to be directly involved in function, while highly conserved sequence are likely to be directly involved.

Comparative analysis of 24 sequences from family 1 strongly supports a hairpin secondary structure for these ligands (FIG. 12). In the figure, consensus nucleotides are specified, with invariant nucleotides in bold type. To the right of the stem is a matrix showing the number of occurrences of particular base pairs for the positions in the stem that are on the same line. The deduced structure consists of a GYTA tetraloop, a 3 nucleotide-pair upper stem and a 6 to 7 nucleotide-pair lower stem. The upper and lower stems are separated by an asymmetrical, AA internal loop or "bulge." Two of the three base pairs in the upper stem and 6 of 7 in the lower stem are validated by covariation. The two invariant pairs, positions 7/20 and 10/19 are both standard Watson/Crick basepairs. This structure provides a plausible basis for the direct involvement of invariant nucleotides (especially, A8, A9 and T15) in binding the target protein.

Figure 14:
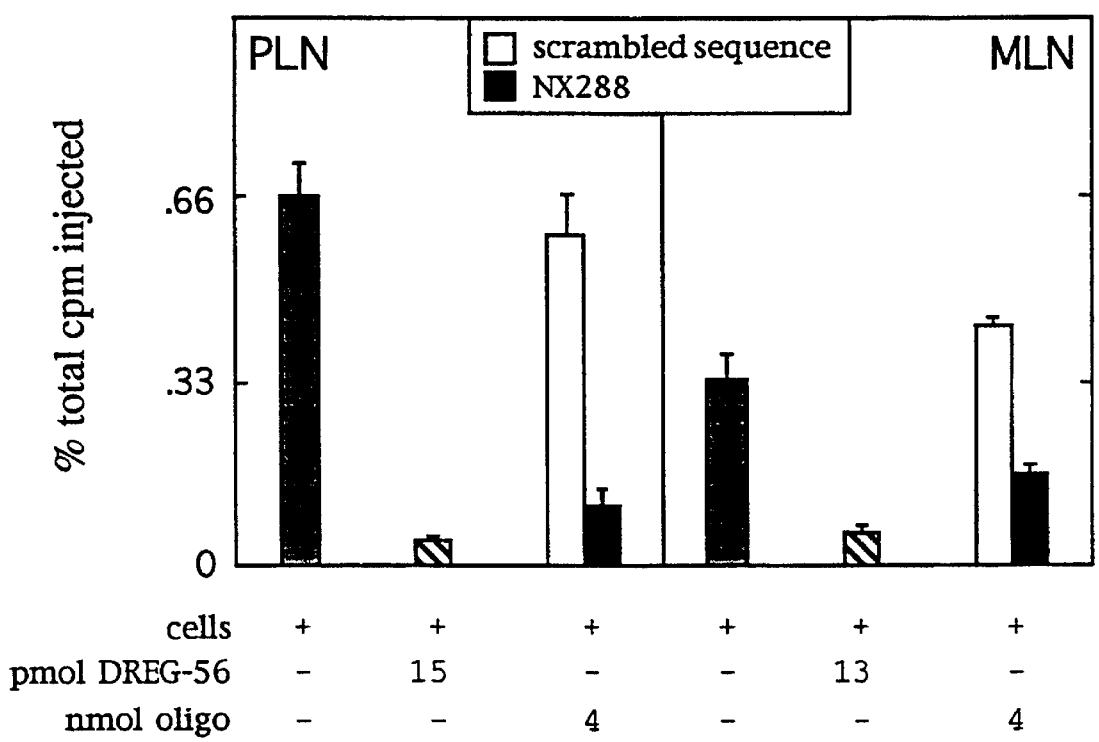
FIG. 14 shows that pre-injection of NX288 (SEQ ID NO: 193) inhibits human lymphocyte trafficking to SCID mouse PLN and MLN. Human PBMC were purified, labeled, and washed as described above. Cells were prepared as described in FIG. 13. Female SCID mice (6–12 weeks of age) were injected intravenously with $2\times10^6$ cells. One to 5 min prior to injecting the cells, the animals were injected with either 15 pmol DREG-56 or 4 nmol modified oligonucleotide. Animals were scarificed 1 hour after injection of cells. Counts incorporated into organs were quantified as described in FIG. 13. Values shown represent the mean±s.e. of triplicate samples, and are representative of 2-experiments.

The site of oligonucleotide binding on L-selectin can be deduced from a set of competition experiments. DREG56 is an anti-L-selectin, adhesion blocking monoclonal antibody that is known to bind to the lectin domain. Binding of three unrelated ligands, LD201T1 (SEQ ID NO: 185), LD174T1 (SEQ ID NO: 194) and LD196T1 (SEQ ID NO: 195), to LS-Rg was blocked by DREG-56, but not by an isotype-matched control. In cross-competition experiments, LD201T1, LD174T1, or LD196T1 prevented radio-labeled LD201T1 from binding to LS-Rg, consistent with the premise that the ligands bind the same or overlapping sites. The blocking and competition experiments, taken together with divalent cation-dependence of binding, suggest that all three ligands bind to the lectin domain. This conclusion has been verified for LD201 by photo-crosslinking experiments.

If T15 of LD201T4 (SEQ ID NO: 187; FIG. 12) is replaced with 5-bromo-uracil, the resulting DNA photo-crosslinks at high yield (17%) to LS-Rg following irradiation with an excimer laser as described in Example 13, paragraph G. The high yield of crosslinking indicates a point contact between the protein and T15. Sequencing of the chymotryptic peptide corresponding to this point contact revealed a peptide deriving from the lectin domain; F82 is the crosslinking amino acid. Thus, F82 contacts T15 in a stacking arrangement that permits high yield photo-crosslinking. By analogy to the structure of the highly related E-selectin (Graves et al, Nature 367, 532–538, 1994), F82 is adjacent to the proposed carbohydrate binding site. Thus, this photo-crosslink provides direct evidence that ligand LD201 makes contact with the lectin domain of LS-Rg and provides an explanation for the function of the oligonucleotides in either sterically hindering access to the carbohydrate binding site or in altering the conformation of the lectin domain upon DNA binding.

EXAMPLE 18

L-Selectin ssDNA Ligand Truncate Data

Initial experiments to define the minimal high affinity sequence of family 1 ligands show that more than the 26 nucleotide hairpin (FIG. 12; Table 13) is required. Ligands corresponding to the hairpin, LD201T4 (SEQ ID NO: 187) and LD227T1 (SEQ ID NO: 192) derived from LD201 (SEQ ID NO: 173) and LD227 (SEQ ID NO: 134), respectively, bind with 20-fold and 100-fold lower affinity than their full length progenitors. The affinity of LD201T3 (SEQ ID NO: 186), a 41 nucleotide truncate of ligand LD201, is reduced about 15-fold compared to the full length ligand, while the affinity of the 49-mer LD201T1 (SEQ ID NO: 185) is not significantly altered (Tables 12 and 13).

Additional experiments shows that truncates LD201T10 (SEQ ID NO: 188) and LD227X1 (SEQ ID NO: 191) bind with affinities similar to their full length counterparts. Both of these ligands have stems that are extended at the base of the consensus stem. Alternations in the sequence of the added stem have little, if any, effect on binding, suggesting that it is not directly involved in binding The added stem is separated from the consensus stem by a single stranded bulge. The two ligands' single stranded bulges differ in length and have unrelated sequences. Furthermore, LD201's bulge is at the 5'-end of the original stem base while that of LD227 is at the 3'-end. Thus, the two ligands do not present an obvious consensus structure. Removal of the loop (LD201) or scrambling or truncating the sequence (LD227) diminishes affinity, suggesting that the bulged sequences may be directly involved in binding. Note that although LD201T3 is longer than LD201T10, it is unable to form the single stranded loop and extended stem because of the position of the truncated ends.

EXAMPLE 19

Inhibition of Binding to Sialyl Lewis$^x$

Sialyl Lewis$^x$ is the minimal carbohydrate ligand bound by selectins. The ability of ssDNA ligands to inhibit the binding of L-selectin to Sialyl Lewis$^x$ was determined in competition ELISA assays as described in Example 13, paragraph I. LD201T1 (SEQ ID NO: 185), LD174T1 (SEQ ID NO: 194) and LD196T1 (SEQ ID NO: 195) inhibited LS-Rg binding to immobilized SLe$^x$ in a dose dependent manner with $IC_{50}$s of approximately 3 nM. This is a $10^5$–$10^6$-fold improvement over the published $IC_{50}$ values for SLe$^x$ in similar plate-binding assays. A scrambled sequence based on LD201T1 showed no activity in this assay. These data verify that DNA ligands compete with sialyl-Lewis$^x$ for LS-Rg binding and support the contention that low concentrations of EDTA specifically elute ligands that bind the lectin domain's carbohydrate binding site.

EXAMPLE 20

Inhibition Of Lymphocyte Trafficking by L-Selectin ssDNA Ligands

Lymphocyte trafficking to peripheral lymph nodes is exquisitely dependent on L-selectin. Since the ssDNA ligands binds to human but not rodent L-selectin, a xenogeneic lymphocyte trafficking system was established to evaluate in vivo efficacy. Human PBMC, labeled with $^{51}Cr$, were injected intravenously into SCID mice. Cell trafficking was determined 1 hour later. In this system, human cells traffic to peripheral and mesenteric lymph nodes (PLN and MLN). This accumulation is inhibited by DREG-56 (FIG. 13) but not MEL-14, a monoclonal antibody that blocks murine L-selectin-dependent trafficking. In initial experiments cells were incubated with either DREG-56 or 3' capped and PEG-modified oligonucleotide before injection. NX288 (SEQ ID NO: 193) inhibited trafficking of cells to PLN (FIG. 13) and MLN in a dose-dependent fashion but had no effect on the accumulation of cells in other organs. At the highest dose tested (4 nmol), inhibition by the DNA ligand was comparable to that of DREG-56 (13 pmol), while a scrambled sequence had no significant effect (FIG. 13). The activity of LD174T1 (SEQ ID NO: 194) was similar to that of NX288.

To determine if the modified oligonucleotide was effective when it was not pre-incubated with cells, DREG-56 (13 pmol/mouse) or the modified oligonucleotide (4 nmol/mouse) was injected intravenously into animals and 1–5 min later the radio-labeled human cells were given intravenously. Again, both NX288 (SEQ ID NO: 193) and DREG-56 inhibited trafficking to PLN and MLN while the scrambled sequence had no effect (FIG. 14). Therefore, the modified oligonucleotide did not require pre-incubation with the cells to effectively block trafficking. These experiments demonstrate, in vivo, the efficacy of oligonucleotide ligands in inhibiting a L-selectin dependent process.

EXAMPLE 21

L-Selectin Nucleic Acid Ligand Multimers

Multivalent Complexes were made in which two nucleic acid ligands to L-selectin were conjugated together. Multivalent Complexes of nucleic acid ligands are described in copending U.S. patent application Ser. No. 08/434,465, filed May 4, 1995, entitled "Nucleic Acid Ligand Complexes" which is herein incorporated by reference in its entirety. These multivalent Complexes were intended to increase the binding energy to facilitate better binding affinities through slower off-rates of the nucleic acid ligands. These multivalent Complexes may be useful at lower doses than their monomeric counterparts. In addition, high molecular weight (20 kD) polyethylene glycol (PEG) was included in some of the Complexes to decrease the in vivo clearance rate of the complexes. Specifically, the nucleic acid ligands incorporated into the Complexes were LD201T1 (SEQ ID NO: 185), LD201T4 (SEQ ID NO: 187), LD201T10 (SEQ ID NO: 188) and NX303 (SEQ ID NO: 196). Multivalent selectin nucleic acid ligand Complexes were produced as described in Example 13, paragraph F.

A variety of monomeric nucleic acid ligands and multivalent Complexes have been examined in flow cytometry. The multivalent Complexes exhibited similar specificity to the monomeric forms, but enhanced affinity as well as improved (i.e., slower) off-rate for human lymphocytes. Titration curves, obtained from incubating fluorescently labeled monomeric FITC-LD201T1 with peripheral blood mononuclear cells (PBMC) purified human lymphocytes, indicated that binding to cells is saturable. Half-saturation fluorescence occurred at 3 nM oligonucleotide. In contrast, the branched dimeric FITC-LD201T1 and bio-LD201T1/SA multivalent Complexes exhibited half-saturation at approximately 0.15 nM, corresponding to an apparent 20-fold increase in affinity. In similar experiments, half saturation of the dumbell and fork dimers of LD201T4 was observed at 0.1 and 0.6 nM, respectively, compared to 20 nM for monomeric LD201T4.

Kinetic competition experiments were performed on monomeric nucleic acid ligands and multivalent Complexes. Kinetic competition experiments were performed with PBMC purified lymphocytes. Cells were stained as described above but used 10 nM oligonucleotide. The off-rate for monomeric, dimeric and multivalent Complexes was determined by addition of 500 nM unlabeled oligonucleotide to cells stained with fluorescently labeled ligand and measurement of the change in the mean fluroescence intensity as a function of time. The dissociation rate of a monomeric LD201T1 from L-selectin expressing human lymphocytes was approximately 0.005 sec-1, corresponding to a half-life of roughly 2.4 minutes. The LD201T1 branched dimer and biotin conjugate multivalent Complexes exhibited apparent off-rates several times slower than that observed for the monomeric ligand and as slow or slower than that observed for the anti-L-selectin blocking antibody DREG56, determined under the same conditions. A multivalent Complex containing a non-binding nucleic acid sequence did not stain cells under identical conditions and did not compete in the off-rate experiments. The off-rate of the LD201T4 dumbell and fork dimers is faster than the LD201T1 branched dimer and is better than all monomers tested. These results confirm the proposition that dimeric and multimeric ligands bind with higher affinities than do monomeric ligands and that the increased affinity results from slower off-rates.

EXAMPLE 22

2'-F RNA Ligands to Human L-Selectin

The experimental procedures outlined in this Example were used to identify and characterize 2'-F RNA ligands to human L-selectin as described in Examples 23–25.
Experimental Procedures
A) Materials Unless otherwise indicated, all materials used in the 2'-F RNA SELEX against the L-selectin/IgG2 chimera, LS-Rg, were identical to those of Examples 7, paragraph A and 13, paragraph A. SHMCK-140 buffer, used for all SELEX and binding experiments, was 1 mM $CaCl_2$, 1 mM $MgCl_2$, 140 mM NaCl, 5 mM KCl, and 20 mM HEPES, pH 7.4. A soluble form of L-selectin, corresponding to the extracellular domains, was purchased from R&D Systems and used for some nitrocellulose filter binding experiments.
B) SELEX The SELEX procedure is described in detail in U.S. Pat. No. 5,270,163 and elsewhere. Procedures are essentially identical to those in Examples 7 and 13 except as noted. The variable regions of synthetic DNA templates were randomized at either 30 or 40 positions and were flanked by N7 5' and 3' fixed regions producing transcripts 30N7 (SEQ ID NO: 292) and 40N7 (SEQ ID NO: 389). The primers for the PCR were the following:

N7 5' Primer 5' taatacgactcactatagggaggacgatgcgg 3' (SEQ ID NO: 65)

N7 3' Primer 5' tcgggcgagtcgtcctg 3' (SEQ ID NO: 66)

The initial RNA pool was made by first Klenow extending 3 nmol of synthetic single stranded DNA and then transcribing the resulting double stranded molecules with T7 RNA polymerase. Klenow extension conditions: 6 nmols primer 5N7, 3 nmols 30N7 or 40n7, 1×Klenow Buffer, 1.8 mM each of dATP, dCTP, dGTP and dTTP in a reaction volume of 0.5 ml.

For subsequent rounds, eluted RNA was the template for AMV reverse transcriptase mediated synthesis of single-stranded cDNA. These single-stranded DNA molecules were converted into double-stranded transcription templates by PCR amplification. PCR conditions were 50 mM KCl, 10 mM Tris-Cl, pH 8.3, 7.5 mM $MgCl_2$, 0.2 mM of each dATP, dCTP, dGTP, and dTTP, and 100 U/ml of Taq DNA polymerase. Transcription reactions contained one third of the purified PCR reaction, 200 nM T7 RNA polymerase, 80 mM HEPES (pH 8.0), 12 mM $MgCl_2$, 5 mM DTT, 2 mM spermidine, 1 mM each of 2'-OH ATP, 2'-OH GTP, 3 mM each of 2'-F CTP, 2'-F UTP, and 250 nM $\alpha$-$^{32}$P 2'-OH ATP. Note that in all transcription reactions 2'-F CTP and 2'-F UTP replaced CTP and UTP.

The strategy for partitioning LS-Rg/RNA complexes from unbound RNA is outlined in Table 15 and is essentially identical to that of Example 7, paragraph B. In the initial SELEX rounds, which were performed at 37° C., the density of immobilized LS-Rg was 10 pmols/μl of Protein A Sepharose 4 Fast Flow beads. LS-Rg was coupled to protein A sepharose beads according to the manufacturer's instructions (Pharmacia Biotech). In later rounds, the density of LS-Rg was reduced (Table 15), as needed, to increase the stringency of selection. At the seventh round, both SELEXes were branched. One branch was continued as previously described (Example 7, paragraph B). In the second branch of both SELEXes, the RNA pool was pre-annealed to oligonucleotides that are complementary to the 5' and 3' fixed sequences. These rounds are termed "counter-selected" rounds. Before each round, RNA was batch adsorbed to 100 µl of protein A sepharose beads for 15 minutes in a 2 ml siliconized column. Unbound RNA and RNA eluted with minimal washing (two volumes) were combined and used for SELEX input material. For SELEX, extensively washed, immobilized LS-Rg was batch incubated with pre-adsorbed RNA for 1 to 2 hours in a 2 ml column with constant rocking. Unbound RNA was removed by extensive batch washing (500 µl SHMCK 140/wash). In addition, the counter selected rounds were extensively washed with buffer containing 200 nM of both complementary oligos. Bound RNA was eluted as two fractions; first, bound RNA was eluted by incubating and washing columns with 100 µL 5 mM EDTA in SHMCK 140 without divalent cations; second, the remaining elutable RNA was removed by incubating and/or washing with 500 µL 50 mM EDTA in SHMCK 140 without divalents. The percentage of input RNA that was eluted is recorded in Table 22. In every round, an equal volume of protein A sepharose beads without LS-Rg was treated identically to the SELEX beads to determine background binding. All unadsorbed, wash and eluted fractions were counted in a Beckman LS6500 scintillation counter in order to monitor each round of SELEX.

The 5 mM EDTA eluates were processed for use in the following round (Table 15). After precipitating with isopropanol/ethanol (1:1, v/v), the RNA was reverse transcribed into cDNA by AMV reverse transcriptase either at 48° C. for 15 minutes and then 65° C. for 15 minutes in 50 mM Tris-Cl pH (8.3), 60 mM NaCl, 6 mM Mg(OAc)$_2$, 10 mM DTT, 200 pmol DNA primer, 0.5 mM each of dNTPs, and 0.4 unit/µL AMV RT. Transcripts of the PCR product were used to initiate the next round of SELEX.

C) Nitrocellulose Filter Binding Assay

As described in SELEX Patent Applications, a nitrocellulose filter partitioning method was used to determine the affinity of RNA ligands for LS-Rg and for other proteins. Filter discs (nitrocellulose/cellulose acetate mixed matrix, 0.45 µm pore size, Millipore) were placed on a vacuum manifold and washed with 3 ml of SHMCK 140 buffer under vacuum. Reaction mixtures, containing $^{32}$P labeled RNA pools and unlabeled LS-Rg, were incubated in SHMCK 140 for 10–20 min at 37° C., and then immediately washed with 3 ml SHMCK 140. The filters were air-dried and counted in a Beckman LS6500 liquid scintillation counter without fluor. Alternatively, binding studies employed 96 well micro-titer manifolds essentially as described in Example 13, paragraph E.

D) Cloning and Sequencing

12th round PCR products were re-amplified with primers which contain either a BamHI or a HinDIII restriction endonuclease recognition site. Using these restriction sites, the DNA sequences were inserted directionally into the pUC9 vector. These recombinant plasmids were transformed into E. coli strain DH5a (Life Technologies, Gaithersburg, Md.). Plasmid DNA was prepared according to the alkaline lysis method (Quiagen, QIAwell, Chattsworth Calif.). Approximately 300 clones were sequenced using the ABI Prism protocol (Perkin Elmer, Foster City, Calif.). Sequences are shown in Table 16.

E) Cell Binding Studies

Binding of evolved ligands to L-selectin presented in the context of a cell surface was tested by flow cytometry experiments with human lymphocytes. Briefly, peripheral blood mononuclear cells (PBMC) were purified on histoplaque by standard techniques. To evaluate leukocyte binding by unlabeled 2'-F ligands, cells (500 cells/mL) were incubated with fluorescein labeled FITC-LD201T1 (SEQ ID NO: 185) in the presence of increasing concentrations of individual, unlabeled 2'-F ligands in 0.25 mL SMHCK buffer (140 mM NaCl, 1 mM MgCl$_2$, 1 mM CaCl$_2$, 5 mM, KCl, 20 mM HEPES pH 7.4, 8.9 mM NaOH, 0.1% (w/v) BSA, 0.1% (w/v) sodium azide) at room temperature for 15 minutes. Fluorescent staining of cells was quantified on a FACSCaliber fluorescent activated cell sorter (Becton Dickinson, San Jose, Calif.). The affinity of the 2'-F competitor was calculated from the flurorescence inhibition curves.

EXAMPLE 23

2'-F RNA Ligands to L-Selectin

A. SELEX

The starting RNA pools for SELEX, randomized 30N7 (SEQ ID NO: 292) or 40N7 (SEQ ID NO: 389) contained approximately $10^{14}$ molecules (0.7 nmol RNA). The SELEX protocol is outlined in Table 15 and Example 22. All rounds were selected at 37° C. The dissociation constant of randomized RNA to LS-Rg is estimated to be approximately 10 µM. After six rounds the pool affinities had improved to approximately 300 nM. An aliquot of the RNA recovered from the seventh round was used as the starting material for the first counter-selected rounds. Five rounds of counter-selection and five additional standard rounds were performed in parallel. Thus, a total of twelve rounds were performed in both branches of both SELEXes: 30N7, counter-selected 30N7, 40N7 and counter-selected 40N7. The affinities of each of the 12th round pools ranged from 60 to 400 pM. Ligands were cloned from these pools.

B. Sequences of 2'-F RNA Ligands to L-Selectin

In Table 16, ligand sequences are shown in standard single letter code (Cornish-Bowden, 1985 NAR 13: 3021–3030). Fixed region sequence is shown in lower case letters. By definition, each clone includes both the evolved sequence and the associated fixed region, unless specifically stated otherwise. A unique sequence is operationally defined as one that differs from all others by three or more nucleotides. Sequences that were isolated more than once are indicated by the parenthetical number, (n), following the ligand isolate number.

The 30N7 and 40N7 SELEX final pools shared a common major sequence family, even though identical sequences from the two SELEXes are rare (Table 16). Most ligands (72 of the 92 unique sequences) from the 30N7 and 40N7 SELEXes contain one of two related sequence motifs, RYGYGUUUUCRAGY or RYGYGUUWWUCRAGY. These motifs define family 1. Within the family there are three subfamilies. Subfamily 1a ligands (53/66) contain an additional sequence motif, CUYARRY, one nucleotide 5' to the family 1 consensus motifs. Subfamily 1b (9/66 unique sequences) lacks the CUYARRY motif. Subfamily 1c (5/66) is also missing the CUYARRY motif, has an A inserted between the Y and G of consensus YGUU and lacks the consensus GA base pair. The significance of the sequence subfamilies is reflected in the postulated secondary structure of the ligands (Example 25).

A second family, composed of 5 sequences, has a relatively well defined consensus: UACUAN$_{0-1}$UGURCG . . . UYCACUAAGN$_{1-2}$CCC (Table 16). Family 3 has a short, unreliable consensus motif (Table 16). In addition, there are approximately 12 orphans or apparently unrelated sequences. Three of the orphan sequences were recovered at least twice (Table 16).

C. Affinities

The dissociation constants of representative ligands from Table 16 are shown in Table 17. These calculations assume two ligand binding sites per chimera. The affinity of random 2'-F RNA cannot be reliably determined but is estimated to be approximately 10 µM.

The dissociation constants range from 34 pM to 315 nM at 37° C. Binding affinity is not expected to be temperature sensitive since selection was at 37° C. and 2'-F RNA forms thermal stable structures, but binding has not been tested at lower temperatures. For the most part, the extreme differences in affinity may be related to predicted secondary structure (Example 25).

The observed affinities of the evolved 2'-F RNA ligands reaffirm our proposition that it is possible to isolate oligonucleotide ligands with affinities that are several orders of magnitude greater than that of carbohydrate ligands.

EXAMPLE 24

Cell Binding Studies

The ability of full length 2'-F ligands to bind to L-selectin presented in the context of a cell surface was tested by competition-flow cytometry experiments with human peripheral blood lymphocytes. Lymphocytes were stained with 10 nM FITC-conjugated DNA ligand FITC-LD201T1 (SEQ ID NO: 185) in the presence of increasing concentrations of unlabeled 2'-F ligands as described in Example 22, paragraph E. Ligands LF1513 (SEQ ID NO: 321), LF1514 (SEQ ID NO: 297), LF1613 (SEQ ID NO: 331) and LF1618 (SEQ ID NO: 351) inhibited the binding of FITC-LD201T1 in a concentration dependent manner, with complete inhibition observed at competitor concentrations of 10 to 300 nM. These results demonstrate that the 2'-F ligands are capable of binding cell surface L-selectin and suggest that the 2'-F ligands and LD201T1 bind the same or overlapping sites. The affinities of the fluoro ligands, calculated from the competition curves, range from 0.2 to 25 nM. The affinity of two of the ligands for L-selectin on human lymphocytes, LF1613 (Kd=0.2 nM) and LF1514 (Kd=0.8 nM), is significantly better than that of the DNA ligand LD201T1 (Kd=3 nM). The reasonable agreement between the affinities for purified protein and lymphocyte L-selectin suggests that binding to lymphocytes is specific for L-selectin. These data validate the feasibility of using immobilized, purified protein to isolate ligands against a cell surface protein.

EXAMPLE 25

Secondary Structure of High Affinity 2'-F RNA Ligands to L-Selectin

In favorable instances, comparative analysis of aligned sequences allows deduction of secondary structure and structure-function relationships. If the nucleotides at two positions in a sequence covary according to Watson-Crick base pairing rules, then the nucleotides at these positions are apt to be paired. Nonconserved sequences, especially those that vary in length are not apt to be directly involved in function, while highly conserved sequence are likely to be directly involved.

The deduced secondary structure of family 1a ligands from comparative analysis of 21 unique sequences is a hairpin motif (FIG. 15) consisting of a 4 to 7 nucleotide terminal loop, a 6 base upper stem and a lower stem of 4 or more base pairs. The consensus terminal loops are either a UUUU tetraloop or a UUWWU pentaloop. Hexa- and heptaloops are relatively rare. The upper and lower stems are delineated by a 7 nucleotide bulge in the 5'-half of the stem. Four of the six base pairs in the upper stem and all base pairs in the lower stem are supported by Watson-Crick covariation. Of the two invariant base pairs in the upper stem one is the loop closing GC, while the other is a non-standard GA. The lower stem is most often 4 or 5 base pairs long but can be extended. While the sequence of the upper stem is strongly conserved, that of the lower stem is not, with the possible exception of the YR' base pair adjacent to the internal bulge. This base pair appears to covary with the 3' position of the 7 nucleotide bulge in a manner which minimizes the likelihood of extending the upper stem. Both the sequence (CUYARRY) and length (7nt) of the bulge are highly conserved.

In terms of comparative analysis, the 7 nucleotide bulge, the upper stem and the 5' and 3' positions of the terminal loop are most apt to be directly involved in L-selectin binding. Specifically, the 5' U and 3' U of the terminal loop, the invariant GC and GA base pairs of the upper stem and the conserved C, U and A of the bulge are the mostly likely candidates. The lower stem, because of its variability in length and sequence, is less likely to be directly involved. The importance of the bulge for binding is supported by the poor affinity of ligand LF1512 (SEQ ID NO: 357; Kd=315 nM); the simplest structure for this ligand is a UUUU tetraloop and a ten base pair, nearly perfect, consensus stem which is missing only the 7 nucleotide bulge.

The deduced secondary structure of family 1b is similar to that of family 1a, except that the upper stem is usually 7 base pairs in length and that the single stranded bulge which does not have a highly conserved consensus is only 4 nucleotide long. This structure may be an acceptable variation of the 1a secondary structure with the upper stem's increased length allowing a shorter bulge; the affinity of ligand LF1511 (SEQ ID NO: 332) is 300 pM.

Although family 1c has a consensus sequence, GUU-UUCNR that is related to 1a and 1b, a convincing consensus secondary structure is not evident, perhaps due to insufficient data. The most highly structured member of the family, LF1618 (SEQ ID NO: 351), permits a UUUU tetraloop and "upper" stem of 7 base pairs but has neither a lower stem nor the consensus 7 nucleotide bulge sequence of 1a. The upper stem differs from those of 1a and 1b in that it has an unpaired A adjacent to the loop closing G and does not have the invariant GA base pair of 1a and 1b. The affinity of LF1618 is a modest 10 nM which suggests that family 1c forms a less successful structure.

Predictions of minimal high affinity sequences for family 1 ligands can be made and serve as a partial test of the postulated secondary structure. Truncates which include only the upper stem and terminal loop, LF1514T1 (SEQ ID NO: 385) or these two elements plus the 7 nucleotide bulge sequence, LF1514T2 (SEQ ID NO: 386), are not expected to bind with high affinity. On the other hand, there is a reasonable, but not rigorous, expectation that ligands truncated at the base of the lower consensus stem, LF1514T4 (SEQ ID NO: 387) and LF1807T4 (SEQ ID NO: 388), will bind with high affinity. In side by side comparisons, the affinities of LF1514T1 and LF1514T2 for LS-Rg were reduced at least 100-fold in comparison to full length LD1514 (SEQ ID NO: 297), while the affinity of LF1514T4 was reduced less than two fold and that of LF1807T4 approximately three-fold. The correspondence between the predicted and observed truncate affinities supports the postulated secondary structure.

Since the ssDNA ligand LD201T1 (SEQ ID NO: 185) and the adhesion blocking anti-human L-selectin antibody DREG56 are known to bind to the lectin domain of L-selectin, competition between radio-labeled LF1807 (SEQ ID NO: 309) and either unlabeled DREG56 or unlabeled LD201T1 can serve to determine if the 2'-F ligands also bind the lectin domain of purified LS-Rg. In these experiments, both DREG56 and LD201T1 gave concentration dependent inhibition of LF1807 binding. Complete inhibition was attained with 300 nM Mab and 1 μM LD201T1. The competitors' affinities of LS-Rg, calculated from the competition curves, were in good agreement with their known affinities. These results are consistent with the premise that LF1807, NX280 and DREG56 have the same or overlapping binding sites and consequently it is expected that 2'-F ligands will be antagonists of L-selectin mediated adhesion. These results also reaffirm the proposition that the SELEX protocol, with 5 mM elution of bound oligonucleotides, preferentially elutes ligands bound at or near the lectin domain's bound calcium.

EXAMPLE 26 ssDNA Ligands to Human P-Selectin

PS-Rg is a chimeric protein in which the lectin, EGF, and the first two CRD domains of human P-selectin are joined to the Fc domain of a human G1 immunoglobulin (R. M. Nelson et al., 1993, supra). Purified chimera is provided by A. Varki. Soluble P-selectin is purchased from R&D Systems. Unless otherwise indicated, all materials used in the ssDNA SELEX against the P-selectin/IgG$_1$ chimera, PS-Rg, are identical to those of Examples 7 and 13.

The SELEX procedure is described in detail in U.S. Pat. No. 5,270,163. The specific strategies and procedures for evolving high affinity ssDNA antagonists to P-selectin are described in Examples 7 and 13.

EXAMPLE 27

2'-F RNA Ligands to Human P-Selectin

The Experimental procedures outlined in this Example were used to identify 2'-F RNA ligands to human P-selectin as described in Examples 28–34. Experimental Procedures
A) Materials PS-Rg is a chimeric protein in which the extracellular domain of human P-selectin is joined to the Fc domain of a human G2 immunoglobulin (Norgard et al., 1993, PNAS 90:1068–1072). ES-Rg and CD22β-Rg are analogous constructs of E-selectin and CD22β joined to a human G1 immunoglobulin Fc domain (R. M. Nelson et al., 1993 supra; I. Stamenkovic et al., 1991, Cell 66, 1133–1144) while LS-Rg has L-selectin joined to an IgG2 Fc domain. Purified chimera were provided by A. Varki. Soluble P-selectin was purchased from R&D Systems. Protein A Sepharose 4 Fast Flow beads were purchased from Pharmacia Biotech. Anti-P-selectin monoclonal antibodies: G1 was obtained from Centocor. The 2'-F modified CTP and UTP were prepared according to Pieken et. al. (1991, Science 253:314–317). DNA oligonucleotides were synthesized by Operon. All other reagents and chemicals were purchased from commercial sources. Unless otherwise indicated, experiments utilized HSMC buffer (1 mM CaCl$_2$, 1 mM MgCl$_2$, 150 mM NaCl, 20.0 mM HEPES, pH 7.4).
B) SELEX The SELEX procedure is described in detail in U.S. Pat. No. 5,270,163 and elsewhere. The nucleotide sequence of the synthetic DNA template for the PS-Rg SELEX was randomized at 50 positions. This variable region was flanked by N8 5' and 3' fixed regions. The transcript 50n8 has the sequence 5' gggagacaagaauaaacgcucaa-50N-uucgacaggaggcucacaacaggc 3' (SEQ ID NO: 390). All C and U have 2'-F substituted for 2'-OH on the ribose. The primers for the PCR were the following:

N8 5' Primer 5'taatacgactcactatagggagacaagaataaacgctcaa 3' (SEQ ID NO: 197)

N8 3' Primer 5'gcctgttgtgagcctcctgtcgaa 3' (SEQ ID NO: 198)

The fixed regions include primer annealing sites for PCr and cDNA synthesis as well as a consensus T7 promoter to allow in vitro transcription. The initial RNA pool was made by first Klenow extending 1 nmol of synthetic single stranded DNA and then transcribing the resulting double stranded molecules with T7 RNA polymerase. Klenow extension conditions: 3.5 nmols primer 5N8, 1.4 nmols 40N8, 1X Klenow Buffer, 0.4 mM each of dATP, dCTP, dGTP and dTTP in a reaction volume of 1 ml.

For subsequent rounds, eluted RNA was the template for AMV reverse transcriptase mediated synthesis of single stranded cDNA. These single-stranded DNA molecules were converted into double-stranded transcription templates by PCR amplification. PCR conditions were 50 mM KCl, 10 mM Tric-Cl, pH 8.3, 7.5 mM MgCl$_2$, 1 mM of each dATP, dCTP, dGTP, and dTTP, and 25 U/ml of Taq DNA polymerase. Transcription reactions contained 0.5 mM DNA template, 200 nM T7 RNA polymerase, 40 mM Tris-HCl (pH 8.0), 12 mM MgCl$_2$, 5 mM DTT, 1 mM spermidine, 4% PEG 8000, 1 mM each of 2'-OH ATP and 2'-OH GTP, 3.3 mM each of 2'-F CTP and 2'-F UTP, and 250 nM α-$^{32}$P 2'-OH ATP.

The strategy for partitioning PS-Rg/RNA complexes from unbound RNA is essentially identical to the strategy detailed in Example 7 for ligands to L-selectin (Table 18).

In the initial SELEX rounds, which were performed at 37° C., the density of immobilized PS-Rg was 20 pmols/μl of Protein A Sepharose 4 Fast Flow beads. In later rounds, the density of PS-Rg was reduced (Table 18), as needed, to increase the stringency of selection. Beginning with the second round, SELEX was often done at more than one PS-Rg density. At each round, the eluted material from only one PS-Rg density was carried forward.

Before each round, RNA was batch adsorbed to 100 μl of protein A sepharose beads for 1 hour in a 2 ml siliconized column. Unbound RNA and RNA eluted with minimal washing (two volumes) were combined and used for SELEX input material. For SELEX, extensively washed, immobilized PS-Rg was batch incubated with pre-adsorbed RNA for 0.5 to 1 hours in a 2 ml siliconized column with frequent mixing. Unbound RNA was removed by extensive batch washing (500 μl HSMC/wash). Bound RNA was eluted as two fractions; first, bound RNA was eluted by incubating and washing columns with 5 mM EDTA in HSMC without divalent cations; second, the remaining elutable RNA was removed by incubating and/or washing with 50 mM EDTA in HSMC without divalents. The percentage of input RNA that was eluted is recorded in Table 18. In every round, an equal volume of protein A sepharose beads without PS-Rg was treated identically to the SELEX beads to determine background binding. All unadsorbed, wash and eluted fractions were counted in a Beckman LS6500 scintillation counter in order to monitor each round of SELEX.

The eluted fractions were processed for use in the following round (Table 18). After precipitating with 300 mM Sodium Acetate pH 7 in ethanol (2.5 volumes), the RNA was resuspended in 80 µl of H$_2$O and 40 µl were reverse transcribed into cDNA by AMV reverse transcriptase at 48° C. for 30 minutes, in 50 mM Tris-Cl pH (8.3), 60 mM NaCl, 6 mM Mg(OAc)$_2$, 10 mM DTT, 200 pmol DNA primer, 0.4 mM each of dNTPs, and 0.4 unit/µl AMV RT. Transcripts of the PCR product were used to initiate the next round of SELEX.

C) Nitrocellulose Filter Binding Assay

As described in SELEX Patent Applications, a nitrocellulose filter partitioning method was used to determine the affinity of RNA ligands for PS-Rg and for other proteins. Filter discs (nitrocellulose/cellulose acetate mixed matrix, 0.45 µm pore size, Millipore) were placed on a vacuum manifold and washed with 2 mL of HSMC buffer under vacuum. Reaction mixtures, containing $^{32}$P labeled RNA pools and unlabeled PS-Rg, were incubated in HSMC for 10–20 min at 4° C., room temperature or 37° C., filtered, and then immediately washed with 4 ml HSMC at the same temperature. The filters were air-dried and counted in a Beckman LS6500 liquid scintillation counter without fluor.

PS-Rg is a dimeric protein that is the expression product of a recombinant gene constructed by fusing the DNA sequence that encodes the extracellular domains of human P-selectin to the DNA that encodes a human IgG$_1$ Fc region. For affinity calculations, one ligand binding site per PS-Rg monomer (two per dimer) were assumed. The monomer concentration is defined as 2 times the PS-Rg dimer concentration. The equilibrium dissociation constant, K$_d$, for an RNA pool or specific ligand is calculated as described in Example 7, paragraph C.

D) Cloning and Sequencing

Twelfth round PCR products were re-amplified with primers which contain either a BamHI or a HinDIII restriction endonuclease recognition site. Using these restriction sites, the DNA sequences were inserted directionally into the pUC9 vector. These recombinant plasmids were transformed into E. coli strain JM109 (Life Technologies, Gaithersburg, Md.). Plasmid DNA was prepared according to the alkaline hydrolysis method (PERFECTprep, 5'-3', Boulder, Colo). Approximately 50 clones were sequenced using the Sequenase protocol (Amersham, Arlington Heights, Ill.). The resulting ligand sequences are shown in Table 19.

E) Boundary Experiments

The minimal high affinity sequence of individual ligands was determined by boundary experiments (Tuerk et. al. 1990, J. Mol. Biol. 213:749). Individual RNA ligands, $^{32}$P-labeled at the 5'-end for the 3' boundary and $^{32}$P-labeled at the 3'-end for the 5' boundary, are hydrolyzed in 50 mM Na$_2$CO$_3$ pH 9 for 8 minutes at 95° C. The resulting partial hydrolysate contains a population of end-labeled molecules whose hydrolyzed ends correspond to each of the purine positions in the full length molecule. The hydrolysate is incubated with PS-Rg (at concentrations 5-fold above, below and at the measured Kd for the ligand). The RNA concentration is significantly lower than the Kd. The reaction is incubated at room temperature for 30 minutes, filtered, and then immediately washed with 5 ml HSMC at the same temperature. The bound RNa is extracted from the filter and then electrophoresed on an 8% denaturing gel adjacent to hydrolyzed RNA which has not been incubated with PS-Rg. Analysis is as described in Tuerk et. al. 1990, J. Mol. Biol. 213:749.

F) 2'-O-Methyl Substitution Experiments

In order to decrease the susceptibility of the 2'-F pyrimidine RNA ligands to nuclease digestion, post-SELEX modification experiments were performed to identify 2'-OH purines that are replaceable with 2'-OMe purines without loss of affinity as described in Green et. al. (1995, J. Mol. Biol. 247:60–68). Briefly, seven oligonucleotides were synthesized, each with three mixed positions. A mixed position is defined as a 2'-OH purine nucleotide within the RNA which has been synthesized with 2:1 ratio of 2'-OH:2'-OMe. Since the coupling efficiency of 2'-OH phosphoramidites is lower than that of 2'-OMes, the resulting RNA has 25–50% 2'-OH at each mixed position. $^{32}$P end-labeled RNA ligands are then incubated with concentrations of PS-Rg 2-fold above and 2.5-fold below the Kd of the unmodified ligand at room temperature for 30 minutes, filtered, and then immediately washed with 5 ml HSMC at the same temperature. The bound RNA (Selected RNA) is extracted from the filter and then hydrolyzed with 50 mM Na$_2$CO$_3$ pH 9 for 8 minutes at 95° C. in parallel with RNA which has not been exposed to binding and filtration (Unselected RNA). The Selected RNA is then electrophoresed on a 20% denaturing gel adjacent to Unselected RNA.

To determine the affect on binding affinity of 2'-OMe substitution at a particular position, the ratio of intensities of the Unselected:Selected bands that correspond to the position in question are calculated. The Unselected:Selected ratio when the position is mixed is compared to the mean ratio for that position from experiments in which the position is not mixed. If the Unselected:Selected ratio of the mixed position is significantly greater than that when the position is not mixed, 2'-OMe may increase affinity. Conversely, if the ratio is significantly less, 2'-OMe may decrease affinity. If the ratios are not significantly different, 2'-OMe substitution has no affect.

G) Cell Binding Studies

The ability of evolved ligand pools and cloned ligands to bind to P-selectin presented in the context of a cell surface was tested in experiments with human platelet suspensions. Whole blood from normal volunteers was collected in Vacutainer 6457 tubes. Within 5 minutes of collection, 485 µl of blood was stimulated with 15 µl Bio/Data THROMBINEX for 5 minutes at room temperature. A 100 µl aliquot of stimulated blood was transferred to 1 ml of BB− (140 mM NaCl, 20 mM HEPES pH 7.35, 5 mM KCl, 0.01% NaN$_3$) at 4° C. and spun at 735 x g for 5 minutes. This step was repeated and the resulting pellet was re-suspended in 1 ml of BB+ (140 mM NaCl, 20 mM HEPES pH 7.35, 5 mM KCl, 0.01% NaN$_3$, 1 mM CaCl$_2$, 1 mM MgCl$_2$) at 4° C.

To detect antigen expression, 15 µl BB+ containing FITC conjugated anti-CD61 or PE conjugated anti-CD62 antibody (Becton Dickinson) was incubated for 20–30 minutes at 4° C. with 10 µl of platelet suspension. This was diluted to 200 µl with 4° C. BB+ and analyzed on a Becton Dickinson FACS Caliber using 488 nm excitation and FL1 (530 nm emission) of FL2 (580 nm emission) with the machine live gated on platelets. Between 1000 and 5000 events in this gate were recorded.

To detect oligonucleotide ligand binding, 15 µl BB+ containing ligand conjugated to either FITC or biotin was incubated 20–30 minutes at 4° C. with 10 µl platelet suspension. The FITC or biotin was incubations were diluted to 200 µl with BB+ and analyzed on a FACSCaliber flow cytometer. The biotinylated-ligand reactions were incubated with streptavidin-phycoerythrin (SA-PE) (Becton Dickinson) for 20 minutes at 4° C., before dilution and analysis. Wash steps with 500 µl BB+ and 700 x g spins have been used without compromising the quality of the results.

The specificity of binding to P-selectin (CD62P) expressed on platelets was tested by competition with the P-selectin specific blocking monoclonal antibody, G1. Saturability of binding was tested by self-competition with unlabeled RNA.

H) Inhibition of Selectin Binding to sialyl-Lewis$^x$

The ability of evolved RNA pools or cloned ligands to inhibit the binding of PS-Rg to sialyl-Lewis$^x$ was tested in competitive ELISA assays (C. Foxall et al., 1992, supra). For these assays, the wells of Corning (25801) 96 well microtiter plates were coated with 100 ng of a sialyl-Lewis$^x$/BSA conjugate, air dried overnight, washed with 300 μl of PBS(-) and then blocked with 1% BSA in HSMC for 60 min at room temperature. RNA ligands were incubated with PS-Rg in HSMC/1% BSA at room temperature for 15 min. After removal of the blocking solution, 50 μl of PS-Rg (10 nM) or a PS-Rg (10 nM)/RNA ligand mix was added to the coated, blocked wells and incubated at room temperature for 60 minutes. The binding solution was removed, wells were washed with 300 μl of PBS(-) and then probed with HRP conjugated anti-human IgG, at room temperature to quantitate PS-Rg binding. After a 30 minute incubation at room temperature in the dark with OPD peroxidase substrate (Sigma P9187), the extent of PS-Rg binding and percent inhibition was determined from the $OD_{450}$.

EXAMPLE 28

2'-F RNA Ligands to Human P-selectin

A. SELEX

The starting RNA pool for SELEX, randomized 50N8 (SEQ ID NO: 390), contained approximately $10^{15}$ molecules (1 nmol RNA). The SELEX protocol is outlined in Table 18. The dissociation constant of randomized RNA to PS-Rg is estimated to be approximately 2.5 μM. An eight-fold difference was observed in the RNA elution profiles with 5 mM EDTA from SELEX and background beads for rounds 1 and 2, while the 50 mM elution produced a 30–40 fold excess over background Table 18. For rounds 1 through 3, the 5 mM and 50 mM eluted RNAs were pooled and processed for the next round. Beginning with round 4, only the 5 mM eluate was processed for the following round. To increase the stringency of selection, the density of immobilized PS-Rg was reduced five fold in round 2 and again in round three without greatly reducing the fraction eluted from the column. The density of immobilized PS-Rg was further reduced 1.6-fold in round 4 and remained at this density until round 8, with further reductions in protein density at later rounds. The affinity of the selected pools rapidly increased and the pools gradually evolved biphasic binding characteristics.

Binding experiments with 12th round RNA revealed that the affinity of the evolving pool for P-selectin was not temperature sensitive. Bulk sequencing of 2nd, 6th, 11th and 12th RNA pools revealed noticeable non-randomness by round twelve. The 6th round RNA bound monophasically at 37° C. with a dissociation constant of approximately 85 nM, while the 11th and 12th round RNAs bound biphasically with high affinity Kds of approximately 100 and 20 pM, respectively. The binding of all tested pools required divalent cations. In the absence of divalent cations, the Kds of the 12th round pools increased to >10 nM. (HSMC, minus $Ca^{++}/Mg^{++}$, plus 2 mM EDTA). The 12th round pool showed high specificity for PS-Rg with measured Kd's of 1.2 μM and 4.9 μM for ES-Rg and LS-Rg, respectively.

B. RNA sequences

In Table 19, ligand sequences are shown in standard single letter code (Cornish-Bowden, 1985 NAR 13:3021–3030). Fixed region sequence is shown in lower case letters. By definition, each clone includes both the evolved sequence and the associated fixed region, unless specifically stated otherwise. From the twelfth round, 21 of 44 sequenced ligands were unique. A unique sequence is operationally defined as one that differs from all others by three or more nucleotides. Sequences that were isolated more than once, are indicated by the parenthetical number, (n), following the ligand isolate number. These clones fall into five sequence families (1–5) and a group of two unrelated sequences (Orphans) (SEQ ID NOs: 199–219).

Family 1 is defined by 23 ligands from 13 independent lineages. The consensus sequence is composed of two variably spaced sequences, CUCAACGAMC and CGCGAG (Table 19). In 11 of 13 ligands the CUCAA of the consensus is from 5' fixed sequence which consequently minimizes variability and in turn reduces confidence in interpreting the importance of CUCAA or the paired GAG (see Example 27).

Families 2–5 are each represented by multiple isolates of a single sequence which precludes determination of consensus sequences.

D. Affinities

The dissociation constants for representative ligands, including all orphans, were determined by nitrocellulose filter binding experiments and are listed in Table 20. These calculations assume two binding sites per chimera. The affinity of random RNA is estimated to be approximately 2.5 μM.

In general, ligands bind monophasically with dissociation constants ranging from 15 pM to 450 pM at 37° C. Some of the highest affinity ligands bind biphasically. Full length ligands of families 1–4 show no temperature dependence. The observed affinities substantiate the proposition that it is possible to isolate oligonucleotide ligands with affinities that are several orders of magnitude greater than that of carbohydrate ligands.

EXAMPLE 29

Specificity of 2'-F RNA Ligands

The affinity of P-selectin ligands to ES-Rg, LS-Rg and CD22β-Rg were determined by nitrocellulose partitioning. As indicated in Table 20, the ligands are highly specific for P-selectin. In general, a ligand's affinity for ES-Rg and LS-Rg is at least $10^4$-fold lower than for PS-Rg. Binding above background is not observed for CD22β-Rg at the highest protein concentration tested (660 nM), indicating that ligands do not bind the Fc domain of the chimeric constructs nor do they have affinity for the sialic acid binding site of this unrelated lectin. The specificity of oligonucleotide ligand binding contrasts sharply with the binding of cognate carbohydrates by the selectins and confirms the proposition that SELEX ligands will have greater specificity than carbohydrate ligands.

EXAMPLE 30

Inhibition of Binding to sialyl-Lewis$^x$

Oligonucleotide ligands, eluted by 2–5 mM EDTA, are expected to derive part of their binding energy from contacts with the lectin domain's bound $Ca^{++}$ and consequently, are expected to compete with sialyl-Lewis$^x$ for binding. In competition assays, the selected oligonucleotide ligands competitively inhibit PS-Rg binding to immobilized sialyl-Lewis$^x$ with IC50s ranging from 1 to 4 nM (Table 20). Specifically, ligand PF377 (SEQ ID NO: 206) has an IC50 of approximately 2 nM. Complete inhibition is attained at 10 nM ligand. This result is typical of high affinity ligands and is reasonable under the experimental conditions. The IC50s of ligands whose Kds are much lower than the PS-Rg concentration (10 nM) are limited by the protein concentration and are expected to be approximately one half the PS-Rg concentration. The specificity of competition is demonstrated by the inability of round 2 RNA (Kd~1 μM) to inhibit PS-Rg binding to immobilized sialyl-Lewis$^x$. These data verify that 2'-F RNA ligands are functional antagonists of PS-Rg.

EXAMPLE 31

Secondary Structure of High Affinity Ligands

In favorable instances, comparative analysis of aligned sequences allows deduction of secondary structure and structure-function relationships. If the nucleotides at two positions in a sequence covary according to Watson-Crick base pairing rules, then the nucleotides at these positions are apt to be paired. Nonconserved sequences, especially those that vary in length are not apt to be directly involved in function, while highly conserved sequences are likely to be directly involved.

Comparative analysis of the family 1 alignment suggests a hairpin motif, the stem of which contains three asymmetrical internal loops (FIG. 16). In the figure, consensus positions are specified, with invariant nucleotides in bold type. To the right of the stem is a matrix showing the number of occurrences of particular base pairs for the positions in the stem that are on the same line. The matrix shows that 6 of the stem's 9 base pairs are supported by Watson-Crick covariation. Portions of the two consensus motifs, CUC and GAG, form the terminus of the stem. Conclusions regarding a direct role of the terminus in binding are tempered by the use of fixed sequence (11 of 13 ligands) which limits variability. The variability of the loop's sequence and length suggests that it is not directly involved in binding. This conclusion is reenforced by ligand PF422 (SEQ ID NO: 202) which is a circular permutation of the consensus motif. Although the loop that connects the stem's two halves is at the opposite end relative to other ligands, PF422 binds with high (Kd=172 pM; Table 21) affinity.

EXAMPLE 32

Boundary Experiments

Boundary experiments were performed on a number of P-selectin ligands as described in Example 27 and the results are shown in Table 21. The results for family 1 ligands are consistent with their proposed secondary structure. The composite boundary species vary in size from 38–90 nucleotides, but are 40–45 nucleotides in family 1. Affinities of these truncated ligands are shown in Table 22. In general, the truncates lose no more than 10-fold in affinity in comparison to the full length, effectively inhibit the binding of PS-Rg to sialyl-Lewis$^x$ and maintain binding specificity for PS-Rg (Table 22). These data validate the boundary method for identifying the minimal high affinity binding element of the RNA ligands.

EXAMPLE 33

Binding of 2'-F RNA Ligands to Human Platelets

Since the P-selectin ligands were isolated against purified protein, their ability to bind P-selectin presented in the context of a cell surface was determined in flow cytometry experiments with activated human platelets. Platelets were gated by side scatter and CD61 expression. CD61 is a constitutively expressed antigen on the surface of both resting and activated platelets. The expression of P-selectin was monitored with anti-CD62P monoclonal antibody (Becton Dickinson). The mean fluorescence intensity of activated platelets, stained with biotintylated-PF377s1 (SEQ ID NO: 223)/SA-PE (Example 27, paragraph G), is 5 times greater than that of similarly stained resting platelets. In titration experiments half maximal fluorescence occurs at approximately 50 pM PF377s1 (EC50) which is consistent with its equilibrium dissociation constant, 60 pM, for PS-Rg. Binding to platelets is specific by the criterion that it is saturable. Saturability has been demonstrated not only by titration but also by competition with unlabeled PF377s1.

Binding to platelets is P-selectin specific by the criteria that 1) oligonucleotides that do not bind PS-Rg do not bind platelets; 2) that binding of PF377s1 to platelets is divalent cation dependent; and most importantly 3) that binding is inhibited by the anti-P-selectin adhesion blocking monoclonal antibody G1, but not by an isotype control antibody. These data validate the feasibility of using immobilized, purified protein to isolate highly specific ligands against a cell surface P-selectin.

EXAMPLE 34

2'-O-Methyl Substitution Experiments

2'-OMe purine substitutions were performed on ligand PF377s1 (SEQ ID NO: 223) as described in Example 27 paragraph F and the results are shown in Table 23. The data indicate that 2'-OMe purines at positions 7–9, 15, 27, 28 and 31 enhance binding while substitutions at positions 13, 14, 16, 18, 21, 22, 24, and 30 have little or no affect on affinity. Thus it appears that up to 15 positions may be substituted with only slight losses in affinity. In partial confirmation of this expectation, the affinity of 377s1 simultaneously substituted with 2'-OMe purines at 11 positions (PF377M6, SEQ ID NO: 235) is 250 pM (Table 22).

EXAMPLE 35

2'-NH$_2$ RNA Ligands to Human P-Selectin

The experimental procedures described in this Example are used in Examples 36–38 to isolate and characterize 2'-NH$_2$ RNA ligands to human P-selectin. Experimental Procedures
A) Materials Unless otherwise indicated, all materials used in the 2'-NH$_2$ RNA SELEX against the P-selectin/IgG$_1$ chimera, PS-Rg, were identical to those of Example 27. The 2'-NH$_2$ modified CTP and UTP were prepared according to Pieken et. al. (1991, science 253:314–317). The buffer for SELEX experiments was 1 mM CaCl$_2$, 1 mM MgCl$_2$, 150 mM NaCl, 10.0 mM HEPES, pH 7.4.
B) SELEX The SELEX procedure is described in detail in U.S. Pat. No. 5,270,163 and elsewhere. The nucleotide sequence of the synthetic DNA template for the PS-Rg SELEX was randomized at 50 positions. This variable region was flanked by N8 5' and 3' fixed regions. The transcript 50N8 has the sequence 5' gggagacaagaauaaac gcucaa-50N-uucgacaggaggcucacaacaggc 3' (SEQ ID NO: 248). All C and U have 2'-NH$_2$ substituted for 2'-OH on the ribose. The primers for the PCR were the following:

N8 5' Primer 5' taatacgactcactatagggagacaa-gaataaacgctcaa 3' (SEQ ID NO: 249)

N8 3' Primer 5' gcctgttgtgagcctcctgtcgaa 3' (SEQ ID NO: 250). The procedures used to isolate 2'-NH$_2$ oligonucleotide ligands to P-selectin are identical to those described 2'-F ligands in Example 27, except that transcription reactions utilized 1 mM each, 2'-NH$_2$-CTP and 2'-NH$_2$-UTP, in place of 3.3 mM each 2'-F-CTP and 2'-F-UTP.

C) Nitrocellulose Filter Binding Assay

As described in SELEX Patent Applications and in Example 27, paragraph C, a nitrocellulose filter partitioning method was used to determine the affinity of RNA ligands for PS-Rg and for other proteins. Either a Gibco BRL 96 well manifold, as described in Example 23 or a 12 well Millipore manifold (Example 7C) was used for these experiments. Binding data were analyzed as described in Example 7, paragraph C.

D) Cloning and Sequencing

Twelfth round PCR products were re-amplified with primers which contain either a DamHI or a HinDIII restriction endonuclease recognition site. Approximately 75 ligands were cloned and sequenced using the procedures described in Example 7, paragraph C. The resulting sequences are shown in Table 25.

E) Cell Binding Studies

The ability of evolved ligand pools to bind to P-selectin presented in the context of a cell surface was tested in flow cytometry experiments with human platelet suspensions as described in Example 7, paragraph E.

EXAMPLE 36

2'-NH$_2$ RNA Ligands to Human P-Selectin

A. SELEX

The starting 2'-NH$_2$ RNA pool for SELEX, randomized 50N8 (SEQ ID NO: 248), contained approximately $10^{15}$ molecules (1 nmol 2'-NH$_2$ RNA). The dissociation constant of randomized RNA to PS-Rg is estimated to be approximately 6.4 $\mu$M. The SELEX protocol is outlined in Table 24.

The initial round of SELEX was performed at 37° C. with an PS-Rg density of 20 pmol/$\mu$l of protein A sepharose beads. Subsequent rounds were all at 37° C. In the first round there was no signal above background for the 5 mM EDTA elution, whereas the 50 mM EDTA elution had a signal 7 fold above background, consequently the two elutions were combined and processed for the next round. This scheme was continued through round 6. Starting with round seven only the 5 mM eluate was processed for the next round. To increase the stringency of selection, the density of immobilized PS-Rg was reduced ten fold in round 6 with further reductions in protein density at later rounds. Under these conditions a rapid increase in the affinity of the selected pools was observed.

Binding experiments with 12th round RNA revealed that the affinity of the evolving pool for P-selectin was temperature sensitive despite performing the selection at 37° C., (Kds: 13 pM, 91 pM and 390 pM at 4° C., room temperature and 37° C., respectively). Bulk sequencing of RNA pools indicated dramatic non-randomness at round 10 with not many visible changes in round 12. Ligands were cloned and sequenced from round 12.

B. 2'-NH$_2$ RNA Sequences

In Table 25, the 2'-NH$_2$ RNA ligand sequences are shown in standard single letter code (Cornish-Bowden, 1985 NAR 13:3021–3030) SEQ ID NOS: 251–290). The evolved random region is shown in upper case letters in Table 25. Any portion of the fixed region is shown in lower case letters. By definition, each clone includes both the evolved sequence and the associated fixed region, unless specifically stated otherwise. From the twelfth round, 40/61 sequenced ligands were unique. A unique sequence is operationally defined as one that differs from all others by three or more nucleotides. Sequences that were isolated more than once are indicated by the parenthetical number, (n), following the ligand isolate number. Ligands from family 1 dominate the final pool containing 16/61 sequences, which are derived from multiple lineages. Families 2 and 3 are represented by slight mutational variations of a single sequence. Sequences labeled as "others" do not have any obvious similarities. Family 1 is characterized by the consensus sequence GGGAAGAAGAC (SEQ ID NO: 291).

C. Affinities

The dissociation constants of representative ligands are shown in Table 26. These calculations assume two RNA ligand binding sites per chimera. The affinity of random 2'-NH$_2$ RNA is estimated to be approximately 10 $\mu$M.

At 37° C., the dissociation constants range from 60 pM to 50 nM which is at least a $1\times10^3$ to $1\times10^5$ fold improvement over randomized 2'-NH$_2$ RNA (Table 26). There is a marked temperature sensitivity for Clone PA350 (SEQ ID NO: 252) with an increase in affinity of 6 fold at 4° C. (Table 26). The observed affinities of the evolved 2'-NH$_2$ ligand pools reaffirm our proposition that it is possible to isolate oligonucleotide ligands with affinities that are several orders of magnitude greater than that of carbohydrate ligands.

EXAMPLE 37

Specificity of 2'-NH$_2$ RNA Ligands to P-Selectin

The affinity of clone PA350 (SEQ ID NO: 252) for LS-Rg and ES-Rg was determined by nitrocellulose partitioning and the results shown in Table 26. The ligands are highly specific for P-selectin. The affinity for ES-Rg is about 600-fold lower and that for LS-Rg is about $5\times10^5$-fold less than for PS-Rg. Binding above background is not observed for CD22$\beta$-Rg indicating that ligands neither bind the Fc domain of the chimeric constructs nor have affinity for unrelated sialic acid binding sites.

The specificity of oligonucleotide ligand binding contrasts sharply with the binding of cognate carbohydrates by the selectins and reconfirms the proposition that SELEX ligands will have greater specificity than carbohydrate ligands.

EXAMPLE 38

Cell Binding Studies

FITC-labeled ligand PA350 (FITC-350) (SEQ ID NO: 252) was tested for its ability to bind to P-selectin presented in the context of a platelet cell surface by flow cytometry experiments as described in Example 23, paragraph G.

The specificity of FITC-PA350 for binding to P-selectin was tested by competition experiments in which FITC-PA350 and unlabeled blocking monoclonal antibody G1 were simultaneously added to stimulated platelets. G1 effectively competes with FITC-PA350 for binding to platelets, while an isotype matched control has little or no effect which demonstrates that FITC-PA350 specifically binds to P-selectin. The specificity of binding is further verified by the observation that oligonucleotide binding is saturable; binding of 10 nM FITC-PA350 is inhibited by 200 nM unlabeled PA350. In addition, the binding of FITC-PA350 is dependent on divalent cations; at 10 nM FITC-PA350 activated platelets are not stained in excess of autofluorescence in the presence of 5 mM EDTA.

These data validate the feasibility of using immobilized, purified protein to isolate ligands against a cell surface protein and the binding specificity of 2'-NH$_2$ ligands to P-selectin in the context of a cell surface.

EXAMPLE 39

Inhibition of P-selectin Binding to Sialyl Lewis$^x$

In competition assays, ligands PA341 (SEQ ID NO: 251) and PA350 (SEQ ID NO: 252) competitively inhibit PS-Rg binding to immobilized sialyl-Lewis$^x$ with IC50s ranging from 2 to 5 nM (Table 26). This result is typical of high affinity ligands and is reasonable under the experimental conditions. The IC50s of ligands whose Kds are much lower than the PS-Rg concentration (10 nM) are limited by the protein concentration and are expected to be approximately one half the PS-Rg concentration. The specificity of competition is demonstrated by the inability of round 2 RNA (Kd~1 $\mu$M) to inhibit PS-Rg binding to immobilized sialyl-Lewis$^x$. These data verify that 2-NH$_2$ RNA ligands are functional antagonists of P-selectin.

EXAMPLE 40

2'-NH$_2$ RNA Ligands to Human E-Selectin

ES-Rg is a chimeric protein in which the extracellular domain of human E-selectin is joined to the Fc domain of a human G1 immunoglobulin (R. M. Nelson et al., 1993, supra). Purified chimera were provided by A. Varki. Unless otherwise indicated, all materials used in this SELEX are similar to those of Examples 7 and 13.

The SELEX procedure is described in detail in U.S. Pat. No. 5,270,163 and elsewhere. The rationale and experimental procedures are the same as those described in Examples 7 and 13.

TABLE 1

Wheat Germ Agglutinin Selex

| Round | Total Protein (pmole) | Total RNA (pmole) | Gel Volume ($\mu$l) | Total Volume ($\mu$l) | % RNA Eluted | % RNA Amplified | Kd (nM) |
|---|---|---|---|---|---|---|---|
| 1 | 5,800 | 2,020 | 50 | 276 | 0.05 | 0.05 | 6,000,000 |
| 2 | 5,800 | 1,070 | 50 | 276 | 0.12 | 0.12 | |
| 3 | 5,800 | 1,770 | 50 | 280 | 0.21 | 0.21 | |
| 4 | 5,800 | 900 | 50 | 263 | 3 | 3 | |
| 5 | 5,800 | 500 | 50 | 271 | 28.5 | 28.5 | 600 |
| 6a | 5,800 | 1,000 | 50 | 282 | 28.8 | | |
| 6b | 580 | 1,000 | 5 | 237 | 5.7 | 0.18 | 400 |
| 7 | 580 | 940 | 5 | 245 | 12.8 | 0.87 | 320 |
| 8 | 580 | 192 | 5 | 265 | 21.4 | 0.64 | 260 |
| 9 | 58 | 170 | 0.5 | 215 | 3.8 | 0.06 | 130 |
| 10 | 58 | 184 | 0.5 | 210 | 5.2 | 0.12 | 94 |
| 11 | 58 | 180 | 0.5 | 210 | 2.3 | 0.07 | 68 |

Wheat Germ Lectin Sepharose 6 MB, WGA density, approximately 5 mg/ml of gel or 116 $\mu$M. RNA Loading Conditions: Rounds 1–5, 2 hrs @ room temperature on roller; incubation time reduced to 1 hr. for Rounds 6–11.
RNA Elution Conditions: Rounds 1–5, 200 $\mu$l of 2 mM (GlcNAc)3, 15 min. @ room temperature on roller; 2× 200 $\mu$l wash with same buffer. Rounds 6: 200 $\mu$l of 0.2 mM (GlcNAc)3, incubated as above; washed sequentially with 200 $\mu$l of 0.5, 1, 1.5, 2 and 10 mM (GlcNAc)3. Rounds 7–8: 200 $\mu$l of 0.2 mM (GlcNAc)3, incubated as in round 6; wash twice with same buffer; washed sequentially with 3× 200 $\mu$l each, of 0.5, 1.0, 1.5, 2.0 and 10 mM (GlcNAc)3. Rounds 9–11: incubated 15 @ room temperature in 200 $\mu$l of 1 mM (GlcNAc); washed 2× with 200 $\mu$l of same buffer; incubation and washes repeated with 1.5, 2.0 and 10 mM (GlcNAc).
% RNA Eluted: percentage of input RNA eluted with (GlcNAc)3
% RNA Amplified: percentage of input RNA amplified; Rounds 1–5: entire eluted RNA sample amplified. Rounds 6–11: pooled 2 mM and 10 mM RNA, amplified for subsequent round. Rounds 9–11: 1.5 mM RNA amplified separately.

TABLE 2

Wheat Germ Agglutinin 2'NH$_2$ RNA Ligands

| Ligand | SEQ ID NO. | SEQUENCE |
|---|---|---|
| | | FAMILY 1 |
| 11.8 | 4 | AUGGUUGGCCUGGGCGCAGGCUUCGAAGACUCGGCGGGAA CGGGAAUGgcuccgcc |
| 11.4(3) | 5 | CAGGCACUG AAAACUCGGCGGGAA CG AAAG UAGUGCCGACUCAGACGCGU |
| 11.10 | 6 | AGUCUGGCCAAAGACUCGGCGGGAA CGUAAAACGGCCAGAAUU |
| 11.35 | 7 | GUAGGAGGUUCCAUCACC AGGACUCGGCGGGAA CG GAA GGUGAUGS |
| 11.5 | 8 | ACAAGGAUCGAUGGCGAGCCGGGGAGG GCUCGGCGGGAA CG AAA UCUgcuccgcc |
| 11.26 | 9 | UUGGGCAGGCAGAGCGAGACCGGGGCUCGGCGGGAA CG GAACAGGAAUcgcuccgcc |
| 11.19 | 10 | AAGGGAUGGGAUUGGGACGAGCGGCC AAGACUCGGCGGGAA CG AAG GGUcgcuccgcc |
| 11.15 | 11 | aaucauacac aagaCUCGGCGGGAA CG AAA GUGUCAUGGUAGCAAGUCCAAUGGUGGACUCUc |
| 11.34 | 12 | aaucauacac aagaCUCGGCGGGAA CGUGAA GUGGGUAGGUAGCUGAAGACGGUCUGGGCGCCA |

TABLE 2-continued

Wheat Germ Agglutinin 2'NH₂ RNA Ligands

| Ligand | SEQ ID NO. | SEQUENCE |
|---|---|---|
| 6.8 | 13 | AAGGGAUGGGAUUGGGACGAGCGGCC AAGACUCGGCGGGAA CG AAG GGUCCgcuccgcc |
| 6.9 | 14 | aaucauacaca agaCUCGGCGGGAA CG AAG UGUGUGAGUAACGAUCACUUGGUACUAAAAGCCC |
| 6.23 | 15 | aaucauacac aagaCUCGGCGGGAAUCG AAA GUGUACUGAAUUAGAACGUGGGCCUGCUCAUCGU |
| 6.26 | 16 | aaucauacaca agaCUCGGCGGGAAUCGUAA UGUGGAUGAUAGCACGAUGGCAGYAGUAGUCGGACCGC |
| 6.14 | 17 | aaucauacacaagaCAGCGGCGG AGUC A GUGAAAGCGUGGGGGGYGCGGGAGGUCUACCCUGAC |
| CON-SENSUS: | 56 | AAGACUCGGCGGGAA CG AAA |

FAMILY 2

| Ligand | SEQ ID NO. | SEQUENCE |
|---|---|---|
| 11.12 | 18 | CGGCUGUGUGUGGU AGCGUCAUAGUAGGAGUCGUCACGAACCAA GGCgcuccgcc |
| 11.24(2) | 19 | CGGCUGU GUGGUGUUGGAGCGUCAUAGUAGGAGUCGUCACGAACCAA GGCgcuccgcc |
| 11.27(2) | 20 | CGAUGCGAGGCAAGAA AUGGAGUCGUUACGAACCC UCUUGCAGUGCGCGc |
| 11.32 | 21 | CGUGCGGAGCAAAUAGGGGAUC AUGGAGUCGU ACGAACCGUUAUCGCcgcuccgcc |
| 11.6 | 22 | CUGGGGAGCAGGAUAUGAGAUGUGCGGGGCA AUGGAGUCGUGACGAACC gcuccgcc |
| CON-SENSUS: | 57 | GGAGUCGUGACGAACC |

FAMILY 3

| Ligand | SEQ ID NO. | SEQUENCE |
|---|---|---|
| 11.13 | 23 | GUCCGCCCCCAGGGAUGCAACGGGGUGGCUCUAAAAGGCUUGGCUAA |
| 11.23 | 24 | GAGAAUGAGCAUGGCCGGGGCAGGAAGUGGGUGGCAACGGAGGCCA |
| 6.3 | 25 | GAUACAGCGCGGGUCUAAAGACCUUGCCCCUAGG AUGCAACGGGGUGCGUCCGCC |
| 6.7 | 26 | UGAAGGGUGGUAAGAGAGAGUCUGAGCUCGUCCUAGGGAUGCAACGGCACGUCCGCC |
| 6.20 | 27 | CAAACCUGCAGUCGCGCGGUGAAACCUAGGGUUGCAACGGUACAUCGCUGUCGUCCGCC |
| 6.34 | 28 | GUGGACUGGAAUCUUCGAGGACAGGAACGUUCCUAGGGAUGCAACGGACCGUCCGCC |
| 6.35 | 29 | GUGUACCAAUGGAGGCAAUGCUGCGGGAAUGGAGGCCUAGGGAUGCAAC |
| 6.5 | 30 | GUCCCUAGGGAUGCAACGGGCAGCAUUCGCAUAGGAGUAAUCGGAGGUC |
| 6.16 | 31 | GCCUAGGGAUGCAACGGCGAAUGGAUAGCGAUGUCGUGGACAGCCAGGU |
| 6.19 | 32 | AUCGAACCUAGGGAUGCAACGGUGAAGGUUGUGAGGAUUCGCCAUUAGGC |
| 6.21 | 33 | GCUAGGGAUGCCGCAGAAUGGUCGCGGAUGUAAUAGGUGAAGAUUGUUGC |
| 6.25 | 34 | GGACCUAGGGAUGCAACGGUCCGACCUUGAUGCGCGGGUGUCCAAGCUAC |
| 6.33 | 35 | AAGGGAGGAGCUAGAGAGGGAAAGGUUACUACGCGCCAGAAUAGGAUGU |
| CON-SENSUS: | 58 | CCUAGGGAUGCAACGG |

FAMILY 4

| Ligand | SEQ ID NO. | SEQUENCE |
|---|---|---|
| 11.2 | 36 | CCAACGUA CAUCGCGAGCUGGUG GAGAGUUCAUGA GGGUGUUACGGGU |
| 11.33 | 37 | CCCAACGUGUCAUCGCGAGCUGGCG GAGAGUUCAUGA GGGU UACGGGU |
| 11.28 | 38 | GUUGGUGCGAGCUGGGGCGGCGA GAAGGUAGGCGGUCCGAGUGUU CGAAU |
| 11.7(4) | 39 | aCUGGCAAGRAGUGCGUGAGGGUACGUUAG GGGUGUU UGGGCCGAUCGCAU |
| CON-SENSUS: | 59 | RCUGG GAGRGU GGGUGUU |

FAMILY 5

| Ligand | SEQ ID NO. | SEQUENCE |
|---|---|---|
| 11.20(5) | 40 | UUGGUCGUACUGGACAGAGCCGUGGUAGAGGGAUUGGGACAAAGUGUCA |

FAMILY 6

| Ligand | SEQ ID NO. | SEQUENCE |
|---|---|---|
| 6.15 | 41 | UGUGAGAAAGUGGCCAACUUUAGGACGUCGGUGGACUGYCGGGUAGGCUC |
| 6.28 | 42 | CAGGCAGAUGUGUCUGAGUUCGUCGGAGUA GACGUCGGUGGAC GCGGAAC |

TABLE 2-continued

Wheat Germ Agglutinin 2'NH₂ RNA Ligands

| Ligand | SEQ ID NO. | SEQUENCE |
|---|---|---|
| CONSENSUS: | 60 | UGUGNNNNAGUNNNNNNNNNUA GACGUCGGUGGACNNNGCGG |

FAMILY 7

| Ligand | SEQ ID NO. | SEQUENCE |
|---|---|---|
| 6.24 | 43 | UGUGAUUAGGCAGUUGCAGCCGCC GU GCGGAGACGU GA CUCGAG GAUUC |
| 6.27 | 44 | UGCCGGUGGAAAGGCGGGUAGGU GA CCCGAG GAUUCCUACCAAGCCAU |
| 11.3 | 45 | GAGGUGRA UGGGAGAGUGGAGCCCGGGUGACUCGAGGAUUCCCGU |
| CONSENSUS: | 61 | GGGNNNGU GA CYCGRG GAYUC |

FAMILY 8

| Ligand | SEQ ID NO. | SEQUENCE |
|---|---|---|
| 6.2 | 46 | GUCAUGCUGUGGCUGAACAUACUGGUGAAAGUUCAGUAGGGUGGAUACAgcuccgcc |
| 6.6(2) | 47 | CCGGGGAUGGUGAGUCGGGCAGUGUGACCGAACUGGUGCCCGCUGAGAgcucc |
| CONSENSUS: | 62 | UGANCNNACUGGUGNNNGNGNAG |

FAMILY 9

| Ligand | SEQ ID NO. | SEQUENCE |
|---|---|---|
| 6.11 | 48 | ACACUAACCAGGUCUCU GAACGCGGGAC GGAGGUG UGGGCGAGGUGGAA |
| 6.13 | 49 | CCGUCUCCCGAGAACCAGGCAGAGGACGUGCUGAAGGAGCUG CAUCUAGAA |
| 6.17 | 50 | CCGUCUCC GAGAACCAGGCAGAGGAGGUGCUGAAGGRGCUGGCAUCUACAA |
| CONSENSUS: | 63 | GUCUCY GAACNNGGNA GGANGUGNUG GAGNUG |

ORPHANS

| Ligand | SEQ ID NO. | SEQUENCE |
|---|---|---|
| 6.1 | 51 | CCCGCACAUAAUGUAGGGAACAAUGUUAUGGCGGAAUUGAUAACCGGU |
| 6.4 | 52 | CGAUGUUAGCGCCUCCGGGAGAGGUUAGGGUCGUGCGGNAAGAGUGAGGU |
| 6.18 | 53 | GGUACGGGCGAGACGAGAUGGACUUAUAGGUCGAUGAACGGGUAGCAGCUC |
| 11.30 | 54 | CGGUUGCUGAACAGAACGUGAGUCUUGGUGAGUCGCACAGAUUGUCCU |
| 11.29 | 55 | ACUGAGUAAGGUCUGGCGUGGCAUUAGGUUAGUGGGAGGCUUGGAGUAGc |

TABLE 3

Dissociation Constants of RNA Ligands to WGA

| Ligand | SEQ ID NO: | Kd |
|---|---|---|
| Family 1 | | |
| 11.8 | 4 | 9.2 nM |
| 11.4 | 5 | 32 nM |
| 11.35 | 7 | 90 nM |
| 11.5 | 8 | 44 nM |
| 11.26 | 9 | 38 nM |
| 11.19 | 10 | 22 nM |
| 11.15 | 11 | 54 nM |
| 11.34 | 12 | 92 nM |
| 6.8 | 13 | 11 nM |
| 6.9 | 14 | 396 nM |
| 6.23 | 15 | 824 nM |
| 6.14 | 17 | <5% |
| Family 2 | | |
| 11.12 | 18 | 15.2 nM |
| 11.24 | 19 | 19.4 nM |
| 11.27 | 20 | 30 nM |
| 11.32 | 21 | 274 nM |
| 11.6 | 22 | 702 nM |
| Family 3 | | |
| 11.13 | 23 | <5% |
| 11.23 | 24 | <5% |
| 6.3 | 25 | 120 nM |
| 6.2 | 27 | <5% |
| 6.34 | 28 | <5% |
| 6.35 | 29 | <5% |
| 6.5 | 30 | 678 nM |
| 6.16 | 31 | <5% |
| 6.19 | 32 | 74 nM |
| Family 4 | | |
| 11.2 | 36 | 62 nM |
| 11.33 | 37 | <5% |
| 11.28 | 38 | 9.2 nM |
| 11.7 | 39 | 16 nM |
| Family 5 | | |
| 11.2 | 40 | 1.4 nM |
| Family 7 | | |
| 6.27 | 44 | 56 nM |
| 11.3 | 45 | 410 nM |
| Family 8 | | |
| 6.6 | 47 | <5% |

TABLE 3-continued

Dissociation Constants of RNA Ligands to WGA

| Ligand | SEQ ID NO: | Kd |
|---|---|---|
| | Family 9 | |
| 6.11 | 48 | <5% |
| | Orphans | |
| 11.3 | 54 | 56 nM |
| 11.29 | 55 | 32 nM |

The Kds of ligands that show <5% binding at 1 μM WGA is estimated to be >20 μM.

TABLE 4

Specificity of RNA Ligands to WGA

| | Kds for N-acetyl-glucosamine Binding Lectins | | |
|---|---|---|---|
| LECTIN | Ligand 6.8 (SEQ ID NO:13) | Ligand 11.20 (SEQ ID NO:40) | Ligand 11.24 (SEQ ID NO:19) |
| Triticum vulgare (WGA) | 11.4 nM | 1.4 nM | 19.2 nM |
| Canavalia ensiformis (Con A)** | <5%* | <5%* | <5%* |
| Datura stramonium | <5%* | 11.2 μM | <5%* |
| Ulex europaeus (UEA-II) | 4.4 μM | 2.2 μM | <5%* |

*Less than 5% binding at 1 μM protein; estimated Kd > 20 μM
**succinylated Con A

TABLE 5

INHIBITION OF RNA LIGAND BINDING TO WHEAT GERM AGGULTININ

| Ligand | SEQ ID NO: | Competitor | $IC_{50}$ (μM) | Max Inhib | $K_c$ (μM) |
|---|---|---|---|---|---|
| 6.8 | 13 | $(GlcNAc)_3$ | 95 | >95% | 10.9 |
| 11.20 | 40 | $(GlcNAc)_3$ | 120 | >95% | 8.4 |
| 11.24 | 19 | $(GlcNAc)_3$ | 120 | >95% | 19.4 |

$K_c$ is the dissociation constant of $(GlcNAc)_3$ calculated from these data, assuming competitive inhibition and two RNA ligand binding sites per dimer.

TABLE 6

INHIBITION OF WGA MEDIATED AGGLUTINATION OF SHEEP ERYTHROCYTES

| | | Inhibitory Concentration (μM) | |
|---|---|---|---|
| Inhibitor | SEQ ID NO: | Complete | Partial |
| 6.8 | 13 | 0.5 | 0.12 |
| 11.20 | 40 | 0.5 | 0.12 |
| 11.24 | 19 | * | 2 |
| $(GlcNAc)_3$ | | 8 | 2 |
| GlcNAc | | 780 | 200 |

* Complete inhibition of agglutination by ligand 11.24 was not observed in this experiment.

TABLE 7a

L-Selectin 2'NH$_2$-RNA SELEX at 4° C.

| SELEX Round # | Total RNA pmoles | Total Protein pmoles | RNA:LS-Rg Ratio | Bead Volume | Total Volume | % 5 mM EDTA Eluted RNA | % 50 mM EDTA Eluted RNA | Kd (nM) |
|---|---|---|---|---|---|---|---|---|
| Rnd 0 | | | | | | | | 10,000 |
| Rnd 1 | 1060 | 167.0 | 6.3 | 10 μL | ~100 μL | 0.498 | 0.301 | |
| Rnd 2 | 962 | 167.0 | 5.8 | 10 μL | ~100 μL | 0.306 | 0.114 | |
| Rnd 3 | 509 | 167.0 | 3.0 | 10 μL | ~100 μL | 1.480 | 0.713 | |
| Rnd 4 | 407 | 167.0 | 2.4 | 10 μL | ~100 μL | 5.010 | 1.596 | 434 |
| Rnd 5 | 429 | 167.0 | 2.6 | 10 μL | ~100 μL | 8.357 | 7.047 | |
| | 439 | 16.7 | 26.3 | 10 μL | ~100 μL | 0.984 | 0.492 | 133 |
| Rnd 6 | 452 | 167.0 | 2.7 | 10 μL | ~100 μL | 7.409 | 6.579 | |
| | 46 | 16.7 | 2.8 | 10 μL | ~100 μL | 3.468 | 1.312 | 37 |
| Rnd 7 | 43 | 16.7 | 2.6 | 10 μL | ~100 μL | 8.679 | 2.430 | |
| | 44 | 16.7 | 2.6 | 10 μL | ~100 μL | 7.539 | 2.358 | |
| | 22 | 4.2 | 5.2 | 10 μL | ~100 μL | 2.748 | 1.298 | |
| Rnd 8 | 43 | 16.7 | 2.6 | 10 μL | ~100 μL | 8.139 | 1.393 | 33 |
| | 23 | 4.2 | 5.5 | 10 μL | ~100 μL | 2.754 | 0.516 | |
| Rnd 9 | 23 | 4.2 | 5.5 | 10 μL | ~100 μL | 4.352 | 0.761 | |
| Rnd 10 | 21 | 4.2 | 5.0 | 10 μL | ~100 μL | 6.820 | 1.123 | 13 |
| | 23 | 8.4 | 2.7 | 50 μL | ~150 μL | 14.756 | 1.934 | |
| Rnd 11 | 30 | 10.5 | 2.9 | 250 μL | ~500 μL | 0.707 | 0.033 | |
| Rnd 12 | 12 | 10.5 | 1.1 | 250 μL | ~500 μL | 3.283 | 0.137 | |
| Rnd 13 | 7 | 1 | 7 | 250 μL | ~500 μL | 4.188 | 0.136 | 0.3 |
| Rnd 14 | 9 | 1 | 9 | 250 μL | ~500 μL | 4.817 | 0.438 | 0.7 |

L-Selectin Rg was immobilized on Protein A Sepharose 4 Fast Flow. Protein A density is approximately 6 mg/ml drained gel (143 μM).
RNA Loading Conditions:

TABLE 7a-continued

L-Selectin 2'NH$_2$-RNA SELEX at 4° C.

| SELEX Round # | Total RNA pmoles | Total Protein pmoles | RNA:LS-Rg Ratio | Bead Volume | Total Volume | % 5 mM EDTA Eluted RNA | % 50 mM EDTA Eluted RNA | Kd (nM) |
|---|---|---|---|---|---|---|---|---|

All selections were carried out in the cold room. The RNA used in each selection was first incubated for 30 minutes with 100 μL Protein A Sepharose in the cold room on a roller. Only RNA which flowed through this column was used on the LS-Rg selection column. The RNA was incubated on the selection column for 90 minutes on a roller before being washed extensively with binding buffer (20 mM HEPES pH 7.4 150 mM NaCl, 1 mM MgCl$_2$, 1 mM CaCl$_2$.)
RNA Elution Conditions:
RNA was eluted by incubating the extensively-washed columns in 100 μL of HEPES buffered EDTA (pH 7.4) for 30 minutes on a roller followed by three 1.00 μL HEPES buffered EDTA washes.

TABLE 7b

L-Selectin 2'NH$_2$-RNA SELEX at Room Temperature

| SELEX Round # | Total RNA pmoles | Total Protein pmoles | RNA:LS-Rg Ratio | Bead Volume | Total Volume | % 5 mM EDTA Eluted RNA | % 50 mM EDTA Eluted RNA | Kd (nM) |
|---|---|---|---|---|---|---|---|---|
| Rnd 7 | 43 | 10.0 | 4.3 | 10 μL | ~100 μL | 1.205 | 0.463 | |
| Rnd 8 | 35 | 10 | 3.5 | 10 μL | ~100 μL | 6.642 | 0.401 | |
|  | 35 | 10 | 3.5 | 10 μL | ~100 μL | 5.540 | 0.391 | |
| Rnd 9 | 24 | 2.5 | 9.6 | 10 μL | ~100 μL | 1.473 | 0.383 | 13 |
| Rnd 10 | 30 | 6.3 | 4.9 | 250 μL | ~500 μL | 0.707 | 0.033 | |
| Rnd 11 | 12 | 6.3 | 1.9 | 250 μL | ~500 μL | 3.283 | 0.134 | |
| Rnd 12 | 6 | 0.6 | 9.4 | 250 μL | ~500 μL | 0.877 | 0.109 | 0.3 |
| Rnd 13 | 1 | 0.6 | 1.4 | 250 μL | ~500 μL | 5.496 | 0.739 | 0.7 |

L-Selectin Rg was immobilized on Protein A Sepharose 4 Fast Flow. Protein A density is approximately 6 mg/ml drained gel (143 μM).
RNA Loading Conditions:
Selections were carried out at room temperature. The RNA used in each selection was first incubated for 30 minutes with 100 μL Protein A Sepharose at room temp. Only RNA which flowed through this column was used on the LS-Rg selection column. The RNA was incubated on the selection column for 90 minutes on a roller before being washed extensively with binding buffer (20 mM HEPES pH 7.4 150 mM NaCl, 1 mM MgCl$_2$, 1 mM CaCl$_2$.)
RNA Elution Conditions:
RNA was eluted by incubating the extensively-washed columns in 100 μL of HEPES buffered EDTA (pH 7.4) for 30 minutes on a roller followed by three 100 μL HEPES buffered EDTA washes.

TABLE 8

L-Selectin 2'NH$_2$ RNA LIGANDS

| Ligand | SEQ ID NO. | Sequences |
|---|---|---|
| | | Family I |
| F13.32(5) | 67 | CGCGUAUGUGUGAAAGCGUGUGCACGGAGGCGU-CUACAAU |
| 6.60(2) | 68 | GGCAUUGUGUGAAUAGCUGAUCCCACAGGUAACAACAGCA |
| 6.50 (3) | 69 | UAAUGUGUGAAUCAAGCAGUCUGAAUAGAUUAGACAAAAU |
| 6.79 | 70 | AUGUGUGAGUAGCUGAGCGCCCGAGUAUGAWACCUGACUA |
| F14.9 | 71 | AAACCUUGAUGUGUGAUAGAGCAUCCCCCAGGCGACGUAC |
| F14.21 | 72 | UUGAGAUGUGUGAGUACAAGCUCAAAAUCCCGUUGGAGG |
| F14.25 | 73 | UAGAGGUAGUAUGUGUGGGAGAUGAAAAUACUGUGGAAAG |
| F13.48(2) | 74 | AAAGUUAUGAGUCCGUAUAUCAAGGUCGACAUGUGUGAAU |
| 6.71 | 75 | CACGAAAAACCCGAAUUGGGUCGCCCAUAAGGAUGUGUGA |
| 6.28 | 76 | GUAAAGAGAUCCUAAUGGCUCGCUAGAUGUGAUGUGAAAC |
| CONSENSUS: | 118 | AUGUGUGA |
| | | Family II |
| F14.20(26) | 77 | UAACAA CAAUCAAGGCGGGUUCACCGCCCCAGUAUGAGUG |

TABLE 8-continued

L-Selectin 2'NH$_2$ RNA LIGANDS

| Ligand | SEQ ID NO. | Sequences |
|---|---|---|
| F14.12(22) | 78 | UAACAA CAAUCAAGGCGGGUUYACCGCCCCAGUAUGAGUA |
| F14.11(12) | 79 | UAACAA CAAUCAAGGCGGGUUYACCGCUCCAGUAUGAGUA |
| F13.45(9) | 80 | UAACAA CAAUCAAGGCGGGUUCACCGCCCCAGUAUGAGUG |
| 6.80 | 81 | ACCAAGCAAUCUAU GGUCGAACGCUACA CAUGAAUGACGUc |
| CONSENSUS: | 119 | CAA CAAUC AUGAGUR |

Family III

| | | |
|---|---|---|
| 6.17 | 82 | GAACAUGAAGUAAUCAAAGUCGUACC AAUAUACAGGAAGC |
| 6.49 | 83 | GAACAUGAAGUAAGAC CGUCAC AAUUCGAAUGAUUGAAUA |
| 6.16 | 84 | GAAQAUGAAGUAAAA AGUCGACG AAUUAGCUGUAACCAAAA |
| 6.37 | 85 | GAACAUGAAGUAAA AGUCUG AGUUAGUAAAUUACAGUGAU |
| 6.78 | 86 | GAACUUGAAGUUGA ANUCGCUAA GGUUAUGGAUUCAAGAUU |
| 6.26 | 87 | AACAUGAAGUAAUA AGUC GACGUAAUUAGCUGUAACUAAA |
| 6.40 | 88 | AACAUGAAGUAAA AGUCUG AGUUAGAAAUUACAAGUGAU- |
| F13.57 | 89 | UAACAUAAAGUAGCG CGUCUGUGAGAGGAAGUGCCUGGAU |
| CONSENSUS: | 120 | AACAUGAAGUA AGUC ARUUAG |

Family IV

| | | |
|---|---|---|
| 6.58 | 90 | AUAGAACCGCAAGGAUAACCUCGACCGUGGUCAACUGAGA |
| 6.69 | 91 | UAAGAACCGCUAGCGCACGAUCAAACAAAGAGAAACAAA- |
| CONSENSUS: | 121 | AGAACCGCWAG |

Family V

| | | |
|---|---|---|
| 6.56 | 92 | UUCUCUCCAAGAACYGAGCGAAUAAACSACCGGASUCACA |
| F13.55 | 93 | UGUCUCUCCUGACUUUUAUUCUUAGUUCGAGCUGUCCUGG |
| CONSENSUS: | 122 | UCUCUCC |

Family VI

| | | |
|---|---|---|
| F14.27 | 94 | CCGUACAUGGUAARCCU CGAAGGAUUCCCGGGAUGAUCCC |
| F14.53 | 95 | UCCCAGAGUCCCGUGAUGCGAAGAAUCCAUUAGUACCAGA |
| CONSENSUS: | 123 | CGAAGAAUYC |

Family VII

| | | |
|---|---|---|
| F13.42 | 96 | GAUGUAAAUGACAAAUGAACCUCGAAAGAUUGCACACUC |
| F13.51 | 97 | AUGUAAAUCUAGGCAGAAACGUAGGGCAUCCACCGCAACGA |
| CONSENSUS: | 124 | AUGUAAAU |

Family VIII

| | | |
|---|---|---|
| 6.33(11) | 98 | AUAACCCAAGCAGCNUCGAGAAAGAGCUCCAUAGAUGAU |
| E.41 | 99 | CAAAGCACGCGUAUGGCAUGAAACUGGCANCCCAAGUAAG |
| CONSENSUS: | 125 | AACCCAAG |

Family IX

| | | |
|---|---|---|
| F13.46(4) | 100 | CAAAAGGUUGACGUAGCGAAGCUCUCAAAAUGGUCAUGAC |

Family X

| | | |
|---|---|---|
| F14.2 | 101 | AAGUGAAGCUAAAGCGGAGGG CCAUUCAGUUUCNCACCA |
| F14.13(2) | 102 | AAGUGAAGCUAAAGSGGAGGG CCACUCAGAAACGCACCA |

Family XI

| | | |
|---|---|---|
| 6.72(2) | 103 | CACCGCUAAGCAGUGGCAUAGCCCAGUAACCUGUAAGAGA |

TABLE 8-continued

L-Selectin 2'NH₂ RNA LIGANDS

| Ligand | SEQ ID NO. | Sequences |
|---|---|---|
| 6.42 | 104 | CAC-GCUAAGCAGUGGCAUAGC---GWAACCUGUAAGAGA |
| | | Family XII |
| 6.30(5) | 105 | AGAUUACCAUAACCGCGUAGUCGAAGACAUAUAGUAGCGA |
| | | Family XIII |
| 6.52(2) | 106 | ACUCGGGUAGAACGCGACUUGCCACCACUCCCAUAAAGAC |
| | | Orphans |
| 6.14 | 107 | UCAGAACUCUGCCGCUGUAGACAAAGAGGAGCUUAGCGAA |
| 6.36 | 108 | AAUGAGCAUCGAGAGAGCGCGAACUCAUCGAGCGUACUAA |
| 6.41 | 119 | CAAAGCACGCGUAUGGCAUGAAACUGGCANCCCAAGUAAG |
| 6.44 | 110 | GAUGCAGCAACCUGAAAACGGCGUCCACAGGUAAUAACAG |
| 6.70 | 111 | AAACUCGCUACAAACACCCAAUCCUAGAACGUUAUGGAGA |
| 6.76 | 112 | CUAGCAUAGCCACCGGAACAGACAGAUACGAGCACGAUCA |
| 6.89 | 113 | GAUUCGGAGUACUGAAAAACAACCCUCAAAAGUGCAUAGG |
| 6.81 | 114 | GUCCAGGACGGACCGCAGCUGUGAUACAAUCGACUUACAC |
| 6.70 | 115 | AAACUCGCUACAAACACCCAAUCCUAGAACGUUAUGGAGA |
| F13.59 | 116 | CGGCCCUUAUCGGAGGUCUGCGCCACUAAUUACAUCCAC |
| F14.70 | 117 | UCCAGAGCGUGAAGAUCAACGUCCCGGNGUCGAAGA |

TABLE 9

Dissociation Constants of 2'NH₂ RNA Ligands to L-Selectin*

| Ligand | SEQ ID NO: | 4° C. | Rm Temp |
|---|---|---|---|
| Family I | | | |
| F13.32 | 67 | 15.7 nM | 14.9 nM |
| F13.48 | 74 | 15.9 nM | 9.2 nM |
| F14.9 | 71 | 8.2 nM | 15.4 nM |
| F14.21 | 72 | 2.3 nM | 15.9 nM |
| F14.25 | 73 | 1300 nM | |
| Family II | | | |
| F14.12 | 78 | 5.8 pM | 1.7 nM |
| | | (0.68) | (0.62) |
| | | 16.2 nM | 94 nM |
| F14.20 | 77 | 58 pM | 1.0 nM |
| | | (0.68) | (0.28) |
| | | 60 nM | 48 nM |
| Family III | | | |
| F13.57 | 89 | 3.0 nM | 75 nM |
| Family V | | | |
| F13.55 | 93 | 62 pM | 1.5 nM |
| Family VI | | | |
| F14.53 | 95 | 97 pM | 142 nM |
| | | (0.65) | |
| | | 14.5 nM | |
| F14.27 | 94 | 145 nM | |
| Family VII | | | |
| F13.42 | 96 | 2.0 nM | 5.5 nM |
| F13.51 | 97 | 8.8 nM | 18 nM |
| Family X | | | |
| F14.2 | 101 | 1.8 nM | 7.2 nM |
| F14.13 | 102 | 1.3 nM | |
| | | (0.74) | |
| | | 270 nM | |
| Orphans | | | |
| F13.59 | 116 | <5% | <5% |
| F14.70 | 117 | 2.0 nM | 7.8 nM |
| | | (0.75) | (0.58) |
| | | 254 nM | 265 nM |

*Kds of monophasic binding ligands are indicated by a single number; the high affinity $K_d$ (ie., $K_{d1}$), the mole fraction binding with $K_{d1}$, and the low affinity $K_d$ (ie., $K_2$) are presented for biphasic binding ligands.

TABLE 10

Specificity of 2'NH₂ RNA Ligands to L-Selectin*

| Ligand | SEQ ID NO: | LS-Rg | ES-Rg | PS-Rg | CD22-Rg |
|---|---|---|---|---|---|
| Family I | | | | | |
| F13.32 | 67 | 15.7 nM | <5% | 17 μM | <5% |
| F13.48 | 74 | 15.9 nM | <5% | 720 μM | <5% |
| F14.9 | 71 | 8.2 nM | <5% | | <5% |
| F14.21 | 72 | 2.3 nM | 2.6 μM | | <5% |
| F14.25 | 73 | 1300 nM | | | |

TABLE 10-continued

Specificity of 2'NH$_2$ RNA Ligands to L-Selectin*

| Ligand | SEQ ID NO: | LS-Rg | ES-Rg | PS-Rg | CD22-Rg |
|---|---|---|---|---|---|
| Family II |
| F14.12 | 78 | 60 pM | 47 nM | 910 nM | <5% |
| F14.20 | 77 | 58 pM (0.68) 60 nM | 70 nM | | <5% |
| Family III |
| F13.57 | 89 | 3.0 nM | 2.7 μM | | <5% |
| Family V |
| F13.55 | 93 | 62 pM | 49 nM | 5.8 μM | <5% |
| Family VI |
| F14.53 | 95 | 97 pM (0.65) 14.5 nM | 355 nM | 5.2 μM | <5% |
| Family VII |
| F13.42 | 96 | 2.0 nM | 4.4 μM | | <5% |
| F13.51 | 97 | 8.8 nM | 2.0 μM | | |
| Family X |
| F14.2 | 101 | 1.8 nM | 1.9 μM | 450 nM | <5% |
| Orphans |
| F13.59 | 116 | <5% | <5% | | <5% |
| F14.70 | 117 | 2.0 nM (0.75) 254 nM | 5.9 μM | | <5% |

*Dissociation constants were determined at 4° C. in HSMC buffer. When <5% binding was observed at the highest protein concentration, the Kd is estimated to be >20 μM.

TABLE 11

L-SELECTIN ssDNA SELEX

| Round | Temp. | Total DNA pmol | Total Prot. pmol | DNA:Protein | Bead Vol. | Total Vol. | % Eluted 2 mM EDTA | % Eluted 50 mM EDTA | Kd, nM 4 degrees | signal:bkgd 2 mM |
|---|---|---|---|---|---|---|---|---|---|---|
| Rnd 0 | | | | | | | | | 10,000 | |
| Rnd 1 | 4 | 930 | 167 | 5.6 | 10 μL | ~100 μL | n/a | 5.5 | | 50 |
| Rnd 2 | 25 | 400 | 167 | 2.4 | 10 μL | ~100 μL | n/a | 2.19 | | 12 |
| Rnd 3 | 25 | 460 | 167 | 2.8 | 10 μL | ~100 μL | n/a | 2.55 | | 25 |
| Rnd 4 | 25 | 100 | 16.7 | 6 | 10 μL | ~100 μL | 0.35 | 0.29 | | 1.3 |
| Rnd 5 | 25 | 100 | 16.7 | 6 | 10 μL | ~100 μL | 0.23 | 0.08 | 967 | 3 |
| Rnd 6 | 25 | 1000 | 167 | 60 | 10 μL | ~100 μL | 1.42 | 0.38 | | 4 |
| Rnd 7 | 25 | 100 | 16.7 | 6 | 10 μL | ~100 μL | 6.9 | 0.93 | 60 | 18 |
| Rnd 8 | 37 | 100 | 16.7 | 6 | 10 μL | ~100 μL | 1.9 | 0.31 | | 9 |
| Rnd 9 | 25 | 10 | 1.67 | 6 | 10 μL | ~100 μL | 0.5 | 0.16 | 2.1 | 1.6 |
| Rnd 10 | 25 | 10 | 1.67 | 6 | 10 μL | ~100 μL | 2.2 | 0.57 | | 5 |
| Rnd 11 | 25 | 2.5 | 0.42 | 6 | 10 μL | ~100 μL | 0.37 | 0.07 | 1.3 @ 25° C. | 8 |
| Rnd 12 | 25 | 2.5 | 0.42 | 6 | 10 μL | ~100 μL | 0.86 | 0.13 | | 11 |
| Rnd 13 | 37 | 2.5 | 0.42 | 6 | 10 μL | ~100 μL | 0.7 | 0.35 | 0.44 @ 25° C. | 5 |
| Rnd 14 | 25 | 5 | 0.84 | 6 | 50 μL | ~100 μL | 2.8 | 0.76 | | 4 |
| Rnd 15 | 25 | 1.25 | 0.21 | 6 | 50 μL | ~100 μL | 1.7 | 0.5 | 0.16 @ 25° C. | 7 |

Binding Buffer, Rounds 1–9    10 mM HEPES, pH at room temp w/NaOH to 7.4
100 mM NaCl
1 mM MgCl$_2$
1 mM CaCl$_2$
5 mM KCl
Elution Buffers: replace divalent cations with EDTA

TABLE 12

L-Selectin ssDNA Ligands

| Ligand | SEQ ID NO | SEQUENCE |
|---|---|---|
| Family 1 | | |
| LD204(3) | 129 | GGAACACGTGAG<u>GTTTAC</u> AAGGCACTCGAC <u>GTAAACACTT</u> |
| LD145 | 130 | CCCCGAAGAAC<u>ATTTTAC</u> AAGGTGCTAAAC <u>GTAAAATCAG</u> |
| LD183(2) | 131 | GGCATCCCTGAGT<u>CATTAC</u> AAGGTTCTTAAC <u>GTAATGTAC</u> |

TABLE 12-continued

L-Selectin ssDNA Ligands

| Ligand | SEQ ID NO | SEQUENCE |
|---|---|---|
| LD230(2) | 132 | TGCACACCTGAGGGTTAC AAGGCGCTAGAC GTAACCTCTC |
| LD208(7) | 133 | CACGTTTC AAGGGGTTACAC GAAACGATTCACTCCTTGGC |
| LD227(5) | 134 | CGGACATGAGCGTTAC AAGGTGCTAAAC GTAACGTACTT |
| LD112 | 135 | CGCATCCACATAGTTC AAGGGGCTACAC GAAATATTGCA |
| LD137 | 136 | TACCCCTTGgGCCTCATAGAC AAGGTCTTAAAC GTTAGC |
| LD179(2) | 137 | CACATGCCTGACGCGGTAC AAGGCCTGG AC GTAACGTTG |
| LD182 | 138 | TAGTGCTCCACGTATTC AAGGTGCTAAAC GAAGACGGCCT |
| LD190 | 139 | AGCGATGC AAGGGGCTACAC GCAACGATTTAGATGCTCT |
| LD193(2) | 140 | CCAGGAGCACAGTAC AAGGTGTTAAAC GTAATGTCTGGT |
| LD199 | 141 | ACCACACCTGGGCGGTAC AAGGAGTTATCC GTAACGTGT |
| LD201(2) | 142 | CAAGGTAACCAGTAC AAGGTGCTAAAC GTAATGGCTTCG |
| LD203 | 143 | ACCCCCGACCCGAGTAC AAGGCATTCGAC GTAATCTGGT |
| LD207 | 144 | CAGTAC AAGGTGTTAAAC GTAATGCCGATCGAGTTGTAT |
| LD216 | 145 | ACAACGAGTAC AAGGAGATAGAC GTAATCGGCGCAGGTATC |
| LD233(5) | 146 | CACGACAGAGAAC AAGGCGTTAGAC GTTATCCGACCACG |
| LD191 | 147 | AGGGAGAAC AAGGTGCTAAAC GTTTATCTACACTTCACCT |
| LD128(3) | 148 | AGGACC AAGGTGTTAAAC GGCTCCCCTGGCTATGCCTCTT |
| LD111(2) | 149 | gcTACAC AAGGTGCTAAAC GTAGAGCCAGATCGGATCTGAGC |
| LD139 | 150 | GGAC AAGGCACTCGAC GTAGTTTATAACTCCCTCCGGgCC |
| LD237 | 151 | gcTACAC AAGGGGCCAAAC GGAGAGCCAGACGCGGATCTGACA |
| LD173 | 152 | CGGCTATAC NNGGTGCTAAAC GCAGAGACTCGATCAACA |
| LD209 | 153 | GAGTAGCC AAGGCGTTAGAC GGAGGGGGAATGGAAGCTTG |
| LD221 | 154 | GAGTAGCC AAGGCGTTAGAC GGAGGGGGAATGG |
| LD108 | 155 | GAGTAGCC AAGGCGTTAGAC GGAGGGGGAATGTGAGCACA |
| LD141 | 156 | TAGCTCCACACAC AASSCGCRGCAC ATAGGGGATATCTGG |
| LD539 | 175 | CGGCAGGGCACTAAC AAGGTGTTAAAC GTTACGGATGCC |
| LD547 | 176 | TGCACACCGGCCCACCCGGAC AAGGCGCTAGAC GAAATGACTCTGTTCTG |
| LD516 | 177 | GACGAAGAGGCC AAGGTGATAACC GGAGTTTCCGTCCGC |
| LD543 | 178 | AAGGACTTAGCTATCC AAGGCACTCGAC GAAGAGCCCGA |
| LD545 | 179 | ATGCCCAGTTC AAGGTTCTGACC GAAATGACTCTGTTCTG |
| Truncates | | |
| LD201T1 | 185 | tagcCAAGGTAACCAGTAC AAGGTGCTAAAC GTAATGGCTTCGgcttac |
| LD201T3 | 186 | GTAACCAGTAC AAGGTGCTAAAC GTAATGGCTTCGgcttac |
| LD201T4 | 187 | CCAGTAC AAGGTGCTAAAC GTAATGG |
| LD201T10 | 188 | CGCGGTAACCAGTAC AAGGTGCTAAAC GTAATGGCGCG |
| LD201T12 | 189 | GCGGTAACCAGTAC AAGGTGCTAAAC GTAATGGCGC |
| LD227t5 | 190 | ACATGAGCGTTAC AAGGTGCTAAAC GTAACGTACTTgcttactctcatgt |
| LD227x1 | 191 | cgcGCGTTAC AAGGTGCTAAAC GTAACGTACTTgcttactcgcg |
| LD227t1 | 192 | GCGTTAC AAGGTGCTAAAC GTAACGT |

TABLE 12-continued

L-Selectin ssDNA Ligands

| Ligand | SEQ ID NO | SEQUENCE |
|---|---|---|
| Nx288 | 193 | dt<sub>a</sub>tagcCAAGGTAACCAGTAC AAGGTGCTAAAC GTAATGGCTTCGgcttact [3'3']t |
| Nx303 | 196 | dt<sub>a</sub>CCAGTAC AAGGTGCTAAAC GTAATGGt[3'3']t |
| Consensus: | 181 | TAC AAGGYGYTAVAC GTA |
| *Family 2* | | |
| LD181(3) | 157 | CAT CAAGGACTTTGCCCGAAACCCTAGGTTCACG TGTGGG |
| *Family 4* | | |
| LD174(2) | 158 | CATTCACCATGGCCCCTTCCTACGTATGTTCTGCGGGTG |
| LD122 | 159 | GCAACGTGGCCCCGTT TAGCTCATTTGACCGTTCCATCCG |
| LD239 | 160 | CCACAGACAATCGCAGTCCCCGTG TAGCTCTGGGTGTCT |
| LD533 | 180 | GCAGCGTGGCCCTGTT TAGCTCATTTGACCGTTCCATCCG |
| Truncates | | |
| LD174t1 | 194 | tagcCATTCACCATGGCCCCTTCCTACGTATGTTCTGCGGGTGgcttta |
| Consensus: | 182 | GGCCCCGT |
| *Family 5* | | |
| LD109 | 161 | CCACCGTGATGCACGATACATGAGGGTGTGTCAGCGCAT |
| LD127 | 162 | CGAGGTAGTCGTTATAGGGTGCGCACGACACACAGCGGTRG |
| Consensus: | 183 | RCACGAYACA |
| *Family 6* | | |
| LD196 | 163 | TGGCGGTACGGGCCGTGCACCCACTTACCTGGGAAGTGA |
| LD229 | 164 | CTCTGCTTACCTCATGTAGTTCCAAGCTTGGCGTAATCATG |
| Truncate | | |
| LD196t1 | 195 | agcTGGCGGTACGGGCCGTGCACCCACTTACCTGGGAAGTGAgctta |
| Consensus: | 184 | CTTACCT |
| *Family 7* | | |
| LD206(2) | 165 | AGCGTTGT ACGGGGTTACAC ACAACGATTTAGATGCTCT |
| Orphans | | |
| LD214 | 166 | TGATGCGACTTTAGTCGAACGTTACTGGGGCTCAGAGGACA |
| LD102 | 167 | CGAGGATCTGATACTTATTGAACATAMCCGCACNCAGGCTT |
| LD530 | 168 | CGATCGTGTGTCATGCTACCTACGATCTGACTA |
| LD504 | 169 | GCACACAAGTCAAGCATGCGACCTTCAACCATCGACCCGA |
| LD509 | 170 | ATGCCAGTGCAGGCTTCCATCCATCAGTCTGACANNNNNN |
| LD523 | 171 | CACTTCGGCTCTACTCCACCTCGGTCCTCCACTCCACAG- |
| LD527 | 172 | CGCTAACTGACCCTCGATCCCCCAAGCCATCCTCATCGC |
| LD541 | 173 | ATCTGACTAGCTCGGCGAGAGTACCCGCTCATGGCTTCGGCGAATGCCCT |
| LD548 | 174 | TCCTGAGACGTTACAATAGGCTGCGGTACTGCAACGTGGA |

TABLE 13

Dissociation Constants of ssDNA Ligands to L-Selectin

| Ligand | SEQ ID NO: | Room Temperature | 37° C. |
|---|---|---|---|
| *Family 1* | | | |
| LD111 | 149 | 330 pM | 11.8 nM |
| LD128 | 148 | 310 pM | 1.8 nM |
| LD108 | 155 | 160 pM | 8.5 nM |
| LD112 | 135 | 300 pM | 23.2 nM |
| LD137 | 136 | 520 pM | 0.65 nM |
| LD139 | 150 | 210 pM | 6.8 nM |

TABLE 13-continued

Dissociation Constants of ssDNA Ligands to L-Selectin

| Ligand | SEQ ID NO: | Room Temperature | 37° C. |
|---|---|---|---|
| LD145 | 130 | 920 pM | 8.8 nM |
| LD179 | 137 | 180 pM | 590 pM |
| LD182 | 138 | 130 pM | 2.0 nM |
| LD183 | 131 | 170 pM | 1.0 nM |
| LD193 | 140 | 88 pM | 970 pM |
| LD201 | 142 | 110 pM | 1.2 nM |
| LD204 | 129 | 100 pM | 3.7 nM |
| LD208 | 155 | 110 pM | 380 pM |
| LD227 | 134 | 43 pM | 160 pM |
| LD230 | 132 | 57 pM | 260 pM |
| LD233 | 146 | 110 nM | 380 pM |
| Family 2 | | | |
| LD181 | 157 | 84 pM | 1.8 nM |
| Family 4 | | | |
| LD122 | 159 | 1.8 nM | 2.1 nM |
| LD174 | 158 | 43 pM | 370 pM |
| LD239 | 160 | 170 pM | 1.6 nM |
| Family 5 | | | |
| LD109 | 161 | 190 pM | 9.6 nM |
| LD127 | 162 | 1.0 nM | 890 pM |
| Family 6 | | | |
| LD196 | 163 | 130 pM | 3.4 nM |
| Family 7 | | | |
| LD206 | 165 | 330 pM | 6.0 nM |
| Orphans | | | |
| LD102 | 167 | not determined | 7.9 nM |
| LD214 | 166 | 660 pM | 8.4 nM |
| Round 15 Pool | | 160 pM | 660 pM |
| LD201T1* | | | 4.8 nM |
| LD201T3* | | | 43 nM |

*LD201T1 and LD201T3 were made by solid state synthesis; the Kd of the synthetic full length LD201 control was 3.8 nM while that of enzymatically synthesized LD201 was 1.8 nM.

TABLE 14

Specificities of ssDNA Ligands to L-Selectin*

| Ligand | SEQ ID NO: | LS-Rg | ES-Rg | PS-Rg |
|---|---|---|---|---|
| Family 1 | | | | |
| LD111 | 149 | 1.1 nM | 1.2 μM | 840 nM |
| LD201 | 142 | 110 nM | 37 nM | 1.0 μM |
| LD204 | 129 | 450 pM | 1.5 μM | 2.9 μM |
| LD227 | 134 | 64 pM | 33 nM | 560 nM |
| LD230 | 132 | 44 pM | 19 nM | 600 nM |
| LD233 | 146 | 120 pM | 39 nM | 420 nM |
| Family 2 | | | | |
| LD181 | 157 | 200 pM | 37 nM | 1.6 μM |
| Family 4 | | | | |
| LD122 | 159 | 340 pM | 400 nM | 420 nM |
| LD174 | 158 | 46 pM | 28 nM | 380 nM |
| Family 5 | | | | |
| LD127 | 162 | 250 pM | 1.3 μM | 780 nM |
| Family 6 | | | | |
| LD196 | 163 | 220 pM | 50 nM | 34 μM |
| Family 7 | | | | |
| LD206 | 165 | 120 pM | 100 nM | 600 nM |

*Kds were determined at room temperature. In assays with 700 nM CD22 β-Rg and 1.4 μM WGA less than 1% and 3% binding, respectively, was observed for all ligands suggesting that the dissociation constants are greater than 100 μM for these proteins.

TABLE 15

Summary of Selection Conditions and Results from 2'F RNA Human L-selectin SELEXes

| SELEX Round | Total RNA pmoles | Total Protein pmoles | Temp., Time, Vol. | % Bound LS-Rg Sites | % 5 mM EDTA Eluted | EDTA Signal/ Bkgnd | Kd (nM) |
|---|---|---|---|---|---|---|---|
| 30n7 2'Fluro SELEX | | | | | | | |
| 1 | 630 | 100 | 37° C. 15' 10 μl | 0.7 | 0.1 | 20 | |
| 2 | 656 | 100 | 37° C. 15' 10 μl | 2.8 | 0.4 | 24 | |
| 3 | 608 | 100 | 37° C. 15' 10 μl | 11.6 | 1.9 | 68 | 10000 |
| 4 | 193 | 20 | 37° C. 15' 10 μl | 7.4 | 0.8 | 24 | |
| 5 | 193 | 20 | 37° C. 15' 10 μl | 19.7 | 2.1 | 17 | 850 |
| 6 | 86 | 10 | 37° C. 15' 10 μl | 15.7 | 1.9 | 8 | 360 |
| 7 | 17 | 2 | 37° C. 15' 10 μl | 12.1 | 1.4 | 3 | |
| 8 | 17 | 2 | 37° C. 15' 10 μl | 55.1 | 6.6 | 2 | |
| 9 | 19 | 2 | 37° C. 15' 10 μl | 40.1 | 4.2 | 4 | |
| 10 | 18 | 2 | 37° C. 15' 10 μl | 28.4 | 3.3 | 3 | 3 |
| 11 | 103 | 12.5 | 37° C. 15' 50 μl | 647.7 | 8.3 | 65 | |
| 11 | 27 | 2.5 | 37° C. 15' 50 μl | 63.1 | 5.9 | 3 | 0.5 |
| 12 | 89 | 5 | 37° C. 15' 50 μl | 53.2 | 3.0 | 7 | |
| 12 | 79 | 5 | 37° C. 15' 50 μl | 54.8 | 3.5 | 65 | 0.4 |
| 40n7 2'Fluro SELEX | | | | | | | |
| 1 | 677 | 100 | 37° C. 15' 10 μl | 1.8 | 0.3 | 31 | |

TABLE 15-continued

Summary of Selection Conditions and Results from
2'F RNA Human L-selectin SELEXes

| SELEX Round | Total RNA pmoles | Total Protein pmoles | Temp., Time., Vol. | % Bound LS-Rg Sites | % 5 mM EDTA Eluted | EDTA Signal/ Bkgnd | Kd (nM) |
|---|---|---|---|---|---|---|---|
| 2 | 659 | 100 | 37° C. 15' 10 µl | 5.8 | 0.9 | 19 | |
| 3 | 499 | 100 | 37° C. 15' 10 µl | 9.6 | 1.9 | 25 | 10000 |
| 4 | 187 | 20 | 37° C. 15' 10 µl | 4.3 | 0.5 | 7 | |
| 5 | 179 | 20 | 37° C. 15' 10 µl | 19.7 | 2.2 | 8 | 1024 |
| 6 | 89 | 10 | 37° C. 15' 10 µl | 17.7 | 2.0 | 12 | 240 |
| 7 | 19 | 2 | 37° C. 15' 10 µl | 17.3 | 1.8 | 2 | |
| 8 | 17 | 2 | 37° C. 15' 10 µl | 78.9 | 10.4 | 5 | |
| 9 | 19 | 2 | 37° C. 15' 10 µl | 36.5 | 4.1 | 3 | |
| 10 | 18 | 2 | 37° C. 15' 10 µl | 14.1 | 2.3 | 2 | 0.9 |
| 11 | 99 | 12.5 | 37° C. 15' 50 µl | 60.3 | 7.7 | 16 | |
| 11 | 22 | 2.5 | 37° C. 15' 50 µl | 90.1 | 10.4 | 18 | 0.3 |
| 12 | 89 | 5 | 37° C. 15' 50 µl | 53.2 | 3.0 | 7 | |
| 12 | 92 | 5 | 37° C. 15' 50 µl | 92.2 | 5.0 | 80 | 0.1 |
| 30n7 Primer Competition Counter-SELEX | | | | | | | |
| 1 | 168 | 20 | 37° C. 15' 100 µl | 2.1 | 0.25 | 6 | |
| 2 | 189 | 20 | 37° C. 15' 100 µl | 15.4 | 1.62 | 119 | |
| 3 | 185 | 20 | 37° C. 15' 100 µl | 9.2 | 0.99 | 66 | 2 |
| 4 | 95 | 5 | 37° C. 15' 100 µl | 44.0 | 2.33 | 6 | 0.3 |
| 5 | 100 | 5 | 37° C. 15' 100 µl | 29.0 | 1.43 | 43 | |
| 5 | 104 | 5 | 37° C. 15' 100 µl | 36.0 | 1.70 | 24 | 0.4 |
| 40n7 Primer Competition Counter-SELEX | | | | | | | |
| 1 | 155 | 20 | 37° C. 15' 100 µl | 1.9 | 0.25 | 5 | |
| 2 | 184 | 20 | 37° C. 15' 100 µl | 26.8 | 2.92 | 172 | |
| 3 | 117 | 20 | 37° C. 15' 100 µl | 12.9 | 2.21 | 78 | 2 |
| 4 | 93 | 5 | 37° C. 15' 100 µl | 46.0 | 2.43 | 3 | 0.2 |
| 5 | 93 | 5 | 37° C. 15' 100 µl | 37.0 | 2.00 | 52 | |
| 5 | 94 | 5 | 37° C. 15' 100 µl | 42.0 | 2.25 | 15 | 0.06 |

TABLE 16

L-selectin 2'F Ligands Sequences

| Ligand | Sequence | SEQ ID NO. |
|---|---|---|
| Family 1a | | |
| LF1518 | gggaggacgau gcggG CAAAUUG CAUGCG UU-UU-- CGAGUG CUUGC UcagacGacucgcccga | 293 |
| LF1817 | gggaggacgaugc ggUG CUUAAAC AACGCG UGAAU-- CGAGUU CAUC CACUCCUCCU cagacgacucgc ccga | 294 |
| LF1813 | gggaggacgaugcgguuAAu UCAGU CUCAAAC GGUGCG UUUAU-- CGAGCC ACUGA UcwgacgacucgcccgaA | 295 |
| LF1822 | gggaggacgaugcggCU UAGAG CUCAAAC GGUGUG ACUUU-- CAAGCC CUCUA UGCCcagacgacucgcccga | 296 |
| LF1514 | gggaggacgaugc ggUAC CUCAAAU UGCGUG UU-UU-- CAAGCA GUAUc agacgacucgcccga | 297 |
| LF1529 | gggaggacgaugcg gACC CUCAAAU AACGUG UCUUU-- CAAGUU GGUc agacgacucgcccga | 298 |
| LF1527 (2) | gggaggacgaugcg gACC CUCAAAU AGCGUG CAUUU-- CAAGCU GGUc agacgacucgcccga | 299 |
| LF1536 (2) | gggaAgacgaugc ggCG CUCAAAU AAUGCG UUAAU-- CGAAUU CGCC cagacgacucgcccga | 300 |
| LF1614 | gggaggacgaugcggCA AACAAG CUCAAAU GACGUG UUUUU-- CAAGUC CUUGUU GUcagacgacucgcccga | 301 |
| LF1625 | gggaggacgaugcggUA GUAAGU CUCAAAU GUUGCG UUUUU-- CGAAAC ACUUAC AucaGacgacucgcccga | 302 |
| LF1728 | gggaggacgaugc ggAGA CUCAAAU GGUGUG UU-UU-- CAAGCC CUCC cagUcgacucgcccga | 303 |

TABLE 16-continued

L-selectin 2'F Ligands Sequences

| Ligand | Sequence | SEQ ID NO. |
|---|---|---|
| LF1729 | gggaggacgaugc ggUG CUCAAAU GAUGCG UUUCU-- CGAAUC CACC cAgacgacucgcccga GG | 304 |
| LF1815 | gggaggacgaugc ggCCAUCGGU CUUGGGC AACGCG UU-UU-- CGAGUU ACCUAUGGUc agacgacucgcccga | 305 |
| LF1834 | gggaggacgaugcggCCAUC GGU CUUGGGC AACGCG UU-UU-- CGAGUU aCC UACAUcagacgacucgcccga | 306 |
| LF1508 | gggaggacgaugcg gGACC CUUAGGC AACGUG UU-UU-- CAAGUU GGUC agacgacucgcccga | 307 |
| LF1828 | gggaggacgaugcgg ACGUAGCU CUUAGGC AAUGCG UAUUU-- CGAAUU AGCUGUGU cagacgacucgcccga | 308 |
| LF1807 | gggaggacgaugc ggAGU CUUAGGC AGCGCG UU-UU-- CGAGCU ACUCC AUCGCCAGUcagacgacucgcccga | 309 |
| LF1825 | gggaAgacgaugcgg AAUGCU CUUAGGC AGCGCG UUAAU-- CGAGCU AGCACAUCCUcagacgacucgcccga | 310 |
| LF1855 | gggaggacgaugG ggAGU CUUAGGC AGCGCG UU-UU-- CGAGCU ACUCC AuCGCCAGUcagacgacucgcccga | 311 |
| LF1811 | gggaggacgaugcgg UAAUCU CUUAGGC AUCGCG UAAU-- CGAGAU AGAUCACCGU cagacgacucgcccga | 312 |
| LF1626 | gggaggacgaugcgg CAAUGUCh CUUAGGC CACGCG UUAAU-- CGAGCG UGACUGU cagacgacucgcccgag | 313 |
| LF1808 (3) | gggaggacgaugc ggCAUGGU CUUAGGC GACGCG UUUAUAU CGAGUC ACCAUGCU cagacgacucgcccga | 314 |
| LF1719 (2)* | gggaggacgaugcgg GAUG CUUAGGC GCCGUG UU-UU-- CAAGGC CAUc agacgacucgcccga | 315 |
| LF1619 | gggaggacgaugcggU AAUUGU CUUAGGC GCCGUG UU-AU-- CAAGGC ACAAUU UCCCUcagacgacucgcccga | 316 |
| LF1620 | gggaagacgaugcggCUACUA GUGU CUUAGGC GGAGUG UUUAU-- CAAUCC ACAC aUcagacgacucgcccga | 317 |
| LF1756 | gggaggacgaugcggA CUGA CUUAGGC UGCGCG CACUU-- CGAGCA UcaG acgacucgcccga | 318 |
| LF1629 (2) | gggaggacgaugcgg UGGUGUGU CUUUGGC ACCGCG UAUUUU- CGAGGU ACACAUca dacgacucgcccga | 319 |
| LF1821 | gggaggacgaugcggUG GUGUGU CUUUGGC ACCGCG UA-UU-- CUCGAG GUACAC AUcagacgacucgcccga | 320 |
| LF1513 | gggaggacgaugcg gGCU CUUCAGC AACGUG UU-AU-- CAAGUU AGCCc agacgacucgcccga | 321 |
| LF1615 | gggaggacgaugc ggCGUAA CUUCAGC GGUGUG UUAAU-- CAAGCC UUACGCC AUCUcagacgacucgcccga | 322 |
| LF1521 (2) | gaggacgaugc ggGCU CUUAAGC AACGUG UU#AU-- CAAGUU AGCCc agacgacucgcccga | 323 |
| LF1651 | gggaggacga ugcggU CUCAAGC aAUGCG UUUAU-- CGAAUU ACCGUA CGCCuCCGUcagacgacucgcccga | 324 |
| LF1830 | gggaggacgaugcggAA AUCU CUUAAGC AGCGUG UAAAU-- CAAGCU AGAU CUUCGUcAgacgacucgcccga | 325 |
| LF1523 (2)* | gggaggacgaugc ggUU CUUAAGC AGCGCG UCAAU-- CGAGCU AACC cagacgacucgcccga | 326 |
| LF 1708** | gggaggacgaugc ggAU CUUAAGC AGCGCG UCAAU-- CGAGCU AACC cagacgacucgcccgag | 327 |
| LF1851 | ACAGCUGAUGACCAUGAUUACGCCAAG CUUAAGC AGCGCG UU-UU-- CGAGCU CAUcuUGGUcagacgacucgcccga | 328 |
| LF1610 (3)** | gggaggac gaugcggAGGGU CUUAAGC AGUGUG AUAAU-- CAAACU ACUCUCCGUGUc agacgacucgcccga | 329 |
| LF1712 | gggaggacgaugc ggGAU CUUAAGC AGUGCG UUAUU-- CGAACU AUCCc agacgacucgcccga | 330 |
| LF1613 (3) | gggaggacgaugcggUGC UAUU CUUAAGC GGCGUG UUUUU-- CAAGCC AAUA UCAUcagacgacucgcccga | 331 |
| LF1735 | gggaggac gaugcggU CUUAAGC GGCGCG AUUUUL CGAGCC ACCGCAUCCUC CGUGcaGacgacucgcccga | 332 |
| LF1731 | gggaggacgaugcg gCCU CUUAAGC GUCGUG UUUUU-- CAAGCU GGUc agacgacucgcccga | 333 |
| LF1853 | ggga ggacgaugcggAUACCACCU CUUAAGC GACGUG CAUUU-- CAAGUC AGAUGGUcagacgacUcgcccga | 334 |
| LF1816 | gggaggacgAugcgUGCuA UU CUUAAGC GGCGUG UAAAU-- CAAGCU AG AUCAUCGUcagacgacucgcccga | 335 |
| LF1622 | gggaggacgaugcggA ACGACU CUUAAGC UGUGCG UU-UU-- CGAACA AGUCGU AACUcagacgacucgcccga | 336 |

TABLE 16-continued

L-selectin 2'F Ligands Sequences

| Ligand | Sequence | SEQ ID NO. |
|---|---|---|
| (3)* | | |
| LF1725 | gggaggacgaugc ggCU CUCAUUU wGCGCG UAAAU-- CGAGCU AGCC cagacgacucgcccga | 337 |
| LF1632 | gggaggacgaugcggAG UCwCU CUCcacC AkCGUG UkUUAAU CAAGCU AnUG CCUcagacGacucgcccga | 338 |
| LF1856 | gggaggacGaugcggUCUAC GGUCU CUCUGGC GGUGCG UAAAU-- CkAACC AGAUCG cagacgacucgcccga | 339 |
| LF1631 | gggaggacgaugc ggUdAUUU CyUAAUC hGAGCG UUUAU-- CUAUCU mAAUkAUC CUcagacgacucgcccga | 340 |
| LF1730 | gggaggacgaugc ggaU CgCAAUmU GUwGCG UU-CU-- CkAAAC AGCC Ucagacgacucgcccga | 341 |
| LF1852 | gggaggacgaugc ggAACUU CUUAGGC AGCGUG CUAGU-- CAAGCU AAGUUCC ACCUcagacgacucgcccga | 371 |
| LF1653 | gggaggacgaugcggC ACAAU CUUCGGC AGCGUG CAAGAU- CAAGCU AUUGU UGUcagacgacucgcccga | 372 |
| LF1554 | gggaggacgaugc ggCGGU CUUAAGC AGUGUG UCAAU-- CAAACU AUCGUC agacgacucgcccga | 366 |
| LF1722 | gggaggacgaugc ggUU CUUAAGC AGCGCG UCAAU-- CGAGCU AACC cagacgacucgcccga | 367 |
| Truncates | | |
| LF 1514T1 | UGCGUG UU-UU-- CAAGCA | 385 |
| LF 1514T2 | CUCAAAU UGCGUG UU-UU-- CAAGCA | 386 |
| LF 1514T4 | ggUAC CUCAAAU UGCGUG UU-UU-- CAAGCA GUAUc | 387 |
| LF 1807T5 | ggAGU CUUAGGC AGCGCG UU-UU-- CGAGCU ACUCC | 388 |
| Family 1b | | |
| LF1511 (4) | gggaggacgaugcgg UGGUU CUAG GCACGUG UU-UU-- CAAGUGU AAUca gacgacucgcccga | 342 |
| LF1753 | gggaggac gaugc ggAA ACAUGUG UU-UU-- CGAAUGU gCUC UCCUCCCCAAACAACYCCCCAA | 343 |
| LF1524 | gggaggacg augc ggAA GGCCGUG UUAAU-- CAAGGCU GCAAU AAAUCAUCCUCCC cagacgacucgcccga | 344 |
| LF1810 | g ggaggacgaugc ggAG GAUCGUG UUCAU-- CAAGAUU GCUCGUUCUUU ACUGCGUcagacgacucgcccga | 345 |
| LF1621 (2)* | gggaggacgaugcgguCAA AGUGAAG AAUG GACaGCG UU-UU-- CGAGUU GCUUCACU cagacGacucgcccga | 346 |
| LF1826 (2)* | gggaggacgaugcgg GGAG AAUG GCCAGCG UUUAU-- CGAGGU GCUCCGUUAACCGG cAgacgacucgcccga | 347 |
| LF1713 | gggaggacgaugcgg GAGG AAUG GACWGCG UAUAU-- CGAGUUG CCUC agacgacucgcccga | 348 |
| LF1520 | gggaggacgaugcg gAUCG AUU UCAUGCG UUUUU-- CGAGUGA CGAUc agacgacucgcccga | 349 |
| LF1552 | gggaggacgaugcggA GACc CUA AGrnGsG UksUUUU CAAsCU GGUc wgacgacucgcccga | 350 |
| Family 1c | | |
| LF1618 (2) | gggaggacgaugcgg UUAGCCUACACUCUAGGUUCAG UU-UU-- CGAAUCUUCCACCG cwgacgacucgcccga | 351 |
| LF1528 (3) | gggaggacgaugcgg UUAGGUCAAUGAUCUUAG UU-UU-- CGAUUCGU cagacgacucgcccga | 352 |
| LF1718 | gggaggacga ucggA CGUGUG UAUCrAr UU-UU-- CCGCUG UUUGUG cagacgacucgcccga | 353 |
| LF1623 | gggaggacGaugcgg ACAGGGUUCUUAG GCGGAG UG-UU-- CAUCAA UCCAACCAUGU cagacgacucgcccga | 354 |
| LF1557 | gggaggacgaugcgg CGAUUUCCAC AGUUUG UCUUAUU CCGCAU AU cagacgacucgcccga | 355 |

TABLE 16-continued

L-selectin 2'F Ligands Sequences

| Ligand | Sequence | SEQ ID NO. |
|---|---|---|
| Family 1 (Unclassified) | | |
| LF1707 | gggaggacgaugcgg AUAyUCAgCUyGUGUk UU-UU-- C#UCUUCCC cagacgacucgcccga | 356 |
| LF1512 | gggaggacgaugc ggCACACGUG UU-UU-- CAAGUGUGCU CCUGGGAU cagacgacucgcccga | 357 |
| LF1535 (2) | gggaggacgaugc ggCAAUGUG UUUCU-- CAAAUUGCU UUCUCCCUU cagacgacucgcccga | 358 |
| LF1711 | gggaAgacg augcggUG UUGAU-- CAAUG AAUGUCCUCCUCCUACCC cagacgacucgcccga | 364 |
| LF1517 | gggaggacgau gcggUG UUUGU-- CAAUGU CAUGAUUAGUUUUCCCA cagacgacucgcccga | 365 |
| Family 2 | | |
| LF1627 (2) | gggaggacgaugc ggAUACUACCGUGCG AACaCUAAG UCCCGUCUGUCCACUCCU cagacgacucgcccga | 359 |
| LF1724 (2) | gggaggacgaugc ggAUaCUA-UGUGCG UUCACUAAG UCCCGUC-GUCCCCU cagacgacucgcccga | 360 |
| LF1652 (2) | gggaggacgaugc ggGUACUA UGUACG AUCaCUAAG CCCCAUCACCCUUCUCACU cagacnacucgcccga | 361 |
| LF1519 | gggaggacgaugc ggUUACUA UGUACA UUUACUAAG ACCCAACGU cagacgacucgcccga | 362 |
| LF1608 | gggaggacgaugc ggUUWCUA UGUwCGCCUUACUAAGUACCCGUCGACUGUCCCAU cagacgacucgcccga | 363 |
| Family 3 | | |
| LF1710 | gggaggacgaugcgg AAUGrCCCGUUACCAwCAAUGCGCCUCdUUGrnCCCCAAACAACyCCCCCAA | 368 |
| LF1829 | gacgaugcgg AAUyUCGUGyUAcGCGUyyyCUAUCCAAUCUACCCCrnUCUCCAAU cagacgacyc----- | 369 |
| LF1509 | gggaggacgaugcgg CGCUUACAAUAAUUCUCCCUGAGUACAGCucag acgacucgcccga | 370 |
| Orphans | | |
| LF1507 | gggaggacgaugcgg UCAUUAACCAAGAUAUGCGAAUCACCUCCU cagacgacucgcccga | 373 |
| LF1516 (2) | g ggaggacgaugcgg UCAUUCUCU#GUAUUCCGUACCUCCa cagacgacucgcccga | 374 |
| LF1530 (2)* | gggaggacgaugcgg GUGAUCUUUUAUGCUCCUCUUGUUUCCUGU cagacgacucgcccga | 375 |
| LF1835 (4)* | gggaggacnaugcgg UCUAGGCaUCGCUAUUCUUUACUGAUAUAAUUACUCCCCU cagacgacucgcccga | 376 |
| monster | gggaggacgaugcgg AGUwwGCNCGGUCCAGUCACAUCCWAUCCC cagacGacucgcccga | 377 |
| LF1522 | gggaggacgAugcgg CUCUCAUAUkGwGUrUUyUUCinUUCsrGGCUCAAACAAyyCCCCCAA | 378 |
| LF1727 | gggaggacgaugcgg CUUGUUAGUUAAACUCGAGUCUCCACCCCU cagacgacucgcccga | 379 |
| LF1510 | gggaggacgaugcgg UCUCUwCUVACVUGUrUUCACAUUUUCGCyUCAAACAACyCCCCCAA | 380 |
| LF1715 | gggaggacgaugcgg UUrACAAUGrssCUCrCCUUCCCwGGUCCU cagacgacucgcccga | 381 |
| LF1809 | AggaggacGaugcgg UUAUCUGAArCWUGCGUAArnCUArUGUsAAAsUGCAACrA cRaacaacYcScccaa | 382 |
| LF1533 | Aggaagacgaugcgg UUCGAUUUAUUUGUGUCAUUGUUCUUCCAU cagacgacucgcccga | 383 |
| LF1720 | --------------- -----------GUGAUGACAUGGAUUACGC cagacgacucgcccga | 384 |

TABLE 17

2'Fluoro L-selectin SELEXes:
Full Length Transcribed Ligands:
Protein and Lymphocyte Binding Affinity

| LIGAND | SEQ ID NO | L-selectin # Kd (nM) | Lymphocytes ## Kd (nM) |
|---|---|---|---|
| LF1508 | 307 | 0.5 | |
| LF1511 | 342 | 0.48 | |
| LF1512 | 357 | 315 | |
| LF1513 | 321 | 0.16 | 4 |
| LF1514 | 297 | 0.13 | 0.8 |
| LF1516 | 374 | 1.3* | |
| LF1518 | 293 | 0.42 | |
| LF1520 | 339 | 0.5* | |
| LF1521 | 323 | 0.25* | |
| LF1523 | 326 | 0.25 | |
| LF1524 | 344 | 2.1* | |
| LF1527 | 299 | 0.32 | |
| LF1528 | 352 | —* | |
| LF1529 | 298 | 0.6 | |
| LF1535 | 358 | —* | |
| LF1536 | 300 | 0.22* | |
| LF1610 | 329 | 0.53 | |
| LF1613 | 331 | 0.034 | 0.2 |
| LF1614 | 301 | 0.17 | |
| LF1615 | 322 | 0.32 | |
| LF1618 | 351 | 9.6 | 25 |
| LF1707 | 356 | 0.16* | |
| LF1708 | 327 | 70 | |
| LF1712 | 330 | 0.065* | |
| LF1713 | 338 | 0.22* | |
| LF1718 | 353 | 6.4* | |
| LF1807 | 309 | 0.034 | |
| LF1808 | 314 | 0.6 | |
| LF1810 | 345 | 8.1* | |
| LF1811 | 312 | 0.19 | |
| LF1815 | 305 | 0.18* | |
| LF1816 | 335 | —* | |
| LF1817 | 294 | 2.3* | |
| 40N7 | | — | |
| NX280 | | 1.6 | 3 |

Nitrocellulose filter partitioning @ 37° C.;
*designate soluble L-selectin, others LS-Rg;
—indicates binding was undetectable
Flow cytometry competition @ room temperature;

TABLE 18

P-SELECTIN 2'F RNA SELEX

| SELEX Round # | RNA Load (pmol) | PS-Rg (pmol) | Bead Volume | Total Volume | % RNA eluted 5 mM EDTA | Signal to Noise- 5 mM EDTA | % RNA eluted 50 mM EDTA | Signal to Noise- 50 mM EDTA | % Retained on column | Kd (nM) |
|---|---|---|---|---|---|---|---|---|---|---|
| Rnd 1 | 320 | 200 | 10 µl | 125 µl | 1.4 | 8 | 8.3 | 40 | 0.7 | 2500 |
| Rnd 2 | 510 | 100 | 10 µl | 125 µl | 1.8 | 9 | 3.5 | 30 | 0.6 | |
| | 200 | 40 | 10 µl | 125 µl | 1.7 | 5 | 2.6 | 12 | 0.3 | |
| Rnd 3 | 200 | 40 | 10 µl | 125 µl | 2.3 | 15 | 3.0 | 13 | 0.1 | |
| | 40 | 8 | 10 µl | 125 µl | 1.3 | 4 | 0.8 | 8 | 0.3 | 1200 |
| Rnd 4 | 25 | 5 | 10 µl | 125 µl | 1.2 | 3 | 0.6 | 3 | 0.7 | |
| Rnd 5 | 25 | 5 | 10 µl | 125 µl | 0.9 | 3 | 0.15 | 1.5 | 0.3 | 280–900 |
| Rnd 6 | 25 | 5 | 10 µl | 125 µl | 0.8 | 2 | 0.0 | 1 | 0.4 | 85 |
| Rnd 7 | 50 | 5 | 10 µl | 125 µl | 4.0 | 8 | 1.0 | 4.3 | 0.5 | 13 |
| Rnd 8 | 50 | 5 | 10 µl | 125 µl | 4.6 | 16 | 0.4 | 6.7 | 0.3 | 5 |
| | 10 | 1 | 10 µl | 125 µl | 4.5 | 6 | 0.2 | 2.3 | 1.4 | 5 |
| Rnd 9 | 10 | 1 | 10 µl | 125 µl | 5.3 | 28 | 0.05 | 1.5 | 1.2 | |
| | 10 | 1 | 100 µl | 250 µl | 2.8 | 6 | 0.3 | 2 | 0.8 | |
| Rnd 10 | 5 | 0.5 | 10 µl | 500 µl | 5.6 | 20 | 0.2 | 5 | 1.2 | |
| Rnd 11 | 5 | 1 | 250 µl | 500 µl | 10 | 11 | 0.4 | 2 | 2.5 | 0.1–2 |
| | 1 | 0.2 | 10 µl | 500 µl | 14.2 | 15 | 0.6 | 3 | 13 | |
| Rnd 12 | 1 | 0.1 | 250 µl | 500 µl | 4.5 | 4 | 0.8 | 2 | 4.7 | 0.02–20 |
| Rnd 13 | 0.1 | 0.01 | 250 µl | 500 µl | 2.6 | 2 | ND | ND | 3.6 | |

TABLE 19

P-Selectin 2'-F RNA Ligands

| Ligand | Sequence | SEQ ID NO. |
|---|---|---|
| Family 1 | | |
| PF373(6) | gggagacaagaauaaacgcucaaCGAAUCAGUAAACAUAACACCAUGAAACAUAAUAGCAGCGAGACGUC-uucgaccaggaggcacacaacaggc | 199 |

TABLE 19-continued

P-Selectin 2'-F RNA Ligands

| Ligand | Sequence | SEQ ID NO. |
|---|---|---|
| PF424 | gggagacaagaauaaacgcucaaCGAGUUCACAUGGGAGCAAUCUCCGAAUAAACAACACGCKAKCGCAAA-uucgacaggaggcucacaacaggc | 200 |
| PF412 | gggagacaagaauaaacgcucaaCGACCACAAUACAAACUCGUAUGGAACACGCGAGCGACAGUGACGCAUU-uucgacaggaggcucacaacaggc | 201 |
| PF422 | gggagacaagaauaaacgcucaaCGUCAAGCCAGAAUCCGGAACACGCGAGAAAACAAUCAACGACCAAUCGA-uucgacaggaggcucacaaaggc | 202 |
| PF426 | gggagacaagaauaaacNcucaaCGACCACAAUAACCGGAAAUCCCCGCGGUUACGGAACACGCGAACAUGAA-uucgacaggaggcucacaacaggc | 203 |
| PF398 | gggagacaagaaucaaCGAACCACGGGGAAAUCCACCAGUAACACGCGAGGCAAACAGACCCUC-uucgacaggaggcucacaacaggc | 203 |
| PF380(2) | gggagacaagaauaaacgcucaaCGAGCAAAGUACUCA CGGGACCAGGAGAUCAGCAACACGCGAGACGAAA-uucgacaggaggcucacaacaggc | 204 |
| PF377(2) | gggagacaagaauaaacgcucaaCGAGCCAGGACAUCGACGUCAGCAAACGCGAGCGCAACCAGUAACACC-uucgacaggaggcucacaacaggc | 205 |
| PF387(2) | gggagacaagaauaaacgcucaaCGCACCAGGAACAACGAGAACCAUCAGUAAACGCGAGCGAUUGCAUG-uucgacaggaggcucacaacaggc | 207 |
| PF383 | gggagacaagaauaaacgcucaaCGCACCAGGAACAACAAGAACCAUCAGUAAGCGCGAGCGAUUGCAUA-uucgacaggaggcucacaacaggc | 208 |
| PF395 | gggagacaagaauaaacgcucaaCGAGCAAGGAACGAAUACAAACCAGGAAACUCAGCAACACGGAGCAGUAACA-uucgacaggaggcucacaacaggc | 209 |
| PF416(2) | gggagacaagaauaaacgcucaaCAGUUCACUCAACCGGCACCAGACUACGAUCAGCAUUGGCGAGUGAACAC-uucgacaggaggcucacaacaggc | 210 |
| PF388(2) | gggagacaagaauaaacgcucaaCUGGCAACGGGAUAACAACAAAUGU CACCAGCACUAGCGAGACGGAAGG-uucgacaggaggcucaacaggc | 211 |
| Family 1 Truncates | | |
| PF373s1 | CUCAACGAAUCAGUAAACAUAACACCAUGAAACAUAAAUAGCACGCGAG | 220 |
| PF424s1 | CUCAACGAGUUCACAUGGGAGCAAUCUCCGAAUAAACAACACGCGAG | 221 |
| PF3981 | CUCAACGAACCACGGGGAAAUCCACCAGUAACACGCGAG | 222 |
| PF377s1 | CUCAACGAGCCAGGAACAUCGACGUCAGCAAACGCGAG | 223 |
| PF377s2 | CGCUCAACGAGCCAGGAACAUCGACGUCAGCAAACGCGAGCG | 224 |
| PF377L1 | CUCAACGAGCCAGGACUACGAUCAGCAAACGCGAG | 225 |
| PF387s1 | CUCAACGCACCAGGAACAACGAGAACCAUCAGUAAACGCGAG | 226 |
| PF383s1 | CUCAACGCACCAGGAACAACAAGAACCAUCAGUAAGCGCGAG | 227 |
| PF416s2 | CACUCAACCGGCACCAGACUACGAUCAGCAUUGGCGAGUG | 228 |
| PF422s1 | GAAUCCGGAACACGCGAGAAAACAAAUCAACGACCAAUCGAUUCG | 229 |
| 2'-O-Methyl Substituted Truncates | | |
| PF377M1 | CUCAAC<u>GAG</u>CCAG<u>GA</u>AC<u>A</u>UC<u>GA</u>CGUC<u>A</u>GC<u>AA</u>ACGCGAG | 230 |
| PF3772 | CUCAAC<u>GAG</u>CCAG<u>GA</u>AC<u>A</u>UC<u>GA</u>C<u>G</u>UC<u>A</u>GC<u>AAA</u>CGCGAG | 231 |
| PF377M3 | CUCAAC<u>GAG</u>CCAG<u>GAA</u>CAGC<u>A</u>AACGC<u>GA</u>G | 232 |
| PF377M4 | CUCAAC<u>GAG</u>CCAG<u>GA</u>AC<u>A</u>UC<u>GA</u>CGUC<u>A</u>GC<u>AAA</u>CGCGAG | 233 |
| PF377M5 | CUCA<u>A</u>C<u>GAG</u>CCAG<u>GA</u>AC<u>A</u>UC<u>GA</u>CGUC<u>A</u>GC<u>AA</u>ACGCGAG | 234 |
| PF377M6 | CUCAAC<u>GAG</u>CCA<u>GGAA</u>C<u>A</u>UC<u>GA</u>C<u>G</u>UC<u>A</u>GC<u>AAA</u>CGCGAG | 235 |

TABLE 19-continued

P-Selectin 2'-F RNA Ligands

| Ligand | Sequence | SEQ ID NO. |
|---|---|---|
| Family 2 | | |
| PF378(8) | gggagacaagaauaaacgcucaaCGAUGAGCGUGACCGAAGCUAUAAUCAGGUCGAUUCACCAAGCAAUCUUA-uucgacaggaggcucacaacaggc | 212 |
| Family 3 | | |
| PF381(5) | gggagacaagaauaaacgcucaaAGGAUCACACAAACAUCGGUCAAUAAAUAAGUAUUGAUAGCGGGGAUA-uucgacaggaggcucacaacaggc | 213 |
| Family 4 | | |
| PF411(2) | gggagacaagaauaaacgcucaaCAACCCAACCAUCUAGAGCUUCGAACCAUGGUAUACAAGGGAACACAAAA-uucgcggaggcuccaacaggcggc | 214 |
| Family 5 | | |
| PF396(2) | gggagacaagaauaaaccgcucaaGCGGUCAGAAACAAUAGCUGGAUACAUACCGCGCAUCCGAUGGGCGAUA-uucgacaggaggcucucaacaggc | 215 |
| Orphans | | |
| PF386 | gggagacaagaauaaacgcucaaACAAGAGAGUCAAACCAAGUGAGAUCAGAGCGUUUAGCGCGGAAAGCACA-uucgacaggaggcucacaacaggc | 216 |
| PF382 | gggagacaagaauaaacacucaaACUCGACUAGUAAUCACCCUAGCAUAAAUCUCCUCGAGCACAGACGAUA-uucagcaggaggcucacaacagga | 217 |
| PF404 | gggagacaagaauaaacgcucaaUCAGCAGUAAGCGAUCCUAUAAAGAUCAACUAGCCAAAGAUGACUUA-uucgacaggaggcucacaacagc | 218 |
| PF417 | gggagacaagaauaaacgcucaaAAAGACGUAUUCGAUUCGAAACGAGAAAGACUUCAAGUGAGCCCGCAG-uucgacaggaggcucacaaccaggc | 219 |

TABLE 20

Dissociation Constants and Specificity of 2'F RNA Ligands to P-Selectin

| Ligand | Kd (PS-Rg) | S LeX (IC50) | Kd (ES-Rg) | Kd (LS-Rg) | Tm (°C.) | SEQ ID NO. |
|---|---|---|---|---|---|---|
| PF373 | 49.5 pM | | >3 μM | >3 μM | | 199 |
| PF377 | 18.5 pM | 3 nM | 2.3 μM | >3 μM | 53° C. | 206 |
| PF378 | 51.5 pM | | | | | 212 |
| PF380 | 74.5 pM | 4 nM | | | | 205 |
| PF381 | 16.5 pM | 1 nM | | | | 213 |
| PF386 | 45.5 pM | | | | | 216 |
| PF387 | 16 pM | | | | | 207 |
| PF388 | 90 pM | | | | | 211 |
| PF395 | 26 pM | | | | | 209 |
| PF396 | 24 pM | | | | | 215 |
| PF398 | 46 pM | | | | | 204 |
| PF404 | 47.5 pM | | | | | 218 |
| PF411 | 13 pM | 2 nM | | | | 214 |
| PF412 | 450 pM | | | | | 201 |
| PF416 | 63 pM | | | | | 210 |
| PF417 | 69 pM | | | | | 219 |
| PF422 | 172 pM | 3 nM | | | | 202 |
| PF424 | 36.5 pM | | | | | 200 |

TABLE 21

Boundary Results for 2'F RNA Ligands to P-selectin

| Kd(pM) | Clone # | | SEQ ID NO. |
|---|---|---|---|
| FAMILY 1 | | | |
| 56 | PF373s1 | cucaaCGAAUCAG UA AACAUAACACCAUGAAACA UAAAUAGCACGCGAG | 220 |
| 178 | PF424s1 | cucaaCGAGUUCACAUG GGAGCAAUCUCCGAA UAAACAACACGCGAG | 221 |
| 63 | PF398s1 | cucaaCGAACCA GG GGAAAUCCA CCAGUAACACGCGAG | 222 |
| ND | PF380s1 | cucaaCGAGCAAAAGUACUCACGGGACCAGGAGA UCAGCAACACGCGAG ACGAAAuucg | 236 |
| 50 | PF377s1 | cucaaCGAGCCAG GA ACAUCGACG UCAGCAAA CGAGAG | 223 |
| 50 | PF377s2 | cg cucaaCGAGCCAG GA ACAUCGACG UCAGCAAA CGCGAG CG | 224 |
| | PF412 | cg cucaaCGACCACAA UA CAAACUCG UAUGGAACACGCGAG CG | 237 |
| 63 | PF387s1 | cg cucaaCGCACCAG GA ACAACGAGAACCA UCAGUAAA CGCGAG CG | 226 |
| 10000 | PF383s1 | acg cucaaCCCACCAG GA ACAACAAGAACCA UCAGUAAG CGCCGAG CG | 227 |
| | PF388 | cg cucaaCUGGCAAC GG GAUAACAACAAAUGCA CCAGCACU AGCGAG ACG | 238 |
| 150 | PF416s1 | UCA CUCAACCGGCACCA GACUACGA UCAGCAUU GGCGAG UG | 239 |
| | PF395 | gggagacaagaauaaacg cucaaCGAGCAAG GA ACGAAUACAAACCAGGAAACUCACAAACACGCGAG CA | 240 |
| | PF426 | cucaaCGACCACAA UA ACCGGAAAUCCCGCGGU UACGGAAACACGAA CA | 241 |
| 1000 | PF422s1 | AUCAACGACCAAUC GA uucg3' 5'GAAUCCGGAACACGCGAG AAAACAA | 229 |
| FAMILY 2 | | | |
| | PF378 | agaauaaacgcucaaCGAUGAGCGUGACCGAAGCUAUAAUCAGGUCGAUCACCAAGCAAUCUUAuucg | 242 |
| FAMILY 3 | | | |
| | PF381 | aacgcucaaAGGAUCACACAAACAUCGGUCAAUAAAUAAGUAUUGAUAGCG | 243 |
| FAMILY 4 | | | |
| | PF396 | gcucaaGCGGUCAGAAUAGCUGGAGAAACAUACCCGCGCAUCCGCUGGCG | 244 |
| FAMILY 5 | | | |
| | PF411 | ACCAUCUAGAGCUUCGACCAUGGUAUACAAGGAAACACAAAAuucgcggaggcucca | 245 |
| ORPHANS | | | |
| | PF386 | gggagacaagaauaacgcucaaACAAGAGUCAAACCAAGUGAGAGAUCAGAGCGUUUAGCCGGAAACACAuucgacgaggagcucaacaggc | 246 |
| | PF417 | gggagacaagaauaaacgcucaaAAAGACGUAUUCGAAACGAGAAAGAC UUCAAGUGAGCCCCGAGuucgacaggaggcuca | 247 |

TABLE 22

Dissociation Constants and Specificity of Truncated 2'F RNA Ligands to P-Selectin

| Ligand | Kd (PS-Rg) | SLeX (IC50) | Kd (ES-Rg) | Kd (LS-Rg) | Tm (° C.) | Bases | SEQ ID NO. |
|---|---|---|---|---|---|---|---|
| PF373s1 | 56 pM | 3 nM | >3 μM | >3 μM | | | 220 |
| PF377s1 | 60 pM | 2 nM | >3 μM | >3 μM | 59° C. | 38 | 223 |
| PF377s2 | 45 pM | 4 nM | | | | 42 | 224 |
| PF383s1 | 10000 pM | 25 nM | | | | 46 | 227 |
| PF387s1 | 63 pM | 2 nM | >3 μM | >3 μM | | 46 | 226 |
| PF398s1 | 178 pM | 2 nM | >3 μM | >3 μM | | 39 | 222 |
| PF416s2 | 150 pM | 3 nM | | | | 42 | 228 |
| PF422s1 | 1000 pM | 8 nM | >3 μM | >3 μM | | 44 | 229 |
| PF377s1B | 65 pM | 3 nM | >3 μM | >3 μM | | 38 | 223 |
| PF377s1B:SA | 30 pM | | | | | 38 | 223 |
| PF377s1F | 60 pM | 3 nM | | | | 38 | 223 |
| PF377s1-5'NH2 | 125 pM | 2 nM | | | | 41 | 223 |
| PF377L1 | 220 pM | 4 nM | >3 μM | >3 μM | | 35 | 225 |
| PF377t3' | 30 pM | 2 nM | | | | 59 | 223 |
| PF377M1 | 120 pM | | >3 μM | | | 38 | 230 |
| PF377M2 | 1700 pM | | | | | 38 | 231 |
| PF377M3 | 900 pM | 10 nM | >3 μM | | | 38 | 232 |
| PF377M4 | 1700 pM | | | | | 38 | 233 |
| PF377M5 | 60 pM | 2 nM | >3 μM | | | 38 | 234 |
| PF377MG | 250 pM | | | | | 38 | 235 |

Table 23

2'OMe Substitution of 2'F RNA Ligands to P-Selectin

| Purine Position | Unmixed Ratio | Std. Dev. | Mixed 40 pM | Mixed 200 pM | Predicted Pref. | Actual Pref. |
|---|---|---|---|---|---|---|
| 4 | 1.07 | 0.12 | 0.3 | 0.4 | 2'-OH | untested |
| 5 | 1.00 | 1.00 | 0.4 | 0.7 | 2'-OH | untested |
| 7 | 1.00 | 0.13 | 1.2 | 1.5 | 2'-O—Me | 2'-O—Me |
| 8 | 1.00 | 0.20 | 2.3 | 1.3 | 2'-O—Me | 2'-O—Me |
| 12 | 0.83 | 0.12 | 0.4 | 0.5 | 2'-OH | untested |
| 13 | 0.90 | 0.17 | 0.8 | 0.8 | neutral | 2'-O—Me |
| 14 | 0.73 | 0.15 | 0.8 | 0.9 | neutral | 2'-O—Me |
| 15 | 0.63 | 0.15 | 0.8 | 1.3 | 2'-O—Me | 2'-O—Me |
| 16 | 0.67 | 0.10 | 0.5 | 0.7 | neutral | untested |
| 18 | 0.60 | 0.10 | 0.7 | 0.7 | neutral | 2'-O—Me |
| 21 | 0.87 | 0.30 | 0.5 | 0.7 | neutral | 2'-O—Me |
| 22 | 0.72 | 0.16 | 0.7 | 0.8 | neutral | 2'-O—Me |
| 24 | 0.70 | 0.16 | 0.6 | 0.8 | neutral | 2'-O—Me |
| 27 | 0.83 | 0.12 | 1.3 | 1.5 | 2'-O—Me | 2'-O—Me |
| 28 | 0.69 | 0.09 | 0.6 | 1.0 | 2'-O—Me | ? |
| 30 | 0.90 | 0.00 | 0.8 | 1.0 | neutral | ? |
| 31 | 0.92 | 0.16 | 1.2 | 1.5 | 2'-O—Me | 2'-O—Me |
| 32 | 1.10 | 0.06 | 0.5 | 0.8 | 2'-OH | untested |
| 34 | 0.93 | 0.06 | 0.7 | 0.9 | 2'-OH | untested |

TABLE 24

P-Selectin 2'NH₂ RNA SELEX

| SELEX Round # | RNA Load (pmol) | PS-Rg (pmol) | Bead Volume | Total Volume | % RNA eluted 5 mM EDTA | Signal to Noise- 5 mM EDTA | % RNA eluted 50 mM EDTA | Signal to Noise- 50 mM EDTA | % Retained on column | Kd (nM) |
|---|---|---|---|---|---|---|---|---|---|---|
| Rnd 1 | 330 | 200 | 10 μl | 125 μl | 0.0 | 1 | 1.3 | 6.5 | 0.2 | 6350 |
| Rnd 2 | 300 | 100 | 10 μl | 100 μl | 0.8 | 8 | 0.3 | 2.7 | 0.6 | |
| Rnd 3 | 550 | 100 | 10 μl | 125 μl | 0.6 | 21 | 0.2 | 8 | 0.1 | 1900 |
| Rnd 4 | 500 | 100 | 10 μl | 125 μl | 1.0 | 33 | 0.8 | 10 | 0.4 | |
| Rnd 5 | 365 | 100 | 10 μl | 125 μl | 1.5 | 30 | 1.6 | 32 | 0.4 | 470 |
| Rnd 6 | 500 | 50 | 10 μl | 125 μl | 1.9 | 22 | 0.9 | 17 | 0.3 | |
| | 50 | 5 | 10 μl | 125 μl | 2.3 | 5 | 0.4 | 2.3 | 1.2 | 103 |
| Rnd 7 | 50 | 5 | 10 μl | 125 μl | 1.8 | 7 | 0.05 | 1.8 | 0.6 | 31 |
| Rnd 8 | 50 | 5 | 10 μl | 125 μl | 3.6 | 7 | 0.0 | <1 | 0.6 | |

TABLE 24-continued

P-Selectin 2'NH₂ RNA SELEX

| SELEX Round # | RNA Load (pmol) | PS-Rg (pmol) | Bead Volume | Total Volume | % RNA eluted 5 mM EDTA | Signal to Noise- 5 mM EDTA | % RNA eluted 50 mM EDTA | Signal to Noise- 50 mM EDTA | % Retained on column | Kd (nM) |
|---|---|---|---|---|---|---|---|---|---|---|
| Rnd 9 | 10 | 1 | 10 µl | 125 µl | 3.3 | 5 | 0.1 | 2 | 1.2 | |
| Rnd 10 | 1 | 0.2 | 10 µl | 500 µl | 2.5 | 3 | 0.0 | <1 | 0.3 | 0.2–6 |
| Rnd 11 | 1 | 0.1 | 10 µl | 500 µl | 2.0 | 2 | 0.0 | <1 | 5.0 | |
|  | 1 | 0.1 | 250 µl | 500 µl | 1.5 | 2 | 0.0 | <1 | 12.0 | |
| Rnd 12 | 1 | 0.1 | 10 µl | 500 µl | 4.1 | 5 | 0.2 | 2 | 3.2 | |
|  | 1 | 0.1 | 250 µl | 500 µl | 3.1 | 2 | 0.2 | 1 | 14.0 | |

TABLE 25

P-Selectin 2'NH₂ RNA Ligands

| Ligand | Sequence | SEQ ID NO. |
|---|---|---| family 1

| PA341(7) | gggagacaagaauaaacacucuaaGCCCCAAACGCAAGCGAGCAUCCGCAACAGGGAAGAAGACAGACGAAUGA-uucgacaggaggcucacaacaggc | 251 |
| PA350 | gggagacaagaauaaacgcucaaGCCCCAAACGCAAGUGAGCAUCCGCAACAGGGAAGAAGACAGACGAUUGA-uucgacaggaggcucacaacaggc | 252 |
| PA466 | gggagacaagaaauaaacncucaaGCCCCAAACGCAAGUGAGCAUCCGCAACAGGGAAGAAGACAGAUGAAUGA-uucgacaggaggcucacaacaggc | 253 |
| PA473 | gggagacaagaauaaacncucaaGc-cccAA   GCAAGUGAGCAUCCGCAACAGGGAAGAAGACAGACGAGUGAUUC-gacaggaggcucacaacaggc | 254 |
| PA477(3) | gggagacaagaauaaacncucaaGCCCCAA    AGCAUCCGCAACAGGGAAGAAGACAGACGAAUGAUU-cgacaggaggcucacaacaggc | 255 |
| PA328(3) | gggagacaagaauaaacgcucaaGCAAAAGGCGAAAuACACC UCCGCAACUGGGAAGAAGACGCAGGGACGG-uucgacaggNggcucacaacaggc | 256 | family 2

| PA337(6) | gggagacaagaauaaacgcucaaACAGCUACAAGUGGGACAACAGGGUACAGCGGAGAGAAACAUCCAAACAAG-uucgacaggaggcucacaacaggc | 257 | family 3

| PA448(7) | gggagacaagaauaaacgcucaaAUCAACUAAACAACGCAGUCACGAGAACGACCGGKCUGACUCCGAAAG uucgacaggaggcucacaacaggc | 258 | others

| PA325 | gggagacaagaauaaacgcucaaACGAGAGCACCAAGGAACAGAUGCAGAAGAAGUGUGCGCGCGAA uucgacaggaggcucacaacaggc | 259 |
| PA327 | gggagacaagaauaaacgcucaaUAAGACAACGAACAGACAGAAGCGAAAAAGGGGCGCCGCAGCAACAACAAA-uucgacaggaggcucacaacaggc | 260 |
| PA446 | gggagacaagaauaaacgcucaaCGUGUACCACAACAGUUCCACG GAAGCUGGAAUAGGACGCAGAGGAA uucgacaggaggcucacaacaggc | 261 |
| PA313 | gggagacaagaauaaacgcucaaACAAAAUUWUGGUGGGCCCCGcAACMGGGRGGRAGRCCGUUGAAGGC uucgacaggaggcucacaacaggc | 262 |
| PA336 | gggagacaagaauaaacgcucaaGAUCAUAACGAGAGGAGAGGGAGAACUACACGCGCGCGCAGGAAAGAG uucgacaggaggcucacaacaggc | 263 |
| PA301 | gggagacaagaauaaacgcucaaACACAAAUCGGGCAGGGUUGGGCACGGCACGGCAGGGCGCC uucgacaggaggcucacaacaggc | 264 |
| PA305 | gggagacaagaauaaacgcucaaGUGGGCUCGGGCCGGAUGUCUACGGGUGUGAAGAAACCCCUAGGGCAGGG uucgacaggaggcucacaacaggc | 265 |
| PA309 | gggagacaagaauaaacgcucaaGAUCAGCGGAACUAAGAAAUGGAAGGCUAGCACCGGGAUCGGGAGAA uucgacaggaggcucacaacaggc | 266 |

TABLE 25-continued

P-Selectin 2'NH₂ RNA Ligands

| Ligand | Sequence | SEQ ID NO. |
|---|---|---|
| PA315 | gggagacaagaauaaacgcucaaUAACAAAGCAGCAAAGUACCAGAGGAGAGUUGGCAGC uucgacaggaggcucacaacaggc | 267 |
| PA318 | gggagaca-gaauaaacgcucaaAGACCAAGGGACAGCAGCGGGGAAAAACAGAUCACAGCUGUAAGAGGGCP uucgacaggaggcucacaacaggc | 268 |
| PA319 | gggagacaagaauaaacgcucaaAGUCGGGGAUAGAAACACACUAAGAAGUGCAUCAGGUAGGAGAUAA uucgacaggnggcucacaacaggc | 269 |
| PA320 | gggagacaagaauaaacgcycaaGAGUAUCACACAAACCGGCAGGACUAAGCAGAAGGAGGUACGGAGA uucgacaggaggcucacaacaggc | 270 |
| PA321 | gggagacaagaauaaacNcucaaCGAAAUAGAAGGAACAGAAGAAUGGBGAWGNGGGAAAUgGCAACGAA uucgacaggnggcucacaacaggc | 271 |
| PA324 | gggagacaagaauaaacgcucaaACGAGACCUGGAUACGAGGCUGAGGGAAAGGGGAGMMMRRAMCUARRCKC uucgacaggaggcucacaacaggc | 272 |
| PA329 | gggagacaagaauaaacgcucaaGAAGGAUACAAAGGACUACGUGGGAUGGGAUGAAUGGGAGAACGGGAG uucgacaggaggcucacaacaggc | 273 |
| PA330 | gggagacaagaauaaacgcucaaAACGCACAAAGUAAGGGAUGGAUCGCCCUAGGCUGGAAGGGAAC uucgacaggaggcucacaacaggc | 274 |
| PA332 | gggagacaagaauaaacgcucaaGGUGAACGGCAGCAAGGCCCAAAACGUAAGGCCGGAAACNGGAGAGGGA uucgacaggnggcucacaacaggc | 275 |
| PA335 | gggagacaagaauaacgcucaaUGAUAUACACGUAAGCACUGAACCAGGCUGAGAUCCAUGCGUGCCCAGG uucgacaggaggcucacaacaggc | 276 |
| PA336 | gggagacaagaauaaacgcucaaGAUCAUAACGAGAGGAGAGGGAGAACUACACGCGCGCGAGGAAAGAG uucgacaggaggcucacaacaggc | 277 |
| PA338 | gggagacaagaauaaacgcucaaUCAAGUAAGGAGGAAGGGUCGUGACAGAAAAACGAGCAAAAACGCGAG uucgacaggaggcucacaacaggc | 278 |
| PA339 | gggagacaagaauaaacgcucaaAAGGUGCCGGGUUGGAGGGGUAGCAAGAAAUGGCUAGGGCGCASGA uucgacaggnggcucacaacaggc | 279 |
| PA342 | gggagacaagaauaaacgcucaaCCAACGCGCACCCCGCAGCAAACGAAAUUGGGGAGACAGGUGCAAGACAG uucgacaggaggcucacaacaggc | 280 |
| PA349 | gggagacaagaauaaackcucaaCAAACAAUAUCGGCGCAGGAAAACGUAGAAACGAAAMGGAGCUGCGYGGA uucgacaggaggcucacaacaggc | 281 |
| PA351 | gggagacaagaauaaacgcucaaUGAUAGCACAGUGUAUAAGAAAACGCAACACCGCGCGCGGAAAGAG uucgacaggaggcucacaacaggc | 282 |
| PA352 | gggagacaagaauaaacgcucaaGAUCAUCGCAGUAUCGGAAUCGACCCUCAGUGGGUGACAUGCdGACAAG uucgacaggaggcucacaacaggc | 283 |
| PA353 | gggagacaagaauaaacgcucaaGUACCGGGAAGGGAUGAACUGGGAUAUGGGAACGGAGGUCAGAGGCACGA uucgacaggaggcucacaacaggc | 284 |
| PA354 | gggagacaagaauaaacgcucaaGCAAUGGAACGCUAGGAGGGAACAUAAGCAGGGCGAGCGGAGUCGAUAGC uucgacaggaggcucacaacaggc | 285 |
| PA447 | gggagacaagaauaaacgcucaaAACAGAACUGAUCGGCGCAGGUUGAUAAAGGGGCAGCGCGAAGAUCACAA uucgacaggaggcucacaacaggc | 286 |
| PA463 | gggagacaagaauaaacgcucaaGGGAAACGGAAAGGGACAAGGCGAACAGACGAGAAGUAGACGGAGUAGGA uucgacaggaggcucacaacaggc | 287 |
| PA465 | gggagacaagaauaaacgcucaaNNNGAGGAAGGGCACGCAAGGAAACAAAACACAAAGCAGAAGUAGUAAGA uucgacaggaggcucacaacaggc | 288 |
| PA467 | gggagacaagaauaaacgcucaaGUACRCAGUGAGCAGAAGCAGAGAGACUUGGGAUGGGAUGAAAUGGKC uucgacaggaggcucacaacaggc | 289 |
| PA479 | gggagacaagaauaaacNcucaaCCGACGUGGACDCGCAUCGGCAUCCAGACCAGGCUGNBCNGCACCASACG uucgacaggaggcucacaacaggc | 290 |

TABLE 26

Dissociation Constants and Specificity of 2'NH2 RNA Ligands to P-Selectin

| Ligand | Kd (PS-Rg) | Kd (4° C.) | SLeX (IC50) | Kd (ES-Rg) | Kd (LS-Rg) | SEQ ID NO. |
|---|---|---|---|---|---|---|
| PA301 | 2.5 nM | | | | | 264 |
| PA305 | 0.21 pM | | | | | 265 |
| PA309 | 0.656 pM | | | | | 266 |
| PA315 | 5 nM | | | | | 267 |
| PA318 | 2 nM | | | | | 268 |
| PA319 | 11 nM | | | | | 269 |
| PA320 | 4.5 nM | | | | | 270 |
| PA321 | 8 nM | | | | | 271 |
| PA325 | >10 nM | | | | | 259 |
| PA327 | 13.5 nM | | | | | 260 |
| PA328 | 3 nM | | | | | 256 |
| PA329 | 4 nM | | | | | 273 |
| PA330 | 0.237 nM | | | | | 274 |
| PA335 | 10.5 nM | | | | | 276 |
| PA336 | 15 nM | | | | | 277 |
| PA337 | 4.5 nM | | | | | 257 |
| PA338 | 57 nM | | | | | 278 |
| PA339 | 13.5 nM | | | | | 279 |
| PA341 | 0.44 nM | | 3 nM | | 251 | |
| PA342 | 4 nM | | | | | 280 |
| PA350 | 0.06 nM | 0.01 nM | 2 nM | 375 nM | >3 μM | 252 |
| PA351 | 2 nM | | | | | 282 |
| PA352 | 6 nM | | | | | 283 |
| PA353 | 9 nM | | | | | 284 |
| PA354 | 5 nM | | | | | 285 |
| PA447 | 50 nM | | | | | 286 |
| PA448 | 5 nM | | | | | 258 |
| PA463 | 8 nM | | | | | 287 |
| PA465 | >50 nM | | | | | 288 |
| PA466 | 0.43 nM | | | | | 253 |
| PA467 | 24 nM | | | | | 289 |
| PA473 | 0.36 nM | | | | | 254 |
| PA477 | 0.57 nM | | | | | 255 |

SEQUENCE LISTING (1) GENERAL INFORMATION:

(iii) NUMBER OF SEQUENCES: 390

(2) INFORMATION FOR SEQ ID NO:1:

(i) SEQUENCE CHARACTERISTICS:
      (A) LENGTH: 98 base pairs
      (B) TYPE: nucleic acid
      (C) STRANDEDNESS: single
      (D) TOPOLOGY: linear (ii) MOLECULE TYPE: RNA (ix) FEATURE:
      (D) OTHER INFORMATION: All C's are 2'-NH2 cytosine (ix) FEATURE:
      (D) OTHER INFORMATION: All U's are 2'-NH2 uracil (xi) SEQUENCE DESCRIPTION: SEQ ID NO:1:

```
GGGAAAAGCG AAUCAUACAC AAGANNNNNN NNNNNNNNNN NNNNNNNNNN        50
NNNNNNNNNN NNNNNNNNNN NNNNGCUCCG CCAGAGACCA ACCGAGAA          98
```

(2) INFORMATION FOR SEQ ID NO:2:

(i) SEQUENCE CHARACTERISTICS:
      (A) LENGTH: 41 base pairs
      (B) TYPE: nucleic acid
      (C) STRANDEDNESS: single (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:2:

UAAUACGACU CACUAUAGGG AAAAGCGAAU CAUACACAAG A                            41

(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:3:

UUCUCGGUUG GUCUCUGGCG GAGC                                              24

(2) INFORMATION FOR SEQ ID NO:4:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:4:

GGGAAAAGCG AAUCAUACAC AAGAAUGGUU GGCCUGGGCG CAGGCUUCGA                   50

AGACUCGGCG GGAACGGGAA UGGCUCCGCC AGAGACCAAC CGAGAA                       96

(2) INFORMATION FOR SEQ ID NO:5:

(i) SEQUENCE CHARACTERISTICS:
        (A) LENGTH: 98 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:5:

GGGAAAAGCG AAUCAUACAC AAGACAGGCA CUGAAAACUC GGCGGGAACG                   50

AAAGUAGUGC CGACUCAGAC GCGUGCUCCG CCAGAGACCA ACCGAGAA    98

(2) INFORMATION FOR SEQ ID NO:6:

(i) SEQUENCE CHARACTERISTICS:
        (A) LENGTH: 91 base pairs
        (B) TYPE: nucleic acid
        (C) STRANDEDNESS: single
        (D) TOPOLOGY:  linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:6:

GGGAAAAGCG AAUCAUACAC AAGAAGUCUG GCCAAAGACU CGGCGGGAAC    50

GUAAAACGGC CAGAAUUGCU CCGCCAGAGA CCAACCGAGA A    91

(2) INFORMATION FOR SEQ ID NO:7:

(i) SEQUENCE CHARACTERISTICS:
        (A) LENGTH: 94 base pairs
        (B) TYPE: nucleic acid
        (C) STRANDEDNESS: single
        (D) TOPOLOGY:  linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:7:

GGGAAAAGCG AAUCAUACAC AAGAGUAGGA GGUUCCAUCA CCAGGACUCG    50

GCGGGAACGG AAGGUGAUGS GCUCCGCCAG AGACCAACCG AGAA    94

(2) INFORMATION FOR SEQ ID NO:8:

(i) SEQUENCE CHARACTERISTICS:
        (A) LENGTH: 95 base pairs
        (B) TYPE: nucleic acid
        (C) STRANDEDNESS: single
        (D) TOPOLOGY:  linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:8:

GGGAAAAGCG AAUCAUACAC AAGAACAAGG AUCGAUGGCG AGCCGGGGAG    50

GGCUCGGCGG GAACGAAAUC UGCUCCGCCA GAGACCAACC GAGAA    95

(2) INFORMATION FOR SEQ ID NO:9:

(i) SEQUENCE CHARACTERISTICS:
        (A) LENGTH: 97 base pairs
        (B) TYPE: nucleic acid
        (C) STRANDEDNESS: single
        (D) TOPOLOGY:  linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:9:

GGGAAAAGCG AAUCAUACAC AAGAUUGGGC AGGCAGAGCG AGACCGGGGG           50

CUCGGCGGGA ACGGAACAGG AAUGCUCCGC CAGAGACCAA CCGAGAA             97

(2) INFORMATION FOR SEQ ID NO:10:

(i) SEQUENCE CHARACTERISTICS:
        (A) LENGTH: 97 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:10:

GGAAAAGCG AAUCAUACAC AAGAAAGGGA UGGGAUUGGG ACGAGCGGCC           50

AGACUCGGC GGGAACGAAG GGUGCUCCGC CAGAGACCAA CCGAGAA              97

(2) INFORMATION FOR SEQ ID NO:11:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:11:

GGGAAAAGCG AAUCAUACAC AAGACUCGGC GGGAACGAAA GUGUCAUGGU           50

AGCAAGUCCA AUGGUGGACU CUGCUCCGCC AGAGACCAAC CGAGAA              96

(2) INFORMATION FOR SEQ ID NO:12:

(i) SEQUENCE CHARACTERISTICS:
        (A) LENGTH: 98 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:12:

```
GGGAAAAGCG AAUCAUACAC AAGACUCGGC GGGAACGUGA AGUGGGUAGG            50

UAGCUGAAGA CGGUCUGGGC GCCAGCUCCG CCAGAGACCA ACCGAGAA             98

(2) INFORMATION FOR SEQ ID NO:13:

(i) SEQUENCE CHARACTERISTICS:
        (A) LENGTH: 99 base pairs
        (B) TYPE: nucleic acid
        (C) STRANDEDNESS: single
        (D) TOPOLOGY:   linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:13:

GGGAAAAGCG AAUCAUACAC AAGAAAGGGA UGGGAUUGGG ACGAGCGGCC            50

AAGACUCGGC GGGAACGAAG GGUCCGCUCC GCCAGAGACC AACCGAGAA             99

(2) INFORMATION FOR SEQ ID NO:14:

(i) SEQUENCE CHARACTERISTICS:
        (A) LENGTH: 98 base pairs
        (B) TYPE: nucleic acid
        (C) STRANDEDNESS: single
        (D) TOPOLOGY:   linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:14:

GGGAAAAGCG AAUCAUACAC AAGACUCGGC GGGAACGAAG UGUGUGAGUA            50

ACGAUCACUU GGUACUAAAA GCCCGCUCCG CCAGAGACCA ACCGAGAA              98

(2) INFORMATION FOR SEQ ID NO:15:

(i) SEQUENCE CHARACTERISTICS:
        (A) LENGTH: 100 base pairs
        (B) TYPE: nucleic acid
        (C) STRANDEDNESS: single
        (D) TOPOLOGY:   linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:15:

GGGAAAAGCG AAUCAUACAC AAGACUCGGC GGGAAUCGAA AGUGUACUGA            50

AUUAGAACGG UGGGCCUGCU CAUCGUGCUC CGCCAGAGAC CAACCGAGAA           100

(2) INFORMATION FOR SEQ ID NO:16:

(i) SEQUENCE CHARACTERISTICS:
        (A) LENGTH: 103 base pairs
```

(B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:16:

GGGAAAAGCG AAUCAUACAC AAGACUCGGC GGGAAUCGUA AUGUGGAUGA           50

UAGCACGAUG GCAGYAGUAG UCGGACCGCG CUCCGCCAGA GACCAACCGA           100

GAA                                                             103

(2) INFORMATION FOR SEQ ID NO:17:

(i) SEQUENCE CHARACTERISTICS:
        (A) LENGTH: 98 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:17:

GGGAAAAGCG AAUCAUACAC AAGACAGCGG CGGAGUCAGU GAAAGCGUGG           50

GGGGYGCGGG AGGUCUACCC UGACGCUCCG CCAGAGACCA ACCGAGAA            98

(2) INFORMATION FOR SEQ ID NO:18:

(i) SEQUENCE CHARACTERISTICS:
        (A) LENGTH: 95 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:18:

GGGAAAAGCG AAUCAUACAC AAGACGGCUG UGUGUGGUAG CGUCAUAGUA           50

GGAGUCGUCA CGAACCAAGG CGCUCCGCCA GAGACCAACC GAGAA               95

(2) INFORMATION FOR SEQ ID NO:19:

(i) SEQUENCE CHARACTERISTICS:
        (A) LENGTH: 98 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
              (D) OTHER INFORMATION: All U's are 2'-NH2 uracil (xi) SEQUENCE DESCRIPTION: SEQ ID NO:19:

GGGAAAAGCG AAUCAUACAC AAGACGGCUG UGUGGUGUUG GAGCGUCAUA            50

GUAGGAGUCG UCACGAACCA AGGCGCUCCG CCAGAGACCA ACCGAGAA              98

(2) INFORMATION FOR SEQ ID NO:20:

(i) SEQUENCE CHARACTERISTICS:
              (A) LENGTH: 97 base pairs
              (B) TYPE: nucleic acid
              (C) STRANDEDNESS: single
              (D) TOPOLOGY:   linear (ii) MOLECULE TYPE: RNA (ix) FEATURE:
              (D) OTHER INFORMATION: All C's are 2'-NH2 cytosine (ix) FEATURE:
              (D) OTHER INFORMATION: All U's are 2'-NH2 uracil (xi) SEQUENCE DESCRIPTION: SEQ ID NO:20:

GGGAAAAGCG AAUCAUACAC AAGACGAUGC GAGGCAAGAA AUGGAGUCGU            50

UACGAACCCU CUUGCAGUGC GCGGCUCCGC CAGAGACCAA CCGAGAA               97

(2) INFORMATION FOR SEQ ID NO:21:

(i) SEQUENCE CHARACTERISTICS:
              (A) LENGTH: 95 base pairs
              (B) TYPE: nucleic acid
              (C) STRANDEDNESS: single
              (D) TOPOLOGY:   linear (ii) MOLECULE TYPE: RNA (ix) FEATURE:
              (D) OTHER INFORMATION: All C's are 2'-NH2 cytosine (ix) FEATURE:
              (D) OTHER INFORMATION: All U's are 2'-NH2 uracil (xi) SEQUENCE DESCRIPTION: SEQ ID NO:21:

GGGAAAAGCG AAUCAUACAC AAGACGUGCG GAGCAAAUAG GGGAUCAUGG            50

AGUCGUACGA ACCGUUAUCG CGCUCCGCCA GAGACCAACC GAGAA                 95

(2) INFORMATION FOR SEQ ID NO:22:

(i) SEQUENCE CHARACTERISTICS:
              (A) LENGTH: 97 base pairs
              (B) TYPE: nucleic acid
              (C) STRANDEDNESS: single
              (D) TOPOLOGY:   linear (ii) MOLECULE TYPE: RNA (ix) FEATURE:
              (D) OTHER INFORMATION: All C's are 2'-NH2 cytosine (ix) FEATURE:
              (D) OTHER INFORMATION: All U's are 2'-NH2 uracil (xi) SEQUENCE DESCRIPTION: SEQ ID NO:22:

GGGAAAAGCG AAUCAUACAC AAGACUGGGG AGCAGGAUAU GAGAUGUGCG            50

GGGCAAUGGA GUCGUGACGA ACCGCUCCGC CAGAGACCAA CCGAGAA               97

(2) INFORMATION FOR SEQ ID NO:23:

(i) SEQUENCE CHARACTERISTICS:
       (A) LENGTH: 95 base pairs
       (B) TYPE: nucleic acid
       (C) STRANDEDNESS: single
       (D) TOPOLOGY: linear (ii) MOLECULE TYPE: RNA (ix) FEATURE:
       (D) OTHER INFORMATION: All C's are 2'-NH2 cytosine (ix) FEATURE:
       (D) OTHER INFORMATION: All U's are 2'-NH2 uracil (xi) SEQUENCE DESCRIPTION: SEQ ID NO:23:

GGGAAAAGCG AAUCAUACAC AAGAGUCCGC CCCCAGGGAU GCAACGGGGU          50

GGCUCUAAAA GGCUUGGCUA AGCUCCGCCA GAGACCAACC GAGAA              95

(2) INFORMATION FOR SEQ ID NO:24:

(i) SEQUENCE CHARACTERISTICS:
       (A) LENGTH: 94 base pairs
       (B) TYPE: nucleic acid
       (C) STRANDEDNESS: single
       (D) TOPOLOGY: linear (ii) MOLECULE TYPE: RNA (ix) FEATURE:
       (D) OTHER INFORMATION: All C's are 2'-NH2 cytosine (ix) FEATURE:
       (D) OTHER INFORMATION: All U's are 2'-NH2 uracil (xi) SEQUENCE DESCRIPTION: SEQ ID NO:24:

GGGAAAAGCG AAUCAUACAC AAGAGAGAAU GAGCAUGGCC GGGGCAGGAA         50

GUGGGUGGCA ACGGAGGCCA GCUCCGCCAG AGACCAACCG AGAA               94

(2) INFORMATION FOR SEQ ID NO:25:

(i) SEQUENCE CHARACTERISTICS:
       (A) LENGTH: 95 base pairs
       (B) TYPE: nucleic acid
       (C) STRANDEDNESS: single
       (D) TOPOLOGY: linear (ii) MOLECULE TYPE: RNA (ix) FEATURE:
       (D) OTHER INFORMATION: All C's are 2'-NH2 cytosine (ix) FEATURE:
       (D) OTHER INFORMATION: All U's are 2'-NH2 uracil (xi) SEQUENCE DESCRIPTION: SEQ ID NO:25:

GGGAAAAGCG AAUCAUACAC AAGAGAUACA GCGCGGGUCU AAAGACCUUG         50

CCCCUAGGAU GCAACGGGGU GGCUCCGCCA GAGACCAACC GAGAA              95

(2) INFORMATION FOR SEQ ID NO:26:

(i) SEQUENCE CHARACTERISTICS:
       (A) LENGTH: 97 base pairs
       (B) TYPE: nucleic acid
       (C) STRANDEDNESS: single
       (D) TOPOLOGY: linear (ii) MOLECULE TYPE: RNA (ix) FEATURE:
              (D) OTHER INFORMATION: All C's are 2'-NH2 cytosine (ix) FEATURE:
              (D) OTHER INFORMATION: All U's are 2'-NH2 uracil (xi) SEQUENCE DESCRIPTION: SEQ ID NO:26:

GGGAAAAGCG AAUCAUACAC AAGAUGAAGG GUGGUAAGAG AGAGUCUGAG           50

CUCGUCCUAG GGAUGCAACG GCAGCUCCGC CAGAGACCAA CCGAGAA              97

(2) INFORMATION FOR SEQ ID NO:27:

(i) SEQUENCE CHARACTERISTICS:
              (A) LENGTH: 99 base pairs
              (B) TYPE: nucleic acid
              (C) STRANDEDNESS: single
              (D) TOPOLOGY:  linear (ii) MOLECULE TYPE: RNA (ix) FEATURE:
              (D) OTHER INFORMATION: All C's are 2'-NH2 cytosine (ix) FEATURE:
              (D) OTHER INFORMATION: All U's are 2'-NH2 uracil (xi) SEQUENCE DESCRIPTION: SEQ ID NO:27:

GGGAAAAGCG AAUCAUACAC AAGACAAACC UGCAGUCGCG CGGUGAAACC           50

UAGGGUUGCA ACGGUACAUC GCUGUGCUCC GCCAGAGACC AACCGAGAA            99

(2) INFORMATION FOR SEQ ID NO:28:

(i) SEQUENCE CHARACTERISTICS:
              (A) LENGTH: 97 base pairs
              (B) TYPE: nucleic acid
              (C) STRANDEDNESS: single
              (D) TOPOLOGY:  linear (ii) MOLECULE TYPE: RNA (ix) FEATURE:
              (D) OTHER INFORMATION: All C's are 2'-NH2 cytosine (ix) FEATURE:
              (D) OTHER INFORMATION: All U's are 2'-NH2 uracil (xi) SEQUENCE DESCRIPTION: SEQ ID NO:28:

GGGAAAAGCG AAUCAUACAC AAGAGUGGAC UGGAAUCUUC GAGGACAGGA           50

ACGUUCCUAG GGAUGCAACG GACGCUCCGC CAGAGACCAA CCGAGAA              97

(2) INFORMATION FOR SEQ ID NO:29:

(i) SEQUENCE CHARACTERISTICS:
              (A) LENGTH: 97 base pairs
              (B) TYPE: nucleic acid
              (C) STRANDEDNESS: single
              (D) TOPOLOGY:  linear (ii) MOLECULE TYPE: RNA (ix) FEATURE:
              (D) OTHER INFORMATION: All C's are 2'-NH2 cytosine (ix) FEATURE:
              (D) OTHER INFORMATION: All U's are 2'-NH2 uracil (xi) SEQUENCE DESCRIPTION: SEQ ID NO:29:

GGGAAAAGCG AAUCAUACAC AAGAGUGUAC CAAUGGAGGC AAUGCUGCGG           50

GAAUGGAGGC UAGGGAUGC AACGCUCCGC CAGAGACCAA CCGAGAA          97

(2) INFORMATION FOR SEQ ID NO:30:

(i) SEQUENCE CHARACTERISTICS:
        (A) LENGTH: 97 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:30:

GGGAAAAGCG AAUCAUACAC AAGAGUCCCU AGGGAUGCAA CGGGCAGCAU          50

UCGCAUAGGA GUAAUCGGAG GUCGCUCCGC CAGAGACCAA CCGAGAA            97

(2) INFORMATION FOR SEQ ID NO:31:

(i) SEQUENCE CHARACTERISTICS:
        (A) LENGTH: 97 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:31:

GGGAAAAGCG AAUCAUACAC AAGAGCCUAG GGAUGCAACG GCGAAUGGAU          50

AGCGAUGUCG UGGACAGCCA GGUGCUCCGC CAGAGACCAA CCGAGAA            97

(2) INFORMATION FOR SEQ ID NO:32:

(i) SEQUENCE CHARACTERISTICS:
        (A) LENGTH: 98 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:32:

GGGAAAAGCG AAUCAUACAC AAGAAUCGAA CCUAGGGAUG CAACGGUGAA          50

GGUUGUGAGG AUUCGCCAUU AGGCGCUCCG CCAGAGACCA ACCGAGAA           98

(2) INFORMATION FOR SEQ ID NO:33:

(i) SEQUENCE CHARACTERISTICS:
        (A) LENGTH: 98 base pairs
        (B) TYPE: nucleic acid
        (C) STRANDEDNESS: single (D) TOPOLOGY:  linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:33:

GGGAAAAGCG AAUCAUACAC AAGAGCUAGG GAUGCCGCAG AAUGGUCGCG           50

GAUGUAAUAG GUGAAGAUUG UUGCGCUCCG CCAGAGACCA ACCGAGAA             98

(2) INFORMATION FOR SEQ ID NO:34:

(i) SEQUENCE CHARACTERISTICS:
        (A) LENGTH: 98 base pairs
        (B) TYPE: nucleic acid
        (C) STRANDEDNESS: single
        (D) TOPOLOGY:  linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:34:

GGGAAAAGCG AAUCAUACAC AAGAGGACCU AGGGAUGCAA CGGUCCGACC           50

UUGAUGCGCG GGUGUCCAAG CUACGCUCCG CCAGAGACCA ACCGAGAA             98

(2) INFORMATION FOR SEQ ID NO:35:

(i) SEQUENCE CHARACTERISTICS:
        (A) LENGTH: 97 base pairs
        (B) TYPE: nucleic acid
        (C) STRANDEDNESS: single
        (D) TOPOLOGY:  linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:35:

GGGAAAAGCG AAUCAUACAC AAGAAAGGGA GGAGCUAGAG AGGGAAAGGU           50

UACUACGCGC CAGAAUAGGA UGUGCUCCGC CAGAGACCAA CCGAGAA              97

(2) INFORMATION FOR SEQ ID NO:36:

(i) SEQUENCE CHARACTERISTICS:
        (A) LENGTH: 97 base pairs
        (B) TYPE: nucleic acid
        (C) STRANDEDNESS: single
        (D) TOPOLOGY:  linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:36:

GGGAAAAGCG AAUCAUACAC AAGACCAACG UACAUCGCGA GCUGGUGGAG                50

AGUUCAUGAG GGUGUUACGG GGUGCUCCGC CAGAGACCAA CCGAGAA                   97

(2) INFORMATION FOR SEQ ID NO:37:

(i) SEQUENCE CHARACTERISTICS:
        (A) LENGTH: 96 base pairs
        (B) TYPE: nucleic acid
        (C) STRANDEDNESS: single
        (D) TOPOLOGY:  linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:37:

GGGAAAAGCG AAUCAUACAC AAGACCCAAC GUGUCAUCGC GAGCUGGCGG                50

AGAGUUCAUG AGGGUUACGG GUGCUCCGCC AGAGACCAAC CGAGAA                    96

(2) INFORMATION FOR SEQ ID NO:38:

(i) SEQUENCE CHARACTERISTICS:
        (A) LENGTH: 98 base pairs
        (B) TYPE: nucleic acid
        (C) STRANDEDNESS: single
        (D) TOPOLOGY:  linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:38:

GGGAAAAGCG AAUCAUACAC AAGAGUUGGU GCGAGCUGGG GCGGCGAGAA                50

GGUAGGCGGU CCGAGUGUUC GAAUGCUCCG CCAGAGACCA ACCGAGAA                  98

(2) INFORMATION FOR SEQ ID NO:39:

(i) SEQUENCE CHARACTERISTICS:
        (A) LENGTH: 98 base pairs
        (B) TYPE: nucleic acid
        (C) STRANDEDNESS: single
        (D) TOPOLOGY:  linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:39:

GGGAAAAGCG AAUCAUACAC AAGACUGGCA AGRAGUGCGU GAGGGUACGU                50

UAGGGGUGUU UGGGCCGAUC GCAUGCUCCG CCAGAGACCA ACCGAGAA                  98

(2) INFORMATION FOR SEQ ID NO:40:

(i) SEQUENCE CHARACTERISTICS:

(A) LENGTH: 97 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:40:

GGGAAAAGCG AAUCAUACAC AAGAUUGGUC GUACUGGACA GAGCCGUGGU          50

AGAGGGAUUG GGACAAAGUG UCAGCUCCGC CAGAGACCAA CCGAGAA            97

(2) INFORMATION FOR SEQ ID NO:41:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:41:

GGGAAAAGCG AAUCAUACAC AAGAUGUGAG AAAGUGGCCA ACUUUAGGAC          50

GUCGGUGGAC UGYGCGGGUA GGCUCGCUCC GCCAGAGACC AACCGAGAA          99

(2) INFORMATION FOR SEQ ID NO:42:

(i) SEQUENCE CHARACTERISTICS:
        (A) LENGTH: 98 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:42:

GGGAAAAGCG AAUCAUACAC AAGACAGGCA GAUGUGUCUG AGUUCGUCGG          50

AGUAGACGUC GGUGGACGCG GAACGCUCCG CCAGAGACCA ACCGAGAA           98

(2) INFORMATION FOR SEQ ID NO:43:

(i) SEQUENCE CHARACTERISTICS:
        (A) LENGTH: 97 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:43:

GGGAAAAGCG AAUCAUACAC AAGAUGUGAU UAGGCAGUUG CAGCCGCCGU          50

GCGGAGACGU GACUCGAGGA UUCGCUCCGC CAGAGACCAA CCGAGAA             97

(2) INFORMATION FOR SEQ ID NO:44:

(i) SEQUENCE CHARACTERISTICS:
        (A) LENGTH: 96 base pairs
        (B) TYPE: nucleic acid
        (C) STRANDEDNESS: single
        (D) TOPOLOGY:  linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:44:

GGGAAAAGCG AAUCAUACAC AAGAUGCCGG UGGAAAGGCG GGUAGGUGAC          50

CCGAGGAUUC CUACCAAGCC AUGCUCCGCC AGAGACCAAC CGAGAA              96

(2) INFORMATION FOR SEQ ID NO:45:

(i) SEQUENCE CHARACTERISTICS:
        (A) LENGTH: 93 base pairs
        (B) TYPE: nucleic acid
        (C) STRANDEDNESS: single
        (D) TOPOLOGY:  linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:45:

GGGAAAAGCG AAUCAUACAC AAGAGAGGUG RAUGGGAGAG UGGAGCCCGG          50

GUGACUCGAG GAUUCCCGUG CUCCGCCAGA GACCAACCGA GAA                 93

(2) INFORMATION FOR SEQ ID NO:46:

(i) SEQUENCE CHARACTERISTICS:
        (A) LENGTH: 97 base pairs
        (B) TYPE: nucleic acid
        (C) STRANDEDNESS: single
        (D) TOPOLOGY:  linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:46:

GGGAAAAGCG AAUCAUACAC AAGAGUCAUG CUGUGGCUGA ACAUACUGGU          50

GAAAGUUCAG UAGGGUGGAU ACAGCUCCGC CAGAGACCAA CCGAGAA             97

```
(2) INFORMATION FOR SEQ ID NO:47:

(i) SEQUENCE CHARACTERISTICS:
        (A) LENGTH: 96 base pairs
        (B) TYPE: nucleic acid
        (C) STRANDEDNESS: single
        (D) TOPOLOGY:  linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:47:

GGGAAAAGCG AAUCAUACAC AAGACCGGGG AUGGUGAGUC GGGCAGUGUG           50

ACCGAACUGG UGCCCGCUGA GAGCUCCGCC AGAGACCAAC CGAGAA              96

(2) INFORMATION FOR SEQ ID NO:48:

(i) SEQUENCE CHARACTERISTICS:
        (A) LENGTH: 97 base pairs
        (B) TYPE: nucleic acid
        (C) STRANDEDNESS: single
        (D) TOPOLOGY:  linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:48:

GGGAAAAGCG AAUCAUACAC AAGAACACUA ACCAGGUCUC UGAACGCGGG           50

ACGGAGGUGU GGGCGAGGUG GAAGCUCCGC CAGAGACCAA CCGAGAA             97

(2) INFORMATION FOR SEQ ID NO:49:

(i) SEQUENCE CHARACTERISTICS:
        (A) LENGTH: 99 base pairs
        (B) TYPE: nucleic acid
        (C) STRANDEDNESS: single
        (D) TOPOLOGY:  linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:49:

GGGAAAAGCG AAUCAUACAC AAGACCGUCU CCCGAGAACC AGGCAGAGGA           50

CGUGCUGAAG GAGCUGCAUC UAGAAGCUCC GCCAGAGACC AACCGAGAA           99

(2) INFORMATION FOR SEQ ID NO:50:

(i) SEQUENCE CHARACTERISTICS:
        (A) LENGTH: 99 base pairs
        (B) TYPE: nucleic acid
        (C) STRANDEDNESS: single
        (D) TOPOLOGY:  linear (ii) MOLECULE TYPE: RNA
```

```
    (ix) FEATURE:
         (D) OTHER INFORMATION: All C's are 2'-NH2 cytosine (ix) FEATURE:
         (D) OTHER INFORMATION: All U's are 2'-NH2 uracil (xi) SEQUENCE DESCRIPTION: SEQ ID NO:50:

GGGAAAAGCG AAUCAUACAC AAGACCGUCU CCGAGAACCA GGCAGAGGAG          50

GUGCUGAAGG RGCUGGCAUC UACAAGCUCC GCCAGAGACC AACCGAGAA           99

(2) INFORMATION FOR SEQ ID NO:51:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: RNA (ix) FEATURE:
         (D) OTHER INFORMATION: All C's are 2'-NH2 cytosine (ix) FEATURE:
         (D) OTHER INFORMATION: All U's are 2'-NH2 uracil (xi) SEQUENCE DESCRIPTION: SEQ ID NO:51:

GGGAAAAGCG AAUCAUACAC AAGACCCGCA CAUAAUGUAG GGAACAAUGU          50

UAUGGCGGAA UUGAUAACCG GUGCUCCGCC AGAGACCAAC CGAGAA              96

(2) INFORMATION FOR SEQ ID NO:52:

(i) SEQUENCE CHARACTERISTICS:
        (A) LENGTH: 98 base pairs
        (B) TYPE: nucleic acid
        (C) STRANDEDNESS: single
        (D) TOPOLOGY: linear (ii) MOLECULE TYPE: RNA (ix) FEATURE:
         (D) OTHER INFORMATION: All C's are 2'-NH2 cytosine (ix) FEATURE:
         (D) OTHER INFORMATION: All U's are 2'-NH2 uracil (xi) SEQUENCE DESCRIPTION: SEQ ID NO:52:

GGGAAAAGCG AAUCAUACAC AAGACGAUGU UAGCGCCUCC GGGAGAGGUU          50

AGGGUCGUGC GGNAAGAGUG AGGUGCUCCG CCAGAGACCA ACCGAGAA            98

(2) INFORMATION FOR SEQ ID NO:53:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (ii) MOLECULE TYPE: RNA (ix) FEATURE:
         (D) OTHER INFORMATION: All C's are 2'-NH2 cytosine (ix) FEATURE:
         (D) OTHER INFORMATION: All U's are 2'-NH2 uracil (xi) SEQUENCE DESCRIPTION: SEQ ID NO:53:

GGGAAAAGCG AAUCAUACAC AAGAGGUACG GGCGAGACGA GAUGGACUUA          50
```

```
UAGGUCGAUG AACGGGUAGC AGCUCGCUCC GCCAGAGACC AACCGAGAA            99
```

(2) INFORMATION FOR SEQ ID NO:54:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:54:

```
GGGAAAAGCG AAUCAUACAC AAGACGGUUG CUGAACAGAA CGUGAGUCUU            50

GGUGAGUCGC ACAGAUUGUC CUGCUCCGCC AGAGACCAAC CGAGAA                96
```

(2) INFORMATION FOR SEQ ID NO:55:

(i) SEQUENCE CHARACTERISTICS:
        (A) LENGTH: 97 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:55:

```
GGGAAAAGCG AAUCAUACAC AAGAACUGAG UAAGGUCUGG CGUGGCAUUA            50

GGUUAGUGGG AGGCUUGGAG UAGGCUCCGC CAGAGACCAA CCGAGAA               97
```

(2) INFORMATION FOR SEQ ID NO:56:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:56:

```
AAGACUCGGC GGGAACGAAA                                             20
```

(2) INFORMATION FOR SEQ ID NO:57:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: RNA (ix) FEATURE:
         (D) OTHER INFORMATION: All C's are 2'-NH2 cytosine (ix) FEATURE:
         (D) OTHER INFORMATION: All U's are 2'-NH2 uracil (xi) SEQUENCE DESCRIPTION: SEQ ID NO:57:

GGAGUCGUGA CGAACC                                                            16

(2) INFORMATION FOR SEQ ID NO:58:

(i) SEQUENCE CHARACTERISTICS:
         (A) LENGTH: 16 base pairs
         (B) TYPE: nucleic acid
         (C) STRANDEDNESS: single
         (D) TOPOLOGY: linear (ii) MOLECULE TYPE: RNA (ix) FEATURE:
         (D) OTHER INFORMATION: All C's are 2'-NH2 cytosine (ix) FEATURE:
         (D) OTHER INFORMATION: All U's are 2'-NH2 uracil (xi) SEQUENCE DESCRIPTION: SEQ ID NO:58:

CCUAGGGAUG CAACGG                                                            16

(2) INFORMATION FOR SEQ ID NO:59:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: RNA (ix) FEATURE:
         (D) OTHER INFORMATION: All C's are 2'-NH2 cytosine (ix) FEATURE:
         (D) OTHER INFORMATION: All U's are 2'-NH2 uracil (xi) SEQUENCE DESCRIPTION: SEQ ID NO:59:

RCUGGGAGRG UGGGUGUU                                                          18

(2) INFORMATION FOR SEQ ID NO:60:

(i) SEQUENCE CHARACTERISTICS:
         (A) LENGTH: 42 base pairs
         (B) TYPE: nucleic acid
         (C) STRANDEDNESS: single
         (D) TOPOLOGY: linear (ii) MOLECULE TYPE: RNA (ix) FEATURE:
         (D) OTHER INFORMATION: All C's are 2'-NH2 cytosine (ix) FEATURE:
         (D) OTHER INFORMATION: All U's are 2'-NH2 uracil (xi) SEQUENCE DESCRIPTION: SEQ ID NO:60:

UGUGNNNNAG UNNNNNNNNN UAGACGUCGG UGGACNNNGC GG                                42

(2) INFORMATION FOR SEQ ID NO:61:

(i) SEQUENCE CHARACTERISTICS:
         (A) LENGTH: 21 base pairs (B) TYPE: nucleic acid
        (C) STRANDEDNESS: single
        (D) TOPOLOGY:  linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:61:

GGGNNNGUGA CYCGRGGAYU C                                              21

(2) INFORMATION FOR SEQ ID NO:62:

(i) SEQUENCE CHARACTERISTICS:
        (A) LENGTH: 23 base pairs
        (B) TYPE: nucleic acid
        (C) STRANDEDNESS: single
        (D) TOPOLOGY:  linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:62:

UGANCNNACU GGUGNNNGNG NAG                                            23

(2) INFORMATION FOR SEQ ID NO:63:

(i) SEQUENCE CHARACTERISTICS:
        (A) LENGTH: 32 base pairs
        (B) TYPE: nucleic acid
        (C) STRANDEDNESS: single
        (D) TOPOLOGY:  linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:63:

GUCUCYGAAC NNGGNAGGAN GUGNUGGAGN UG                                  32

(2) INFORMATION FOR SEQ ID NO:64:

(i) SEQUENCE CHARACTERISTICS:
        (A) LENGTH: 71 base pairs
        (B) TYPE: nucleic acid
        (C) STRANDEDNESS: single
        (D) TOPOLOGY:  linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:64:

GGGAGGACGA UGCGGNNNNN NNNNNNNNNN NNNNNNNNNN NNNNNNNNNN                50

NNNNNCAGAC GACUCGCCCG A                                              71

(2) INFORMATION FOR SEQ ID NO:65:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:65:

TAATACGACT CACTATAGGG AGGACGATGC GG                                  32

(2) INFORMATION FOR SEQ ID NO:66:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:66:

TCGGGCGAGT CGTCCTG                                                   17

(2) INFORMATION FOR SEQ ID NO:67:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:67:

GGGAGGACGA UGCGGCGCGU AUGUGUGAAA GCGUGUGCAC GGAGGCGUCU               50

ACAAUCAGAC GACUCGCCCG A                                              71

(2) INFORMATION FOR SEQ ID NO:68:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:

(D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:68:

GGGAGGACGA UGCGGGGCAU UGUGUGAAUA GCUGAUCCCA CAGGUAACAA           50

CAGCACAGAC GACUCGCCCG A                                          71

(2) INFORMATION FOR SEQ ID NO:69:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:69:

GGGAGGACGA UGCGGUAAUG UGUGAAUCAA GCAGUCUGAA UAGAUUAGAC           50

AAAAUCAGAC GACUCGCCCG A                                          71

(2) INFORMATION FOR SEQ ID NO:70:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:70:

GGGAGGACGA UGCGGAUGUG UGAGUAGCUG AGCGCCCGAG UAUGAWACCU           50

GACUACAGAC GACUCGCCCG A                                          71

(2) INFORMATION FOR SEQ ID NO:71:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:71:

GGGAGGACGA UGCGGAAACC UUGAUGUGUG AUAGAGCAUC CCCCAGGCGA           50

CGUACCAGAC GACUCGCCCG A                                          71

(2) INFORMATION FOR SEQ ID NO:72:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:72:

GGGAGGACGA UGCGGUUGAG AUGUGUGAGU ACAAGCUCAA AAUCCCGUUG          50

GAGGCAGACG ACUCGCCCGA                                          70

(2) INFORMATION FOR SEQ ID NO:73:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:73:

GGGAGGACGA UGCGGUAGAG GUAGUAUGUG UGGGAGAUGA AAAUACUGUG          50

GAAAGCAGAC GACUCGCCCG A                                        71

(2) INFORMATION FOR SEQ ID NO:74:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:74:

GGGAGGACGA UGCGGAAAGU UAUGAGUCCG UAUAUCAAGG UCGACAUGUG          50

UGAAUCAGAC GACUCGCCCG A                                        71

(2) INFORMATION FOR SEQ ID NO:75:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
             (D) OTHER INFORMATION: All C's are 2'-NH2 cytosine (ix) FEATURE:
             (D) OTHER INFORMATION: All U's are 2'-NH2 uracil (xi) SEQUENCE DESCRIPTION: SEQ ID NO:75:

GGGAGGACGA UGCGGCACGA AAACCCGAA UUGGGUCGCC CAUAAGGAUG          50

UGUGACAGAC GACUCGCCCG A                                        71

(2) INFORMATION FOR SEQ ID NO:76:

(i) SEQUENCE CHARACTERISTICS:
            (A) LENGTH: 71 base pairs
            (B) TYPE: nucleic acid
            (C) STRANDEDNESS: single
            (D) TOPOLOGY:  linear (ii) MOLECULE TYPE: RNA (ix) FEATURE:
             (D) OTHER INFORMATION: All C's are 2'-NH2 cytosine (ix) FEATURE:
             (D) OTHER INFORMATION: All U's are 2'-NH2 uracil (xi) SEQUENCE DESCRIPTION: SEQ ID NO:76:

GGGAGGACGA UGCGGGUAAA GAGAUCCUAA UGGCUCGCUA GAUGUGAUGU          50

GAAACCAGAC GACUCGCCCG A                                        71

(2) INFORMATION FOR SEQ ID NO:77:

(i) SEQUENCE CHARACTERISTICS:
            (A) LENGTH: 71 base pairs
            (B) TYPE: nucleic acid
            (C) STRANDEDNESS: single
            (D) TOPOLOGY:  linear (ii) MOLECULE TYPE: RNA (ix) FEATURE:
             (D) OTHER INFORMATION: All C's are 2'-NH2 cytosine (ix) FEATURE:
             (D) OTHER INFORMATION: All U's are 2'-NH2 uracil (xi) SEQUENCE DESCRIPTION: SEQ ID NO:77:

GGGAGGACGA UGCGGUAACA ACAAUCAAGG CGGGUUCACC GCCCCAGUAU          50

GAGUGCAGAC GACUCGCCCG A                                        71

(2) INFORMATION FOR SEQ ID NO:78:

(i) SEQUENCE CHARACTERISTICS:
            (A) LENGTH: 71 base pairs
            (B) TYPE: nucleic acid
            (C) STRANDEDNESS: single
            (D) TOPOLOGY:  linear (ii) MOLECULE TYPE: RNA (ix) FEATURE:
             (D) OTHER INFORMATION: All C's are 2'-NH2 cytosine (ix) FEATURE:
             (D) OTHER INFORMATION: All U's are 2'-NH2 uracil (xi) SEQUENCE DESCRIPTION: SEQ ID NO:78:

GGGAGGACGA UGCGGUAACA ACAAUCAAGG CGGGUUYACC GCCCCAGUAU         50

GAGUACAGAC GACUCGCCCG A                                       71

(2) INFORMATION FOR SEQ ID NO:79:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:79:

GGGAGGACGA UGCGGUAACA ACAAUCAAGG CGGGUUYACC GCUCCAGUAU         50

GAGUACAGAC GACUCGCCCG A                                       71

(2) INFORMATION FOR SEQ ID NO:80:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:80:

GGGAGGACGA UGCGGUAACA ACAAUCAAGG CGGGUUCACC GCCCCAGUAU         50

GAGUGCAGAC GACUCGCCCG A                                       71

(2) INFORMATION FOR SEQ ID NO:81:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:81:

GGGAGGACGA UGCGGACCAA GCAAUCUAUG GUCGAACGCU ACACAUGAAU         50

GACGUCAGAC GACUCGCCCG A                                       71

(2) INFORMATION FOR SEQ ID NO:82:

(i) SEQUENCE CHARACTERISTICS:
        (A) LENGTH: 71 base pairs
        (B) TYPE: nucleic acid (C) STRANDEDNESS: single
            (D) TOPOLOGY: linear (ii) MOLECULE TYPE: RNA (ix) FEATURE:
            (D) OTHER INFORMATION: All C's are 2'-NH2 cytosine (ix) FEATURE:
            (D) OTHER INFORMATION: All U's are 2'-NH2 uracil (xi) SEQUENCE DESCRIPTION: SEQ ID NO:82:

GGGAGGACGA UGCGGGAACA UGAAGUAAUC AAAGUCGUAC CAAUAUACAG          50

GAAGCCAGAC GACUCGCCCG A                                        71

(2) INFORMATION FOR SEQ ID NO:83:

(i) SEQUENCE CHARACTERISTICS:
            (A) LENGTH: 70 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All C's are 2'-NH2 cytosine (ix) FEATURE:
            (D) OTHER INFORMATION: All U's are 2'-NH2 uracil (xi) SEQUENCE DESCRIPTION: SEQ ID NO:83:

GGGAGGACGA UGCGGGACAU GAAGUAAGAC CGUCACAAUU CGAAUGAUUG          50

AAUACAGACG ACUCGCCCGA                                          70

(2) INFORMATION FOR SEQ ID NO:84:

(i) SEQUENCE CHARACTERISTICS:
            (A) LENGTH: 72 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All C's are 2'-NH2 cytosine (ix) FEATURE:
            (D) OTHER INFORMATION: All U's are 2'-NH2 uracil (xi) SEQUENCE DESCRIPTION: SEQ ID NO:84:

GGGAGGACGA UGCGGGAACA UGAAGUAAAA AGUCGACGAA UUAGCUGUAA          50

CCAAAACAGA CGACUCGCCC GA                                       72

(2) INFORMATION FOR SEQ ID NO:85:

(i) SEQUENCE CHARACTERISTICS:
            (A) LENGTH: 71 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All C's are 2'-NH2 cytosine (ix) FEATURE:
            (D) OTHER INFORMATION: All U's are 2'-NH2 uracil (xi) SEQUENCE DESCRIPTION: SEQ ID NO:85:

GGGAGGACGA UGCGGGAACA UGAAGUAAAA GUCUGAGUUA GUAAAUUACA            50

GUGAUCAGAC GACUCGCCCG A                                          71

(2) INFORMATION FOR SEQ ID NO:86:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:86:

GGGAGGACGA UGCGGGAACU UGAAGUUGAA NUCGCUAAGG UUAUGGAUUC            50

AAGAUUCAGA CGACUCGCCC GA                                         72

(2) INFORMATION FOR SEQ ID NO:87:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:87:

GGGAGGACGA UGCGGAACAU GAAGUAAUAA GUCGACGUAA UUAGCUGUAA            50

CUAAACAGAC GACUCGCCCG A                                          71

(2) INFORMATION FOR SEQ ID NO:88:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:88:

GGGAGGACGA UGCGGAACAU GAAGUAAAAG UCUGAGUUAG AAAUUACAAG            50

UGAUCAGACG ACUCGCCCGA                                            70

(2) INFORMATION FOR SEQ ID NO:89:

(i) SEQUENCE CHARACTERISTICS:
            (A) LENGTH: 71 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All C's are 2'-NH2 cytosine (ix) FEATURE:
            (D) OTHER INFORMATION: All U's are 2'-NH2 uracil (xi) SEQUENCE DESCRIPTION: SEQ ID NO:89:

GGGAGGACGA UGCGGUAACA UAAAGUAGCG CGUCUGUGAG AGGAAGUGCC            50

UGGAUCAGAC GACUCGCCCG A                                          71

(2) INFORMATION FOR SEQ ID NO:90:

(i) SEQUENCE CHARACTERISTICS:
            (A) LENGTH: 71 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All C's are 2'-NH2 cytosine (ix) FEATURE:
            (D) OTHER INFORMATION: All U's are 2'-NH2 uracil (xi) SEQUENCE DESCRIPTION: SEQ ID NO:90:

GGGAGGACGA UGCGGAUAGA ACCGCAAGGA UAACCUCGAC CGUGGUCAAC            50

UGAGACAGAC GACUCGCCCG A                                          71

(2) INFORMATION FOR SEQ ID NO:91:

(i) SEQUENCE CHARACTERISTICS:
            (A) LENGTH: 70 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All C's are 2'-NH2 cytosine (ix) FEATURE:
            (D) OTHER INFORMATION: All U's are 2'-NH2 uracil (xi) SEQUENCE DESCRIPTION: SEQ ID NO:91:

GGGAGGACGA UGCGGUAAGA ACCGCUAGCG CACGAUCAAA CAAAGAGAAA            50

CAAACAGACG ACUCGCCCGA                                            70

(2) INFORMATION FOR SEQ ID NO:92:

(i) SEQUENCE CHARACTERISTICS:
            (A) LENGTH: 71 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All C's are 2'-NH2 cytosine (ix) FEATURE:
    (D) OTHER INFORMATION: All U's are 2'-NH2 uracil (xi) SEQUENCE DESCRIPTION: SEQ ID NO:92:

GGGAGGACGA UGCGGUUCUC UCCAAGAACY GAGCGAAUAA ACSACCGGAS      50

UCACACAGAC GACUCGCCCG A      71

(2) INFORMATION FOR SEQ ID NO:93:

(i) SEQUENCE CHARACTERISTICS:
        (A) LENGTH: 71 base pairs
        (B) TYPE: nucleic acid
        (C) STRANDEDNESS: single
        (D) TOPOLOGY:  linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:93:

GGGAGGACGA UGCGGUGUCU CUCCUGACUU UUAUUCUUAG UUCGAGCUGU      50

CCUGGCAGAC GACUCGCCCG A      71

(2) INFORMATION FOR SEQ ID NO:94:

(i) SEQUENCE CHARACTERISTICS:
        (A) LENGTH: 71 base pairs
        (B) TYPE: nucleic acid
        (C) STRANDEDNESS: single
        (D) TOPOLOGY:  linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:94:

GGGAGGACGA UGCGGCCGUA CAUGGUAARC CUCGAAGGAU UCCCGGGAUG      50

AUCCCCAGAC GACUCGCCCG A      71

(2) INFORMATION FOR SEQ ID NO:95:

(i) SEQUENCE CHARACTERISTICS:
        (A) LENGTH: 71 base pairs
        (B) TYPE: nucleic acid
        (C) STRANDEDNESS: single
        (D) TOPOLOGY:  linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:95:

GGGAGGACGA UGCGGUCCCA GAGUCCCGUG AUGCGAAGAA UCCAUUAGUA      50

CCAGACAGAC GACUCGCCCG A      71

(2) INFORMATION FOR SEQ ID NO:96:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:96:

```
GGGAGGACGA UGCGGGAUGU AAAUGACAAA UGAACCUCGA AAGAUUGCAC          50

ACUCCAGACG ACUCGCCCGA                                          70
```

(2) INFORMATION FOR SEQ ID NO:97:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:97:

```
GGGAGGACGA UGCGGAUGUA AAUCUAGGCA GAAACGUAGG GCAUCCACCG          50

CAACGACAGA CGACUCGCCC GA                                       72
```

(2) INFORMATION FOR SEQ ID NO:98:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:98:

```
GGGAGGACGA UGCGGAUAAC CCAAGCAGCN UCGAGAAAGA GCUCCAUAGA          50

UGAUCAGACG ACUCGCCCGA                                          70
```

(2) INFORMATION FOR SEQ ID NO:99:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
   (D) OTHER INFORMATION: All C's are 2'-NH2 cytosine (ix) FEATURE:
   (D) OTHER INFORMATION: All U's are 2'-NH2 uracil (xi) SEQUENCE DESCRIPTION: SEQ ID NO:99:

GGGAGGACGA UGCGGCAAAG CACGCGUAUG GCAUGAAACU GGCANCCCAA       50

GUAAGCAGAC GACUCGCCCG A       71

(2) INFORMATION FOR SEQ ID NO:100:

(i) SEQUENCE CHARACTERISTICS:
      (A) LENGTH: 71 base pairs
      (B) TYPE: nucleic acid
      (C) STRANDEDNESS: single
      (D) TOPOLOGY: linear (ii) MOLECULE TYPE: RNA (ix) FEATURE:
      (D) OTHER INFORMATION: All C's are 2'-NH2 cytosine (ix) FEATURE:
      (D) OTHER INFORMATION: All U's are 2'-NH2 uracil (xi) SEQUENCE DESCRIPTION: SEQ ID NO:100:

GGGAGGACGA UGCGGCAAAA GGUUGACGUA GCGAAGCUCU CAAAAUGGUC       50

AUGACCAGAC GACUCGCCCG A       71

(2) INFORMATION FOR SEQ ID NO:101:

(i) SEQUENCE CHARACTERISTICS:
      (A) LENGTH: 70 base pairs
      (B) TYPE: nucleic acid
      (C) STRANDEDNESS: single
      (D) TOPOLOGY: linear (ii) MOLECULE TYPE: RNA (ix) FEATURE:
      (D) OTHER INFORMATION: All C's are 2'-NH2 cytosine (ix) FEATURE:
      (D) OTHER INFORMATION: All U's are 2'-NH2 uracil (xi) SEQUENCE DESCRIPTION: SEQ ID NO:101:

GGGAGGACGA UGCGGAAGUG AAGCUAAAGC GGAGGGCCAU UCAGUUUCNC       50

ACCACAGACG ACUCGCCCGA       70

(2) INFORMATION FOR SEQ ID NO:102:

(i) SEQUENCE CHARACTERISTICS:
      (A) LENGTH: 70 base pairs
      (B) TYPE: nucleic acid
      (C) STRANDEDNESS: single
      (D) TOPOLOGY: linear (ii) MOLECULE TYPE: RNA (ix) FEATURE:
      (D) OTHER INFORMATION: All C's are 2'-NH2 cytosine (ix) FEATURE:
      (D) OTHER INFORMATION: All U's are 2'-NH2 uracil (xi) SEQUENCE DESCRIPTION: SEQ ID NO:102:

GGGAGGACGA UGCGGAAGUG AAGCUAAAGS GGAGGGCCAC UCAGAAACGC       50

ACCACAGACG ACUCGCCCGA                                              70

(2) INFORMATION FOR SEQ ID NO:103:

(i) SEQUENCE CHARACTERISTICS:
        (A) LENGTH: 71 base pairs
        (B) TYPE: nucleic acid
        (C) STRANDEDNESS: single
        (D) TOPOLOGY:  linear (ii) MOLECULE TYPE: RNA (ix) FEATURE:
         (D) OTHER INFORMATION: All C's are 2'-NH2 cytosine (ix) FEATURE:
         (D) OTHER INFORMATION: All U's are 2'-NH2 uracil (xi) SEQUENCE DESCRIPTION: SEQ ID NO:103:

GGGAGGACGA UGCGGCACCG CUAAGCAGUG GCAUAGCCCA GUAACCUGUA            50

AGAGACAGAC GACUCGCCCG A                                           71

(2) INFORMATION FOR SEQ ID NO:104:

(i) SEQUENCE CHARACTERISTICS:
        (A) LENGTH: 67 base pairs
        (B) TYPE: nucleic acid
        (C) STRANDEDNESS: single
        (D) TOPOLOGY:  linear (ii) MOLECULE TYPE: RNA (ix) FEATURE:
         (D) OTHER INFORMATION: All C's are 2'-NH2 cytosine (ix) FEATURE:
         (D) OTHER INFORMATION: All U's are 2'-NH2 uracil (xi) SEQUENCE DESCRIPTION: SEQ ID NO:104:

GGGAGGACGA UGCGGCACGC UAAGCAGUGG CAUAGCGWAA CCUGUAAGAG            50

ACAGACGACU CGCCCGA                                                67

(2) INFORMATION FOR SEQ ID NO:105:

(i) SEQUENCE CHARACTERISTICS:
        (A) LENGTH: 71 base pairs
        (B) TYPE: nucleic acid
        (C) STRANDEDNESS: single
        (D) TOPOLOGY:  linear (ii) MOLECULE TYPE: RNA (ix) FEATURE:
         (D) OTHER INFORMATION: All C's are 2'-NH2 cytosine (ix) FEATURE:
         (D) OTHER INFORMATION: All U's are 2'-NH2 uracil (xi) SEQUENCE DESCRIPTION: SEQ ID NO:105:

GGGAGGACGA UGCGGAGAUU ACCAUAACCG CGUAGUCGAA GACAUAUAGU            50

AGCGACAGAC GACUCGCCCG A                                           71

(2) INFORMATION FOR SEQ ID NO:106:

(i) SEQUENCE CHARACTERISTICS:
        (A) LENGTH: 71 base pairs
        (B) TYPE: nucleic acid
        (C) STRANDEDNESS: single (D) TOPOLOGY:  linear (ii) MOLECULE TYPE: RNA (ix) FEATURE:
            (D) OTHER INFORMATION: All C's are 2'-NH2 cytosine (ix) FEATURE:
            (D) OTHER INFORMATION: All U's are 2'-NH2 uracil (xi) SEQUENCE DESCRIPTION: SEQ ID NO:106:

GGGAGGACGA UGCGGACUCG GGUAGAACGC GACUUGCCAC CACUCCCAUA         50

AAGACCAGAC GACUCGCCCG A                                       71

(2) INFORMATION FOR SEQ ID NO:107:

(i) SEQUENCE CHARACTERISTICS:
            (A) LENGTH: 71 base pairs
            (B) TYPE: nucleic acid
            (C) STRANDEDNESS: single
            (D) TOPOLOGY:  linear (ii) MOLECULE TYPE: RNA (ix) FEATURE:
            (D) OTHER INFORMATION: All C's are 2'-NH2 cytosine (ix) FEATURE:
            (D) OTHER INFORMATION: All U's are 2'-NH2 uracil (xi) SEQUENCE DESCRIPTION: SEQ ID NO:107:

GGGAGGACGA UGCGGUCAGA ACUCUGCCGC UGUAGACAAA GAGGAGCUUA         50

GCGAACAGAC GACUCGCCCG A                                       71

(2) INFORMATION FOR SEQ ID NO:108:

(i) SEQUENCE CHARACTERISTICS:
            (A) LENGTH: 71 base pairs
            (B) TYPE: nucleic acid
            (C) STRANDEDNESS: single
            (D) TOPOLOGY:  linear (ii) MOLECULE TYPE: RNA (ix) FEATURE:
            (D) OTHER INFORMATION: All C's are 2'-NH2 cytosine (ix) FEATURE:
            (D) OTHER INFORMATION: All U's are 2'-NH2 uracil (xi) SEQUENCE DESCRIPTION: SEQ ID NO:108:

GGGAGGACGA UGCGGAAUGA GCAUCGAGAG AGCGCGAACU CAUCGAGCGU         50

ACUAACAGAC GACUCGCCCG A                                       71

(2) INFORMATION FOR SEQ ID NO:109:

(i) SEQUENCE CHARACTERISTICS:
            (A) LENGTH: 71 base pairs
            (B) TYPE: nucleic acid
            (C) STRANDEDNESS: single
            (D) TOPOLOGY:  linear (ii) MOLECULE TYPE: RNA (ix) FEATURE:
            (D) OTHER INFORMATION: All C's are 2'-NH2 cytosine (ix) FEATURE:
            (D) OTHER INFORMATION: All U's are 2'-NH2 uracil (xi) SEQUENCE DESCRIPTION: SEQ ID NO:109:

GGGAGGACGA UGCGGCAAAG CACGCGUAUG GCAUGAAACU GGCANCCCAA       50

GUAAGCAGAC GACUCGCCCG A                                     71

(2) INFORMATION FOR SEQ ID NO:110:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:110:

GGGAGGACGA UGCGGGAUGC AGCAACCUGA AAACGGCGUC CACAGGUAAU       50

AACAGCAGAC GACUCGCCCG A                                     71

(2) INFORMATION FOR SEQ ID NO:111:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:111:

GGGAGGACGA UGCGGAAACU CGCUACAAAC ACCCAAUCCU AGAACGUUAU       50

GGAGACAGAC GACUCGCCCG A                                     71

(2) INFORMATION FOR SEQ ID NO:112:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:112:

GGGAGGACGA UGCGGCUAGC AUAGCCACCG GAACAGACAG AUACGAGCAC       50

GAUCACAGAC GACUCGCCCG A                                     71

(2) INFORMATION FOR SEQ ID NO:113:

(i) SEQUENCE CHARACTERISTICS:

```
        (A) LENGTH: 71 base pairs
        (B) TYPE: nucleic acid
        (C) STRANDEDNESS: single
        (D) TOPOLOGY:  linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:113:

GGGAGGACGA UGCGGGAUUC GGAGUACUGA AAAACAACCC UCAAAAGUGC           50

AUAGGCAGAC GACUCGCCCG A                                          71

(2) INFORMATION FOR SEQ ID NO:114:

(i) SEQUENCE CHARACTERISTICS:
        (A) LENGTH: 71 base pairs
        (B) TYPE: nucleic acid
        (C) STRANDEDNESS: single
        (D) TOPOLOGY:  linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:114:

GGGAGGACGA UGCGGGUCCA GGACGGACCG CAGCUGUGAU ACAAUCGACU           50

UACACCAGAC GACUCGCCCG A                                          71

(2) INFORMATION FOR SEQ ID NO:115:

(i) SEQUENCE CHARACTERISTICS:
        (A) LENGTH: 71 base pairs
        (B) TYPE: nucleic acid
        (C) STRANDEDNESS: single
        (D) TOPOLOGY:  linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:115:

GGGAGGACGA UGCGGAAACU CGCUACAAAC ACCCAAUCCU AGAACGUUAU           50

GGAGACAGAC GACUCGCCCG A                                          71

(2) INFORMATION FOR SEQ ID NO:116:

(i) SEQUENCE CHARACTERISTICS:
        (A) LENGTH: 70 base pairs
        (B) TYPE: nucleic acid
        (C) STRANDEDNESS: single
        (D) TOPOLOGY:  linear (ii) MOLECULE TYPE: RNA (ix) FEATURE:
        (D) OTHER INFORMATION: All C's are 2'-NH2 cytosine
```

```
    (ix) FEATURE:
         (D) OTHER INFORMATION: All U's are 2'-NH2 uracil (xi) SEQUENCE DESCRIPTION: SEQ ID NO:116:

GGGAGGACGA UGCGGCGGCC CUUAUCGGAG GUCUGCGCCA CUAAUUACAU            50

CCACCAGACG ACUCGCCCGA                                             70

(2) INFORMATION FOR SEQ ID NO:117:

(i) SEQUENCE CHARACTERISTICS:
        (A) LENGTH: 67 base pairs
        (B) TYPE: nucleic acid
        (C) STRANDEDNESS: single
        (D) TOPOLOGY:  linear (ii) MOLECULE TYPE: RNA (ix) FEATURE:
         (D) OTHER INFORMATION: All C's are 2'-NH2 cytosine (ix) FEATURE:
         (D) OTHER INFORMATION: All U's are 2'-NH2 uracil (xi) SEQUENCE DESCRIPTION: SEQ ID NO:117:

GGGAGGACGA UGCGGUCCAG AGCGUGAAGA UCAACGUCCC GGNGUCGAAG            50

ACAGACGACU CGCCCGA                                                67

(2) INFORMATION FOR SEQ ID NO:118:

(i) SEQUENCE CHARACTERISTICS:
        (A) LENGTH:   8 base pairs
        (B) TYPE: nucleic acid
        (C) STRANDEDNESS: single
        (D) TOPOLOGY:  linear (ii) MOLECULE TYPE: RNA (ix) FEATURE:
         (D) OTHER INFORMATION: All C's are 2'-NH2 cytosine (ix) FEATURE:
         (D) OTHER INFORMATION: All U's are 2'-NH2 uracil (xi) SEQUENCE DESCRIPTION: SEQ ID NO:118:

AUGUGUGA                                                          8

(2) INFORMATION FOR SEQ ID NO:119:

(i) SEQUENCE CHARACTERISTICS:
        (A) LENGTH: 15 base pairs
        (B) TYPE: nucleic acid
        (C) STRANDEDNESS: single
        (D) TOPOLOGY:  linear (ii) MOLECULE TYPE: RNA (ix) FEATURE:
         (D) OTHER INFORMATION: All C's are 2'-NH2 cytosine (ix) FEATURE:
         (D) OTHER INFORMATION: All U's are 2'-NH2 uracil (xi) SEQUENCE DESCRIPTION: SEQ ID NO:119:

CAACAAUCAU GAGUR                                                  15

(2) INFORMATION FOR SEQ ID NO:120:

(i) SEQUENCE CHARACTERISTICS:
        (A) LENGTH: 21 base pairs
```

```
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:120:

AACAUGAAGU AAGUCARUUA G                                         21

(2) INFORMATION FOR SEQ ID NO:121:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:121:

AGAACCGCWA G                                                    11

(2) INFORMATION FOR SEQ ID NO:122:

(i) SEQUENCE CHARACTERISTICS:
        (A) LENGTH: 7 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:122:

UCUCUCC                                                          7

(2) INFORMATION FOR SEQ ID NO:123:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:123:

CGAAGAAUYC                                                      10
```

(2) INFORMATION FOR SEQ ID NO:124:

(i) SEQUENCE CHARACTERISTICS:
       (A) LENGTH: 8 base pairs
       (B) TYPE: nucleic acid
       (C) STRANDEDNESS: single
       (D) TOPOLOGY:  linear (ii) MOLECULE TYPE: RNA (ix) FEATURE:
       (D) OTHER INFORMATION: All C's are 2'-NH2 cytosine (ix) FEATURE:
       (D) OTHER INFORMATION: All U's are 2'-NH2 uracil (xi) SEQUENCE DESCRIPTION: SEQ ID NO:124:

AUGUAAAU                                                                  8

(2) INFORMATION FOR SEQ ID NO:125:

(i) SEQUENCE CHARACTERISTICS:
       (A) LENGTH: 8 base pairs
       (B) TYPE: nucleic acid
       (C) STRANDEDNESS: single
       (D) TOPOLOGY:  linear (ii) MOLECULE TYPE: RNA (ix) FEATURE:
       (D) OTHER INFORMATION: All C's are 2'-NH2 cytosine (ix) FEATURE:
       (D) OTHER INFORMATION: All U's are 2'-NH2 uracil (xi) SEQUENCE DESCRIPTION: SEQ ID NO:125:

AACCCAAG                                                                  8

(2) INFORMATION FOR SEQ ID NO:126:

(i) SEQUENCE CHARACTERISTICS:
       (A) LENGTH: 80 base pairs
       (B) TYPE: nucleic acid
       (C) STRANDEDNESS: single
       (D) TOPOLOGY:  linear (ii) MOLECULE TYPE: DNA (xi) SEQUENCE DESCRIPTION: SEQ ID NO:126:

CTACCTACGA TCTGACTAGC NNNNNNNNNN NNNNNNNNNN NNNNNNNNNN                    50

NNNNNNNNNN GCTTACTCTC ATGTAGTTCC                                          80

(2) INFORMATION FOR SEQ ID NO:127:

(i) SEQUENCE CHARACTERISTICS:
       (A) LENGTH: 20 base pairs
       (B) TYPE: nucleic acid
       (C) STRANDEDNESS: single
       (D) TOPOLOGY:  linear (ii) MOLECULE TYPE: DNA (xi) SEQUENCE DESCRIPTION: SEQ ID NO:127:

CTACCTACGA TCTGACTAGC                                                    20

(2) INFORMATION FOR SEQ ID NO:128:

(i) SEQUENCE CHARACTERISTICS:
       (A) LENGTH: 25 base pairs (B) TYPE: nucleic acid
        (C) STRANDEDNESS: single
        (D) TOPOLOGY:  linear (ii) MOLECULE TYPE: DNA (xi) FEATURE:
        (D) OTHER INFORMATION: N AT POSITION 2 AND 4 IS BIOTIN (xi) SEQUENCE DESCRIPTION: SEQ ID NO:128:

ANANAGGAAC TACATGAGAG TAAGC                                                25

(2) INFORMATION FOR SEQ ID NO:129:

(i) SEQUENCE CHARACTERISTICS:
        (A) LENGTH: 80 base pairs
        (B) TYPE: nucleic acid
        (C) STRANDEDNESS: single
        (D) TOPOLOGY:  linear (ii) MOLECULE TYPE: DNA (xi) SEQUENCE DESCRIPTION: SEQ ID NO:129:

CTACCTACGA TCTGACTAGC GGAACACGTG AGGTTTACAA GGCACTCGAC                     50

GTAAACACTT GCTTACTCTC ATGTAGTTCC                                           80

(2) INFORMATION FOR SEQ ID NO:130:

(i) SEQUENCE CHARACTERISTICS:
        (A) LENGTH: 80 base pairs
        (B) TYPE: nucleic acid
        (C) STRANDEDNESS: single
        (D) TOPOLOGY:  linear (ii) MOLECULE TYPE: DNA (xi) SEQUENCE DESCRIPTION: SEQ ID NO:130:

CTACCTACGA TCTGACTAGC CCCCGAAGAA CATTTTACAA GGTGCTAAAC                     50

GTAAAATCAG GCTTACTCTC ATGTAGTTCC                                           80

(2) INFORMATION FOR SEQ ID NO:131:

(i) SEQUENCE CHARACTERISTICS:
        (A) LENGTH: 80 base pairs
        (B) TYPE: nucleic acid
        (C) STRANDEDNESS: single
        (D) TOPOLOGY:  linear (ii) MOLECULE TYPE: DNA (xi) SEQUENCE DESCRIPTION: SEQ ID NO:131:

CTACCTACGA TCTGACTAGC GGCATCCCTG AGTCATTACA AGGTTCTTAA                     50

CGTAATGTAC GCTTACTCTC ATGTAGTTCC                                           80

(2) INFORMATION FOR SEQ ID NO:132:

(i) SEQUENCE CHARACTERISTICS:
        (A) LENGTH: 80 base pairs
        (B) TYPE: nucleic acid
        (C) STRANDEDNESS: single
        (D) TOPOLOGY:  linear (ii) MOLECULE TYPE: DNA (xi) SEQUENCE DESCRIPTION: SEQ ID NO:132:

CTACCTACGA TCTGACTAGC TGCACACCTG AGGGTTACAA GGCGCTAGAC                     50

```
GTAACCTCTC GCTTACTCTC ATGTAGTTCC                                             80

(2) INFORMATION FOR SEQ ID NO:133:

(i) SEQUENCE CHARACTERISTICS:
          (A) LENGTH: 80 base pairs
          (B) TYPE: nucleic acid
          (C) STRANDEDNESS: single
          (D) TOPOLOGY:  linear (ii) MOLECULE TYPE: DNA (xi) SEQUENCE DESCRIPTION: SEQ ID NO:133:

CTACCTACGA TCTGACTAGC CACGTTTCAA GGGGTTACAC GAAACGATTC                       50

ACTCCTTGGC GCTTACTCTC ATGTAGTTCC                                             80

(2) INFORMATION FOR SEQ ID NO:134:

(i) SEQUENCE CHARACTERISTICS:
          (A) LENGTH: 79 base pairs
          (B) TYPE: nucleic acid
          (C) STRANDEDNESS: single
          (D) TOPOLOGY:  linear (ii) MOLECULE TYPE: DNA (xi) SEQUENCE DESCRIPTION: SEQ ID NO:134:

CTACCTACGA TCTGACTAGC CGGACATGAG CGTTACAAGG TGCTAAACGT                       50

AACGTACTTG CTTACTCTCA TGTAGTTCC                                              79

(2) INFORMATION FOR SEQ ID NO:135:

(i) SEQUENCE CHARACTERISTICS:
          (A) LENGTH: 79 base pairs
          (B) TYPE: nucleic acid
          (C) STRANDEDNESS: single
          (D) TOPOLOGY:  linear (ii) MOLECULE TYPE: DNA (xi) SEQUENCE DESCRIPTION: SEQ ID NO:135:

CTACCTACGA TCTGACTAGC CGCATCCACA TAGTTCAAGG GGCTACACGA                       50

AATATTGCAG CTTACTCTCA TGTAGTTCC                                              79

(2) INFORMATION FOR SEQ ID NO:136:

(i) SEQUENCE CHARACTERISTICS:
          (A) LENGTH: 79 base pairs
          (B) TYPE: nucleic acid
          (C) STRANDEDNESS: single
          (D) TOPOLOGY:  linear (ii) MOLECULE TYPE: DNA (xi) SEQUENCE DESCRIPTION: SEQ ID NO:136:

CTACCTACGA TCTGACTAGC TACCCCTTGG GCCTCATAGA CAAGGTCTTA                       50

AACGTTAGCG CTTACTCTCA TGTAGTTCC                                              79

(2) INFORMATION FOR SEQ ID NO:137:

(i) SEQUENCE CHARACTERISTICS:
          (A) LENGTH: 79 base pairs
          (B) TYPE: nucleic acid
          (C) STRANDEDNESS: single
          (D) TOPOLOGY:  linear
```

(ii) MOLECULE TYPE: DNA (xi) SEQUENCE DESCRIPTION: SEQ ID NO:137:

CTACCTACGA TCTGACTAGC CACATGCCTG ACGCGGTACA AGGCCTGGAC          50

GTAACGTTGG CTTACTCTCA TGTAGTTCC                                79

(2) INFORMATION FOR SEQ ID NO:138:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:138:

CTACCTACGA TCTGACTAGC TAGTGCTCCA CGTATTCAAG GTGCTAAACG          50

AAGACGGCCT GCTTACTCTC ATGTAGTTCC                               80

(2) INFORMATION FOR SEQ ID NO:139:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:139:

CTACCTACGA TCTGACTAGC AGCGATGCAA GGGGCTACAC GCAACGATTT          50

AGATGCTCTG CTTACTCTCA TGTAGTTCC                                79

(2) INFORMATION FOR SEQ ID NO:140:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:140:

CTACCTACGA TCTGACTAGC CCAGGAGCAC AGTACAAGGT GTTAAACGTA          50

ATGTCTGGTG CTTACTCTCA TGTAGTTCC                                79

(2) INFORMATION FOR SEQ ID NO:141:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:141:

CTACCTACGA TCTGACTAGC ACCACACCTG GGCGGTACAA GGAGTTATCC          50

GTAACGTGTG CTTACTCTCA TGTAGTTCC                                79

(2) INFORMATION FOR SEQ ID NO:142:

(i) SEQUENCE CHARACTERISTICS:
    (A) LENGTH: 79 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:142:

CTACCTACGA TCTGACTAGC CAAGGTAACC AGTACAAGGT GCTAAACGTA        50

ATGGCTTCGG CTTACTCTCA TGTAGTTCC                              79

(2) INFORMATION FOR SEQ ID NO:143:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:143:

CTACCTACGA TCTGACTAGC ACCCCCGACC CGAGTACAAG GCATTCGACG        50

TAATCTGGTG CTTACTCTCA TGTAGTTCC                              79

(2) INFORMATION FOR SEQ ID NO:144:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:144:

CTACCTACGA TCTGACTAGC CAGTACAAGG TGTTAAACGT AATGCCGATC        50

GAGTTGTATG CTTACTCTCA TGTAGTTCC                              79

(2) INFORMATION FOR SEQ ID NO:145:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:145:

CTACCTACGA TCTGACTAGC ACAACGAGTA CAAGGAGATA GACGTAATCG        50

GCGCAGGTAT CGCTTACTCT CATGTAGTTC C                           81

(2) INFORMATION FOR SEQ ID NO:146:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:146:

CTACCTACGA TCTGACTAGC CACGACAGAG AACAAGGCGT TAGACGTTAT        50

```
CCGACCACGG CTTACTCTCA TGTAGTTCC                                         79
```

(2) INFORMATION FOR SEQ ID NO:147:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:147:

```
CTACCTACGA TCTGACTAGC AGGGAGAACA AGGTGCTAAA CGTTTATCTA                  50

CACTTCACCT GCTTACTCTC ATGTAGTTCC                                        80
```

(2) INFORMATION FOR SEQ ID NO:148:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:148:

```
CTACCTACGA TCTGACTAGC AGGACCAAGG TGTTAAACGG CTCCCCTGGC                  50

TATGCCTCTT GCTTACTCTC ATGTAGTTCC                                        80
```

(2) INFORMATION FOR SEQ ID NO:149:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:149:

```
CTACCTACGA TCTGACTAGC TACACAAGGT GCTAAACGTA GAGCCAGATC                  50

GGATCTGAGC GCTTACTCTC ATGTAGTTCC                                        80
```

(2) INFORMATION FOR SEQ ID NO:150:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:150:

```
CTACCTACGA TCTGACTAGC GGACAAGGCA CTCGACGTAG TTTATAACTC                  50

CCTCCGGGCC GCTTACTCTC ATGTAGTTCC                                        80
```

(2) INFORMATION FOR SEQ ID NO:151:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:151:

CTACCTACGA TCTGACTAGC TACACAAGGG GCCAAACGGA GAGCCAGACG         50

CGGATCTGAC AGCTTACTCT CATGTAGTTC C                            81

(2) INFORMATION FOR SEQ ID NO:152:

(i) SEQUENCE CHARACTERISTICS:
        (A) LENGTH: 79 base pairs
        (B) TYPE: nucleic acid
        (C) STRANDEDNESS: single
        (D) TOPOLOGY:  linear (ii) MOLECULE TYPE: DNA (xi) SEQUENCE DESCRIPTION: SEQ ID NO:152:

CTACCTACGA TCTGACTAGC CGGCTATACN NGGTGCTAAA CGCAGAGACT         50

CGATCAACAG CTTACTCTCA TGTAGTTCC                               79

(2) INFORMATION FOR SEQ ID NO:153:

(i) SEQUENCE CHARACTERISTICS:
        (A) LENGTH: 80 base pairs
        (B) TYPE: nucleic acid
        (C) STRANDEDNESS: single
        (D) TOPOLOGY:  linear (ii) MOLECULE TYPE: DNA (xi) SEQUENCE DESCRIPTION: SEQ ID NO:153:

CTACCTACGA TCTGACTAGC GAGTAGCCAA GGCGTTAGAC GGAGGGGAA          50

TGGAAGCTTG GCTTACTCTC ATGTAGTTCC                              80

(2) INFORMATION FOR SEQ ID NO:154:

(i) SEQUENCE CHARACTERISTICS:
        (A) LENGTH: 73 base pairs
        (B) TYPE: nucleic acid
        (C) STRANDEDNESS: single
        (D) TOPOLOGY:  linear (ii) MOLECULE TYPE: DNA (xi) SEQUENCE DESCRIPTION: SEQ ID NO:154:

CTACCTACGA TCTGACTAGC GAGTAGCCAA GGCGTTAGAC GGAGGGGAA          50

TGGGCTTACT CTCATGTAGT TCC                                     73

(2) INFORMATION FOR SEQ ID NO:155:

(i) SEQUENCE CHARACTERISTICS:
        (A) LENGTH: 80 base pairs
        (B) TYPE: nucleic acid
        (C) STRANDEDNESS: single
        (D) TOPOLOGY:  linear (ii) MOLECULE TYPE: DNA (xi) SEQUENCE DESCRIPTION: SEQ ID NO:155:

CTACCTACGA TCTGACTAGC GAGTAGCCAA GGCGTTAGAC GGAGGGGAA          50

TGTGAGCACA GCTTACTCTC ATGTAGTTCC                              80

(2) INFORMATION FOR SEQ ID NO:156:

(i) SEQUENCE CHARACTERISTICS:
           (A) LENGTH: 80 base pairs
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:156:

CTACCTACGA TCTGACTAGC TAGCTCCACA CACAASSCGC RGCACATAGG           50

GGATATCTGG GCTTACTCTC ATGTAGTTCC                                 80

(2) INFORMATION FOR SEQ ID NO:157:

(i) SEQUENCE CHARACTERISTICS:
           (A) LENGTH: 80 base pairs
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:157:

CTACCTACGA TCTGACTAGC CATCAAGGAC TTTGCCCGAA ACCCTAGGTT           50

CACGTGTGGG GCTTACTCTC ATGTAGTTCC                                 80

(2) INFORMATION FOR SEQ ID NO:158:

(i) SEQUENCE CHARACTERISTICS:
           (A) LENGTH: 79 base pairs
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:158:

CTACCTACGA TCTGACTAGC CATTCACCAT GGCCCCTTCC TACGTATGTT           50

CTGCGGGTGG CTTACTCTCA TGTAGTTCC                                  79

(2) INFORMATION FOR SEQ ID NO:159:

(i) SEQUENCE CHARACTERISTICS:
           (A) LENGTH: 80 base pairs
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:159:

CTACCTACGA TCTGACTAGC GCAACGTGGC CCCGTTTAGC TCATTTGACC           50

GTTCCATCCG GCTTACTCTC ATGTAGTTCC                                 80

(2) INFORMATION FOR SEQ ID NO:160:

(i) SEQUENCE CHARACTERISTICS:
           (A) LENGTH: 79 base pairs
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:160:

```
CTACCTACGA TCTGACTAGC CCACAGACAA TCGCAGTCCC CGTGTAGCTC          50

TGGGTGTCTG CTTACTCTCA TGTAGTTCC                                 79

(2) INFORMATION FOR SEQ ID NO:161:

(i) SEQUENCE CHARACTERISTICS:
            (A) LENGTH: 79 base pairs
            (B) TYPE: nucleic acid
            (C) STRANDEDNESS: single
            (D) TOPOLOGY:  linear (ii) MOLECULE TYPE: DNA (xi) SEQUENCE DESCRIPTION: SEQ ID NO:161:

CTACCTACGA TCTGACTAGC CCACCGTGAT GCACGATACA TGAGGGTGTG          50

TCAGCGCATG CTTACTCTCA TGTAGTTCC                                 79

(2) INFORMATION FOR SEQ ID NO:162:

(i) SEQUENCE CHARACTERISTICS:
            (A) LENGTH: 80 base pairs
            (B) TYPE: nucleic acid
            (C) STRANDEDNESS: single
            (D) TOPOLOGY:  linear (ii) MOLECULE TYPE: DNA (xi) SEQUENCE DESCRIPTION: SEQ ID NO:162:

CTACCTACGA TCTGACTAGC CGAGGTAGTC GTTATAGGGT RCRCACGACA          50

CAAARCRGTR GCTTACTCTC ATGTAGTTCC                                80

(2) INFORMATION FOR SEQ ID NO:163:

(i) SEQUENCE CHARACTERISTICS:
            (A) LENGTH: 79 base pairs
            (B) TYPE: nucleic acid
            (C) STRANDEDNESS: single
            (D) TOPOLOGY:  linear (ii) MOLECULE TYPE: DNA (xi) SEQUENCE DESCRIPTION: SEQ ID NO:163:

CTACCTACGA TCTGACTAGC TGGCGGTACG GGCCGTGCAC CCACTTACCT          50

GGGAAGTGAG CTTACTCTCA TGTAGTTCC                                 79

(2) INFORMATION FOR SEQ ID NO:164:

(i) SEQUENCE CHARACTERISTICS:
            (A) LENGTH: 81 base pairs
            (B) TYPE: nucleic acid
            (C) STRANDEDNESS: single
            (D) TOPOLOGY:  linear (ii) MOLECULE TYPE: DNA (xi) SEQUENCE DESCRIPTION: SEQ ID NO:164:

CTACCTACGA TCTGACTAGC CTCTGCTTAC CTCATGTAGT TCCAAGCTTG          50

GCGTAATCAT GGCTTACTCT CATGTAGTTC C                              81

(2) INFORMATION FOR SEQ ID NO:165:

(i) SEQUENCE CHARACTERISTICS:
            (A) LENGTH: 79 base pairs
            (B) TYPE: nucleic acid
            (C) STRANDEDNESS: single
```

(D) TOPOLOGY:  linear (ii) MOLECULE TYPE: DNA (xi) SEQUENCE DESCRIPTION: SEQ ID NO:165:

CTACCTACGA TCTGACTAGC AGCGTTGTAC GGGGTTACAC ACAACGATTT          50

AGATGCTCTG CTTACTCTCA TGTAGTTCC                                79

(2) INFORMATION FOR SEQ ID NO:166:

(i) SEQUENCE CHARACTERISTICS:
        (A) LENGTH: 81 base pairs
        (B) TYPE: nucleic acid
        (C) STRANDEDNESS: single
        (D) TOPOLOGY:  linear (ii) MOLECULE TYPE: DNA (xi) SEQUENCE DESCRIPTION: SEQ ID NO:166:

CTACCTACGA TCTGACTAGC TGATGCGACT TTAGTCGAAC GTTACTGGGG          50

CTCAGAGGAC AGCTTACTCT CATGTAGTTC C                             81

(2) INFORMATION FOR SEQ ID NO:167:

(i) SEQUENCE CHARACTERISTICS:
        (A) LENGTH: 81 base pairs
        (B) TYPE: nucleic acid
        (C) STRANDEDNESS: single
        (D) TOPOLOGY:  linear (ii) MOLECULE TYPE: DNA (xi) SEQUENCE DESCRIPTION: SEQ ID NO:167:

CTACCTACGA TCTGACTAGC CGAGGATCTG ATACTTATTG AACATAMCCG          50

CACNCAGGCT TGCTTACTCT CATGTAGTTC C                             81

(2) INFORMATION FOR SEQ ID NO:168:

(i) SEQUENCE CHARACTERISTICS:
        (A) LENGTH: 73 base pairs
        (B) TYPE: nucleic acid
        (C) STRANDEDNESS: single
        (D) TOPOLOGY:  linear (ii) MOLECULE TYPE:DNA (xi) SEQUENCE DESCRIPTION: SEQ ID NO:168:

CTACCTACGA TCTGACTAGC CGATCGTGTG TCATGCTACC TACGATCTGA          50

CTAGCTTACT CTCATGTAGT TCC                                      73

(2) INFORMATION FOR SEQ ID NO:169:

(i) SEQUENCE CHARACTERISTICS:
        (A) LENGTH: 80 base pairs
        (B) TYPE: nucleic acid
        (C) STRANDEDNESS: single
        (D) TOPOLOGY:  linear (ii) MOLECULE TYPE:  DNA (xi) SEQUENCE DESCRIPTION: SEQ ID NO:169:

CTACCTACGA TCTGACTAGC GCACACAAGT CAAGCATGCG ACCTTCAACC          50

ATCGACCCGA GCTTACTCTC ATGTAGTTCC                               80

```
(2) INFORMATION FOR SEQ ID NO:170:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:170:

CTACCTACGA TCTGACTAGC ATGCCAGTGC AGGCTTCCAT CCATCAGTCT          50

GACANNNNNN GCTTACTCT CATGTAGTTCC                               80

(2) INFORMATION FOR SEQ ID NO:171:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:171:

CTACCTACGA TCTGACTAGC CACTTCGGCT CTACTCCACC TCGGTCCTCC          50

ACTCCACAG GCTTACTCTCA TGTAGTTCC                                79

(2) INFORMATION FOR SEQ ID NO:172:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:172:

CTACCTACGA TCTGACTAGC CGCTAACTGA CCCTCGATCC CCCCAAGCCA          50

TCCTCATCGC GCTTACTCTC ATGTAGTTCC                               80

(2) INFORMATION FOR SEQ ID NO:173:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:173:

CTACCTACGA TCTGACTAGC ATCTGACTAG CTCGGCGAGA GTACCCGCTC          50

ATGGCTTCGG CGAATGCCCT GCTTACTCTC ATGTAGTTCC                    90

(2) INFORMATION FOR SEQ ID NO:174:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:174:
```

CTACCTACGA TCTGACTAGC TCCTGAGACG TTACAATAGG CTGCGGTACT          50

GCAACGTGGA GCTTACTCTC ATGTAGTTCC                                80

(2) INFORMATION FOR SEQ ID NO:175:

(i) SEQUENCE CHARACTERISTICS:
        (A) LENGTH: 79 base pairs
        (B) TYPE: nucleic acid
        (C) STRANDEDNESS: single
        (D) TOPOLOGY:  linear (ii) MOLECULE TYPE:  DNA (xi) SEQUENCE DESCRIPTION: SEQ ID NO:175:

CTACCTACGA TCTGACTAGC CGGCAGGGCA CTAACAAGGT GTTAAACGTT          50

ACGGATGCCG CTTACTCTCA TGTAGTTCC                                79

(2) INFORMATION FOR SEQ ID NO:176:

(i) SEQUENCE CHARACTERISTICS:
        (A) LENGTH: 90 base pairs
        (B) TYPE: nucleic acid
        (C) STRANDEDNESS: single
        (D) TOPOLOGY:  linear (ii) MOLECULE TYPE:  DNA (xi) SEQUENCE DESCRIPTION: SEQ ID NO:176:

CTACCTACGA TCTGACTAGC TGCACACCGG CCCACCCGGA CAAGGCGCTA          50

GACGAAATGA CTCTGTTCTG GCTTACTCTC ATGTAGTTCC                    90

(2) INFORMATION FOR SEQ ID NO:177:

(i) SEQUENCE CHARACTERISTICS:
        (A) LENGTH: 79 base pairs
        (B) TYPE: nucleic acid
        (C) STRANDEDNESS: single
        (D) TOPOLOGY:  linear (ii) MOLECULE TYPE:  DNA (xi) SEQUENCE DESCRIPTION: SEQ ID NO:177:

CTACCTACGA TCTGACTAGC GACGAAGAGG CCAAGGTGAT AACCGGAGTT          50

TCCGTCCGCG CTTACTCTCA TGTAGTTCC                                79

(2) INFORMATION FOR SEQ ID NO:178:

(i) SEQUENCE CHARACTERISTICS:
        (A) LENGTH: 79 base pairs
        (B) TYPE: nucleic acid
        (C) STRANDEDNESS: single
        (D) TOPOLOGY:  linear (ii) MOLECULE TYPE:  DNA (xi) SEQUENCE DESCRIPTION: SEQ ID NO:178:

CTACCTACGA TCTGACTAGC AAGGACTTAG CTATCCAAGG CACTCGACGA          50

AGAGCCCGAG CTTACTCTCA TGTAGTTCC                                79

(2) INFORMATION FOR SEQ ID NO:179:

(i) SEQUENCE CHARACTERISTICS:
        (A) LENGTH: 80 base pairs
        (B) TYPE: nucleic acid

```
        (C) STRANDEDNESS: single
        (D) TOPOLOGY:  linear (ii) MOLECULE TYPE:  DNA (xi) SEQUENCE DESCRIPTION: SEQ ID NO:179:

CTACCTACGA TCTGACTAGC ATGCCCAGTT CAAGGTTCTG ACCGAAATGA          50

CTCTGTTCTG GCTTACTCTC ATGTAGTTCC                               80

(2) INFORMATION FOR SEQ ID NO:180:

(i) SEQUENCE CHARACTERISTICS:
        (A) LENGTH: 80 base pairs
        (B) TYPE: nucleic acid
        (C) STRANDEDNESS: single
        (D) TOPOLOGY:  linear (ii) MOLECULE TYPE:  DNA (xi) SEQUENCE DESCRIPTION: SEQ ID NO:180:

CTACCTACGA TCTGACTAGC GCAGCGTGGC CCTGTTTAGC TCATTTGACC          50

GTTCCATCCG GCTTACTCTC ATGTAGTTCC                               80

(2) INFORMATION FOR SEQ ID NO:181:

(i) SEQUENCE CHARACTERISTICS:
        (A) LENGTH: 18 base pairs
        (B) TYPE: nucleic acid
        (C) STRANDEDNESS: single
        (D) TOPOLOGY:  linear (ii) MOLECULE TYPE: DNA (xi) SEQUENCE DESCRIPTION: SEQ ID NO:181:

TACAAGGYGY TAVACGTA                                            18

(2) INFORMATION FOR SEQ ID NO:182:

(i) SEQUENCE CHARACTERISTICS:
        (A) LENGTH: 8 base pairs
        (B) TYPE: nucleic acid
        (C) STRANDEDNESS: single
        (D) TOPOLOGY:  linear (ii) MOLECULE TYPE: DNA (xi) SEQUENCE DESCRIPTION: SEQ ID NO:182:

GGCCCCGT                                                        8

(2) INFORMATION FOR SEQ ID NO:183:

(i) SEQUENCE CHARACTERISTICS:
        (A) LENGTH: 10 base pairs
        (B) TYPE: nucleic acid
        (C) STRANDEDNESS: single
        (D) TOPOLOGY:  linear (ii) MOLECULE TYPE: DNA (xi) SEQUENCE DESCRIPTION: SEQ ID NO:183:

RCACGAYACA                                                     10

(2) INFORMATION FOR SEQ ID NO:184:

(i) SEQUENCE CHARACTERISTICS:
        (A) LENGTH: 7 base pairs
        (B) TYPE: nucleic acid
```

(C) STRANDEDNESS: single
            (D) TOPOLOGY:  linear (ii) MOLECULE TYPE: DNA (xi) SEQUENCE DESCRIPTION: SEQ ID NO:184:

CTTACCT                                                              7

(2) INFORMATION FOR SEQ ID NO:185:

(i) SEQUENCE CHARACTERISTICS:
            (A) LENGTH: 49 base pairs
            (B) TYPE: nucleic acid
            (C) STRANDEDNESS: single
            (D) TOPOLOGY:  linear (ii) MOLECULE TYPE: DNA (xi) SEQUENCE DESCRIPTION: SEQ ID NO:185:

TAGCCAAGGT AACCAGTACA AGGTGCTAAA CGTAATGGCT TCGGCTTAC                 49

(2) INFORMATION FOR SEQ ID NO:186:

(i) SEQUENCE CHARACTERISTICS:
            (A) LENGTH: 41 base pairs
            (B) TYPE: nucleic acid
            (C) STRANDEDNESS: single
            (D) TOPOLOGY:  linear (ii) MOLECULE TYPE: DNA (xi) SEQUENCE DESCRIPTION: SEQ ID NO:186:

GTAACCAGTA CAAGGTGCTA AACGTAATGG CTTCGGCTTA C                         41

(2) INFORMATION FOR SEQ ID NO:187:

(i) SEQUENCE CHARACTERISTICS:
            (A) LENGTH: 26 base pairs
            (B) TYPE: nucleic acid
            (C) STRANDEDNESS: single
            (D) TOPOLOGY:  linear (ii) MOLECULE TYPE:  DNA (xi) SEQUENCE DESCRIPTION: SEQ ID NO:187:

CCAGTACAAG GTGCTAAACG TAATGG                                         26

(2) INFORMATION FOR SEQ ID NO:188:

(i) SEQUENCE CHARACTERISTICS:
            (A) LENGTH: 38 base pairs
            (B) TYPE: nucleic acid
            (C) STRANDEDNESS: single
            (D) TOPOLOGY:  linear (ii) MOLECULE TYPE:  DNA (xi) SEQUENCE DESCRIPTION: SEQ ID NO:188:

CGCGGTAACC AGTACAAGGT GCTAAACGTA ATGGCGCG                             38

(2) INFORMATION FOR SEQ ID NO:189:

(i) SEQUENCE CHARACTERISTICS:
            (A) LENGTH: 36 base pairs
            (B) TYPE: nucleic acid
            (C) STRANDEDNESS: single
            (D) TOPOLOGY:  linear (ii) MOLECULE TYPE:  DNA (xi) SEQUENCE DESCRIPTION: SEQ ID NO:189:

GCGGTAACCA GTACAAGGTG CTAAACGTAA TGGCGC                                      36

(2) INFORMATION FOR SEQ ID NO:190:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:190:

ACATGAGCGT TACAAGGTGC TAAACGTAAC GTACTTGCTT ACTCTCATGT                       50

(2) INFORMATION FOR SEQ ID NO:191:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:191:

CGCGCGTTAC AAGGTGCTAA ACGTAACGTA CTTGCTTACT CGCG                             44

(2) INFORMATION FOR SEQ ID NO:192:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:192:

GCGTTACAAG GTGCTAAACG TAACGT                                                 26

(2) INFORMATION FOR SEQ ID NO:193:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE:

(ix) FEATURE:
        (D) OTHER INFORMATION: N at position 1 is an amino
            modifier C6 dT (ix) FEATURE:
        (D) OTHER INFORMATION: Nucleotide 51 is an inverted-
            orientation (3'3' linkage) phosphoramidite (xi) SEQUENCE DESCRIPTION: SEQ ID NO:193:

NTAGCCAAGG TAACCAGTAC AAGGTGCTAA ACGTAATGGC TTCGGCTTAC                       50

TT                                                                          52

(2) INFORMATION FOR SEQ ID NO:194:

(i) SEQUENCE CHARACTERISTICS:

```
        (A) LENGTH: 48 base pairs
        (B) TYPE: nucleic acid
        (C) STRANDEDNESS: single
        (D) TOPOLOGY:  linear (ii) MOLECULE TYPE:  DNA (xi) SEQUENCE DESCRIPTION: SEQ ID NO:194:

TAGCCATTCA CCATGGCCCC TTCCTACGTA TGTTCTGCGG GTGGCTTA                48

(2) INFORMATION FOR SEQ ID NO:195:

(i) SEQUENCE CHARACTERISTICS:
        (A) LENGTH: 47 base pairs
        (B) TYPE: nucleic acid
        (C) STRANDEDNESS: single
        (D) TOPOLOGY:  linear (ii) MOLECULE TYPE:  DNA (xi) SEQUENCE DESCRIPTION: SEQ ID NO:195:

AGCTGGCGGT ACGGGCCGTG CACCCACTTA CCTGGGAAGT GAGCTTA                 47

(2) INFORMATION FOR SEQ ID NO:196:

(i) SEQUENCE CHARACTERISTICS:
        (A) LENGTH: 29 base pairs
        (B) TYPE: nucleic acid
        (C) STRANDEDNESS: single
        (D) TOPOLOGY:  linear (ii) MOLECULE TYPE: DNA (ix) FEATURE:
        (D) OTHER INFORMATION:  N at position 1 is an amimo
            modifier C6 dT (ix) FEATURE:
        (D) OTHER INFORMATION:  Nucleotide number 28 is an
            inverted-orientation (3'3' linkage) phosphoramidite (xi) SEQUENCE DESCRIPTION: SEQ ID NO:196:

NCCAGTACAA GGTGCTAAAC GTAATGGTT                                     29

(2) INFORMATION FOR SEQ ID NO:197:

(i) SEQUENCE CHARACTERISTICS:
        (A) LENGTH:40 base pairs
        (B) TYPE: nucleic acid
        (C) STRANDEDNESS: single
        (D) TOPOLOGY:  linear (ii) MOLECULE TYPE: DNA (xi) SEQUENCE DESCRIPTION: SEQ ID NO:197:

TAATACGACT CACTATAGGG AGACAAGAAT AAACGCTCAA                         40

(2) INFORMATION FOR SEQ ID NO:198:

(i) SEQUENCE CHARACTERISTICS:
        (A) LENGTH: 24 base pairs
        (B) TYPE: nucleic acid
        (C) STRANDEDNESS: single
        (D) TOPOLOGY:  linear (ii) MOLECULE TYPE: DNA (xi) SEQUENCE DESCRIPTION: SEQ ID NO:198:

GCCTGTTGTG AGCCTCCTGT CGAA                                          24
```

(2) INFORMATION FOR SEQ ID NO:199:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:199:

```
GGGAGACAAG AAUAAACGCU CAACGAAUCA GUAAACAUAA CACCAUGAAA        50

CAUAAAUAGC ACGCGAGACG UCUUCGACAG GAGGCUCACA ACAGGC            96
```

(2) INFORMATION FOR SEQ ID NO:200:

(i) SEQUENCE CHARACTERISTICS:
        (A) LENGTH: 95 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:200:

```
GGGAGACAAG AAUAAACGCU CAACGAGUUC ACAUGGGAGC AAUCUCCGAA        50

UAAACAACAC GCKAKCGCAA AUUCGACAGG AGGCUCACAA CAGGC             95
```

(2) INFORMATION FOR SEQ ID NO:201:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:201:

```
GGGAGACAAG AAUAAACGCU CAACGACCAC AAUACAAACU CGUAUGGAAC        50

ACGCGAGCGA CAGUGACGCA UUUUCGACAG GAGGCUCACA ACAGGC            96
```

(2) INFORMATION FOR SEQ ID NO:202:

(i) SEQUENCE CHARACTERISTICS:
        (A) LENGTH: 97 base pairs
        (B) TYPE: nucleic acid
        (C) STRANDEDNESS: single
        (D) TOPOLOGY: linear (ii) MOLECULE TYPE:RNA (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:202:

GGGAGACAAG AAUAAACGCU CAACGUCAAG CCAGAAUCCG GAACACGCGA          50

GAAAACAAAU CAACGACCAA UCGAUUCGAC AGGAGGCUCA CAAAGGC             97

(2) INFORMATION FOR SEQ ID NO:203:

(i) SEQUENCE CHARACTERISTICS:
              (A) LENGTH: 97 base pairs
              (B) TYPE: nucleic acid
              (C) STRANDEDNESS: single
              (D) TOPOLOGY: linear (ii) MOLECULE TYPE:RNA (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:203:

GGGAGACAAG AAUAAACNCU CAACGACCAC AAUAACCGGA AAUCCCCGCG          50

GUUACGGAAC ACGCGAACAU GAAUUCGACA GGAGGCUCAC AACAGGC             97

(2) INFORMATION FOR SEQ ID NO:204:

(i) SEQUENCE CHARACTERISTICS:
              (A) LENGTH: 95 base pairs
              (B) TYPE: nucleic acid
              (C) STRANDEDNESS: single
              (D) TOPOLOGY: linear (ii) MOLECULE TYPE:RNA (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:204:

GGGAGACAAG AAUAAACGCU CAACGAACCA CGGGGAAAUC CACCAGUAAC          50

ACGCGAGGCA AACAGACCCU CUUCGACAGG AGGCUCACAA CAGGC               95

(2) INFORMATION FOR SEQ ID NO:205:

(i) SEQUENCE CHARACTERISTICS:
              (A) LENGTH: 97 base pairs
              (B) TYPE: nucleic acid
              (C) STRANDEDNESS: single
              (D) TOPOLOGY: linear (ii) MOLECULE TYPE:RNA (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:205:

GGGAGACAAG AAUAAACGCU CAACGAGCAA AAGUACUCAC GGGACCAGGA          50

GAUCAGCAAC ACGCGAGACG AAAUUCGACA GGAGGCUCAC AACAGGC           97

(2) INFORMATION FOR SEQ ID NO:206:

(i) SEQUENCE CHARACTERISTICS:
        (A) LENGTH: 96 base pairs
        (B) TYPE: nucleic acid
        (C) STRANDEDNESS: single
        (D) TOPOLOGY:  linear (ii) MOLECULE TYPE:RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:206:

GGGAGACAAG AAUAAACGCU CAACGAGCCA GGAACAUCGA CGUCAGCAAA         50

CGCGAGCGCA ACCAGUAACA CCUUCGACAG GAGGCUCACA ACAGGC             96

(2) INFORMATION FOR SEQ ID NO:207:

(i) SEQUENCE CHARACTERISTICS:
        (A) LENGTH: 94 base pairs
        (B) TYPE: nucleic acid
        (C) STRANDEDNESS: single
        (D) TOPOLOGY:  linear (ii) MOLECULE TYPE:RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:207:

GGGAGACAAG AAUAAACGCU CAACGCACCA GGAACAACGA GAACCAUCAG         50

UAAACGCGAG CGAUUGCAUG UUCGACAGGA GGCUCACAAC AGGC               94

(2) INFORMATION FOR SEQ ID NO:208:

(i) SEQUENCE CHARACTERISTICS:
        (A) LENGTH: 94 base pairs
        (B) TYPE: nucleic acid
        (C) STRANDEDNESS: single
        (D) TOPOLOGY:  linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:208:

GGGAGACAAG AAUAAACGCU CAACGCACCA GGAACAACAA GAACCAUCAG         50

UAAGCGCGAG CGAUUGCAUA UUCGACAGGA GGCUCACAAC AGGC               94

(2) INFORMATION FOR SEQ ID NO:209:

(i) SEQUENCE CHARACTERISTICS:
        (A) LENGTH: 101 base pairs
        (B) TYPE: nucleic acid
        (C) STRANDEDNESS: single (D) TOPOLOGY:  linear (ii) MOLECULE TYPE:RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:209:

GGGAGACAAG AAUAAACGCU CAACGAGCAA GGAACGAAUA CAAACCAGGA         50

AACUCAGCAA CACGCGAGCA GUAAGAAUUC GACAGGAGGC UCACAACAGG         100

C                                                             101

(2) INFORMATION FOR SEQ ID NO:210:

(i) SEQUENCE CHARACTERISTICS:
        (A) LENGTH: 97 base pairs
        (B) TYPE: nucleic acid
        (C) STRANDEDNESS: single
        (D) TOPOLOGY:  linear (ii) MOLECULE TYPE:

(ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:210:

GGGAGACAAG AAUAAACGCU CAACAGUUCA CUCAACCGGC ACCAGACUAC         50

GAUCAGCAUU GGCGAGUGAA CACUUCGACA GGAGGCUCAC AACAGGC           97

(2) INFORMATION FOR SEQ ID NO:211:

(i) SEQUENCE CHARACTERISTICS:
        (A) LENGTH: 96 base pairs
        (B) TYPE: nucleic acid
        (C) STRANDEDNESS: single
        (D) TOPOLOGY:  linear (ii) MOLECULE TYPE:RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:211:

GGGAGACAAG AAUAAACGCU CAACUGGCAA CGGGAUAACA ACAAAUGUCA         50

CCAGCACUAG CGAGACGGAA GGUUCGACAG GAGGCUCACA ACAGGC            96

(2) INFORMATION FOR SEQ ID NO:212:

(i) SEQUENCE CHARACTERISTICS:
        (A) LENGTH: 97 base pairs
        (B) TYPE: nucleic acid
        (C) STRANDEDNESS: single
        (D) TOPOLOGY:  linear (ii) MOLECULE TYPE:RNA (ix) FEATURE:
        (D) OTHER INFORMATION: All C's are 2'-F cytosine (ix) FEATURE:

(D) OTHER INFORMATION: All U's are 2'-F uracil (xi) SEQUENCE DESCRIPTION: SEQ ID NO:212:

GGGAGACAAG AAUAAACGCU CAACGAUGAG CGUGACCGAA GCUAUAAUCA          50

GGUCGAUUCA CCAAGCAAUC UUAUUCGACA GGAGGCUCAC AACAGGC             97

(2) INFORMATION FOR SEQ ID NO:213:

(i) SEQUENCE CHARACTERISTICS:
        (A) LENGTH: 95 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:213:

GGGAGACAAG AAUAAACGCU CAAAGGAUCA CACAAACAUC GGUCAAUAAA          50

UAAGUAUUGA UAGCGGGGAU AUUCGACAGG AGGCUCACAA CAGGC               95

(2) INFORMATION FOR SEQ ID NO:214:

(i) SEQUENCE CHARACTERISTICS:
        (A) LENGTH: 97 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:214:

GGGAGACAAG AAUAAACGCU CAACAACCCA ACCAUCUAGA GCUUCGAACC          50

AUGGUAUACA AGGGAACACA AAAUUCGCGG AGGCUCCAAC AGGCGGC             97

(2) INFORMATION FOR SEQ ID NO:215:

(i) SEQUENCE CHARACTERISTICS:
        (A) LENGTH: 96 base pairs
        (B) TYPE: nucleic acid
        (C) STRANDEDNESS: single
        (D) TOPOLOGY:linear (ii) MOLECULE TYPE:RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:215:

GGGAGACAAG AAUAAACGCU CAAGCGGUCA GAAACAAUAG CUGGAUACAU          50

ACCGCGCAUC CGCUGGGCGA UAUUCGACAG GAGGCUCACA ACAGGC              96

(2) INFORMATION FOR SEQ ID NO:216:

```
    (i) SEQUENCE CHARACTERISTICS:
        (A) LENGTH: 97 base pairs
        (B) TYPE: nucleic acid
        (C) STRANDEDNESS: single
        (D) TOPOLOGY:  linear (ii) MOLECULE TYPE:RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:216:

GGGAGACAAG AAUAAACGCU CAAACAAGAG AGUCAAACCA AGUGAGAUCA          50

GAGCGUUUAG CGCGGAAAGC ACAUUCGACA GGAGGCUCAC AACAGGC             97

(2) INFORMATION FOR SEQ ID NO:217:

(i) SEQUENCE CHARACTERISTICS:
        (A) LENGTH: 96 base pairs
        (B) TYPE: nucleic acid
        (C) STRANDEDNESS: single
        (D) TOPOLOGY:  linear (ii) MOLECULE TYPE:RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:217:

GGGAGACAAG AAUAAACGCU CAAACUCGAC UAGUAAUCAC CCUAGCAUAA          50

AUCUCCUCGA GCACAGACGA UAUUCGACAG GAGGCUCACA ACAGGC              96

(2) INFORMATION FOR SEQ ID NO:218:

(i) SEQUENCE CHARACTERISTICS:
        (A) LENGTH: 94 base pairs
        (B) TYPE: nucleic acid
        (C) STRANDEDNESS: single
        (D) TOPOLOGY:  linear (ii) MOLECULE TYPE:RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:218:

GGGAGACAAG AAUAAACGCU CAAUCAGCAG UAAGCGAUCC UAUAAAGAUC          50

AACUAGCCAA AGAUGACUUA UUCGACAGGA GGCUCACAAC AGGC                94

(2) INFORMATION FOR SEQ ID NO:219:

(i) SEQUENCE CHARACTERISTICS:
        (A) LENGTH: 95 base pairs
        (B) TYPE: nucleic acid
        (C) STRANDEDNESS: single
        (D) TOPOLOGY:  linear (ii) MOLECULE TYPE:RNA (ix) FEATURE:
```

(D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:219:

GGGAGACAAG AAUAAACGCU CAAAAAGACG UAUUCGAUUC GAAACGAGAA        50

AGACUUCAAG UGAGCCCGCA GUUCGACAGG AGGCUCACAA CAGGC            95

(2) INFORMATION FOR SEQ ID NO:220:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:220:

CUCAACGAAU CAGUAAACAU AACACCAUGA AACAUAAAUA GCACGCGAG         49

(2) INFORMATION FOR SEQ ID NO:221:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:221:

CUCAACGAGU UCACAUGGGA GCAAUCUCCG AAUAAACAAC ACGCGAG           47

(2) INFORMATION FOR SEQ ID NO:222:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:222:

CUCAACGAAC CACGGGGAAA UCCACCAGUA ACACGCGAG                    39

(2) INFORMATION FOR SEQ ID NO:223:

(i) SEQUENCE CHARACTERISTICS:
        (A) LENGTH: 38 base pairs

```
        (B) TYPE: nucleic acid
        (C) STRANDEDNESS: single
        (D) TOPOLOGY:  linear (ii) MOLECULE TYPE:RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:223:

CUCAACGAGC CAGGAACAUC GACGUCAGCA AACGCGAG                                   38

(2) INFORMATION FOR SEQ ID NO:224:

(i) SEQUENCE CHARACTERISTICS:
        (A) LENGTH: 42 base pairs
        (B) TYPE: nucleic acid
        (C) STRANDEDNESS: single
        (D) TOPOLOGY:  linear (ii) MOLECULE TYPE:RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:224:

CGCUCAACGA GCCAGGAACA UCGACGUCAG CAAACGCGAG CG                              42

(2) INFORMATION FOR SEQ ID NO:225:

(i) SEQUENCE CHARACTERISTICS:
        (A) LENGTH: 35 base pairs
        (B) TYPE: nucleic acid
        (C) STRANDEDNESS: single
        (D) TOPOLOGY:  linear (ii) MOLECULE TYPE:RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:225:

CUCAACGAGC CAGGACUACG AUCAGCAAAC GCGAG                                      35

(2) INFORMATION FOR SEQ ID NO:226:

(i) SEQUENCE CHARACTERISTICS:
        (A) LENGTH: 42 base pairs
        (B) TYPE: nucleic acid
        (C) STRANDEDNESS: single
        (D) TOPOLOGY:  linear (ii) MOLECULE TYPE:RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:226:

CUCAACGCAC CAGGAACAAC GAGAACCAUC AGUAAACGCG AG                              42
```

(2) INFORMATION FOR SEQ ID NO:227:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:227:

```
CUCAACGCAC CAGGAACAAC AAGAACCAUC AGUAAGCGCG AG                42
```

(2) INFORMATION FOR SEQ ID NO:228:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:228:

```
CACUCAACCG GCACCAGACU ACGAUCAGCA UUGGCGAGUG                   40
```

(2) INFORMATION FOR SEQ ID NO:229:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:229:

```
GAAUCCGGAA CACGCGAGAA AACAAAUCAA CGACCAAUCG AUUCG             45
```

(2) INFORMATION FOR SEQ ID NO:230:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All C's are 2'-F cytosine (ix) FEATURE:
        (D) OTHER INFORMATION: All U's are 2'-F uracil

```
        (ix) FEATURE:
             (B) LOCATION: 7, 9, 14, 21
             (D) OTHER INFORMATION: G are 2'-O-methyl guanine (ix) FEATURE:
             (B) LOCATION: 8, 15, 18, 22, 27, 31
             (D) OTHER INFORMATION: A are 2'-O-methly adenine (xi) SEQUENCE DESCRIPTION: SEQ ID NO:230:

CUCAACGAGC CAGGAACAUC GACGUCAGCA AACGCGAG                                  38

(2) INFORMATION FOR SEQ ID NO:231:

(i) SEQUENCE CHARACTERISTICS:
             (A) LENGTH: 38 base pairs
             (B) TYPE: nucleic acid
             (C) STRANDEDNESS: single
             (D) TOPOLOGY:  linear (ii) MOLECULE TYPE:RNA (ix) FEATURE:
             (D) OTHER INFORMATION: All C's are 2'-F cytosine (ix) FEATURE:
             (D) OTHER INFORMATION: All U's are 2'-F uracil (ix) FEATURE:
             (B) LOCATION:7, 9, 13, 14, 21, 24, 28
             (D) OTHER INFORMATION: G are 2'-O-methyl-guanine (ix) FEATURE:
             (B) LOCATION:8, 15, 18, 22, 27, 30, 31
             (D) OTHER INFORMATION: A are 2'-O-methyl-adenine (xi) SEQUENCE DESCRIPTION: SEQ ID NO:231:

CUCAACGAGC CAGGAACAUC GACGUCAGCA AACGCGAG                                  38

(2) INFORMATION FOR SEQ ID NO:232:

(i) SEQUENCE CHARACTERISTICS:
             (A) LENGTH: 38 base pairs
             (B) TYPE: nucleic acid
             (C) STRANDEDNESS: single
             (D) TOPOLOGY:  linear (ii) MOLECULE TYPE:RNA (ix) FEATURE:
             (D) OTHER INFORMATION: All C's are 2'-F cytosine (ix) FEATURE:
             (D) OTHER INFORMATION: All U's are 2'-F uracil (ix) FEATURE:
             (B) LOCATION: 7, 9, 14, 21, 36
             (D) OTHER INFORMATION: G are 2'-O-methyl-guanine (ix) FEATURE:
             (B) LOCATION:8, 15, 18, 22, 27, 31, 37
             (D) OTHER INFORMATION: A are 2'-O-methyl-adenine (xi) SEQUENCE DESCRIPTION: SEQ ID NO:232:

CUCAACGAGC CAGGAACAUC GACGUCAGCA AACGCGAG                                  38

(2) INFORMATION FOR SEQ ID NO:233:

(i) SEQUENCE CHARACTERISTICS:
             (A) LENGTH: 38 base pairs
             (B) TYPE: nucleic acid
             (C) STRANDEDNESS: single
             (D) TOPOLOGY:  linear
```

(ii) MOLECULE TYPE:RNA (ix) FEATURE:
    (D) OTHER INFORMATION: All C's are 2'-F cytosine (ix) FEATURE:
    (D) OTHER INFORMATION: All U's are 2'-F uracil (ix) FEATURE:
    (B) LOCATION: 7, 9, 13, 14, 21, 24, 28, 36
    (D) OTHER INFORMATION: G are 2'-O-methyl-guanine (ix) FEATURE:
    (B) LOCATION: 8, 15, 18, 22, 27, 30, 31, 37
    (D) OTHER INFORMATION: A are 2'-O-methyl-adenine (xi) SEQUENCE DESCRIPTION: SEQ ID NO:233:

CUCAACGAGC CAGGAACAUC GACGUCAGCA AACGCGAG                38

(2) INFORMATION FOR SEQ ID NO:234:

(i) SEQUENCE CHARACTERISTICS:
        (A) LENGTH: 38 base pairs
        (B) TYPE: nucleic acid
        (C) STRANDEDNESS: single
        (D) TOPOLOGY:  linear (ii) MOLECULE TYPE:RNA (ix) FEATURE:
        (D) OTHER INFORMATION: All C's are 2'-F cytosine (ix) FEATURE:
        (D) OTHER INFORMATION: All U's are 2'-F uracil (ix) FEATURE:
        (B) LOCATION:7, 9, 14
        (D) OTHER INFORMATION: G are 2'-O-methyl-guanine (ix) FEATURE:
        (B) LOCATION:8, 15, 18, 27, 31
        (D) OTHER INFORMATION: A are 2'-O-methyl-adenine (xi) SEQUENCE DESCRIPTION: SEQ ID NO:234:

CUCAACGAGC CAGGAACAUC GACGUCAGCA AACGCGAG                38

(2) INFORMATION FOR SEQ ID NO:235:

(i) SEQUENCE CHARACTERISTICS:
        (A) LENGTH: 38 base pairs
        (B) TYPE: nucleic acid
        (C) STRANDEDNESS: single
        (D) TOPOLOGY:  linear (ii) MOLECULE TYPE:RNA (ix) FEATURE:
        (D) OTHER INFORMATION: All C's are 2'-F cytosine (ix) FEATURE:
        (D) OTHER INFORMATION: All U's are 2'-F uracil (ix) FEATURE:
        (B) LOCATION: 7, 9, 13, 14, 24
        (D) OTHER INFORMATION: G are 2'-O-methyl-guanine (ix) FEATURE:
        (B) LOCATION: 8, 15, 18, 22, 27, 31
        (D) OTHER INFORMATION: A are 2'-O-methyl-adenine (xi) SEQUENCE DESCRIPTION: SEQ ID NO:235:

CUCAACGAGC CAGGAACAUC GACGUCAGCA AACGCGAG                38

(2) INFORMATION FOR SEQ ID NO:236:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:236:

```
CUCAACGAGC AAAAGUACUC ACGGGACCAG GAGAUCAGCA ACACGCGAGA          50

CGAAAUUCG                                                       59
```

(2) INFORMATION FOR SEQ ID NO:237:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:237:

```
CGCUCAACGA CCACAAUACA AACUCGUAUG GAACACGCGA GCG                 43
```

(2) INFORMATION FOR SEQ ID NO:238:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:238:

```
CGCUCAACUG GCAACGGGAU AACAACAAAU GUCACCAGCA CUAGCGAGAC          50

G                                                               51
```

(2) INFORMATION FOR SEQ ID NO:239:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE:RNA (ix) FEATURE:

```
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:239:

UCACUCAACC GGCACCAGAC UACGAUCAGC AUUGGCGAGU G                  41

(2) INFORMATION FOR SEQ ID NO:240:

(i) SEQUENCE CHARACTERISTICS:
        (A) LENGTH: 70 base pairs
        (B) TYPE: nucleic acid
        (C) STRANDEDNESS: single
        (D) TOPOLOGY:  linear (ii) MOLECULE TYPE:RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:240:

GGGAGACAAG AAUAAACGCU CAACGAGCAA GGAACGAAUA CAAACCAGGA         50

AACUCAGCAA CACGCGAGCA                                          70

(2) INFORMATION FOR SEQ ID NO:241:

(i) SEQUENCE CHARACTERISTICS:
        (A) LENGTH: 51 base pairs
        (B) TYPE: nucleic acid
        (C) STRANDEDNESS: single
        (D) TOPOLOGY:  linear (ii) MOLECULE TYPE:RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:241:

CUCAACGACC ACAAUAACCG GAAAUCCCCG CGGUUACGGA ACACGCGAAC         50

A                                                              51

(2) INFORMATION FOR SEQ ID NO:242:

(i) SEQUENCE CHARACTERISTICS:
        (A) LENGTH: 69 base pairs
        (B) TYPE: nucleic acid
        (C) STRANDEDNESS: single
        (D) TOPOLOGY:  linear (ii) MOLECULE TYPE:RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:242:

AGAAUAAACG CUCAACGAUG AGCGUGACCG AAGCUAUAAU CAGGUCGAUU         50

CACCAAGCAA UCUUAUUCG                                           69
```

(2) INFORMATION FOR SEQ ID NO:243:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:243:

ACGCUCAAAG GAUCACACAA ACAUCGGUCA AUAAAUAAGU AUUGAUAGCG          50

(2) INFORMATION FOR SEQ ID NO:244:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:244:

GCUCAAGCGG UCAGAAACAA UAGCUGGAUA CAUACCGCGC AUCCGCUGGG          50

CG          52

(2) INFORMATION FOR SEQ ID NO:245:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:245:

ACCAUCUAGA GCUUCGAACC AUGGUAUACA AGGGAACACA AAAUUCGCGG          50

AGGCUCCA          58

(2) INFORMATION FOR SEQ ID NO:246:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All C's are 2'-F cytosine (ix) FEATURE:
      (D) OTHER INFORMATION: All U's are 2'-F uracil (xi) SEQUENCE DESCRIPTION: SEQ ID NO:246:

GGGAGACAAG AUAAACGCUC AAACAAGAGA GUCAAACCAA GUGAGAUCAG        50

AGCGUUUAGC GCGGAAAGCA CAUUCGACAG GAGGCUCACA ACAGGC           96

(2) INFORMATION FOR SEQ ID NO:247:

(i) SEQUENCE CHARACTERISTICS:
       (A) LENGTH: 87 base pairs
       (B) TYPE: nucleic acid
       (C) STRANDEDNESS: single
       (D) TOPOLOGY: linear (ii) MOLECULE TYPE:RNA (ix) FEATURE:
      (D) OTHER INFORMATION: All C's are 2'-F cytosine (ix) FEATURE:
      (D) OTHER INFORMATION: All U's are 2'-F uracil (xi) SEQUENCE DESCRIPTION: SEQ ID NO:247:

GGGAGACAAG AAUAAACGCU CAAAAAGACG UAUUCGAUUC GAAACGAGAA        50

AGACUUCAAG UGAGCCCGCA GUUCGACAGG AGGCUCA                     87

(2) INFORMATION FOR SEQ ID NO:248:

(i) SEQUENCE CHARACTERISTICS:
       (A) LENGTH: 97 base pairs
       (B) TYPE: nucleic acid
       (C) STRANDEDNESS: single
       (D) TOPOLOGY: linear (ii) MOLECULE TYPE:RNA (ix) FEATURE:
      (D) OTHER INFORMATION: All C's are 2'-NH2 cytosine (ix) FEATURE:
      (D) OTHER INFORMATION: All U's are 2'-NH2 uracil (xi) SEQUENCE DESCRIPTION: SEQ ID NO:248:

GGGAGACAAG AAUAAACGCU CAANNNNNNN NNNNNNNNNN NNNNNNNNNN        50

NNNNNNNNNN NNNNNNNNNN NNNUUCGACA GGAGGCUCAC AACAGGC           97

(2) INFORMATION FOR SEQ ID NO:249:

(i) SEQUENCE CHARACTERISTICS:
       (A) LENGTH: 40 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:249:

TAATACGACT CACTATAGGG AGACAAGAAT AAACGCTCAA                   40

(2) INFORMATION FOR SEQ ID NO:250:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE:  DNA (xi) SEQUENCE DESCRIPTION: SEQ ID NO:250:

GCCTGTTGTG AGCCTCCTGT CGAA                                           24

(2) INFORMATION FOR SEQ ID NO:251:

(i) SEQUENCE CHARACTERISTICS:
        (A) LENGTH: 97 base pairs
        (B) TYPE: nucleic acid
        (C) STRANDEDNESS: single
        (D) TOPOLOGY:  linear (ii) MOLECULE TYPE:RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:251:

GGGAGACAAG AAUAAACGCU CAAGCCCCAA ACGCAAGCGA GCAUCCGCAA               50

CAGGGAAGAA GACAGACGAA UGAUUCGACA GGAGGCUCAC AACAGGC                  97

(2) INFORMATION FOR SEQ ID NO:252:

(i) SEQUENCE CHARACTERISTICS:
        (A) LENGTH: 97 base pairs
        (B) TYPE: nucleic acid
        (C) STRANDEDNESS: single
        (D) TOPOLOGY:  linear (ii) MOLECULE TYPE:RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:252:

GGGAGACAAG AAUAAACGCU CAAGCCCCAA ACGCAAGUGA GCAUCCGCAA               50

CAGGGAAGAA GACAGACGAU UGAUUCGACA GGAGGCUCAC AACAGGC                  97

(2) INFORMATION FOR SEQ ID NO:253:

(i) SEQUENCE CHARACTERISTICS:
        (A) LENGTH: 98 base pairs
        (B) TYPE: nucleic acid
        (C) STRANDEDNESS: single
        (D) TOPOLOGY:  linear (ii) MOLECULE TYPE:RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:253:

GGGAGACAAG AAAUAAACNC UCAAGCCCCA AACGCAAGUG AGCAUCCGCA               50

ACAGGGAAGA AGACAGAUGA AUGAUUCGAC AGGAGGCUCA CAACAGGC                 98

(2) INFORMATION FOR SEQ ID NO:254:

(i) SEQUENCE CHARACTERISTICS:
            (A) LENGTH: 95 base pairs
            (B) TYPE: nucleic acid
            (C) STRANDEDNESS: single
            (D) TOPOLOGY:  linear (ii) MOLECULE TYPE:RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:254:

```
GGGAGACAAG AAUAAACNCU CAAGCCCCAA GCAAGUGAGC AUCCGCAACA          50

GGGAAGAAGA CAGACGAGUG AUUCGACAGG AGGCUCACAA CAGGC               95
```

(2) INFORMATION FOR SEQ ID NO:255:

(i) SEQUENCE CHARACTERISTICS:
            (A) LENGTH: 97 base pairs
            (B) TYPE: nucleic acid
            (C) STRANDEDNESS: single
            (D) TOPOLOGY:  linear (ii) MOLECULE TYPE:RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:255:

```
GGGAGACAAG AAUAAACNCU CAAGCCCCAA ACGCAAGUGA GCAUCCGCAA          50

CAGGGAAGAA GACAGACGAA UGAUUCGACA GGAGGCUCAC AACAGGC             97
```

(2) INFORMATION FOR SEQ ID NO:256:

(i) SEQUENCE CHARACTERISTICS:
            (A) LENGTH: 97 base pairs
            (B) TYPE: nucleic acid
            (C) STRANDEDNESS: single
            (D) TOPOLOGY:  linear (ii) MOLECULE TYPE:RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:256:

```
GGGAGACAAG AAUAAACGCU CAAGCAAAAG GCGUAAAUAC ACCUCCGCAA          50

CUGGGAAGAA GACGCAGGGA CGGUUCGACA GGNGGCUCAC AACAGGC             97
```

(2) INFORMATION FOR SEQ ID NO:257:

(i) SEQUENCE CHARACTERISTICS:
            (A) LENGTH: 98 base pairs
            (B) TYPE: nucleic acid
            (C) STRANDEDNESS: single
            (D) TOPOLOGY:  linear (ii) MOLECULE TYPE:RNA (ix) FEATURE:
        (D) OTHER INFORMATION: All C's are 2'-NH2 cytosine (ix) FEATURE:
              (D) OTHER INFORMATION: All U's are 2'-NH2 uracil (xi) SEQUENCE DESCRIPTION: SEQ ID NO:257:

GGGAGACAAG AAUAAACGCU CAAACAGCUA CAAGUGGGAC AACAGGGUAC         50

AGCGGAGAGA AACAUCCAAA CAAGUUCGAC AGGAGGCUCA CAACAGGC          98

(2) INFORMATION FOR SEQ ID NO:258:

(i) SEQUENCE CHARACTERISTICS:
              (A) LENGTH: 95 base pairs
              (B) TYPE: nucleic acid
              (C) STRANDEDNESS: single
              (D) TOPOLOGY:  linear (ii) MOLECULE TYPE:RNA (ix) FEATURE:
              (D) OTHER INFORMATION: All C's are 2'-NH2 cytosine (ix) FEATURE:
              (D) OTHER INFORMATION: All U's are 2'-NH2 uracil (xi) SEQUENCE DESCRIPTION: SEQ ID NO:258:

GGGAGACAAG AAUAAACGCU CAAAUCAACU AAACAACGCA GUCACGAGAA         50

CGACCGGKCU GACUCCGAAA GUUCGACAGG AGGCUCACAA CAGGC             95

(2) INFORMATION FOR SEQ ID NO:259:

(i) SEQUENCE CHARACTERISTICS:
              (A) LENGTH: 95 base pairs
              (B) TYPE: nucleic acid
              (C) STRANDEDNESS: single
              (D) TOPOLOGY:  linear (ii) MOLECULE TYPE:RNA (ix) FEATURE:
              (D) OTHER INFORMATION: All C's are 2'-NH2 cytosine (ix) FEATURE:
              (D) OTHER INFORMATION: All U's are 2'-NH2 uracil (xi) SEQUENCE DESCRIPTION: SEQ ID NO:259:

GGGAGACAAG AAUAAACGCU CAAACGAGAG CACCAAGGCA ACAGAUGCAG         50

AAGAAGUGUG CGCGCGCGAA AUUCGACAGG AGGCUCACAA CAGGC             95

(2) INFORMATION FOR SEQ ID NO:260:

(i) SEQUENCE CHARACTERISTICS:
              (A) LENGTH: 98 base pairs
              (B) TYPE: nucleic acid
              (C) STRANDEDNESS: single
              (D) TOPOLOGY:  linear (ii) MOLECULE TYPE:RNA (ix) FEATURE:
              (D) OTHER INFORMATION: All C's are 2'-NH2 cytosine (ix) FEATURE:
              (D) OTHER INFORMATION: All U's are 2'-NH2 uracil (xi) SEQUENCE DESCRIPTION: SEQ ID NO:260:

GGGAGACAAG AAUAAACGCU CAAUAAGACA ACGAACAGAC AGAAGCGAAA         50

AAGGGGCGCC GCAGCAACAA CAAAUUCGAC AGGAGGCUCA CAACAGGC          98

(2) INFORMATION FOR SEQ ID NO:261:

(i) SEQUENCE CHARACTERISTICS:
        (A) LENGTH: 94 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:261:

```
GGGAGACAAG AAUAAACGCU CAACGUGUAC CACAACAGUU CCACGGAAGC        50
UGGAAUAGGA CGCAGAGGAA UUCGACAGGA GGCUCACAAC AGGC              94
```

(2) INFORMATION FOR SEQ ID NO:262:

(i) SEQUENCE CHARACTERISTICS:
        (A) LENGTH: 94 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:262:

```
GGGAGACAAG AAUAAACGCU CAAACAAAAU UWUGGUGGGC CCCGCAACMG        50
GGRGGRAGRC CGUUGAAGGC UUCGACAGGA GGCUCACAAC AGGC              94
```

(2) INFORMATION FOR SEQ ID NO:263:

(i) SEQUENCE CHARACTERISTICS:
        (A) LENGTH: 94 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:263:

```
GGGAGACAAG AAUAAACGCU CAAGAUCAUA ACGAGAGGAG AGGGAGAACU        50
ACACGCGCGC GAGGAAAGAG UUCGACAGGA GGCUCACAAC AGGC              94
```

(2) INFORMATION FOR SEQ ID NO:264:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (ii) MOLECULE TYPE:RNA (ix) FEATURE:
            (D) OTHER INFORMATION: All C's are 2'-NH2 cytosine (ix) FEATURE:
            (D) OTHER INFORMATION: All U's are 2'-NH2 uracil (xi) SEQUENCE DESCRIPTION: SEQ ID NO:264:

GGGAGACAAG AAUAAACGCU CAAACACAAA UCGGGCAGGG ACUGGGUUGG         50

GCACGGCAGG  GCGCCUUCGA CAGGAGGCUC ACAACAGGC                   89

(2) INFORMATION FOR SEQ ID NO:265:

(i) SEQUENCE CHARACTERISTICS:
           (A) LENGTH: 97 base pairs
           (B) TYPE: nucleic acid
           (C) STRANDEDNESS: single
           (D) TOPOLOGY:  linear (ii) MOLECULE TYPE:RNA (ix) FEATURE:
            (D) OTHER INFORMATION: All C's are 2'-NH2 cytosine (ix) FEATURE:
            (D) OTHER INFORMATION: All U's are 2'-NH2 uracil (xi) SEQUENCE DESCRIPTION: SEQ ID NO:265:

GGGAGACAAG AAUAAACGCU CAAGUGGGCU CGGGCCGGAU GUCUACGGGU         50

GUGAAGAAAC CCCUAGGGCA GGGUUCGACA GGAGGCUCAC AACAGGC            97

(2) INFORMATION FOR SEQ ID NO:266:

(i) SEQUENCE CHARACTERISTICS:
           (A) LENGTH: 95 base pairs
           (B) TYPE: nucleic acid
           (C) STRANDEDNESS: single
           (D) TOPOLOGY:  linear (ii) MOLECULE TYPE:

(ix) FEATURE:RNA
            (D) OTHER INFORMATION: All C's are 2'-NH2 cytosine (ix) FEATURE:
            (D) OTHER INFORMATION: All U's are 2'-NH2 uracil (xi) SEQUENCE DESCRIPTION: SEQ ID NO:266:

GGGAGACAAG AAUAAACGCU CAAGAUCAGC GGAACUAAGA AAUGGAAGGC         50

UAAGCACCGG GAUCGGGAGA AUUCGACAGG AGGCUCACAA CAGGC              95

(2) INFORMATION FOR SEQ ID NO:267:

(i) SEQUENCE CHARACTERISTICS:
           (A) LENGTH: 95 base pairs
           (B) TYPE: nucleic acid
           (C) STRANDEDNESS: single
           (D) TOPOLOGY:  linear (ii) MOLECULE TYPE:RNA (ix) FEATURE:
            (D) OTHER INFORMATION: All C's are 2'-NH2 cytosine (ix) FEATURE:
            (D) OTHER INFORMATION: All U's are 2'-NH2 uracil (xi) SEQUENCE DESCRIPTION: SEQ ID NO:267:

GGGAGACAAG AAUAAACGCU CAAUAACAAA GCAGCAAAGU ACCAGAGGAG         50

AGUUGGCAGG GUUUAGGCAG CUUCGACAGG AGGCUCACAA CAGGC                95

(2) INFORMATION FOR SEQ ID NO:268:

(i) SEQUENCE CHARACTERISTICS:
        (A) LENGTH: 95 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:268:

GGGAGACAGA AUAAACGCUC AAAGACCAAG GGACAGCAGC GGGGAAAAAC           50

AGAUCACAGC UGUAAGAGGG CUUCGACAGG AGGCUCACAA CAGGC                95

(2) INFORMATION FOR SEQ ID NO:269:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:269:

GGGAGACAAG AAUAAACGCU CAAAGUCGGG GAUAGAAACA CACUAAGAAG           50

UGCAUCAGGU AGGAGAUAAU UCGACAGGNG GCUCACAACA GGC                  93

(2) INFORMATION FOR SEQ ID NO:270:

(i) SEQUENCE CHARACTERISTICS:
        (A) LENGTH: 95 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:270:

GGGAGACAAG AAUAAACGCU CAAGAGUAUC ACACAAACCG GCACGGACUA           50

AGCAGAAGGA GGUACGGAAG AUUCGACAGG AGGCUCACAA CAGGC                95

(2) INFORMATION FOR SEQ ID NO:271:

(i) SEQUENCE CHARACTERISTICS:
        (A) LENGTH: 94 base pairs
        (B) TYPE: nucleic acid
        (C) STRANDEDNESS: single (D) TOPOLOGY: linear (ii) MOLECULE TYPE:RNA (ix) FEATURE:
           (D) OTHER INFORMATION: All C's are 2'-NH2 cytosine (ix) FEATURE:
           (D) OTHER INFORMATION: All U's are 2'-NH2 uracil (xi) SEQUENCE DESCRIPTION: SEQ ID NO:271:

GGGAGACAAG AAUAAACNCU CAACGAAAUA GAAGGAACAG AAGAAUGGBG           50

AWGNGGGAAA UGGCAACGAA UUCGACAGGN GGCUCACAAC AGGC                94

(2) INFORMATION FOR SEQ ID NO:272:

(i) SEQUENCE CHARACTERISTICS:
          (A) LENGTH: 97 base pairs
          (B) TYPE: nucleic acid
          (C) STRANDEDNESS: single
          (D) TOPOLOGY: linear (ii) MOLECULE TYPE:RNA (ix) FEATURE:
           (D) OTHER INFORMATION: All C's are 2'-NH2 cytosine (ix) FEATURE:
           (D) OTHER INFORMATION: All U's are 2'-NH2 uracil (xi) SEQUENCE DESCRIPTION: SEQ ID NO:272:

GGGAGACAAG AAUAAACGCU CAAACGAGAC CCUGGAUACG AGGCUGAGGG           50

AAAGGGAGMM MRRAMCUARR CKCUUCGACA GGAGGCUCAC AACAGGC             97

(2) INFORMATION FOR SEQ ID NO:273:

(i) SEQUENCE CHARACTERISTICS:
          (A) LENGTH: 96 base pairs
          (B) TYPE: nucleic acid
          (C) STRANDEDNESS: single
          (D) TOPOLOGY: linear (ii) MOLECULE TYPE:RNA (ix) FEATURE:
           (D) OTHER INFORMATION: All C's are 2'-NH2 cytosine (ix) FEATURE:
           (D) OTHER INFORMATION: All U's are 2'-NH2 uracil (xi) SEQUENCE DESCRIPTION: SEQ ID NO:273:

GGGAGACAAG AAUAAACGCU CAAGAAGGAU ACUUAGGACU ACGUGGGAUG           50

GGAUGAAAUG GGAGAACGGG AGUUCGACAG GAGGCUCACA ACAGGC              96

(2) INFORMATION FOR SEQ ID NO:274:

(i) SEQUENCE CHARACTERISTICS:
          (A) LENGTH: 96 base pairs
          (B) TYPE: nucleic acid
          (C) STRANDEDNESS: single
          (D) TOPOLOGY: linear (ii) MOLECULE TYPE:RNA (ix) FEATURE:
           (D) OTHER INFORMATION: All C's are 2'-NH2 cytosine (ix) FEATURE:
           (D) OTHER INFORMATION: All U's are 2'-NH2 uracil (xi) SEQUENCE DESCRIPTION: SEQ ID NO:274:

GGGAGACAAG AAUAAACGCU CAAAACGCAC AAAGUAAGGG ACGGGAUGGA    50

UCGCCCUAGG CUGGAAGGGA ACUUCGACAG GAGGCUCACA ACAGGC    96

(2) INFORMATION FOR SEQ ID NO:275:

(i) SEQUENCE CHARACTERISTICS:
        (A) LENGTH: 96 base pairs
        (B) TYPE: nucleic acid
        (C) STRANDEDNESS: single
        (D) TOPOLOGY:  linear (ii) MOLECULE TYPE:RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:275:

GGGAGACAAG AAUAAACGCU CAAGGUGAAC GGCAGCAAGG CCCAAAACGU    50

AAGGCCGGAA ACNGGAGAGG GAUUCGACAG GNGGCUCACA ACAGGC    96

(2) INFORMATION FOR SEQ ID NO:276:

(i) SEQUENCE CHARACTERISTICS:
        (A) LENGTH: 96 base pairs
        (B) TYPE: nucleic acid
        (C) STRANDEDNESS: single
        (D) TOPOLOGY:  linear (ii) MOLECULE TYPE:RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:276:

GGGAGACAAG AAUAAACGCU CAAUGAUAUA CACGUAAGCA CUGAACCAGG    50

CUGAGAUCCA UCAGUGCCCA GGUUCGACAG GAGGCUCACA ACAGGC    96

(2) INFORMATION FOR SEQ ID NO:277:

(i) SEQUENCE CHARACTERISTICS:
        (A) LENGTH: 94 base pairs
        (B) TYPE: nucleic acid
        (C) STRANDEDNESS: single
        (D) TOPOLOGY:  linear (ii) MOLECULE TYPE:RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:277:

GGGAGACAAG AAUAAACGCU CAAGAUCAUA ACGAGAGGAG AGGGAGAACU    50

ACACGCGCGC GAGGAAAGAG UUCGACAGGA GGCUCACAAC AGGC    94

(2) INFORMATION FOR SEQ ID NO:278:

(i) SEQUENCE CHARACTERISTICS:

(A) LENGTH: 96 base pairs
        (B) TYPE: nucleic acid
        (C) STRANDEDNESS: single
        (D) TOPOLOGY:  linear (ii) MOLECULE TYPE:RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:278:

GGGAGACAAG AAUAAACGCU CAAUCAAGUA AGGAGGAAGG GUCGUGACAG          50

AAAAACGAGC AAAAAACGCG AGUUCGACAG GAGGCUCACA ACAGGC              96

(2) INFORMATION FOR SEQ ID NO:279:

(i) SEQUENCE CHARACTERISTICS:
        (A) LENGTH: 93 base pairs
        (B) TYPE: nucleic acid
        (C) STRANDEDNESS: single
        (D) TOPOLOGY:  linear (ii) MOLECULE TYPE:RNA (ix) FEATURE:
        (D) OTHER INFORMATION: All C's are 2'-NH2 cytosine (ix) FEATURE:
        (D) OTHER INFORMATION: All U's are 2'-NH2 uracil (xi)

(xi) SEQUENCE DESCRIPTION: SEQ ID NO:279:

GGGAGACAAG AAUAAACGCU CAAAAGGUGC CGGGUUGGAG GGGUAGCAAG          50

AAAUGGCUAG GGCGCASGAU UCGACAGGNG GCUCACAACA GGC                 93

(2) INFORMATION FOR SEQ ID NO:280:

(i) SEQUENCE CHARACTERISTICS:
        (A) LENGTH: 97 base pairs
        (B) TYPE: nucleic acid
        (C) STRANDEDNESS: single
        (D) TOPOLOGY:  linear (ii) MOLECULE TYPE:RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:280:

GGGAGACAAG AAUAAACGCU CAACCAACGC GCACCCCGCA GCAAACGAAA          50

UUGGGGAGAC AGGUGCAAGA CAGUUCGACA GGAGGCUCAC AACAGGC             97

(2) INFORMATION FOR SEQ ID NO:281:

(i) SEQUENCE CHARACTERISTICS:
        (A) LENGTH: 97 base pairs
        (B) TYPE: nucleic acid
        (C) STRANDEDNESS: single
        (D) TOPOLOGY:  linear (ii) MOLECULE TYPE:RNA (ix) FEATURE:
        (D) OTHER INFORMATION: All C's are 2'-NH2 cytosine (ix) FEATURE:
    (D) OTHER INFORMATION: All U's are 2'-NH2 uracil (xi) SEQUENCE DESCRIPTION: SEQ ID NO:281:

GGGAGACAAG AAUAAACKCU CAACAAACAA UAUCGGCGCA GGAAAACGUA        50

GAAACGAAAM GGAGCUGCGY GGAUUCGACA GGAGGCUCAC AACAGGC          97

(2) INFORMATION FOR SEQ ID NO:282:
    (i) SEQUENCE CHARACTERISTICS:
        (A) LENGTH: 93 base pairs
        (B) TYPE: nucleic acid
        (C) STRANDEDNESS: single
        (D) TOPOLOGY:  linear (ii) MOLECULE TYPE:RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:282:

GGGAGACAAG AAUAAACGCU CAAUGAUAGC ACAGUGUAUA AGAAAACGCA        50

ACACCGCGCG CGGAAAGAGU UCGACAGGAG GCUCACAACA GGC              93

(2) INFORMATION FOR SEQ ID NO:283:
    (i) SEQUENCE CHARACTERISTICS:
        (A) LENGTH: 96 base pairs
        (B) TYPE: nucleic acid
        (C) STRANDEDNESS: single
        (D) TOPOLOGY:  linear (ii) MOLECULE TYPE:RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:283:

GGGAGACAAG AAUAAACGCU CAAGAUCAUC GCAGUAUCGG AAUCGACCCU        50

CAGUGGGUGA CAUGCGGACA AGUUCGACAG GAGGCUCACA ACAGGC           96

(2) INFORMATION FOR SEQ ID NO:284:
    (i) SEQUENCE CHARACTERISTICS:
        (A) LENGTH: 97 base pairs
        (B) TYPE: nucleic acid
        (C) STRANDEDNESS: single
        (D) TOPOLOGY:  linear (ii) MOLECULE TYPE:RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:284:

GGGAGACAAG AAUAAACGCU CAAGUACCGG GAAGGGAUGA ACUGGGAUAU        50

GGGAACGGAG GUCAGAGGCA CGAUUCGACA GGAGGCUCAC AACAGGC          97

(2) INFORMATION FOR SEQ ID NO:285:

(i) SEQUENCE CHARACTERISTICS:
        (A) LENGTH: 97 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:285:

```
GGGAGACAAG AAUAAACGCU CAAGCAAUGG AACGCUAGGA GGGAACAUAA          50

GCAGGGCGAG CGGAGUCGAU AGCUUCGACA GGAGGCUCAC AACAGGC             97
```

(2) INFORMATION FOR SEQ ID NO:286:

(i) SEQUENCE CHARACTERISTICS:
        (A) LENGTH: 97 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:286:

```
GGGAGACAAG AAUAAACGCU CAAAACAGAA CUGAUCGGCG CAGGUUGAUA          50

AAGGGGCAGC GCGAAGAUCA CAAUUCGACA GGAGGCUCAC AACAGGC             97
```

(2) INFORMATION FOR SEQ ID NO:287:

(i) SEQUENCE CHARACTERISTICS:
        (A) LENGTH: 97 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:287:

```
GGGAGACAAG AAUAAACGCU CAAGGGAAAC GGAAAGGGAC AAGGCGAACA          50

GACGAGAAGU AGACGGAGUA GGAUUCGACA GGAGGCUCAC AACAGGC             97
```

(2) INFORMATION FOR SEQ ID NO:288:

(i) SEQUENCE CHARACTERISTICS:
        (A) LENGTH: 97 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:288:

GGGAGACAAG AAUAAACGCU CAANNNGAGG AAGGGCACGC AAGGAAACAA         50

AACACAAAGC AGAAGUAGUA AGAUUCGACA GGAGGCUCAC AACAGGC           97

(2) INFORMATION FOR SEQ ID NO:289:

(i) SEQUENCE CHARACTERISTICS:
        (A) LENGTH: 95 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:289:

GGGAGACAAG AAUAAACGCU CAAGUACRCA GUGAGCAGAA GCAGAGAGAC         50

UUGGGAUGGG AUGAAAUGGK CUUCGACAGG AGGCUCACAA CAGGC             95

(2) INFORMATION FOR SEQ ID NO:290:

(i) SEQUENCE CHARACTERISTICS:
        (A) LENGTH: 97 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:290:

GGGAGACAAG AAUAAACNCU CAACCGACGU GGACDCGCAU CGGCAUCCAG         50

ACCAGGCUGN BCNGCACCAS ACGUUCGACA GGAGGCUCAC AACAGGC           97

(2) INFORMATION FOR SEQ ID NO:291:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All C's are 2'-NH2 cytosine (ix) FEATURE:
        (D) OTHER INFORMATION: All U's are 2'-NH2 uracil (xi) SEQUENCE DESCRIPTION: SEQ ID NO:291:

GGGAAGAAGA C                                                  11

(2) INFORMATION FOR SEQ ID NO:292:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:292:

```
GGGAGGACGA UGCGGNNNNN NNNNNNNNNN NNNNNNNNNN NNNNNNNNNN          50

CAGACGACUC GCCCGA                                               66
```

(2) INFORMATION FOR SEQ ID NO:293:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:293:

```
GGGAGGACGA UGCGGGCAAA UUGCAUGCGU UUUCGAGUGC UUGCUCAGAC          50

GACUCGCCCG A                                                    61
```

(2) INFORMATION FOR SEQ ID NO:294:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:294:

```
GGGAGGACGA UGCGGUGCUU AAACAACGCG UGAAUCGAGU UCAUCCACUC          50

CUCCUCAGAC GACUCGCCCG A                                         71
```

(2) INFORMATION FOR SEQ ID NO:295:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: RNA (ix) FEATURE:
         (D) OTHER INFORMATION: All C's are 2'-F cytosine (ix) FEATURE:
         (D) OTHER INFORMATION: All U's are 2'-F uracil (xi) SEQUENCE DESCRIPTION: SEQ ID NO:295:

GGGAGGACGA UGCGGUUAAU UCAGUCUCAA ACGGUGCGUU UAUCGAGCCA          50

CUGAUCWGAC GACUCGCCCG AA                                       72

(2) INFORMATION FOR SEQ ID NO:296:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
         (D) OTHER INFORMATION: All C's are 2'-F cytosine (ix) FEATURE:
         (D) OTHER INFORMATION: All U's are 2'-F uracil (xi) SEQUENCE DESCRIPTION: SEQ ID NO:296:

GGGAGGACGA UGCGGCUUAG AGCUCAAACG GUGUGACUUU CAAGCCCUCU          50

AUGCCCAGAC GACUCGCCCG A                                        71

(2) INFORMATION FOR SEQ ID NO:297:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (ix) FEATURE:
         (D) OTHER INFORMATION: All C's are 2'-F cytosine (ix) FEATURE:
         (D) OTHER INFORMATION: All U's are 2'-F uracil (xi) SEQUENCE DESCRIPTION: SEQ ID NO:297:

GGGAGGACGA UGCGGUACCU CAAAUUGCGU GUUUUCAAGC AGUAUCAGAC          50

GACUCGCCCG A                                                   61

(2) INFORMATION FOR SEQ ID NO:298:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (ix) FEATURE:
         (D) OTHER INFORMATION: All C's are 2'-F cytosine (ix) FEATURE:
         (D) OTHER INFORMATION: All U's are 2'-F uracil (xi) SEQUENCE DESCRIPTION: SEQ ID NO:298:

GGGAGGACGA UGCGGACCCU CAAAUAACGU GUCUUUCAAG UUGGUCAGAC          50

```
GACUCGCCCG A                                                  61

(2) INFORMATION FOR SEQ ID NO:299:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:299:

GGGAGGACGA UGCGGACCCU CAAAUAGCGU GCAUUUCAAG CUGGUCAGAC          50

GACUCGCCCG A                                                  61

(2) INFORMATION FOR SEQ ID NO:300:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:300:

GGGAAGACGA UGCGGCGCUC AAAUAAUGCG UUAAUCGAAU UCGCCCAGAC          50

GACUCGCCCG A                                                  61

(2) INFORMATION FOR SEQ ID NO:301:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:301:

GGGAGGACGA UGCGGCAAAC AAGCUCAAAU GACGUGUUUU UCAAGUCCUU          50

GUUGUCAGAC GACUCGCCCG A                                        71

(2) INFORMATION FOR SEQ ID NO:302:

(i) SEQUENCE CHARACTERISTICS:
        (A) LENGTH: 71 base pairs
        (B) TYPE: nucleic acid
        (C) STRANDEDNESS: single
```

(D) TOPOLOGY: linear (ii) MOLECULE TYPE: RNA (ix) FEATURE:
            (D) OTHER INFORMATION: All C's are 2'-F cytosine (ix) FEATURE:
            (D) OTHER INFORMATION: All U's are 2'-F uracil (xi) SEQUENCE DESCRIPTION: SEQ ID NO:302:

GGGAGGACGA UGCGGUAGUA AGUCUCAAAU GUUGCGUUUU UCGAAACACU           50

UACAUCAGAC GACUCGCCCG A                                         71

(2) INFORMATION FOR SEQ ID NO:303:

(i) SEQUENCE CHARACTERISTICS:
            (A) LENGTH: 62 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All C's are 2'-F cytosine (ix) FEATURE:
            (D) OTHER INFORMATION: All U's are 2'-F uracil (xi) SEQUENCE DESCRIPTION: SEQ ID NO:303:

GGGAGGACGA UGCGGAGACU CAAAUGGUGU GUUUUCAAGC CUCUCCCAGU           50

CGACUCGCCC GA                                                   62

(2) INFORMATION FOR SEQ ID NO:304:

(i) SEQUENCE CHARACTERISTICS:
            (A) LENGTH: 63 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All C's are 2'-F cytosine (ix) FEATURE:
            (D) OTHER INFORMATION: All U's are 2'-F uracil (xi) SEQUENCE DESCRIPTION: SEQ ID NO:304:

GGGAGGACGA UGCGGUGCUC AAAUGAUGCG UUUCUCGAAU CCACCCAGAC           50

GACUCGCCCG AGG                                                  63

(2) INFORMATION FOR SEQ ID NO:305:

(i) SEQUENCE CHARACTERISTICS:
            (A) LENGTH: 71 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All C's are 2'-F cytosine (ix) FEATURE:
            (D) OTHER INFORMATION: All U's are 2'-F uracil (xi) SEQUENCE DESCRIPTION: SEQ ID NO:305:

GGGAGGACGA UGCGGCCAUC GGUCUUGGGC AACGCGUUUU CGAGUUACCU        50

AUGGUCAGAC GACUCGCCCG A                                       71

(2) INFORMATION FOR SEQ ID NO:306:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:306:

GGGAGGACGA UGCGGCCAUC GGUCUUGGGC AACGCGUUUU CGAGUUACCU        50

ACAUCAGACG ACUCGCCCGA                                         70

(2) INFORMATION FOR SEQ ID NO:307:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:307:

GGGAGGACGA UGCGGGACCC UUAGGCAACG UGUUUUCAAG UUGGUCAGAC        50

GACUCGCCCG A                                                  61

(2) INFORMATION FOR SEQ ID NO:308:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:308:

GGGAGGACGA UGCGGACGUA GCUCUUAGGC AAUGCGUAUU UCGAAUUAGC        50

UGUGUCAGAC GACUCGCCCG A                                       71

(2) INFORMATION FOR SEQ ID NO:309:

(i) SEQUENCE CHARACTERISTICS:

(A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:309:

GGGAGGACGA UGCGGAGUCU UAGGCAGCGC GUUUUCGAGC UACUCCAUCG         50

CCAGUCAGAC GACUCGCCCG A                                        71

(2) INFORMATION FOR SEQ ID NO:310:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:310:

GGGAAGACGA UGCGGAAUGC UCUUAGGCAG CGCGUUAAUC GAGCUAGCAC         50

AUCCUCAGAC GACUCGCCCG A                                        71

(2) INFORMATION FOR SEQ ID NO:311:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:311:

GGGAGGACGA UGGGGAGUCU UAGGCAGCGC GUUUUCGAGC UACUCCAUCG         50

CCAGUCAGAC GACUCGCCCG A                                        71

(2) INFORMATION FOR SEQ ID NO:312:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:312:

GGGAGGACGA UGCGGUAAUC UCUUAGGCAU CGCGUUAAUC GAGAUAGAUC          50

ACCGUCAGAC GACUCGCCCG A                                         71

(2) INFORMATION FOR SEQ ID NO:313:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:313:

GGGAGGACGA UGCGGCAAUG UCHCUUAGGC CACGCGUUAA UCGAGCGUGA          50

CUGUCAGACG ACUCGCCCGA G                                         71

(2) INFORMATION FOR SEQ ID NO:314:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:314:

GGGAGGACGA UGCGGCAUGG UCUUAGGCGA CGCGUUUAUA UCGAGUCACC          50

AUGCUCAGAC GACUCGCCCG A                                         71

(2) INFORMATION FOR SEQ ID NO:315:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:315:

GGGAGGACGA UGCGGGAUGC UUAGGCGCCG UGUUUUCAAG GCCAUCAGAC          50

GACUCGCCCG A                                                    61

(2) INFORMATION FOR SEQ ID NO:316:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:316:

```
GGGAGGACGA UGCGGUAAUU GUCUUAGGCG CCGUGUUAUC AAGGCACAAU          50

UUCCCUCAGA CGACUCGCCC GA                                       72
```

(2) INFORMATION FOR SEQ ID NO:317:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:317:

```
GGGAAGACGA UGCGGCUACU AGUGUCUUAG GCGGAGUGUU UAUCAAUCCA          50

CACAUCAGAC GACUCGCCCG A                                        71
```

(2) INFORMATION FOR SEQ ID NO:318:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:318:

```
GGGAGGACGA UGCGGACUGA CUUAGGCUGC GCGCACUUCG AGCAUCAGAC          50

GACUCGCCCG A                                                   61
```

(2) INFORMATION FOR SEQ ID NO:319:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: RNA (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:319:

GGGAGGACGA UGCGGUGGUG UGUCUUUGGC ACCGCGUAUU UUCGAGGUAC          50

ACAUCAGACG ACUCGCCCGA                                          70

(2) INFORMATION FOR SEQ ID NO:320:

(i) SEQUENCE CHARACTERISTICS:
              (A) LENGTH: 70 base pairs
              (B) TYPE: nucleic acid
              (C) STRANDEDNESS: single
              (D) TOPOLOGY: linear (ii) MOLECULE TYPE: RNA (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:320:

GGGAGGACGA UGCGGUGGUG UGUCUUUGGC ACCGCGUAUU CUCGAGGUAC          50

ACAUCAGACG ACUCGCCCGA                                          70

(2) INFORMATION FOR SEQ ID NO:321:

(i) SEQUENCE CHARACTERISTICS:
              (A) LENGTH: 61 base pairs
              (B) TYPE: nucleic acid
              (C) STRANDEDNESS: single
              (D) TOPOLOGY: linear (ii) MOLECULE TYPE: RNA (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:321:

GGGAGGACGA UGCGGGCUCU UCAGCAACGU GUUAUCAAGU UAGCCCAGAC          50

GACUCGCCCG A                                                   61

(2) INFORMATION FOR SEQ ID NO:322:

(i) SEQUENCE CHARACTERISTICS:
              (A) LENGTH: 71 base pairs
              (B) TYPE: nucleic acid
              (C) STRANDEDNESS: single
              (D) TOPOLOGY: linear (ii) MOLECULE TYPE: RNA (ix) FEATURE:
              (D) OTHER INFORMATION: All C's are 2'-F cytosine (ix) FEATURE:
              (D) OTHER INFORMATION: All U's are 2'-F uracil (xi) SEQUENCE DESCRIPTION: SEQ ID NO:322:

GGGAGGACGA UGCGGCGUAA CUUCAGCGGU GUGUUAAUCA AGCCUUACGC          50

CAUCUCAGAC GACUCGCCCG A                                              71

(2) INFORMATION FOR SEQ ID NO:323:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:323:

GAGGACGAUG CGGGCUCUUA AGCAACGUGU UAUCAAGUUA GCCCAGACGA               50

CUCGCCCGA                                                           59

(2) INFORMATION FOR SEQ ID NO:324:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:324:

GGGAGGACGA UGCGGUCUCA AGCAAUGCGU UUAUCGAAUU ACCGUACGCC               50

UCCGUCAGAC GACUCGCCCG A                                             71

(2) INFORMATION FOR SEQ ID NO:325:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:325:

GGGAGGACGA UGCGGAAAUC UCUUAAGCAG CGUGUAAAUC AAGCUAGAUC               50

UUCGUCAGAC GACUCGCCCG A                                             71

(2) INFORMATION FOR SEQ ID NO:326:

(i) SEQUENCE CHARACTERISTICS:
        (A) LENGTH: 61 base pairs
        (B) TYPE: nucleic acid
        (C) STRANDEDNESS: single
        (D) TOPOLOGY: linear

```
        (ii) MOLECULE TYPE: RNA (ix) FEATURE:
             (D) OTHER INFORMATION: All C's are 2'-F cytosine (ix) FEATURE:
             (D) OTHER INFORMATION: All U's are 2'-F uracil (xi) SEQUENCE DESCRIPTION: SEQ ID NO:326:

GGGAGGACGA UGCGGUUCUU AAGCAGCGCG UCAAUCGAGC UAACCCAGAC            50

GACUCGCCCG A                                                     61

(2) INFORMATION FOR SEQ ID NO:327:

(i) SEQUENCE CHARACTERISTICS:
             (A) LENGTH: 62 base pairs
             (B) TYPE: nucleic acid
             (C) STRANDEDNESS: single
             (D) TOPOLOGY: linear (ii) MOLECULE TYPE: RNA (ix) FEATURE:
             (D) OTHER INFORMATION: All C's are 2'-F cytosine (ix) FEATURE:
             (D) OTHER INFORMATION: All U's are 2'-F uracil (xi) SEQUENCE DESCRIPTION: SEQ ID NO:327:

GGGAGGACGA UGCGGAUCUU AAGCAGCGCG UCAAUCGAGC UAACCCAGAC            50

GACUCGCCCG AG                                                    62

(2) INFORMATION FOR SEQ ID NO:328:

(i) SEQUENCE CHARACTERISTICS:
             (A) LENGTH: 75 base pairs
             (B) TYPE: nucleic acid
             (C) STRANDEDNESS: single
             (D) TOPOLOGY: linear (ii) MOLECULE TYPE: RNA (ix) FEATURE:
             (D) OTHER INFORMATION: All C's are 2'-F cytosine (ix) FEATURE:
             (D) OTHER INFORMATION: All U's are 2'-F uracil (xi) SEQUENCE DESCRIPTION: SEQ ID NO:328:

ACAGCUGAUG ACCAUGAUUA CGCCAAGCUU AAGCAGCGCG UUUUCGAGCU            50

CAUGUUGGUC AGACGACUCG CCCGA                                      75

(2) INFORMATION FOR SEQ ID NO:329:

(i) SEQUENCE CHARACTERISTICS:
             (A) LENGTH: 71 base pairs
             (B) TYPE: nucleic acid
             (C) STRANDEDNESS: single
             (D) TOPOLOGY: linear (ii) MOLECULE TYPE: RNA (ix) FEATURE:
             (D) OTHER INFORMATION: All C's are 2'-F cytosine (ix) FEATURE:
             (D) OTHER INFORMATION: All U's are 2'-F uracil (xi) SEQUENCE DESCRIPTION: SEQ ID NO:329:
```

GGGAGGACGA UGCGGAGGGU CUUAAGCAGU GUGAUAAUCA AACUACUCUC        50

CGUGUCAGAC GACUCGCCCG A                                      71

(2) INFORMATION FOR SEQ ID NO:330:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:330:

GGGAGGACGA UGCGGGAUCU UAAGCAGUGC GUUAUUCGAA CUAUCCCAGA        50

CGACUCGCCC GA                                                62

(2) INFORMATION FOR SEQ ID NO:331:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:331:

GGGAGGACGA UGCGGUGCUA UUCUUAAGCG GCGUGUUUUU CAAGCCAAUA        50

UCAUCAGACG ACUCGCCCGA                                        70

(2) INFORMATION FOR SEQ ID NO:332:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:332:

GGGAGGACGA UGCGGUCUUA AGCGGCGCGA UUUUCGAGCC ACCGCAUCCU        50

CCGUGCAGAC GACUCGCCCG A                                      71

(2) INFORMATION FOR SEQ ID NO:333:

(i) SEQUENCE CHARACTERISTICS:
        (A) LENGTH: 61 base pairs

```
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All C's are 2'-F cytosine (ix) FEATURE:
            (D) OTHER INFORMATION: All U's are 2'-F uracil (xi) SEQUENCE DESCRIPTION: SEQ ID NO:333:

GGGAGGACGA UGCGGCCUCU UAAGCGUCGU GUUUUUCAAG CUGGUCAGAC        50

GACUCGCCCG A                                                  61

(2) INFORMATION FOR SEQ ID NO:334:

(i) SEQUENCE CHARACTERISTICS:
            (A) LENGTH: 71 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All C's are 2'-F cytosine (ix) FEATURE:
            (D) OTHER INFORMATION: All U's are 2'-F uracil (xi) SEQUENCE DESCRIPTION: SEQ ID NO:334:

GGGAGGACGA UGCGGAUACC ACCUCUUAAG CGACGUGCAU UUCAAGUCAG        50

AUGGUCAGAC GACUCGCCCG A                                       71

(2) INFORMATION FOR SEQ ID NO:335:

(i) SEQUENCE CHARACTERISTICS:
            (A) LENGTH: 72 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All C's are 2'-F cytosine (ix) FEATURE:
            (D) OTHER INFORMATION: All U's are 2'-F uracil (xi) SEQUENCE DESCRIPTION: SEQ ID NO:335:

GGGAGGACGA UGCGGUGCUA UUCUUAAGCG GCGUGUAAAU CAAGCUAGAU        50

CAUCGUCAGA CGACUCGCCC GA                                      72

(2) INFORMATION FOR SEQ ID NO:336:

(i) SEQUENCE CHARACTERISTICS:
            (A) LENGTH: 71 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All C's are 2'-F cytosine (ix) FEATURE:
```

(D) OTHER INFORMATION: All U's are 2'-F uracil (xi) SEQUENCE DESCRIPTION: SEQ ID NO:336:

GGGAGGACGA UGCGGAACGA CUCUUAAGCU GUGCGUUUUC GAACAAGUCG          50

UAACUCAGAC GACUCGCCCG A                                        71

(2) INFORMATION FOR SEQ ID NO:337:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:337:

GGGAGGACGA UGCGGCUCUC AUUUWGCGCG UAAAUCGAGC UAGCCCAGAC          50

GACUCGCCCG A                                                   61

(2) INFORMATION FOR SEQ ID NO:338:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:338:

GGGAGGACGA UGCGGAGUCW CUCUCCACCA KCGUGUKUUA AUCAAGCUAN          50

UGCCUCAGAC GACUCGCCCG A                                        71

(2) INFORMATION FOR SEQ ID NO:339:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:339:

GGGAGGACGA UGCGGUCUAC GGUCUCUCUG GCGGUGCGUA AAUCKAACCA          50

GAUCGCAGAC GACUCGCCCG A                                        71

(2) INFORMATION FOR SEQ ID NO:340:

(i) SEQUENCE CHARACTERISTICS:
            (A) LENGTH: 71 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All C's are 2'-F cytosine (ix) FEATURE:
            (D) OTHER INFORMATION: All U's are 2'-F uracil (xi) SEQUENCE DESCRIPTION: SEQ ID NO:340:

GGGAGGACGA UGCGGUDAUU UCYUAAUCHG AGCGUUUAUC UAUCUMAAUK         50

AUCCUCAGAC GACUCGCCCG A                                       71

(2) INFORMATION FOR SEQ ID NO:341:

(i) SEQUENCE CHARACTERISTICS:
            (A) LENGTH: 62 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All C's are 2'-F cytosine (ix) FEATURE:
            (D) OTHER INFORMATION: All U's are 2'-F uracil (xi) SEQUENCE DESCRIPTION: SEQ ID NO:341:

GGGAGGACGA UGCGGAUCGC AAUMUGUWGC GUUCUCKAAA CAGCCUCAGA        50

CGACUCGCCC GA                                                 62

(2) INFORMATION FOR SEQ ID NO:342:

(i) SEQUENCE CHARACTERISTICS:
            (A) LENGTH: 61 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All C's are 2'-F cytosine (ix) FEATURE:
            (D) OTHER INFORMATION: All U's are 2'-F uracil (xi) SEQUENCE DESCRIPTION: SEQ ID NO:342:

GGGAGGACGA UGCGGUGGUU CUAGGCACGU GUUUUCAAGU GUAAUCAGAC        50

GACUCGCCCG A                                                  61

(2) INFORMATION FOR SEQ ID NO:343:

(i) SEQUENCE CHARACTERISTICS:
            (A) LENGTH: 62 base pairs
            (B) TYPE: nucleic acid
            (C) STRANDEDNESS: single
            (D) TOPOLOGY: linear (ii) MOLECULE TYPE: RNA (ix) FEATURE:

(D) OTHER INFORMATION: All C's are 2'-F cytosine (ix) FEATURE:
    (D) OTHER INFORMATION: All U's are 2'-F uracil (xi) SEQUENCE DESCRIPTION: SEQ ID NO:343:

```
GGGAGGACGA UGCGGAAACA UGUGUUUUCG AAUGUGCUCU CCUCCCCAAA        50

CAACYCCCCC AA                                                 62
```

(2) INFORMATION FOR SEQ ID NO:344:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:344:

```
GGGAGGACGA UGCGGAAGGC CGUGUUAAUC AAGGCUGCAA UAAAUCAUCC        50

UCCCCAGACG ACUCGCCCGA                                         70
```

(2) INFORMATION FOR SEQ ID NO:345:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:345:

```
GGGAGGACGA UGCGGAGGAU CGUGUUCAUC AAGAUUGCUC GUUCUUUACU        50

GCGUUCAGAC GACUCGCCCG A                                       71
```

(2) INFORMATION FOR SEQ ID NO:346:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:346:

```
GGGAGGACGA UGCGGUCAAA GUGAAGAAUG GACAGCGUUU UCGAGUUGCU        50

UCACUCAGAC GACUCGCCCG A                                       71
```

(2) INFORMATION FOR SEQ ID NO:347:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:347:

GGGAGGACGA UGCGGGGAGA AUGGCCAGCG UUUAUCGAGG UGCUCCGUUA        50

ACCGGCAGAC GACUCGCCCG A                                      71

(2) INFORMATION FOR SEQ ID NO:348:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:348:

GGGAGGACGA UGCGGGAGGA AUGGACWGCG UAUAUCGAGU UGCCUCAGAC        50

GACUCGCCCG A                                                 61

(2) INFORMATION FOR SEQ ID NO:349:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:349:

GGGAGGACGA UGCGGAUCGA UUUCAUGCGU UUUUCGAGUG ACGAUCAGAC        50

GACUCGCCCG A                                                 61

(2) INFORMATION FOR SEQ ID NO:350:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (ix) FEATURE:
             (D) OTHER INFORMATION: All C's are 2'-F cytosine (ix) FEATURE:
             (D) OTHER INFORMATION: All U's are 2'-F uracil (xi) SEQUENCE DESCRIPTION: SEQ ID NO:350:

GGGAGGACGA UGCGGAGACC CUAAGMGSGU KSUUUUCAAS CUGGUCWGAC           50

GACUCGCCCG A                                                    61

(2) INFORMATION FOR SEQ ID NO:351:

(i) SEQUENCE CHARACTERISTICS:
            (A) LENGTH: 71 base pairs
            (B) TYPE: nucleic acid
            (C) STRANDEDNESS: single
            (D) TOPOLOGY: linear (ii) MOLECULE TYPE: RNA (ix) FEATURE:
             (D) OTHER INFORMATION: All C's are 2'-F cytosine (ix) FEATURE:
             (D) OTHER INFORMATION: All U's are 2'-F uracil (xi) SEQUENCE DESCRIPTION: SEQ ID NO:351:

GGGAGGACGA UGCGGUUAGC CUACACUCUA GGUUCAGUUU UCGAAUCUUC           50

CACCGCWGAC GACUCGCCCG A                                         71

(2) INFORMATION FOR SEQ ID NO:352:

(i) SEQUENCE CHARACTERISTICS:
            (A) LENGTH: 61 base pairs
            (B) TYPE: nucleic acid
            (C) STRANDEDNESS: single
            (D) TOPOLOGY: linear (ii) MOLECULE TYPE: RNA (ix) FEATURE:
             (D) OTHER INFORMATION: All C's are 2'-F cytosine (ix) FEATURE:
             (D) OTHER INFORMATION: All U's are 2'-F uracil (xi) SEQUENCE DESCRIPTION: SEQ ID NO:352:

GGGAGGACGA UGCGGUUAGG UCAAUGAUCU UAGUUUUCGA UUCGUCAGAC           50

GACUCGCCCG A                                                    61

(2) INFORMATION FOR SEQ ID NO:353:

(i) SEQUENCE CHARACTERISTICS:
            (A) LENGTH: 61 base pairs
            (B) TYPE: nucleic acid
            (C) STRANDEDNESS: single
            (D) TOPOLOGY: linear (ii) MOLECULE TYPE: RNA (ix) FEATURE:
             (D) OTHER INFORMATION: All C's are 2'-F cytosine (ix) FEATURE:
             (D) OTHER INFORMATION: All U's are 2'-F uracil (xi) SEQUENCE DESCRIPTION: SEQ ID NO:353:

GGGAGGACGA UGCGGACGUG UGUAUCRARU UUUCCGCUGU UUGUGCAGAC          50

GACUCGCCCG A          61

(2) INFORMATION FOR SEQ ID NO:354:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:354:

GGGAGGACGA UGCGGACAGG GUUCUUAGGC GGAGUGUUCA UCAAUCCAAC          50

CAUGUCAGAC GACUCGCCCG A          71

(2) INFORMATION FOR SEQ ID NO:355:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:355:

GGGAGGACGA UGCGGCGAUU UCCACAGUUU GUCUUAUUCC GCAUAUCAGA          50

CGACUCGCCC GA          62

(2) INFORMATION FOR SEQ ID NO:356:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:356:

GGGAGGACGA UGCGGAUAYU CAGCUYGUGU KUUUUCDAUC UUCCCCAGAC          50

GACUCGCCCG A          61

(2) INFORMATION FOR SEQ ID NO:357:

(i) SEQUENCE CHARACTERISTICS:
        (A) LENGTH: 61 base pairs
        (B) TYPE: nucleic acid (C) STRANDEDNESS: single
            (D) TOPOLOGY: linear (ii) MOLECULE TYPE: RNA (ix) FEATURE:
            (D) OTHER INFORMATION: All C's are 2'-F cytosine (ix) FEATURE:
            (D) OTHER INFORMATION: All U's are 2'-F uracil (xi) SEQUENCE DESCRIPTION: SEQ ID NO:357:

GGGAGGACGA UGCGGCACAC GUGUUUUCAA GUGUGCUCCU GGGAUCAGAC         50

GACUCGCCCG A                                                  61

(2) INFORMATION FOR SEQ ID NO:358:

(i) SEQUENCE CHARACTERISTICS:
            (A) LENGTH: 61 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All C's are 2'-F cytosine (ix) FEATURE:
            (D) OTHER INFORMATION: All U's are 2'-F uracil (xi) SEQUENCE DESCRIPTION: SEQ ID NO:358:

GGGAGGACGA UGCGGCAAUG UGUUUCUCAA AUUGCUUUCU CCCUUCAGAC         50

GACUCGCCCG A                                                  61

(2) INFORMATION FOR SEQ ID NO:359:

(i) SEQUENCE CHARACTERISTICS:
            (A) LENGTH: 71 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All C's are 2'-F cytosine (ix) FEATURE:
            (D) OTHER INFORMATION: All U's are 2'-F uracil (xi) SEQUENCE DESCRIPTION: SEQ ID NO:359:

GGGAGGACGA UGCGGAUACU ACCGUGCGAA CACUAAGUCC CGUCUGUCCA         50

CUCCUCAGAC GACUCGCCCG A                                       71

(2) INFORMATION FOR SEQ ID NO:360:

(i) SEQUENCE CHARACTERISTICS:
            (A) LENGTH: 66 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All C's are 2'-F cytosine (ix) FEATURE:
            (D) OTHER INFORMATION: All U's are 2'-F uracil (xi) SEQUENCE DESCRIPTION: SEQ ID NO:360:

GGGAGGACGA UGCGGAUACU AUGUGCGUUC ACUAAGUCCC GUCGUCCCCU        50

CAGACGACUC GCCCGA        66

(2) INFORMATION FOR SEQ ID NO:361:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:361:

GGGAGGACGA UGCGGGUACU AUGUACGAUC ACUAAGCCCC AUCACCCUUC        50

UCACUCAGAC NACUCGCCCG A        71

(2) INFORMATION FOR SEQ ID NO:362:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:362:

GGGAGGACGA UGCGGUUACU AUGUACAUUU ACUAAGACCC AACGUCAGAC        50

GACUCGCCCG A        61

(2) INFORMATION FOR SEQ ID NO:363:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:363:

GGGAGGACGA UGCGGUUWCU AUGUWCGCCU UACUAAGUAC CCGUCGACUG        50

UCCCAUCAGA CGACUCGCCC GA        72

(2) INFORMATION FOR SEQ ID NO:364:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:364:

GGGAAGACGA UGCGGUGUUG AUCAAUGAAU GUCCUCCUCC UACCCCAGAC            50

GACUCGCCCG A                                                     61

(2) INFORMATION FOR SEQ ID NO:365:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:365:

GGGAGGACGA UGCGGUGUUU GUCAAUGUCA UGAUUAGUUU UCCCACAGAC            50

GACUCGCCCG A                                                     61

(2) INFORMATION FOR SEQ ID NO:366:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:366:

GGGAGGACGA UGCGGCGGUC UUAAGCAGUG UGUCAAUCAA ACUAUCGUCA            50

GACGACUCGC CCGA                                                  64

(2) INFORMATION FOR SEQ ID NO:367:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
    (D) OTHER INFORMATION: All U's are 2'-F uracil (xi) SEQUENCE DESCRIPTION: SEQ ID NO:367:

GGGAGGACGA UGCGGUUCUU AAGCAGCGCG UCAAUCGAGC UAACCCAGAC          50

GACUCGCCCG A                                                    61

(2) INFORMATION FOR SEQ ID NO:368:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:368:

GGGAGGACGA UGCGGAAUGR CCCGUUACCA WCAAUGCGCC UCDUUGMCCC          50

CAAACAACYC CCCCAA                                               66

(2) INFORMATION FOR SEQ ID NO:369:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:369:

GGGAGGACGA UGCGGAAUYU CGUGYUACGC GUYYYCUAUC CAAUCUACCC          50

CMUCUCCAAU CAGACGACYC                                           70

(2) INFORMATION FOR SEQ ID NO:370:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:370:

GGGAGGACGA UGCGGCGCUU ACAAUAAUUC UCCCUGAGUA CAGCUCAGAC          50

GACUCGCCCG A                                                    61

(2) INFORMATION FOR SEQ ID NO:371:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:371:

```
GGGAGGACGA UGCGGAACUU CUUAGGCAGC GUGCUAGUCA AGCUAAGUUC          50

CACCUCAGAC GACUCGCCCG A                                         71
```

(2) INFORMATION FOR SEQ ID NO:372:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:372:

```
GGGAGGACGA UGCGGCACAA UCUUCGGCAG CGUGCAAGAU CAAGCUAUUG          50

UUGUCAGACG ACUCGCCCGA                                           70
```

(2) INFORMATION FOR SEQ ID NO:373:

(i) SEQUENCE CHARACTERISTICS:
        (A) LENGTH:  61 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:373:

```
GGGAGGACGA UGCGGUCAUU AACCAAGAUA UGCGAAUCAC CUCCUCAGAC          50

GACUCGCCCG A                                                    61
```

(2) INFORMATION FOR SEQ ID NO:374:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: RNA (ix) FEATURE:
    (D) OTHER INFORMATION: All C's are 2'-F cytosine (ix) FEATURE:
    (D) OTHER INFORMATION: All U's are 2'-F uracil (xi) SEQUENCE DESCRIPTION: SEQ ID NO:374:

GGGAGGACGA UGCGGUCAUU CUCUAAAAAA GUAUUCCGUA CCUCCACAGA         50

CGACUCGCCC GA         62

(2) INFORMATION FOR SEQ ID NO:375:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:375:

GGGAGGACGA UGCGGGUGAU CUUUUAUGCU CCUCUUGUUU CCUGUCAGAC         50

GACUCGCCCG A         61

(2) INFORMATION FOR SEQ ID NO:376:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:376:

GGGAGGACNA UGCGGUCUAG GCAUCGCUAU UCUUUACUGA UAUAAUUACU         50

CCCCUCAGAC GACUCGCCCG A         71

(2) INFORMATION FOR SEQ ID NO:377:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:377:

GGGAGGACGA UGCGGAGUWW GCNCGGUCCA GUCACAUCCW AUCCCCAGAC         50

GACUCGCCCG A                                                                    61

(2) INFORMATION FOR SEQ ID NO:378:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:378:

GGGAGGACGA UGCGGCUCUC AUAUKGWGUR UUYUUCMUUC SRGGCUCAAA                          50

CAAYYCCCCC AA                                                                   62

(2) INFORMATION FOR SEQ ID NO:379:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:379:

GGGAGGACGA UGCGGCUUGU UAGUUAAACU CGAGUCUCCA CCCCUCAGAC                          50

GACUCGCCCG A                                                                    61

(2) INFORMATION FOR SEQ ID NO:380:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:380:

GGGAGGACGA UGCGGUCUCU WCUVACVUGU RUUCACAUUU UCGCYUCAAA                          50

CAACYCCCCC AA                                                                   62

(2) INFORMATION FOR SEQ ID NO:381:

(i) SEQUENCE CHARACTERISTICS:
        (A) LENGTH: 61 base pairs
        (B) TYPE: nucleic acid
        (C) STRANDEDNESS: single (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:381:

GGGAGGACGA UGCGGUURAC AAUGRSSCUC RCCUUCCCWG GUCCUCAGAC          50

GACUCGCCCG A                                                   61

(2) INFORMATION FOR SEQ ID NO:382:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:382:

AGGAGGACGA UGCGGUUAUC UGAARCWUGC GUAAMCUARU GUSAAASUGC          50

AACRACRAAC AACYCSCCCA A                                        71

(2) INFORMATION FOR SEQ ID NO:383:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:383:

AGGAAGACGA UGCGGUUCGA UUUAUUUGUG UCAUUGUUCU UCCAUCAGAC          50

GACUCGCCCG A                                                   61

(2) INFORMATION FOR SEQ ID NO:384:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:384:

GUGAUGACAU GGAUUACGCC AGACGACUCG CCCGA                                          35

(2) INFORMATION FOR SEQ ID NO:385:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All C's are 2'-F cytosine (ix) FEATURE:
            (D) OTHER INFORMATION: All U's are 2'-F uracil (xi) SEQUENCE DESCRIPTION: SEQ ID NO:385:

UGCGUGUUUU CAAGCA                                                               16

(2) INFORMATION FOR SEQ ID NO:386:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All C's are 2'-F cytosine (ix) FEATURE:
            (D) OTHER INFORMATION: All U's are 2'-F uracil (xi) SEQUENCE DESCRIPTION: SEQ ID NO:386:

CUCAAAUUGC GUGUUUCAA GCA                                                        23

(2) INFORMATION FOR SEQ ID NO:387:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All C's are 2'-F cytosine (ix) FEATURE:
            (D) OTHER INFORMATION: All U's are 2'-F uracil (xi) SEQUENCE DESCRIPTION: SEQ ID NO:387:

GGUACCUCAA AUUGCGUGUU UUCAAGCAGU AUC                                            33

(2) INFORMATION FOR SEQ ID NO:388:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: RNA (ix) FEATURE:

-continued (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:388:

GGAGUCUUAG GCAGCGCGUU UUCGAGCUAC UCC                          33

(2) INFORMATION FOR SEQ ID NO:389:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:389:

GGGAGGACGA UGCGGNNNNN NNNNNNNNNN NNNNNNNNNN NNNNNNNNNN         50

NNNNNCAGAC GACUCGCCCG A                                       71

(2) INFORMATION FOR SEQ ID NO:390:

(i) SEQUENCE CHARACTERISTICS:
        (A) LENGTH: 97 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All C's are 2'-F cytosine (ix) FEATURE:
        (D) OTHER INFORMATION: All U's are 2'-F uracil (xi) SEQUENCE DESCRIPTION: SEQ ID NO:390:

GGGAGACAAG AAUAAACGCU CAANNNNNNN NNNNNNNNNN NNNNNNNNNN         50

NNNNNNNNNN NNNNNNNNNN NNNUUCGACA GGAGGCUCAC AACAGGC            97

We claim:

1. A method for identifying modified, single-stranded ribonucleic acid ligands to a lectin comprising:
   a) contacting a candidate mixture of modified, single-stranded ribonucleic acids with a lectin, said modified ribonucleic acids selected from the group consisting of 2'-amino (2'-NH$_2$) modified ribonucleic acids and 2'-fluoro (2'-F) modified ribonucleic acids, wherein ribonucleic acids having an increased affinity to said lectin relative to the candidate mixture may be partitioned from the remainder of the candidate mixture;
   b) partitioning the increased affinity ribonucleic acids from the remainder of the candidate mixture; and
   c) amplifying the increased affinity ribonucleic acids to yield a mixture of ribonucleic acids enriched for ribonucleic acid sequences with relatively high affinity and specificity for binding to said lectin, whereby modified, single-stranded ribonucleic acid ligands to said lectin may be identified.

2. A method for forming a multivalent Complex of nucleic acid ligands to a lectin comprising:
   a) contacting a candidate mixture of nucleic acids with a lectin, wherein nucleic acids having an increased affinity to said lectin relative to the candidate mixture may be partitioned from the remainder of the candidate mixture;
   b) partitioning the increased affinity nucleic acids from the remainder of the candidate mixture; and
   c) amplifying the increased affinity nucleic acids to yield a mixture of nucleic acids enriched for nucleic acid sequences with relatively higher affinity and specificity for binding to said lectin, whereby nucleic acid ligands to said lectin may be identified; and
   d) forming a multivalent Complex comprising two nucleic acid ligands identified in step c).

3. A method for identifying single-stranded ribonucleic acid ligands and producing modified ribonucleic acid ligands to a lectin comprising:

a) contacting a candidate mixture of single-stranded ribonucleic acids with a lectin, wherein ribonucleic acids having an increased affinity to said lectin relative to the candidate mixture may be partitioned from the remainder of the candidate mixture;

b) partitioning the increased affinity ribonucleic acids from the remainder of the candidate mixture; and c) amplifying the increased affinity ribonucleic acids to yield a mixture of single-stranded ribonucleic acids enriched for ribonucleic acid sequences with relatively higher affinity and specificity for binding to said lectin, whereby the ribonucleic acid ligands to said lectin may be identified; and d) substituting 2'-O-methyl ribonucleic acids for 2'-OH ribonucleic acids in the ribonucleic acid ligands identified in step c), whereby the modified ribonucleic acids to a ligand are produced.

4. A method for identifying nucleic acid ligands and nucleic acid ligand sequences to a lectin comprising:

a) contacting a candidate mixture of nucleic acids with a lectin, wherein nucleic acids having an increased affinity to said lectin relative to the candidate mixture may be partitioned from the remainder of the candidate mixture;

b) partitioning the increased affinity nucleic acids from the remainder of the candidate mixture; and c) amplifying the increased affinity nucleic acids to yield a mixture of nucleic acids enriched for nucleic acid sequences with relatively higher affinity and specificity for binding to said lectin, whereby nucleic acid ligands to said lectin may be identified, wherein said lectin is a selectin.

5. The method of claim 4 wherein said selectin is selected from the group consisting of L-selectin, E-selectin, and P-selectin.

6. A purified and isolated non-naturally occurring nucleic acid ligand to a lectin.

7. The nucleic acid ligand of claim 6 which is a non-naturally occurring nucleic acid ligand having a specific binding affinity for said lectin, such lectin being a three dimensional chemical structure other than a polynucleotide that binds to said nucleic acid ligand through a mechanism which predominantly depends on Watson/Crick base pairing or triple helix binding, wherein said nucleic acid ligand is not a nucleic acid having the known physiological function of being bound by said lectin.

8. The nucleic acid ligand of claim 6 wherein said lectin is selected from the group consisting of a mammalian lectin, a plant lectin, a microbial lectin and a viral lectin.

9. The nucleic acid ligand of claim 6 wherein said lectin is selected from the group consisting of wheat germ agglutinin, L-selectin, E-selectin and P-selectin.

10. The nucleic acid ligand of claim 6 wherein said lectin is wheat germ agglutinin.

11. The nucleic acid ligand to wheat germ agglutinin of claim 10 wherein said nucleic acid ligand is a ribonucleic acid (RNA) ligand.

12. The nucleic acid ligand of claim 11 which comprises a modified ribonucleic acid.

13. The nucleic acid ligand of claim 12 wherein said modified ribonucleic acid is a 2'-amino ($NH_2$) modified ribonucleic acid.

14. The nucleic acid ligand to wheat germ agglutinin of claim 13 wherein said ligand is an RNA ligand selected from the group consisting of the nucleotide sequences set forth in Table 2.

15. The nucleic acid ligand of claim 14 wherein said ligand is selected from the group consisting of SEQ ID NOS: 4–55.

16. The nucleic acid ligand of claim 11 wherein said ligand comprises sequences selected from the group consisting of SEQ ID NOS: 56–63.

17. The nucleic acid ligand to wheat germ agglutinin of claim 10 wherein said ligand is substantially homologous to a ligand selected from the group consisting of the sequences set forth in Table 2.

18. The nucleic acid ligand to wheat germ agglutinin of claim 10 wherein said ligand has substantially the same structure as a ligand selected from the group consisting of the sequences set forth in Table 2.

19. The nucleic acid ligand of claim 6 wherein said lectin is a selectin.

20. The nucleic acid ligand of claim 19 wherein said selectin is selected from the group consisting of L-selectin, E-selectin and P-selectin.

21. The nucleic acid ligand of claim 20 wherein said selectin is L-selectin.

22. The nucleic acid ligand to L-selectin of claim 21 wherein said nucleic acid ligand is ribonucleic acid (RNA) ligand.

23. The nucleic acid ligand of claim 22 which comprises a modified ribonucleic acid.

24. The nucleic acid ligand of claim 23 wherein said modified ribonucleic acid is selected from the group consisting of a 2'-amino (2'-$NH_2$) modified ribonucleic acid and a 2'-fluoro (2'-F) modified ribonucleic acid.

25. The nucleic acid ligand to L-selectin of claim 24 wherein said ligand is an RNA ligand selected from the group consisting of the nucleotide sequences set forth in Tables 8 and 16.

26. The nucleic acid ligand of claim 25 wherein said ligand is selected from the group consisting of SEQ ID NOS: 67–117 and 293–388.

27. The nucleic acid ligand of claim 22 wherein said ligand comprises sequences selected from the group consisting of SEQ ID NOS: 118–125.

28. The nucleic acid ligand to L-selectin of claim 21 wherein said ligand is substantially homologous to a ligand selected from the group consisting of the sequences set forth in Tables 8, 12 and 16.

29. The nucleic acid ligand to L-selectin of claim 21 wherein said ligand has substantially the same structure as a ligand selected from the group consisting of the sequences set forth in Tables 8, 12 and 16.

30. The nucleic acid ligand to L-selectin of claim 21 wherein said nucleic acid ligand is deoxyribonucleic acid (DNA).

31. The nucleic acid ligand to L-selectin of claim 30 wherein said ligand is an DNA ligand selected from the group consisting of the nucleotide sequences set forth in Table 12.

32. The nucleic acid ligand of claim 31 wherein said ligand is selected from the group consisting of SEQ ID NOS: 129–180 and 185–196.

33. The nucleic acid ligand of claim 30 wherein said ligand comprises sequences selected from the group consisting of SEQ ID NOS: 181–184.

34. The nucleic acid ligand of claim 20 wherein said selectin is P-selectin.

35. The nucleic acid ligand to P-selectin of claim 34 wherein said nucleic acid ligand is ribonucleic acid (RNA) ligand.

36. The nucleic acid ligand of claim 35 which comprises a modified ribonucleic acid.

37. The nucleic acid ligand of claim 36 wherein said modified ribonucleic acid is selected from the group consisting of a 2'-amino (2'-NH$_2$) modified ribonucleic acid, a 2'-fluoro (2'-F) modified ribonucleic acid, and a 2'-O-Methyl (2'-O-Me) modified ribonucleic acid.

38. The nucleic acid ligand to P-selectin of claim 37 wherein said ligand is an RNA ligand selected from the group consisting of the nucleotide sequences set forth in Tables 19, 21 and 25.

39. The nucleic acid ligand of claim 38 wherein said ligand is selected from the group consisting of SEQ ID NOS: 199–219 and 236–290.

40. The nucleic acid ligand of claim 35 wherein said ligand comprises sequences selected from the group consisting of SEQ ID NO: 291.

41. A nucleic acid ligand to P-selectin of claim 34 wherein said ligand is substantially homologous to a ligand selected from the group consisting of the sequences set forth in Tables 19, 21 and 25.

42. The nucleic acid ligand to P-selectin of claim 34 wherein said ligand has substantially the same structure as a ligand selected from the group consisting of the sequences set forth in Tables 19, 21 and 25.

43. The nucleic acid ligand to P-selectin of claim 37 wherein said nucleic acid ligand is deoxyribonucleic acid (DNA).

44. The nucleic acid ligand of claim 6 wherein said ligand is a ribonucleic acid ligand.

45. The nucleic acid ligand of claim 44 which comprises a modified ribonucleic acid.

46. The nucleic acid ligand of claim 45 wherein said modified ribonucleic acid is selected from the group consisting of 2'-amino (2'-NH$_2$) modified ribonucleic acids, 2'-fluoro (2'-F) modified ribonucleic acids and 2'-O-Methyl (2'-O-Me) modified ribonucleic acids.

47. The nucleic acid ligand of claim 6 wherein said ligand is a deoxyribonucleic acid.

48. The nucleic acid ligand of claim 6 wherein said ligand has been chemically modified at a sugar and/or phosphate and/or base.

49. A multivalent Complex comprising a plurality of ligands of claim 6.

50. A nucleic acid ligand to a lectin identified according to the method comprising:

a) contacting a candidate mixture of nucleic acids with a lectin, wherein nucleic acids having an increased affinity to said lectin relative to the candidate mixture may be partitioned from the remainder of the candidate mixture;

b) partitioning the increased affinity nucleic acids from the remainder of the candidate mixture; and c) amplifying the increased affinity nucleic acids to yield a mixture of nucleic acids enriched for nucleic acid sequences with relatively higher affinity and specificity for binding to said lectin, whereby nucleic acid ligand of said lectin may be identified.

\* \* \* \* \*